United States Patent
Stupple et al.

(10) Patent No.: US 11,911,372 B2
(45) Date of Patent: Feb. 27, 2024

(54) COMPOUNDS

(71) Applicant: CTXT PTY LTD, Parkville (AU)

(72) Inventors: Paul Anthony Stupple, Parkville (AU); Helen Rachel Lagiakos, Parkville (AU); Richard Charles Foitzik, Parkville (AU); Michelle Ang Camerino, Parkville (AU); George Nikolakopoulos, Bundoora (AU); Ylva Elisabet Bergman Bozikis, Parkville (AU); Wilhelmus Johannes Antonius Kersten, Bundoora (AU); Scott Raymond Walker, Parkville (AU); Jonathan Grant Hubert, Parkville (AU)

(73) Assignee: CTXT PTY LTD, Parkville (AU)

(*) Notice: Subject to any disclaimer, the term of this patent is extended or adjusted under 35 U.S.C. 154(b) by 44 days.

(21) Appl. No.: 17/059,818

(22) PCT Filed: Jun. 28, 2019

(86) PCT No.: PCT/EP2019/067309
§ 371 (c)(1),
(2) Date: Nov. 30, 2020

(87) PCT Pub. No.: WO2020/002587
PCT Pub. Date: Jan. 2, 2020

(65) Prior Publication Data
US 2021/0213004 A1 Jul. 15, 2021

(30) Foreign Application Priority Data
Jun. 28, 2018 (GB) ...................................... 1810581

(51) Int. Cl.
*A61K 31/4439* (2006.01)
*A61K 31/422* (2006.01)
*A61K 31/4245* (2006.01)
*A61K 31/433* (2006.01)
*A61K 45/06* (2006.01)

(52) U.S. Cl.
CPC ........ *A61K 31/4439* (2013.01); *A61K 31/422* (2013.01); *A61K 31/4245* (2013.01); *A61K 31/433* (2013.01); *A61K 45/06* (2013.01)

(58) Field of Classification Search
CPC .......................... C07D 261/16; A61K 31/4439
See application file for complete search history.

(56) References Cited

U.S. PATENT DOCUMENTS

| 2,358,031 | A | 9/1944 | Roblin et al. |
| 2,525,321 | A | 10/1950 | Hultquist et al. |
| 3,064,003 | A | 11/1962 | Satzinger et al. |
| 3,332,942 | A | 7/1967 | Breivogel et al. |
| 3,951,967 | A | 4/1976 | Novello |
| 3,960,854 | A | 6/1976 | Novello |
| 4,251,664 | A | 2/1981 | Spitzner |
| 6,248,767 | B1 | 6/2001 | Blok et al. |
| 8,071,631 | B2 * | 12/2011 | Muchowski ............ A61P 33/00 514/363 |
| 2006/0025415 | A1 | 2/2006 | Gonzalez et al. |
| 2006/0128706 | A1 | 6/2006 | Bruncko et al. |
| 2006/0258657 | A1 | 11/2006 | Bruncko et al. |
| 2007/0015787 | A1 | 1/2007 | Bruncko et al. |
| 2007/0072860 | A1 | 3/2007 | Bruncko et al. |
| 2009/0042945 | A1 | 2/2009 | Frank et al. |
| 2009/0163545 | A1 | 6/2009 | Goldfarb |
| 2013/0022629 | A1 | 1/2013 | Sharpe et al. |
| 2015/0183802 | A1 | 7/2015 | Chen et al. |
| 2016/0009667 | A1 | 1/2016 | Chen et al. |

FOREIGN PATENT DOCUMENTS

| BE | 617370 A | 11/1962 |
| CA | 2121724 A1 | 10/1994 |
| CN | 101747325 A | 6/2010 |
| CN | 101845043 A | 9/2010 |
| DE | 1102745 B | 3/1961 |
| EP | 181018 A2 | 5/1986 |
| EP | 371438 A2 | 6/1990 |
| EP | 0558258 A1 | 9/1993 |
| EP | 0569193 A1 | 11/1993 |
| EP | 1963295 A1 | 9/2008 |
| FR | 2690160 A1 | 10/1993 |
| GB | 689281 A | 3/1953 |

(Continued)

OTHER PUBLICATIONS

Potkin et al Russian Journal of Organic Chemistry (2009), 45(6),879-883 (Year: 2009).*
J. A. L. Brown et al: "Targeting cancer using KAT inhibitors to mimic lethal knockouts", Biochemical Society Transactions, vol. 44, No. 4, Aug. 15, 2016, pp. 979-986.
Joshi et al., Immunity 2015, 43, 579-590 doi:10.1016/j.immuni.2015.08.006.
Judes et al., Epigenomics, 2015, 7(8), 1351-1363.
Keil et al., ChemMedChem, 2011, 6(4), 633-653.
King et al., Journal of Biological Chemistry, 2009, 284(14), 9059-9065.

(Continued)

*Primary Examiner* — Kamal A Saeed
(74) *Attorney, Agent, or Firm* — Banner & Witcoff, Ltd.

(57) ABSTRACT

A compound of formula (I), or a pharmaceutically acceptable salt thereof.

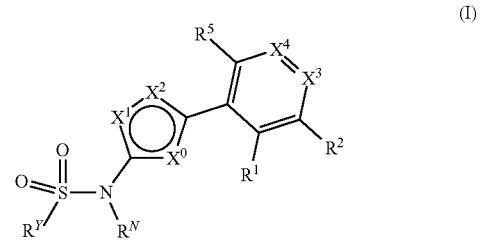

13 Claims, No Drawings

(56) References Cited

FOREIGN PATENT DOCUMENTS

| | | | |
|---|---|---|---|
| JP | 29002834 B | 5/1927 | |
| JP | 36003685 B | 4/1936 | |
| JP | 36019566 B | 10/1936 | |
| JP | 39001229 B | 2/1939 | |
| JP | 49008255 B | 2/1974 | |
| JP | 54052075 A | 4/1979 | |
| JP | 03258771 A | 11/1991 | |
| JP | 63238006 A | 10/1998 | |
| JP | 2003292485 A | 10/2003 | |
| PL | 220630 B1 | 11/2015 | |
| WO | 199321171 A1 | 10/1993 | |
| WO | 199427979 A1 | 12/1994 | |
| WO | 199631492 A1 | 10/1996 | |
| WO | 199739000 A1 | 10/1997 | |
| WO | 199813366 A1 | 4/1998 | |
| WO | 199821186 A1 | 5/1998 | |
| WO | 199849162 A1 | 11/1998 | |
| WO | 2001019798 A2 | 3/2001 | |
| WO | 200149289 A1 | 7/2001 | |
| WO | 200164642 A2 | 9/2001 | |
| WO | 200164643 A2 | 9/2001 | |
| WO | 2003042700 A2 | 5/2003 | |
| WO | 2003044000 A1 | 5/2003 | |
| WO | 2004085385 A2 | 10/2004 | |
| WO | 2004103980 A1 | 12/2004 | |
| WO | 2004113310 A1 | 12/2004 | |
| WO | 2005009967 A2 | 2/2005 | |
| WO | 2005013914 A2 | 2/2005 | |
| WO | 2006044405 A1 | 4/2006 | |
| WO | 2006122799 A1 | 11/2006 | |
| WO | 2006124744 A1 | 11/2006 | |
| WO | 2007039174 A2 | 4/2007 | |
| WO | 2007039175 A1 | 4/2007 | |
| WO | 2007057093 A1 | 5/2007 | |
| WO | 2007075895 A2 | 7/2007 | |
| WO | 2008022286 A2 | 2/2008 | |
| WO | 2008063668 A1 | 5/2008 | |
| WO | 2008064116 A2 | 5/2008 | |
| WO | 2008089307 A2 | 7/2008 | |
| WO | 2009012242 A2 | 1/2009 | |
| WO | 2009058348 A1 | 5/2009 | |
| WO | 2009080223 A1 | 7/2009 | |
| WO | 201019788 A1 | 2/2010 | |
| WO | 2010046780 A2 | 4/2010 | |
| WO | 2010121963 A1 | 10/2010 | |
| WO | 2011017561 A1 | 2/2011 | |
| WO | 2011082400 A2 | 7/2011 | |
| WO | 2011085575 A1 | 7/2011 | |
| WO | 2011137089 A1 | 11/2011 | |
| WO | 2011156610 A2 | 12/2011 | |
| WO | 2012080729 A2 | 6/2012 | |
| WO | 2012088438 A1 | 6/2012 | |
| WO | 2012129562 A2 | 9/2012 | |
| WO | 2014144545 A2 | 9/2014 | |
| WO | 2015112465 A1 | 7/2015 | |
| WO | 2016198507 A1 | 12/2016 | |
| WO | 2017002120 A1 | 1/2017 | |
| WO | 2017098421 A1 | 6/2017 | |
| WO | 2018081167 A1 | 5/2018 | |
| WO | 2018102419 A1 | 6/2018 | |
| WO | 2018226976 A1 | 12/2018 | |

OTHER PUBLICATIONS

Klosa, Archiv der Pharmazie und Berichte der Deutschen Pharmazeutischen Gesellschaft, 1954, 287, 12-14.
Kurihara et al., Yakugaku Zasshi, 1965, 85(10), 920-5.
Kuznetsov et al., Izvestiya Akademii Nauk SSSR, Seriya Khimicheskaya 1976, (2), 319-22.
Lagiakos et al., U.S. Appl. No. 16/445,868, filed Jun. 20, 2019.
Lagiakos et al., U.S. Appl. No. 16/445,868 Notice of Allowance dated Oct. 5, 2020.
Lagiakos et al., U.S. Appl. No. 16/445,868 Response to Non-Final Office Action filed Aug. 19, 2020.
Lalezari et al., Journal of Heterocyclic Chemistry, 1966, 3(3), 336-7.
Lazaris et al., Khimiya Geterotsiklicheskikh Soedinenii, 1973, (10), 1345-50.
Lee, Archives of Pharmacal Research, 2004, 27(3), 305-313.
Li et al., PNAS, 2007, 104, 4571-4576 doi:10.1073/pnas.0700298104.
Liu, Workman and Vignali, The FEBS journal, 2016, 283, 2731-2748.
Malev, Metody Polucheniya Khimicheskikh Reaktivov i Preparatov 1964, No. 8, 44-8.
Melero et al. Nature Reviews Cancer, 2015, 15, 457-472 doi:10.1038/nrc3973.
Meng et al., Zhongguo Yaowu Huaxue Zazhi, 1996, 6(4), 257-261.
Merson et al., J. Neurosci., 2006, 26, 11359-11370 doi :10.1523/JNEUROSCI.2247-6.2006.
Miller, A.M. et al. J. Immunol., 2006, 177, 7398-7405 doi:10.4049/jimmunol.177.10.7398.
Mochona et al, Bioorg. & Med. Chem. Lett., 2016, 26(12), 2847-2851.
Morrow et al., PCT/EP2018/073431 International Search Report and Written Opinion dated Dec. 3, 2018.
Morrow et al., U.S. Appl. No. 16/642,290, filed Feb. 26, 2020.
Morrow et al., U.S. Appl. No. 16/642,290 Preliminary Amendment filed Feb. 26, 2020.
Neidlein & Hausmann, Zeitschrift fur Naturforschung, Teil B. Chemie, Biochemie, Biophysik, Biologie und wervandte Gebeite, 1966, 21(9), 898.
Neidlein & J. Tauber, Pharmazeutische Zentralhalle, 1968, 107(6), 430-432.
Pachhamia J. Indian Chem. Soc., 1988, 65(5), 357-361.
Pattan et al., Asian Journal of Research in Chemistry, 2009, 2(2), 123-126.
Pattan et al., Iranian Journal of Pharmaceutical Sciences, 2009, 5(4), 225-230.
Persa et al., Cancer Letters, 2015 368(2), 252-261 doi:10.1016/j.canlet.2015.03.003.
Polozov et al., Tetrahedron Letters, 2010, 51(4), 575-578.
Potkin et al., Russian Journal of Organic Chemistry, 2009, 45(6), 879-883.
Rosenthal et al., Bioorganic & Medicinal Chemistry Letters, 2013, 23(20), 5660-5666.
Savastre et al., Bulletin of University of Agricultural Sciences and Veterinary Medicine Cluj-Napoca, Veterinary Medicine, 2013, 70(1), 134-139.
Sheikh et al., Blood, 2015, 125(12), 1910-21 doi:10.1182/blood-2014-08-594655.
Shi et al, Nature Biotech, 2015, 33, 661-667 doi:10.1038/nbt.3235.
Singh et al., International Journal of Chemical Sciences, 2012, 10(3), 1487-1492.
Smaine et al., Bioorganic & Medicinal Chemistry Letters, 2008, 18(24), 6332-6335.
Spillane et al., Journal of Agricultural and Food Chemistry (2009), 57(12), 5486-5493.
Stachel, Chemische Berichte, 1963, 96, 1088-97.
Stein et al., Journal of Medicinal Chemistry, 1995, 38, 1344-1354.
Stern et al., Crit. Rev. Oncol. Hematol., 2005, 54, 11-29 doi:10.1016/j.critrevonc.2004.10.011.
Su et al., Int. J. Mol. Sci., 2016, 17, 1-18 doi:10.3390/ijms17101594.
Sugai et al., Chemical & Pharmaceutical Bulletin, 1984, 32(2), 530-7.
Suyama et al., Heterocycles, 2003, 60(1), 121-129.
Tait et al., Bollettino chimico Farmaceutico, 1990, 129(9), 273-275.
Tan et al., Yingyong Huaxue, 2016, 33(9), 1067-1072.
Tao, H. et al., Lung Cancer, 2012, 75, 95-101 doi:10.1016/j.lungcan.2011.06.002.
Thomas et al., Development, 2000, 127, 2537-2548 PMID:10821753.
Aggarwal and Calvi, Nature, 2004, 430, 372-376 doi:10.1038/nature02694.
Aiello et al., Ricerca Scientifica, Parte 2: Rendiconti, Sezione B: Biologica, 1964, 4(4), 575-80.
Avvakumov et al., Oncogene, 2007, 26, 5395-5407 doi:10.1038/sj.onc.1210608.

(56) References Cited

OTHER PUBLICATIONS

Baell et al., Nature, doi:/10.1038/s41586-018-0387-5, 2018.
Berge et al., J. Pharm. Sci., 1977, 66, 1-19 doi:10.1002/jps.2600660104.
Borrow et al., Nat. Genet., 1996, 14, 33-41 doi:10.1038/ng0996-33.
Brown et al., Biocehmical Society Transactions, 2016, 44(4), 979-986.
CAS Registry No. 1808493-75-5.
CAS Registry No. 1808779-04-5.
CAS Registry No. 2094666-45-0.
CAS Registry No. 891026-69-0.
CAS Registry No. 891026-77-0.
CAS Registry No. 891027-89-7.
CAS Registry No. 891028-12-9.
CAS Registry No. 891028-89-0.
CAS Registry No. 892699-39-7.
CAS Registry Nos. 1032507-60-0, 2094317-93-6, 891027-49-9, and 891028-05-0.
Chavan et al., Indian Journal of Heterocyclic Chemistry, 2007, 17(1), 45-48.
Czudor et al., Bioorganic & Med. Chem. Let., 2018, vol. 28, p. 769-773.
Dekker et al., Drug, Discov. Today, 2014, 19, 654-660 doi:10.1016/j.drudis.2013.11.012.
Dhuban et al., Sci. Immunol., 2017, 2, 9297 doi:10.1126/sciimmunol.aai9297.
Doyon et al., Mol. Cell., 2006, 21, 51-64 doi:10.1016/j.molcel.2005.12.007.
Duong et al., Cancer Res., 2013, 73, 5556-5568 doi:10.1158/0008-5472.CAN-13-0013.
Dzhemukhadze et al., Fenol'nye Soedineniya i lkh Biologicheskie Funktsii, Materialy Vsesoyuznogo Simpoziuma po Fenol'nym Soedineniyam 1968, 196-202.
Fairley et al., Synlett, 2013, 24(5), 570-574.
Falk et al., J. Biomolecular Screening 16(10): 2011 DOI:10.1177/1087057111421631.
Fan et al., Oncogene, 2015, 1-12.
Fernandes et al., Journal of the Institution of Chemists (India), 1991, 63(3), 83-4.
Fujita et al., Yakugaku Zasshi, 1964, 84(11), 1061-7.
Geng et al., Nature Immunology, 2017, (online) doi:10.1038/ni.3748.
Ghizzoni et al., Eur. J. Med. Chem., 2012, 47, 337-344 doi:10.1016/j.ejmech.2011.11.001.
Gil et al., J. Proteomics, 2017, 150, 297-309 doi :10.1016/j.jprot.2016.10.003.
Giri et al., Journal of the Indian Chemical Society, 1964, 41(4), 295-8.
Gobert et al., Cancer Research, 2009, 69, 2000-2009 doi:10.1158/0008-5472.CAN-08-2360.
Grashey et al., Chemiker-Zeitung 1976, 100(11), 497-8.
Grashey et al., Chemiker-Zeitung, 1973, 97(11), 623.
Grashey et al., Tetrahedron Letters, 1972, (29), 2943-6.
Gregory J. Wells et al, "1, 2-Benzothiazine 1, 1-Dioxide P2-P3 Peptide Mimetic Aldehyde Calpain I Inhibitors", Journal of Medicinal Chemistry, vol. 44, No. 21, Oct. 1, 2001, pp. 3488-3503.
Hangan et al., Farmacia, 2012, 60(6), 932-938.
Hangan et al., Journal of Chemical Sciences (Berlin, Germany), 2016, 128(5), 815-824.
Hangan et al., Russian Journal of Coordination Chemistry, 2015, 41(6), 395-404.
Hassan et al., Journal of Chemical Technology and Biotechnology, 1982, 32(2), 416-20.
Hategan et al., Bioorganic & Medicinal Chemistry Letters, 2009, 19(23), 6797-6800.
Hirsch et al., J. Mol. Biol., 2017, 429(13), 1958-1977.
Hitchin et al, Med. Chem. Commun., 2013, 4, 1513-1522.
Holbert et al., J. Biol. Chem., 2007, 282, 36603-36613 doi:10.1074/jbc.M705812200.
Hultquist et al., Journal of the American Chemical Society, 1951, 73, 2558-66.
Iizuka et al., Cancer Sci., 2013, 104, 1647-1655 doi:10.1111/cas.12303.
Iizuka et al., Mol. Cell. Biol., 2006, 26, 1098-1108 doi :10.1128/MCB.26.3.1098-1108.2006.
International Search Report and Written Opinion for PCT/EP2018/073431 dated Dec. 3, 2018, 9 pages.
Thomas et al., Genes Dev, 2006, 20(9), 1175.
Turner-Ivey et al., Neoplasia, 2014, 16(8): 644-655 doi:10.1016/j.neo.2014.07.007.
Valerio et al., Cancer Research, 2017, 77(7), 1753-62 doi:10.1158/0008-5472.CAN-16-2374.
Vikani et al., Journal of the Indian Chemical Society, 1990, 67(10), 859-61.
Vizmanos et al., Genes Chromosomes Cancer, 2003, 36(4), 402-405 doi:10.1002/gcc.10174.
Voss et al., BioEssays, 2009, 31(10), 1050-1061 doi:10.1002/bies.200900051.
Wang et al. EBioMedicine, 2016, 13, 99-112 doi:10.1016/j.ebiom.2016.10.018.
Wang et al., Gaodeng Xuexiao Huaxue Xuebao, 1987, 8(2), 133-6.
Wang et al., Oncogene, 2017, 36, 3048-3058 doi:10.1038/onc.2016.458.
Wells et al., Journal of Medicinal Chemistry, 2001, 44(21), 3488-3503.
Xiao et al., Cell reports, 2014, 7, 1471-1480 doi :10.1016/j.celrep.2014.04.021.
Xiao-Jian et al., Frontiers in Oncology, 2015, 5, 108.
Yan et al., Breast Cancer Research, 2011, 13, R47 doi:10.1186/bcr2869.
Yoshida et al., Yakugaku Zasshi 1954, 74, 948-50.
Young et al., Blood Res 2016 51(3), 152-154 doi:10.5045/br.2016.51.3.152.
Zack et al., Nature Genetics 2013 45, 1134-1140 doi: 10.1038/ng.2760.
Zhang et al., Mini. Rev. Med. Chem., 2017, 17, 1-8 doi:10.2174/1389557516666160923125031.
International Search Report for PCT/EP2019/067309 dated Nov. 21, 2019, 17 pages.

* cited by examiner

COMPOUNDS

The present invention relates to compounds which act as Lysine Acetyl Transferase (KAT) inhibitors of the MYST family.

BACKGROUND TO THE INVENTION

The MYST family is the largest family of KATs and is named after the founding members in yeast and mammals: MOZ, Ybf2/Sas3, Sas2 and TIP60 (Dekker 2014). MYST proteins mediate many biological functions including gene regulation, DNA repair, cell-cycle regulation and development (Avvakumov 2007; Voss 2009). The KAT proteins of the MYST family play key roles in post-translational modification of histones and thus have a profound effect on chromatin structure in the eukaryotic nucleus (Avvakumov 2007). The family currently comprises five mammalian KATs: TIP60 (KAT5; HTATIP; MIM 601409), MOZ (KAT6A; MIM 601408; MYST3), MORF (KAT6b; QKF; MYST4), HBO (KAT8; HBO1; MYST2) and MOF (KAT8; MYST1) (Voss 2009). These five members of the MYST family are present in humans and malfunction of MYST proteins is known to be associated with cancer (Avvakumov 2007). The most frequently used names for members of the MYST family are:

| Common name | MYST name | Systematic name |
|---|---|---|
| MOF | MYST1 | KAT8 |
| HBO | MYST2 | KAT7 |
| MOZ | MYST3 | KAT6A |
| MORF | MYST4 | KAT6B |
| TIP60 | | KAT5 |

MYST Functional Domains

MYST proteins function in multisubunit protein complexes including adaptors such as ING proteins that mediate DNA binding (Avvakumov 2007). For instance, TIP60 is affiliated to the NuA4 multiprotein complex (which embraces more than 16 members) (Zhang 2017). However, there have also been some reports of a helix-turn-helix DNA-binding motif within the structure of the MOZ protein itself (Holbert 2007), which suggests the capacity to bind directly to DNA.

The acetyltransferase activity of MYST proteins is effected by the MYST domain (the catalytic domain). The MYST domain contains an acetyl-coenzyme A binding motif, which is structurally conserved with other HATs, and an unusual $C_2HC$-type zinc finger (Voss 2009). The highly conserved MYST domain, including the acetyl-CoA binding motif and zinc finger, is considered to be the defining feature of this family of enzymes (Avvakumov 2007).

Role of MYST Proteins

Acetylation of histone residues is generally associated with transcriptional activation. However, in some instances, transcriptional repression has also been attributed to MYST proteins (Voss 2009). The individual members of the MYST family are known to participate in a broad range of important biochemical interactions:

HBO1 positively regulates initiation of DNA replication (Avvakumov 2007; Aggarwal 2004; Doyon 2006; Iizuka 2006) via acetylation of histone substrates, which presumably leads to a more accessible chromatin conformation (Avvakumov 2007, Iizuka 2006). HBO1 is also known to play a role in the pathogenesis of breast cancer by promoting an enrichment of cancer stem-like cells (Duong 2013) and by destabilising the estrogen receptor a (ERα) through ubiquinitiation, which proceeds via the histone-acetylating activity of HBO1 (Iizuka 2013). HBO1 has also been implicated in Acute myeloid leukaemia (AML) (Shi 2015).

TIP60 (KAT5) is the most studied member of the MYST family. TIP60 plays an important role not only in the regulation of transcription but also in the process of DNA damage repair, particularly in DNA double-strand breaks (DSB) (Gil 2017). TIP60 can acetylate p53, ATM and c-Myc. TIP60 and MOF specifically acetylate lysine 120 (K120) of p53 upon DNA damage (Avvakumov 2007). TIP60 has also been implicated in being important for regulatory T-cell (Treg) biology. FOXP3 is the master regulator in the development and function of Tregs and it has been shown that acetylation of FOXP3 by TIP60 is essential for FOXP3 activity (Li 2007, Xiao 2014). Underscoring this, conditional TIP60 deletion in mice leads to a scurfy-like fatal autoimmune disease, mimicking a phenotype seen in FOXP3 knock out mice (Xiao 2014). In cancer, Treg cells can facilitate tumour progression by suppressing adaptive immunity against the tumour.

MOF ("males absent on the first") was originally identified as one of the components of the dosage compensation in *Drosophila*, and was classified as a member of the MYST family based on functional studies and sequence analysis (Su 2016). The human ortholog exhibits significant similarity to *Drosophila* MOF; containing an acetyl-CoA-binding site, a chromodomain (which binds histones) and a $C_2HC$-type zinc finger (Su 2016). MOF is a key enzyme for acetylating histone H4K16, and MOF-containing complexes are implicated in various essential cell functions with links to cancer (Su 2016). Besides the global reduction of histone acetylation, depletion of MOF in mammalian cells can result in abnormal gene transcription, particularly causing abnormal expression of certain tumor suppressor genes or oncogenes, suggesting a critical role of MOF in tumorigenesis (Su 2016). For example, KAT activity of MOF has been shown to be required to sustain MLL-AF9 leukemia and may be important for multiple AML subtypes (Valerio 2017).

KAT6B (Querkopf) was first identified in a mutation screen for genes regulating the balance between proliferation and differentiation during embryonic development (Thomas 2000). Mice homozygous for the KAT6B mutant allele have severe defects in cerebral cortex development resulting from a severe reduction in both proliferation and differentiation of specifically the cortical progenitor population during embryonic development. KAT6B is required for the maintenance of the adult neural stem cell population and is part of a system regulating differentiation of stem cells into neurons (Merson 2006). KAT6B is also mutated in rare forms of leukaemia (Vizmanos 2003).

The MOZ locus ranks as the 12th most commonly amplified region across all cancer types (Zack 2013). MOZ is within the 8p11-p12 amplicon, which is seen at frequencies around 10-15% in various cancers, especially breast and ovarian (Turner-Ivey 2014). MOZ was first identified as a fusion partner of the CREB-binding protein (CBP) during examination of a specific chromosomal translocation in acute myeloid leukaemia (AML) (Avvakumov 2007; Borrow 1996). MOZ KAT activity is necessary for promoting the expression of MEIS1 and HOXa9, proteins that are typically seen overexpressed in some lymphomas and leukaemias. Increased survival of MOZ$^{+/-}$ heterozygote mice in the Eµ-Myc transgenic model of B-cell lymphoma is seen, where loss of a single MOZ allele leads to a biologically relevant reduction in Meis1 and Hoxa9 levels in pre-B-cells (Sheikh 2015).

Inhibitors of some MYSTs are known. For example, the following Anacardic acid derivative is reported (Ghizzoni 2012) as inhibiting TIP60 ($IC_{50}$=74 µM) and MOF ($IC_{50}$=47 µM):

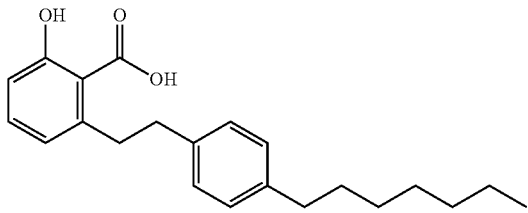 [SMILES: CCCCCCCc1ccc(CCc2cccc(O)c2C(=O)O)cc1]

Other known inhibitors include (Zhang 2017):

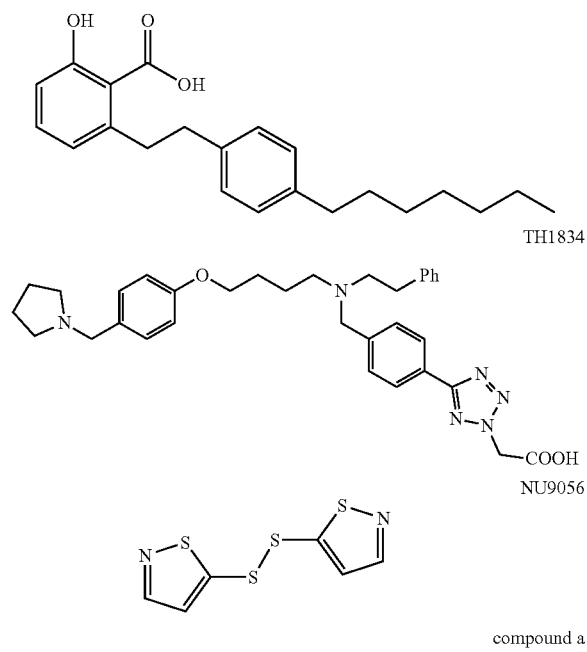

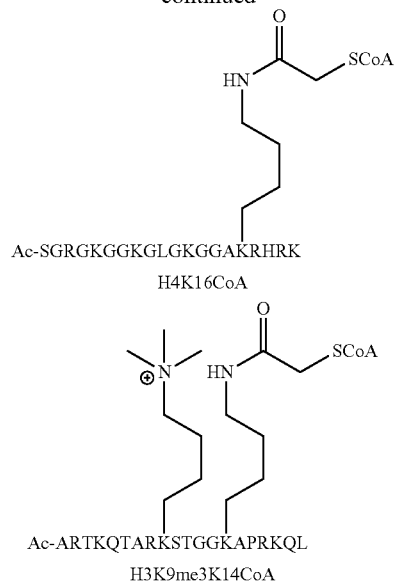

In light of the established role of KATs in general, and MYSTs in particular, in diseases such as cancer, a need exists for new inhibitors of these proteins.

DISCLOSURE OF THE INVENTION

The present invention provides compounds which inhibit the activity of one or more KATs of the MYST family, i.e., TIP60, KAT6B, MOZ, HBO1 and MOF.

A first aspect of the present invention provides a compound of formula (I), or a pharmaceutically acceptable salt thereof, for use in a method of therapy:

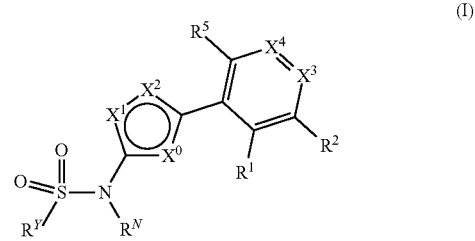

wherein:
(i) $X^0$=$CR^C$, $X^1$=N, $X^2$=O; or
(ii) $X^0$=$CR^C$, $X^1$=O, $X^2$=N; or
(iii) $X^0$=S, $X^1$=N, $X^2$=N; or
(iv) $X^0$=N, $X^1$=N, $X^2$=O; or
(v) $X^0$=O, $X^1$=N, $X^2$=N;
where $R^C$ is H, $CO_2CH_3$ or Cl;
$R^N$ is H or methyl;
$X^3$ is $CR^3$ or N;
$X^4$ is $CR^4$ or N;
$R^1$ to $R^5$ are independently selected from:
(i) H;
(ii) halo;
(iii) cyano;
(iv) $C_{1-3}$ alkyl, optionally substituted by one or more fluoro groups;
(v) $(CH_2)_{n0}$—$C_{3-6}$ cycloalkyl, where n0=0 or 1;

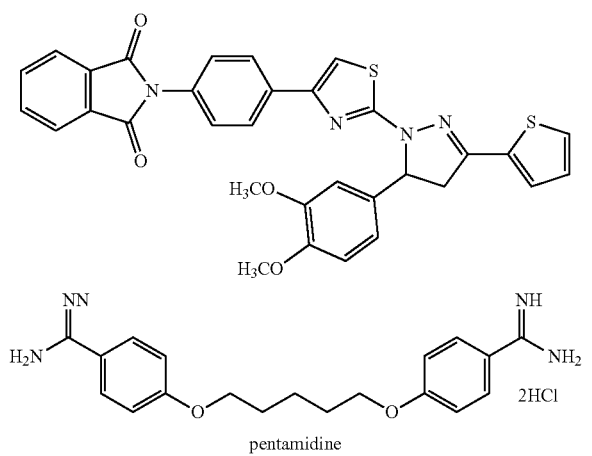

(vi) $(CH_2)_{n1}$—$C_{1-3}$ alkoxy, where n1=0 or 1, optionally substituted by one or more fluoro groups;
(vii) $C_{1-3}$ alkylester;
(vii) $(CH_2)_{n2}$-phenyl, where n2=0-2; and
(viii) $(CH_2)_{n3}$—$C_5$ heteroaryl, where n3=0-1, optionally substituted by methyl; and $R^Y$ is selected from:
(i) $(CH_2)_{n4}$-phenyl, where n4=0-2, where phenyl is optionally substituted by:
   (a) $C_{1-4}$ alkyl, optionally substituted by one or more fluoro groups;
   (b) $C_{1-4}$ alkoxy, optionally substituted by phenyl, or one or more fluoro groups;
   (c) halo;
   (d) cyano, nitro or amido;
   (e) phenyl; or
   (f) —$(CH_2)_{n5}$—, where n5 is 3 or 4;
(ii) pyridyl;
(iii) $C_{3-4}$ alkyl;
(iv) $(CH_2)_{n6}$—$C_{3-6}$ cycloalkyl, where n6=0-2;
(v) $C_6$ heterocyclyl, optionally substituted by $C_{1-4}$ alkylester; and
(vi) $NHR^{YN}$, where $R^{YN}$ is selected from phenyl or cyclohexyl.

A first aspect also provides a pharmaceutical composition comprising a compound of formula (I), or a pharmaceutically acceptable salt thereof, as defined and a pharmaceutically acceptable excipient.

A second aspect of the present invention provides a method of treatment of cancer, comprising administering to a patient in need of treatment, a compound, or a pharmaceutically acceptable salt thereof, as defined in the first aspect of the invention or a pharmaceutical composition of the first aspect of the invention. The second aspect of the present invention also provides the use of a compound, or a pharmaceutically acceptable salt thereof, as defined in the first aspect of the invention in the manufacture of a medicament for treating cancer, and a compound, or a pharmaceutically acceptable salt thereof, as defined in the first aspect of the invention or pharmaceutical composition thereof for use in the treatment of cancer.

As described below, the compound as defined in the first aspect may be administered simultaneously or sequentially with radiotherapy and/or chemotherapy in the treatment of cancer.

A third aspect of the invention provides a compound of formula (I) or a pharmaceutically acceptable salt thereof:

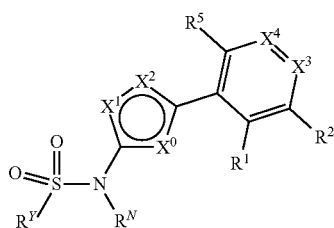
(I)

wherein either:
(i) $X^0=CR^C$, $X^1=N$, $X^2=O$; or
(ii) $X^0=CR^C$, $X^1=O$, $X^2=N$; or
(iii) $X^0=S$, $X^1=N$, $X^2=N$; or
(iv) $X^0=N$, $X^1=N$, $X^2=O$; or
(v) $X^0=O$, $X^1=N$, $X^2=N$;
where $R^C$ is H, $CO_2CH_3$ or Cl;
$R^N$ is H or methyl;

$X^3$ is $CR^3$ or N;
$X^4$ is $CR^4$ or N;
$R^1$ to $R^5$ are independently selected from:
(i) H;
(ii) halo;
(iii) cyano;
(iv) $C_{1-3}$ alkyl, optionally substituted by one or more fluoro groups;
(v) $(CH_2)_{n0}$—$C_{3-6}$ cycloalkyl, where n0=0 or 1;
(vi) $(CH_2)_{n1}$—$C_{1-3}$ alkoxy, where n1=0 or 1, optionally substituted by one or more fluoro groups;
(vii) $C_{1-3}$ alkylester;
(vii) $(CH_2)_{n2}$-phenyl, where n2=0-2; and
(viii) $(CH_2)_{n3}$—$C_5$ heteroaryl, where n3=0-1, optionally substituted by methyl; and
$R^Y$ is selected from:
(i) $(CH_2)_{n4}$-phenyl, where n4=0-2, where phenyl is optionally substituted by:
   (a) $C_{1-4}$ alkyl, optionally substituted by one or more fluoro groups;
   (b) $C_{1-4}$ alkoxy, optionally substituted by phenyl, or one or more fluoro groups;
   (c) halo;
   (d) cyano, nitro or amido;
   (e) phenyl; or
   (f) —$(CH_2)_{n5}$—, where n5 is 3 or 4;
(ii) pyridyl;
(iii) $C_{3-4}$ alkyl;
(iv) $(CH_2)_{n6}$—$C_{3-6}$ cycloalkyl, where n6=0-2;
(v) $C_6$ heterocyclyl, optionally substituted by $C_{1-4}$ alkylester; and
(vi) $NHR^{YN}$, where $R^{YN}$ is selected from phenyl or cyclohexyl, with the proviso that:
   (a) at least one of $R^1$ to $R^5$ is not H.
   (b) $R^2$ and $R^5$ are not H.
   (c) $R^Y$ is not $(CH_2)_{n3}$-phenyl, wherein the phenyl is substituted by a single group which is Cl, F or $NO_2$.
   (d) $R^Y$ is not $(CH_2)_{n3}$-phenyl, wherein the phenyl is substituted by $NO_2$.

A fourth aspect of the present invention provides the synthesis of compounds as defined in the first or third aspects of the invention, as described below.

In the above aspects of the invention, if $X^0=CR^C$, $X^1=N$, $X^2=O$, the compound is of formula (I-i):

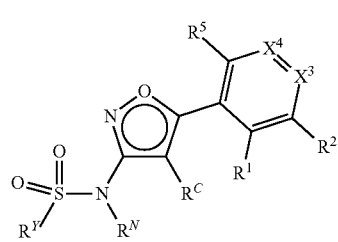
(I-i)

In the above aspects of the invention, if $X^0=CR^C$, $X^1=O$, $X^2=N$, the compound is of formula (I-ii):

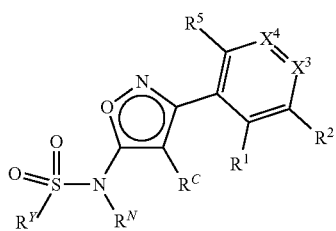
(I-ii)

In the above aspects of the invention, if $X^0$=S, $X^1$=N, $X^2$=N, the compound is of formula (I-iii):

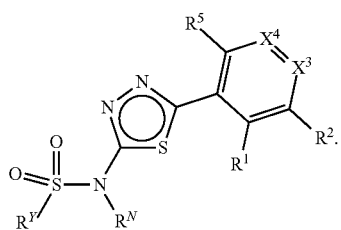
(I-iii)

In the above aspects of the invention, if $X^0$=N, $X^1$=N, $X^2$=O, the compound is of formula (I-iv):

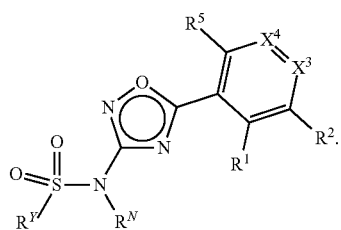
(I-iv)

In the above aspects of the invention, if $X^0$=O, $X^1$=N, $X^2$=N, the compound is of formula (I-v):

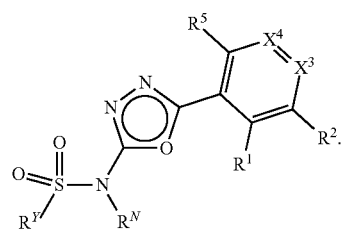
(I-v)

Definitions

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. The phrase "optionally substituted" as used herein, pertains to a parent group which may be unsubstituted or which may be substituted.

$C_5$ heteroaryl: The term "$C_5$ heteroaryl" as used herein, pertains to a monovalent moiety obtained by removing a hydrogen atom from an aromatic structure having from 5 ring atoms, of which from 1 to 3 are ring heteroatoms. The term 'aromatic structure' is used to denote a single ring or fused ring systems having aromatic properties, and the term 'ring heteroatom' refers to a nitrogen, oxygen or sulphur atom.

In this context, the suffix denote the number of atoms making up the aromatic structure, or range of number of atoms making up the aromatic structure, whether carbon atoms or heteroatoms.

Examples of $C_5$ heteroaryl structures include, but are not limited to, those derived from:

$N_1$: pyrrole (azole) ($C_5$);
$O_1$: furan (oxole) ($C_5$);
$S_1$: thiophene (thiole) ($C_5$);
$N_1O_1$: oxazole ($C_5$), isoxazole ($C_5$);
$N_2O_1$: oxadiazole (furazan) ($C_5$);
$N_1S_1$: thiazole ($C_5$), isothiazole ($C_5$);
$N_2S_1$: thiadiazole ($C_5$)
$N_2$: imidazole (1,3-diazole) ($C_5$), pyrazole (1,2-diazole) ($C_5$);
$N_3$: triazole ($C_5$).

Halo: The term "halo" as used herein, refers to a group selected from fluoro, chloro, bromo and iodo.

Cyano: The term "cyano" as used herein, refers to a group —C≡N.

Nitro: The term "nitro" as used herein, refers to a group —NO$_2$.

Amido: The term "amido" as used herein, refers to a group —C(=O)NH$_2$.

$C_{1-4}$ alkyl: The term "$C_{1-4}$ alkyl" as used herein, pertains to a monovalent moiety obtained by removing a hydrogen atom from a carbon atom of a saturated hydrocarbon compound having from 1 to 4 carbon atoms. Similarly the term "$C_{1-3}$ alkyl" as used herein, pertains to a monovalent moiety obtained by removing a hydrogen atom from a carbon atom of a saturated hydrocarbon compound having from 1 to 3 carbon atoms. Similarly the term "$C_{3-4}$ alkyl" as used herein, pertains to a monovalent moiety obtained by removing a hydrogen atom from a carbon atom of a saturated hydrocarbon compound having from 3 to 4 carbon atoms.

Examples of saturated alkyl groups include, but are not limited to, methyl ($C_1$), ethyl ($C_2$), propyl ($C_3$), and butyl ($C_4$).

Examples of saturated linear alkyl groups include, but are not limited to, methyl ($C_1$), ethyl ($C_2$), n-propyl ($C_3$), and n-butyl ($C_4$).

Examples of saturated branched alkyl groups include iso-propyl ($C_3$), iso-butyl ($C_4$), sec-butyl ($C_4$) and tert-butyl ($C_4$).

$C_{3-6}$ cycloalkyl: The term "$C_{3-6}$ cycloalkyl" as used herein, pertains to a monovalent moiety obtained by removing a hydrogen atom from a carbon atom of a saturated cyclic hydrocarbon compound having from 3 to 6 carbon atoms. Examples of $C_{3-6}$ cycloalkyl groups include, but are not limited to, cyclopropyl ($C_3$), cyclobutyl ($C_4$), cyclopentyl ($C_5$) and cyclohexyl ($C_6$).

$C_{1-4}$ alkoxy: The term "$C_{1-4}$ alkoxy as used herein, pertains to a monovalent moiety obtained by removing a hydrogen atom from an oxygen atom of a saturated alcohol compound having from 1 to 4 carbon atoms. It can be represented as —O—$C_{1-4}$ alkyl. Examples of $C_{1-4}$ alkoxy groups include, but are not limited to, methoxy ($C_1$), ethoxy ($C_2$), propyloxy ($C_3$), and butyloxy ($C_4$). Similarly, the term "$C_{1-3}$ alkoxy as used herein, pertains to a monovalent moiety obtained by removing a hydrogen atom from an oxygen atom of a saturated alcohol compound having from 1 to 3 carbon atoms.

$C_{1-4}$ alkylester: The term "$C_{1-4}$ alkylester" as used herein, pertains to a monovalent moiety obtained by removing a hydrogen atom from an oxygen atom of a saturated carboxylic acid compound having from 1 to 5 carbon atoms. It can be represented as —O—C(=O)—$C_{1-4}$ alkyl. Examples of $C_{1-4}$ alkylester groups include, but are not limited to acetoxy (—O—C(O)—CH$_3$), propanoyloxy (—O—C(O)—CH$_2$CH$_3$), butanoyloxy (—O—C(O)—CH$_2$CH$_2$CH$_3$), pentanoyloxy (—O—C(O)—CH$_2$CH$_2$CH$_2$CH$_3$) and tert-butanoyloxy (—O—C(O)—C(CH$_3$)$_3$). Similarly the term "$C_{1-3}$ alkylester" as used herein, pertains to a monovalent moiety obtained by removing a hydrogen atom from an oxygen atom of a saturated carboxylic acid compound having from 1 to 5 carbon atoms. It can be represented as —O—C(=O)—$C_{1-3}$ alkyl.

Phenyl: the term "phenyl" as used herein, pertains to a monovalent moiety obtained by removing a hydrogen atom from a single aromatic ring structure having 6 carbon ring atoms (—C$_6$H$_5$).

$C_6$ heterocyclyl: The term "$C_6$ heterocyclyl" as used herein, pertains to a monovalent moiety obtained by removing a hydrogen atom from a ring atom of a heterocyclic compound, which moiety has 6 ring atoms, of which from 1 to 3 are ring heteroatoms. In this context, the prefixes (e.g. $C_6$) denote the number of ring atoms, whether carbon atoms or heteroatoms. For example, the term "$C_6$ heterocyclyl", as used herein, pertains to a heterocyclyl group having 6 ring atoms.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge 1977.

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Isomers

Certain compounds of the invention may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

In the present invention, the carbon atom to which $R^1$ and Cy are bound may be a stereochemical centre, i.e. when $R^1$ is not H and $R^1$ and Cy are different. The compounds of the present invention may be a racemic mixture, or may be in enantiomeric excess or substantially enantiomerically pure.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

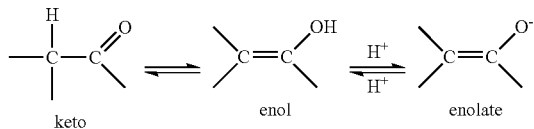

keto    enol    enolate

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Examples of isotopes that can be incorporated into compounds of the invention include isotopes of hydrogen, carbon, nitrogen, oxygen, phosphorous, fluorine, and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Inhibition

The compounds of the present invention inhibit the activity of one or more KATs of the MYST family, i.e., TIP60, KAT6B, MOZ, HBO1 and MOF.

The inhibitory activity of the compounds of the invention is likely to vary between the KATs of the MYST family.

The compounds of the present invention may selectively inhibit the activity of one or more KATs of the MYST family over other KATs of the MYST family, i.e. the inhibitory activity of the compound may be higher for one or more of the KATs of the MYST family over one or more of the other KATs of the MYST family.

Compounds of the present invention may (selectively) inhibit the activity of a single KAT of the MYST family.

Thus, compounds of the present invention may inhibit the activity of TIP60, MORF, MOZ, HBO1 or MOF.

Compounds of the present invention may inhibit the activity of two KATs of the MYST family, for example MOZ and MORF.

Compounds of the present invention may inhibit the activity of three KATs of the MYST family, for example MOZ, MORF and HBO1.

Compounds of the present invention may inhibit the activity of four KATs of the MYST family, for example MOZ, MORF, HBO1 and TIP60.

Compounds of the present invention may inhibit the activity of all five KATs of the MYST family, thus the compounds may inhibit the activity of TIP60, MORF, MOZ, HBO1 and MOF.

Compounds of the present invention may, in particular, inhibit the activity of MOZ and/or KAT6B and/or HBO1.

Therapeutic Indications

Compounds disclosed herein may provide a therapeutic benefit in a number of disorders, in particular, in the treatment or prevention of cancers.

Cancer

Inhibitors of post-translational lysine acetylation mediated by KATs of the MYST family are considered to be promising anti-neoplastic agents and therefore may be useful therapeutic agents, e.g. for use in the treatment of cancer. Such agents may also be useful as therapeutic agents for the treatment of cancers which exhibit overexpression of MYST proteins.

A "cancer" may be any form of cancer. In particular, a cancer can comprise any one or more of the following: leukemia, acute lymphocytic leukemia (ALL), acute myeloid leukemia (AML), chronic lymphocytic leukemia (CLL), chronic myeloid leukemia (CML), non-Hodgkin's lymphoma, Hodgkin's disease, prostate cancer, lung cancer, melanoma, breast cancer, colon and rectal cancer, colon cancer, squamous cell carcinoma and gastric cancer.

Alternatively, the cancer may comprise adrenocortical cancer, anal cancer, bladder cancer, blood cancer, bone cancer, brain tumor, cancer of the female genital system, cancer of the male genital system, central nervous system lymphoma, cervical cancer, childhood rhabdomyosarcoma, childhood sarcoma, endometrial cancer, endometrial sarcoma, esophageal cancer, eye cancer, gallbladder cancer, gastrointestinal tract cancer, hairy cell leukemia, head and neck cancer, hepatocellular cancer, hypopharyngeal cancer, Kaposi's sarcoma, kidney cancer, laryngeal cancer, liver cancer, malignant fibrous histiocytoma, malignant thymoma, mesothelioma, multiple myeloma, myeloma, nasal cavity and paranasal sinus cancer, nasopharyngeal cancer, nervous system cancer, neuroblastoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, rectal cancer, respiratory system, retinoblastoma, salivary gland cancer, skin cancer, small intestine cancer, soft tissue sarcoma, stomach cancer, stomach cancer, testicular cancer, thyroid cancer, urinary system cancer, uterine sarcoma, vaginal cancer, vascular system, Waldenstrom's macroglobulinemia and/or Wilms' tumor.

Cancers may be of a particular type. Examples of types of cancer include lymphoma, melanoma, carcinoma (e.g. adenocarcinoma, hepatocellular carcinoma, medullary carcinoma, papillary carcinoma, squamous cell carcinoma), astrocytoma, glioma, medulloblastoma, myeloma, meningioma, neuroblastoma, sarcoma (e.g. angiosarcoma, chondrosarcoma, osteosarcoma).

The cancer may be a MYST overexpressing cancer. The cancer may over-express MYST protein relative to non-cancerous tissue. In some cases, the cancer overproduces MYST mRNA relative to non-cancerous tissue. The overexpressed MYST protein or MYST mRNA may be any one KATs of the MYST family, i.e. any one of TIP60, KAT6B, MOZ, HBO1 and MOF. In some embodiments, the cancer may overexpress more than one KATs of the MYST family, e.g. two or more selected from the group consisting of TIP60, KAT6B, MOZ, HBO1 and MOF. The cancer may be a cancer that evades immune recognition, e.g. via tumor-associated Treg cells.

Alternatively or additionally, the cancer may be a bromodomain overexpressing cancer: The cancer cell may overexpress one or more bromodomain-containing proteins (herein referred to as "bromodomain proteins") relative to non-cancerous tissue. It may overproduce one or more bromodomain mRNA as compared to non-cancerous tissue. In some cases, the level of bromodomain protein and/or mRNA in the cell is at a level approximately equivalent to that of a non-cancerous cell. The cancer may overexpress one or more bromodomain proteins selected from the group consisting of; a bromodomain protein (namely BRD2, BRD3, BRD4, BRD7, BRD8, BRD9 and BRDT), TAF1/TAF1L, TFIID, SMARC2 (also called BRM) and SMARC4 (also called BRG1). For example, some colon cancers overexpress BRD8. Some acute myeloid leukemia cells overexpress BRD4.

Treg Cells as a Cancer Target

Treg cells are immunosuppressive cells, which act to prevent autoimmunity in the healthy mammalian immune system. However, some cancers act to upregulate Treg activity to evade the host immune system. Infiltration of Tregs in many tumour types correlates with poor patient prognoses and Treg cell depletion in tumour models demonstrates increased anti-tumour immune responses (Melero 2015). Tumour-associated Treg suppression of the host immune system has been reported in lung (Joshi 2015), (Tso 2012), breast (Gobert 2009; Yan 2011), prostate (Miller 2006) & pancreatic (Wang X 2016) cancers. FOXP3 is considered to be the master regulator of Treg differentiation, development and function of Treg cells.

Several studies have demonstrated that acetylation of FOXP3 plays a critical role in the stability of the FOXP3 protein and in regulating its ability to access DNA; and FOXP3 acetylation is mediated by KATs (Dhuban 2017). Decreases in TIP60-mediated FOXP3 acetylation has been shown to attenuate Treg development, suggesting a further mechanism by which the inhibition of the acetylating activity of MYST proteins could be used to intervene in diseases such as cancer.

Combination Therapies

The agents described herein may be useful in combination with other anti-cancer therapies. They may act synergistically with chemo- or radiotherapy, and/or with targeted therapies, including but not limited to FGFR1 inhibitors and therapies targeting nuclear hormone receptors. For example, the agents described herein may be useful in combination with bromodomain targeted drugs including BET inhibitors. BET inhibitors reversibly bind the bromodomains of the BET proteins BRD2, BRD3, BRD4 and BRDT.

Inhibition of KAT proteins of the MYST family, to reduce the extent of lysine acetylation of histones (and other nuclear proteins described herein) will likely sensitize tumour cells to chemo- and radiotherapy by attenuating the process of DNA damage repair, e.g. the repair of DNA double-strand breaks (DSB), thus increasing the frequency of chemo- and radiotherapy induced cancer cell death. Therefore, it is likely that inhibition of KAT proteins of the MYST family would synergize well with low dose chemo- or radiotherapy.

Thus, in some cases, a MYST protein antagonist disclosed herein may be administered in conjunction with a radiotherapeutic or chemotherapeutic regime. It may be administered simultaneously or sequentially with radio and/or chemotherapy. Suitable chemotherapeutic agents and radiotherapy protocols will be readily appreciable to the skilled person. In particular, the compound described herein may be combined with low dose chemo or radio therapy. Appropriate dosages for "low dose" chemo or radio therapy will be readily appreciable to the skilled practitioner.

In particular, where the compounds of the present application are used to abrogate Treg suppression, these may be combined with immune checkpoint inhibitors (Melero 2015, Wang L 2016). Furthermore, where compounds of the present invention which abrogate Treg suppression may be used in combination with radiotherapy, to reduce the depletion of Treg function in tumours (Persa 2015, Jeong 2016)

Methods of Treatment

The compounds of the present invention may be used in a method of therapy. Also provided is a method of treatment, comprising administering to a subject in need of treatment a therapeutically-effective amount of a compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

As described above, the anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and docetaxel (Taxotere) and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661 and 4-((2,4-dichloro-5-methoxyphenyl)amino)-6-methoxy-7-(3-(4-methylpiperazin-1-yl)propoxy)quinoline-3-carbonitrile (bosutinib, SKI-606; Cancer research (2003), 63(2), 375-81), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [HerceptinT], the anti-EGFR antibody panitumumab, the anti erbB1 antibody cetuximab [Erbitux, C225] and any growth factor or growth factor receptor antibodies disclosed by Stern 2005; such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic and antilymphangiogenic agents such as those which inhibit the effects of vascular endothelial growth factor, [for example the anti vascular endothelial cell growth factor A (VEGFA) antibody bevacizumab (AvastinT), the anti vascular endothelial cell growth factor A (VEGFA) antibody ranibizumab, the anti-VEGF aptamer pegaptanib, the anti vascular endothelial growth factor receptor 3 (VEGFR3) antibody IMC-3C5, the anti vascular endothelial cell growth factor C (VEGFC) antibody VGX-100, the anti vascular endothelial cell growth factor D (VEGFD) antibody VGX-200, the soluble form of the vascular endothelial growth factor receptor 3 (VEGFR3) VGX-300 and VEGF receptor tyrosine kinase inhibitors such as 4-(4-bromo-2-fluoroanilino)-6-methoxy-7-(1-methylpiperidin-4-ylmethoxy)quinazoline (vandetanib; ZD6474; Example 2 within WO 01/32651), 4-(4-fluoro-2-methylindol-5-yloxy)-6-methoxy-7-(3-pyrrolidin-1-ylpropoxy)quinazoline (cediranib; AZD2171; Example 240 within WO 00/47212), vatalanib (PTK787; WO 98/35985), pazopanib (GW786034), axitinib (AG013736), sorafenib and sunitinib (SU11248; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies Administration The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intravitreal and intrasternal; by implant of a depot, for example, subcutaneously, intravitreal or intramuscularly. The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences*, 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include lozenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichlorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/mL to about 10 µg/mL, for example from about 10 ng/ml to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated by one of skill in the art that appropriate dosages of the compound, and compositions comprising the compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the active compound is administered to a human patient according to the following dosage regime: about 50 or about 75 mg, 3 or 4 times daily.

In one embodiment, the active compound is administered to a human patient according to the following dosage regime: about 100 or about 125 mg, 2 times daily.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

General Synthesis Methods

The compounds of the invention can be prepared employing the following general methods and using procedures described in detail in the examples. The reaction conditions referred to are illustrative and non-limiting, for example one skilled in the art may use a diverse range of synthetic methods to synthesis the desired compounds such as but not limited to methods described in literature (for example but not limited to March's Advanced Organic Chemistry: Reactions, Mechanisms, and Structure, 7th Edition or Larock's Comprehensive Organic Transformations: Comprehensive Organic Transformations: A Guide to Functional Group Preparations).

Compounds of formula I, as described above, can be prepared by synthetic strategies outlined below, wherein the definitions above apply.

General Synthesis 1—Synthesis of the Sulfonyl Chloride & Sulfonamide

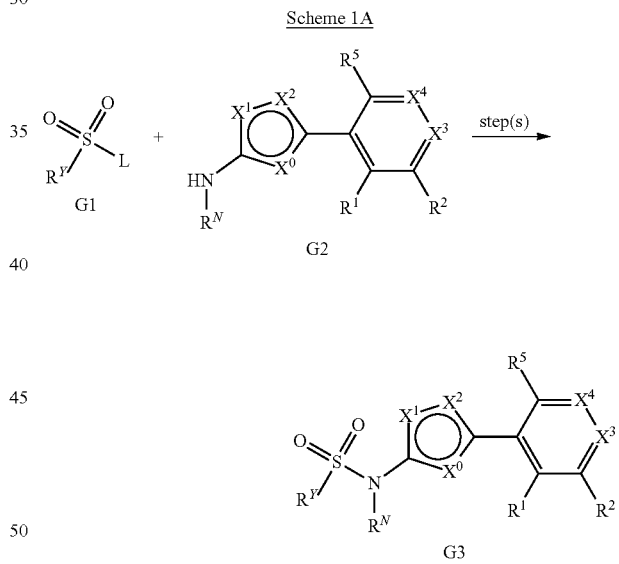

Scheme 1A illustrates the formation of a sulfonamide bond by coupling the relevant sulfonyl chloride, such as (G1), with a primary or secondary amine, such as heterocyclic amine (G2). Methods to form such sulfonamides will be apparent to those skilled in the art, but include for example the use of a suitable base such as but not limited to pyridine, LiHMDS, n-BuLi or NaH and the use of activated forms of the sulfonic acid such as the corresponding sulfonyl halide G1. Formation of the sulfonyl chloride G1 from the corresponding acid G4 can be achieved by for example use of thionyl chloride or cyanuric chloride (Scheme 1B). For compounds where $R_Y$=alkyl, formation of the sulfonic acid G4 can be achieved by treatment of alkyl halide or alkyl mesylate G50 with for example sodium sulphite.

Scheme 1B

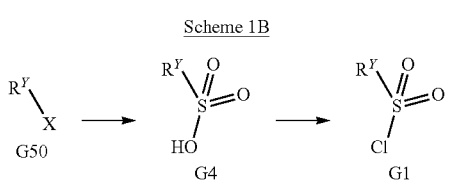

Alternatively, the activated sulfonate ester G6, such as but not limited to a pentafluorophenyl sulfonate ester or trichlorophenyl sulfonate ester can be coupled with the relevant primary or secondary amine, such as heterocyclic amine G2 (Scheme 1C). Methods to form the sulfonamides will be apparent to those skilled in the art, but include for example the use of a suitable base such as but not limited to LiHMDS. Formation of the activated sulfonate ester G6 from the corresponding sulfonyl chloride G1 can be achieved by using a suitable phenol G5 and base such as but not limited to pyridine or triethylamine.

Scheme 1C

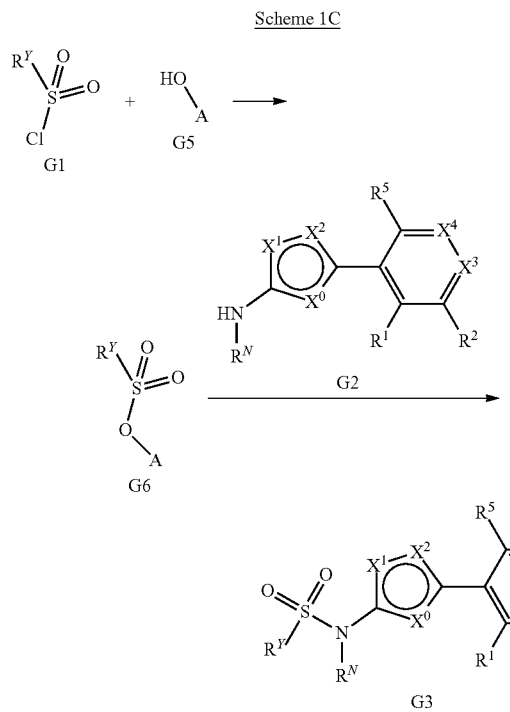

Examples of A that can be used to activate the sulfonic acid include, but are not limited to, those shown below.

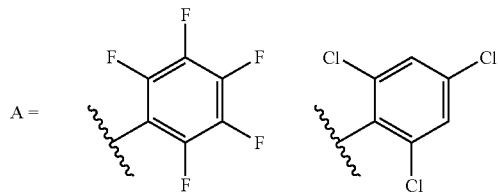 [SMILES: *c1c(F)c(F)c(F)c(F)c1F ; *c1c(Cl)cc(Cl)cc1Cl]

Scheme 1D illustrates the formation of a sulfonyl chloride, where $R^Y$=Ar. This can be achieved by reacting a relevant aryl compound (G7) with for example but not limited to chlorosulfonic acid. Alternatively, the aryl G7 may be sequentially treated with a base, such as but not limited to n-BuLi, and sulfur dioxide to furnish the lithium arylsulfinate which is further oxidised by for example sulfuryl chloride to give the desired sulfonyl chloride G8. The product G8 may be isolated or may be formed in situ and used immediately in subsequent step without being isolated.

Scheme 1D

where $R^Y$ = Ar

Alternatively, as shown in Scheme 1E, sulfonylation of an aryl compound such as G7 may give the corresponding sulfonic acid G9. This can be achieved by any suitable reagent known to someone skilled in the art, for example sulfur trioxide or sulfuric acid. The sulfonic acid G9 may be converted to the sulfonyl chloride G8 by methods outlined in General Synthesis 1, Scheme 1B.

Scheme 1E

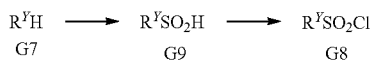

where $R^Y$ = Ar

In addition, as shown in scheme 1F, the sulfonyl chloride G8 may be formed from the aryl thiol G11. Methods to form G8 include for example the use of a suitable oxidant such as but not limited to hydrogen peroxide and potassium nitrate in the presence of a chloride source such as but not limited to chlorotrimethylsilane or thionyl chloride. A thiol of structure G11 may be synthesised from a compound of structure G10, where (X) may be a halogen, by methods known to those skilled in the art, including but not limited to nucleophilic displacement in the presence or absence of a transition metal.

Scheme 1F

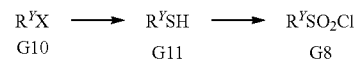

where $R^Y$ = Ar

General Synthesis 2—Synthesis of the 3 and 5 Aminoisoxazole Intermediates

Scheme 2A

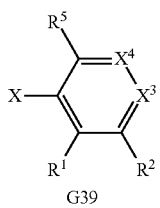

↓

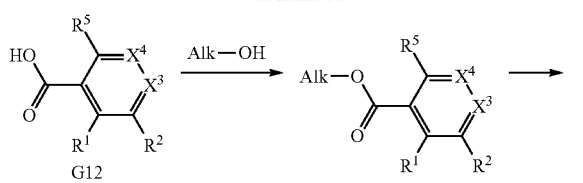

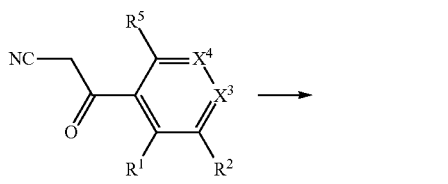

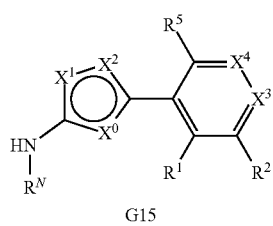

where $X^1 = N$, $X^2 = O$, $X^0 = CR^C$
or
where $X^1 = O$, $X^2 = N$, $X^0 = CR^C$ Scheme 2A illustrates the synthesis of intermediate aminoisoxazoles G15 where $R^N$=H and $X^1$=N, $X^2$=O, $X^0$=CH or $X^1$=O, $X^2$=N, $X^0$=CH. Initially, conversion of X in G39 to an ester in G13 via a carbonylation reaction can be achieved by the use of carbon monoxide in the presence of a transition metal catalyst such as but not limited to PdCl$_2$dppf·DCM; and an alcoholic solvent such as but not limited to methanol, ethanol, isopropanol or tert-butyl alcohol. The groups denoted by X are chosen to be suitable for the reaction and may be a halogen, triflate or other suitable group. Alternatively, conversion of G12 into ester G13 can be performed with an alcoholic solvent, Alk-OH, such as but not limited to MeOH or EtOH in the presence of an acid such as but not limited to H$_2$SO$_4$. Condensation of the ester of structure G13 with acetonitrile to give a beta-ketonitrile of structure G14 will be apparent to those skilled in the art and includes the use of a base such as but not limited to LDA, NaH, NaOMe, n-BuLi, or f-BuOK. Ring closure to form the aminoisoxazole G15 is achieved by reacting the beta-ketonitrile G14 with hydroxylamine or a hydroxylamine salt in the presence of a base such as but not limited to NaOH followed by treatment with an acid such as but not limited to HCl.

Scheme 2B

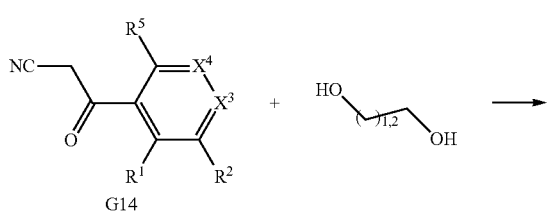

where $X^1 = N$, $X^2 = O$, $X^0 = CR^C$

Scheme 2B illustrates the exclusive formation of 3-aminoisoxazole intermediates G15 where $X^1$=N, $X^2$=O, $X^0$=CH. Introduction of a ketone protecting group in G16 such as a cyclic acetal will be apparent to those skilled in the art (for example Greene's Protective Groups in Organic Synthesis, 4th Edition). Formation of the 3-aminoisoxazole of structure G15 is achieved by reacting G16 under conditions analogous to those described in scheme 2A.

General Synthesis 3—Synthesis of the
2-Amino-5-Substituted 1,3,4-Thiadiazole and
2-Amino-5-Substituted 1,3,4-Oxadiazole
Intermediates Scheme 3A

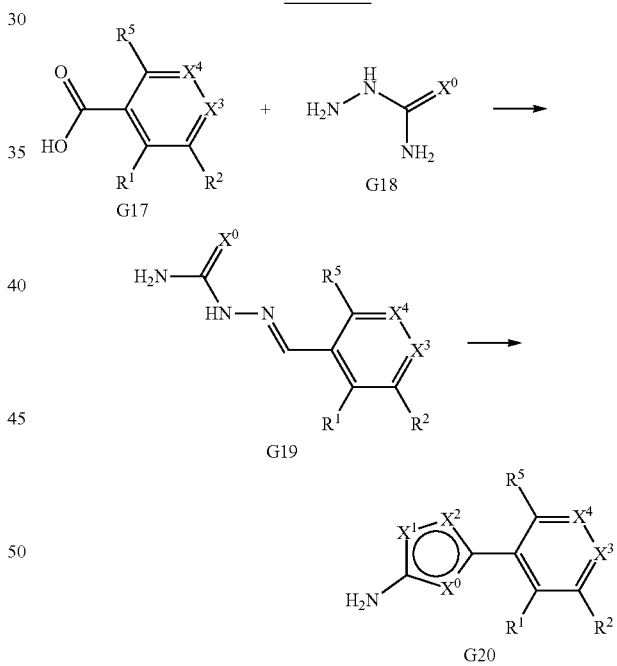

where $X^1 = N$, $X^2 = N$, $X^0 = S$ or $O$

Scheme 3A illustrates the synthesis of intermediates with the structure G20 where $X^1$=N, $X^2$=N, $X^0$=S or O. Formation of the carbazone/semicarbazone G19 can be achieved by condensation of semicarbazide/thiosemicarbazide G18 with aldehydes of the structure G17 in the presence of a reagent such as but not limited to, NaOAc. Formation of the aminoheterocycle G20 is achieved by oxidative cyclisation of G19 in the presence of reagents such as but not limited to molecular iodine and a base such as but not limited to K$_2$CO$_3$ or CS$_2$CO$_3$.

Scheme 3B

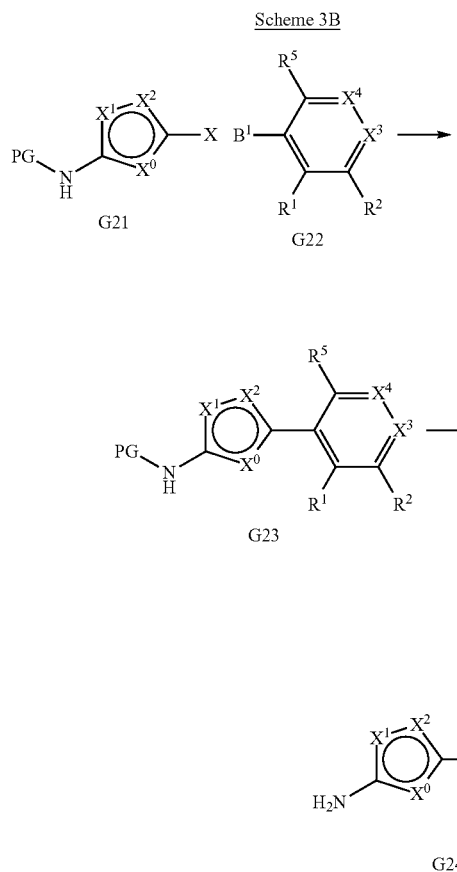

where $X^1 = N, X^2 = N, X^0 = S$
$X^1 = N, X^2 = N, X^0 = O$
$X^1 = N, X^2 = O, X^0 = CR^C$
$X^1 = O, X^2 = N, X^0 = CR^C$ In addition to Scheme 3A, Scheme 3B illustrates the formation of G24 achieved using any suitable coupling reaction known to a person skilled in the art, for example by Suzuki coupling. The groups denoted by X and $B^1$ are chosen to be suitable for the coupling reaction employed. For example, in the case of a Suzuki coupling reaction, (X) may be a halogen, triflate or other suitable group and $B^1$ represents a suitable boron compound including, but not limited to, a boronic acid or boronate ester.

Examples of $B^1$ that can be used in the Suzuki coupling include, but are not limited to, those shown below.

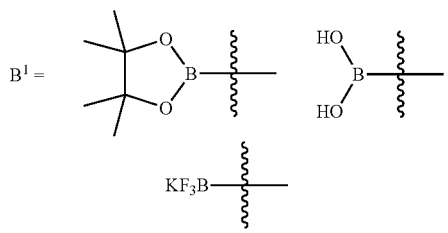

Removal of the protecting group will be apparent to those skilled in the art (for example *Greene's Protective Groups in Organic Synthesis*, 4th Edition) and gives intermediate G24.

Scheme 3C

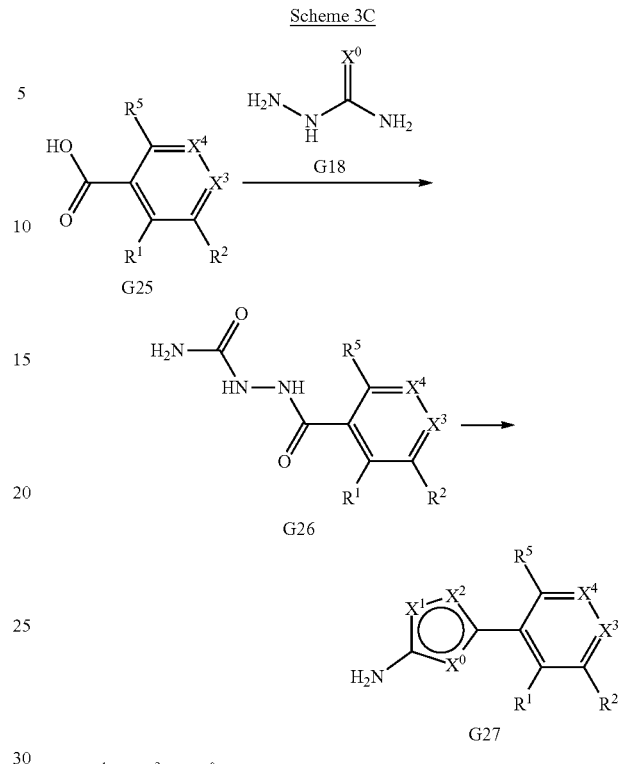

where $X^1 = N, X^2 = N, X^0 = O$ or $S$

Scheme 3C illustrates the alternative synthesis of intermediates with the structure G27 where $X^1=N$, $X^2=N$, $X^0=O$ or S. Beginning with G25, methods to form the acyl semicarbazide/acyl thiosemicarbazide G26 will be apparent to those skilled in the art, but include for example reaction of semicarbazide/thiosemicarbazide G18 or an appropriate salt form with an activated form of the carboxylic acid such as but not limited to, the corresponding acyl halide. Cyclodehydration of the acyl semicarbazide G26 to the 2-amino-1,3,4-oxadiazole G27 is achieved by reaction in the presence of a dehydrating reagent such as but not limited to $SOCl_2$, $Ph_3P$, $PCl_5$ or $POCl_3$. Where suitable the conversion of G25 to G27 may be performed in one-pot.

Scheme 3D

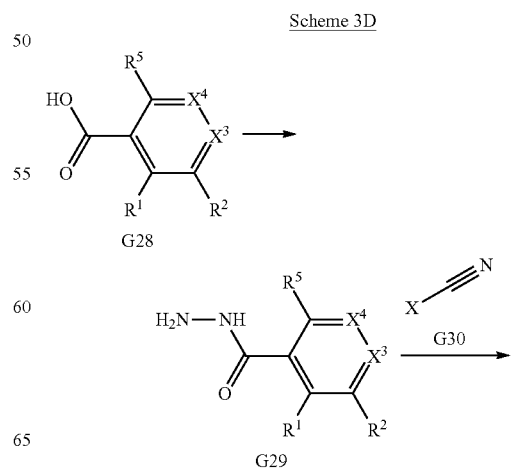

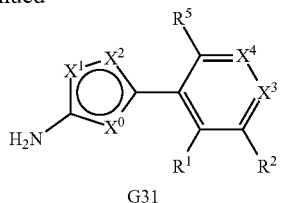

where $X^1 = N$, $X^2 = N$, $X^0 = O$

Scheme 3D illustrates the synthesis of 2-amino-5-substituted 1,3,4-oxadiazole intermediates with the structure G31 where $X^1$=N, $X^2$=N, $X^0$=O. Formation of the hydrazide G29 will be apparent to those skilled in the art and may be performed by reaction of hydrazine or hydrazine hydrate with an appropriate acid G28. Synthesis of intermediates with the structure G31 is performed by reacting hydrazide G29 with a reagent of structure G30 such as but not limited to cyanogen bromide or cyanogen chloride.

General Synthesis 4—Synthesis of the 3-Amino-5-Substituted 1,2,4-Oxadiazole Intermediates Scheme 4A illustrates the synthesis of 3-amino-5-substituted 1,2,4-oxadiazole intermediates with the structure G34 where $X^1$=N, $X^2$=O, $X^0$=N. Beginning with a relevant carboxylic acid G32, formation of G33 can be achieved by coupling to guanidine or a guanidine salt. Methods to form such amides will be apparent to those skilled in the art, but include for example the use of reagents such as HATU, HBTU, T3P and EDCl/HOBt, and the use of activated forms of the carboxylic acid such as the corresponding acyl halide, mixed anhydride or N-hydroxysuccinimide ester. Formation of the heterocyclic ring in G34 may be achieved via cyclisation with a suitable oxidant such as but not limited to PhI(OAc)$_2$.

Alternatively, G34 could also be synthesised starting from 3-amino-5-methyloxadiazole G35. Methods to form amide G37 will be apparent to those skilled in the art and as described previously. Thermal equilibration of G37 can yield G38 and may be performed by heating in an alcoholic solvent such as but not limited to EtOH. Final hydrolysis of the acetyl group in G38 to give 3-amino-5-substituted 1,2,4-oxadiazole G34 will be apparent to those skilled in the art (for example *Greene's Protective Groups in Organic Synthesis*, 4th Edition).

Scheme 4A

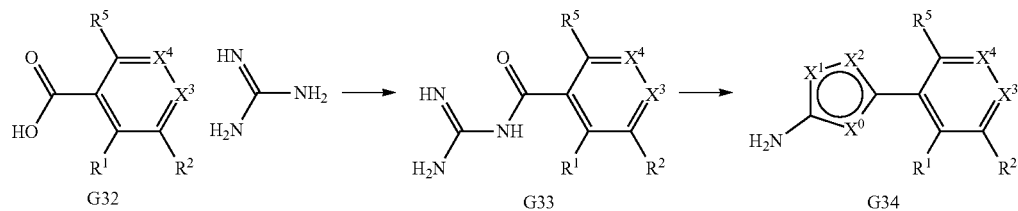

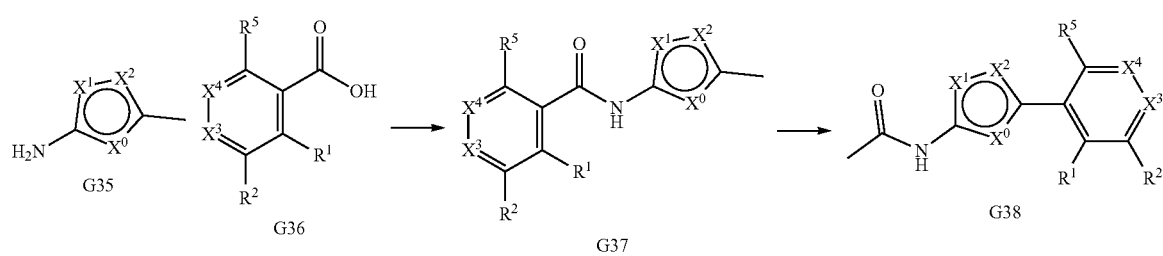

where $X^1 = N$, $X^2 = O$, $X^0 = N$

General Synthesis 5—Late Stage Diversification of the Sulfonamide with or without a Protecting Group Scheme 5A

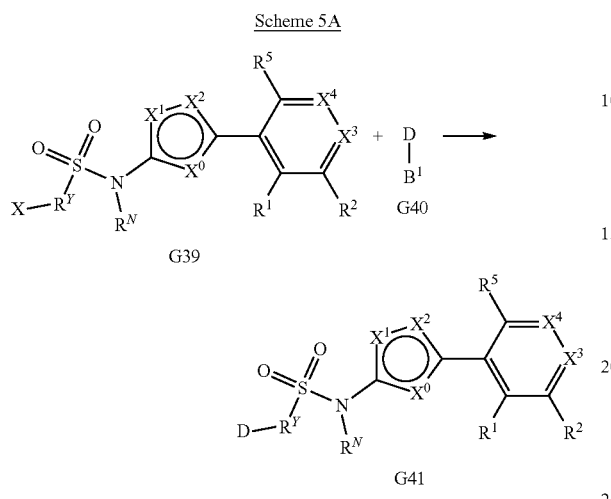

G39

G40

G41

Scheme 5A illustrates the addition of a D group, as a substituent which is part of $R^Y$, to sulfonamide G39 (where $R^N$ represents H or a suitable protecting group including but not limited to 2,4-dimethoxybenzyl, DMB). This can be achieved using any suitable coupling reaction known to the person skilled in the art, for example Suzuki coupling. The groups $DB^1$ and X are chosen to be suitable for the coupling reaction employed. For example, in the case of a Suzuki coupling reaction, (X) may be a halogen, triflate or other suitable group and $B^1$ represents a suitable boron compound including but not limited to a boronic acid or boronate ester.

Examples of $B^1$ that can be used in the Suzuki coupling include, but are not limited to, those shown below.

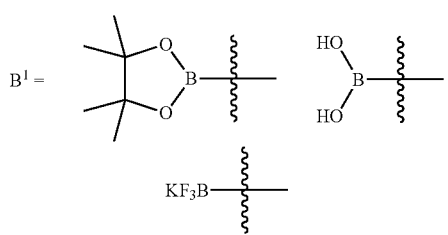

The types of $DB^1$ compounds that can be used in the Suzuki coupling include, but are not limited to, those shown in the table below.

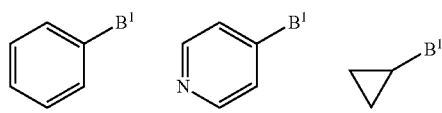

Methods for the removal of protecting groups (if employed) will be known to those skilled in the art (for example *Greene's Protective Groups in Organic Synthesis, 4th Edition*).

In addition to scheme 5A, the position of the (X) and ($B^1$) can be reversed as shown below in scheme 5B, to give the same final compound G41. Similarly to Scheme 5A, the groups denoted by DX and $B^1$ are chosen to be suitable for the coupling reaction employed. For example, in the case of a Suzuki coupling reaction (X) may be a halogen, triflate or other suitable group and $B^1$ represents a suitable boron compound including, but not limited to, a boronic acid or boronate ester.

Scheme 5B

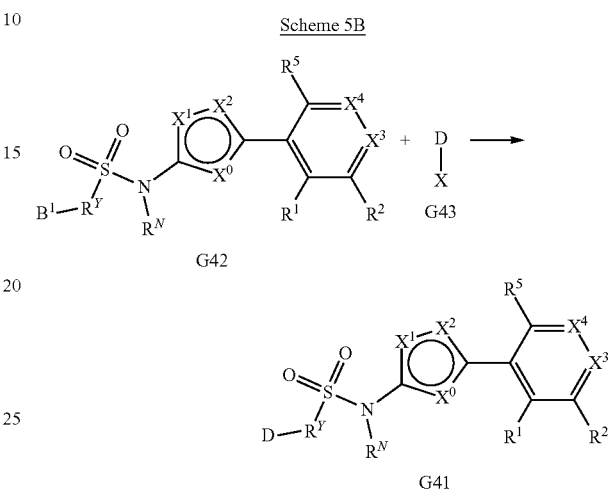

G42

G43

G41

A variety of coupling reactions may be used to introduce the D group other than Suzuki coupling, such as for example transition metal catalysed coupling reactions offer example tin (Stille type reaction) and zinc (Negishi type reaction) compounds.

The transitions described in Scheme 5A and 5B may also be carried out with substituent $R^1$, $R^2$, $R^3$, $R^4$ or $R^5$, represented by Scheme 5C below.

Scheme 5C

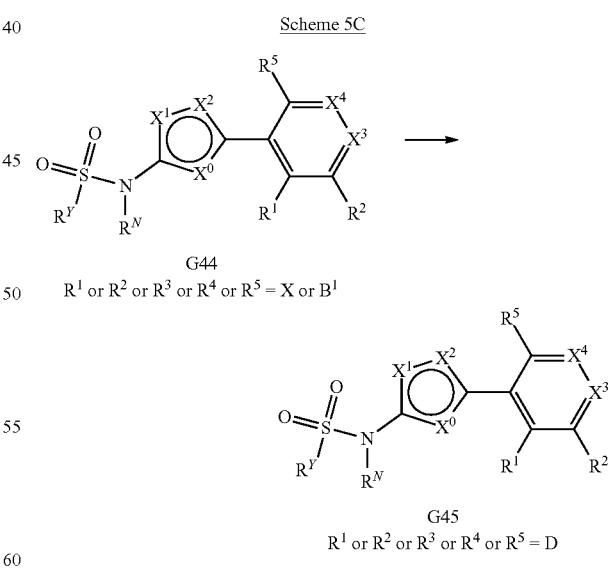

G44
$R^1$ or $R^2$ or $R^3$ or $R^4$ or $R^5$ = X or $B^1$

G45
$R^1$ or $R^2$ or $R^3$ or $R^4$ or $R^5$ = D

Alternatively, to synthesise ether linked compounds, a similar strategy can be employed as shown in scheme 5D. This can be achieved using any suitable coupling reaction known to a person skilled in the art, for example by SnAr displacement or an Ullman-type coupling to give compounds of structure G47. The group in G46 denoted by (X)

may be but is not limited to halogen and are chosen to be suitable for the coupling reaction employed.

Scheme 5D

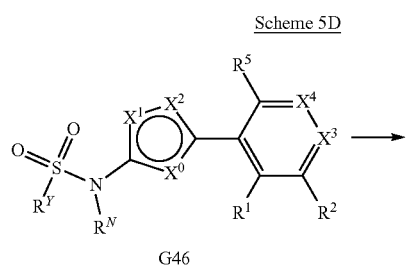

G46

R$^1$ or R$^2$ or R$^3$ or R$^4$ or R$^5$ = X

G47

R$^1$ or R$^2$ or R$^3$ or R$^4$ or R$^5$ = OR$^Z$

The above coupling may also be reversed, such that the group added is R$^z$—X.

Scheme 5E illustrates the addition of a nitrogen linked R" group, as a substituent which is part of R$^1$-R$^5$ to give a compound of structure G49. This can be achieved using any suitable coupling reaction known to the person skilled in the art, for example, by SnAr displacement, Buchwald or Ullmann coupling. The group in G48 denoted by (X) may be, but not limited to, a halogen and is chosen to be suitable for the coupling reaction employed.

Scheme 5E

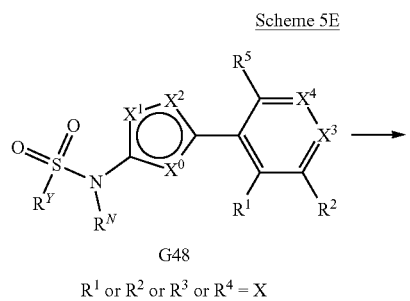

G48

R$^1$ or R$^2$ or R$^3$ or R$^4$ = X

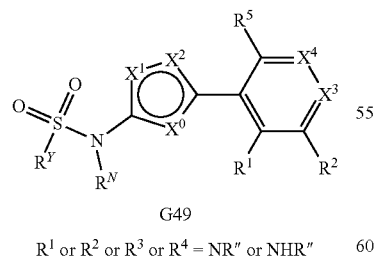

G49

R$^1$ or R$^2$ or R$^3$ or R$^4$ = NR" or NHR"

Where appropriate, the transitions used for the introduction of groups R$^1$-R$^5$ described in schemes 5C, 5D and 5E may also be performed on earlier intermediates represented in Schemes 2A, 3A, 3C & 4A; prior to formation of the desired 5-membered aminoheterocycle.

Genera/Synthesis 6—Synthesis of the Sulfamoyl Chloride and Sulfamide

Scheme 6A illustrates the synthesis of compounds where R$^Y$ is NHR$^{YN}$. Formation of amino sulfonic acid G52 may be achieved by treatment of amine G51 with chlorosulfonic acid and a base such as but not limited to triethylamine. Conversion of G52 to the sulfamoyl chloride G53 can be achieved using any suitable chlorinating agent known to the person skilled in the art, for example PCIs, thionyl chloride or POCl$_3$. Conversion to the sulfamide G54 may be achieved by coupling the relevant sulfamoyl chloride, such as (G53), with a primary or secondary amine, such as heterocyclic amine (G2) and may require the addition of base such as but not limited to K$_2$CO$_3$ or triethylamine.

Scheme 6A

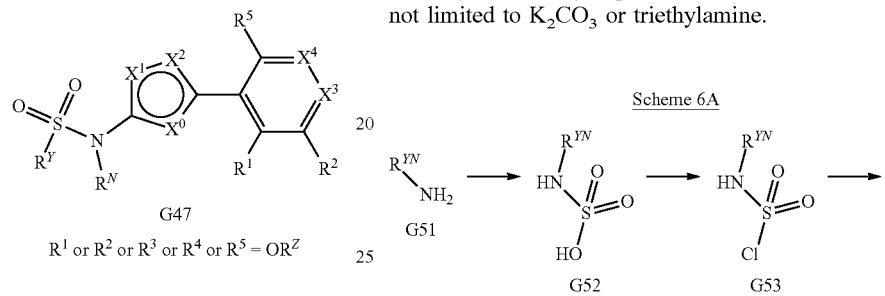

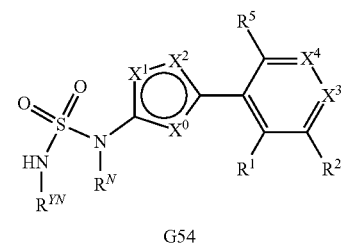

G54

Further Preferences

The following preferences may apply to all aspects of the invention as described above, or may relate to a single aspect. The preferences may be combined together in any combination.

X$^0$, X$^1$, X$^2$

In some embodiments of the invention, X$^0$=CR$^C$, X$^1$=N and X$^2$=O, i.e. the compound is of formula (I-i):

(I-i)

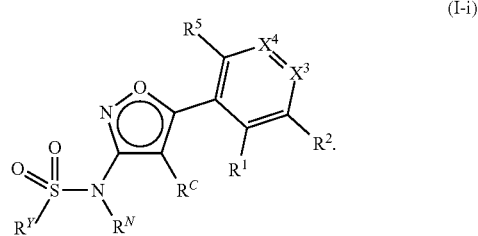

In some of these embodiments, R$^C$ is H. In others of these embodiments, R$^C$ is CO$_2$CH$_3$. In others of these embodiments, R$^C$ is Cl. It may be preferred that R$^C$ is H.

In other embodiments of the invention, X$^0$=CR$^C$, X$^1$=O and X$^2$=N, i.e. the compound is of formula (I-ii):

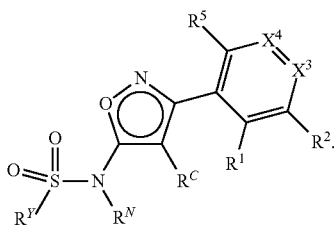

(I-ii)

In some of these embodiments, $R^C$ is H. In others of these embodiments, $R^C$ is $CO_2CH_3$. In others of these embodiments, $R^C$ is Cl. It may be preferred that $R^C$ is H.

In other embodiments of the invention, $X^0$=S, $X^1$=N and $X^2$=N, i.e. the compound is of formula (I-iiii):

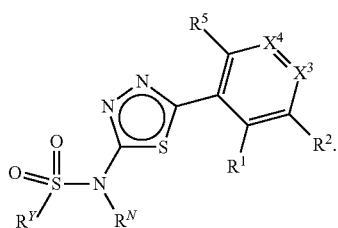

(I-iii)

In other embodiments of the invention, $X^0$=N, $X^1$=N and $X^2$=O, i.e. the compound is of formula (I-iv):

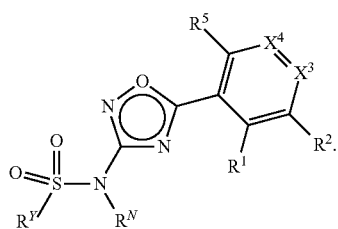

(I-iv)

In other embodiments of the invention, $X^0$=O, $X^1$=N and $X^2$=N, i.e. the compound is of formula (I-v):

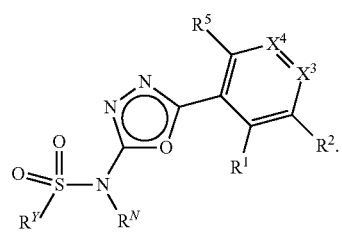

(I-v)

$R^N$

In some embodiments, $R^N$ is H.
In other embodiments, $R^N$ is methyl.
It may be preferred that $R^N$ is H.

$X^3$, $X^4$

In some embodiments, $X^3$ is $CR^3$. In other embodiments $X^3$ is N.
In some embodiments, $X^4$ is $CR^4$. In other embodiments $X^4$ is N.

It some embodiments only one of $X^3$ and $X^4$ is N.
It may be preferred that $X^3$ is $CR^3$ and $X^4$ is $CR^4$.

$R^1$ to $R^5$

In some embodiments, when $R^1$ to $R^5$ is halo, it may be selected from F, Cl and Br.

In some embodiments, when $R^1$ to $R^5$ is $C_{1-3}$ alkyl, optionally substituted by one or more fluoro groups, it may be unsubstituted by fluorine, i.e. be selected from methyl, ethyl and propyl. In other embodiments, the $C_{1-3}$ alkyl is substituted by one or more fluoro groups. In some of these embodiments, the $C_{1-3}$ alkyl is perfluorinated, for example, $CF_3$, $C_2F_5$ or $C_3F_7$. These groups may be substituted by one, two, three, four, or five fluoro groups. In some embodiments, these groups may be substituted by one; one or two; or one, two or three fluoro groups.

In some embodiments, when $R^1$ to $R^5$ is $(CH_2)_{n0}$—$C_{3-6}$ cycloalkyl, where n0=0 or 1, n0 is 0, such that the group is $C_{3-6}$ cycloalkyl, for example, cyclopropyl or cyclohexyl. In other embodiments n0 is 1, such that the group is —($CH_2$)— $C_{3-6}$ cycloalkyl, for example, —($CH_2$)-cyclopropyl or —($CH_2$)-cyclohexyl.

In some embodiments, when $R^1$ to $R^5$ is $(CH_2)_{n1}$—$C_{1-3}$ alkoxy, where n1=0 or 1, optionally substituted by one or more fluoro groups, n1 is 0, such that the group is $C_{1-3}$ alkoxy, optionally substituted by one or more fluoro groups, for example methoxy, ethoxy, isopropoxy, $OCF_3$. In other embodiments n1 is 1, such that the group is —($CH_2$)—$C_{1-3}$ alkoxy, optionally substituted by one or more fluoro groups, for example $CH_2OCH_3$, $CH_2OCF_3$. These groups may be substituted by one, two, three, four, or five fluoro groups. In some embodiments, these groups may be substituted by one; one or two; or one, two or three fluoro groups.

In some embodiments, when $R^1$ to $R^5$ is $C_{1-3}$ alkylester, it may be selected from $CO_2CH_3$, $CO_2CH_2CH_3$ and $CO_2CH_2CH_2CH_3$.

In some embodiments, when $R^1$ to $R^5$ is $(CH_2)_{n2}$-phenyl, where n2=0-2, it may be selected from phenyl, $CH_2$-phenyl and $C_2H_5$-phenyl.

In some embodiments, when $R^1$ to $R^5$ is $(CH_2)_{n3}$—$C_5$ heteroaryl, where n3=0-1, optionally substituted by methyl, when n3=0 it may be selected from oxazolyl, isoxazolyl, thiazolyl, isothiazolyl, imidazolyl and pyrazolyl. In some of these embodiments, it may be selected from oxazolyl and pyrazolyl. In some embodiments when $R^1$ to $R^5$ is —($CH_2$)$_{n3}$—$C_5$ heteroaryl, where n3=0-1, optionally substituted by methyl, when n3=1 it may be selected from —($CH_2$)-oxazolyl, —($CH_2$)-isoxazolyl, —($CH_2$)-thiazolyl, —($CH_2$)-isothiazolyl, —($CH_2$)-imidazolyl and —($CH_2$)-pyrazolyl. In some of these embodiments, it may be selected from —($CH_2$)-oxazolyl and —($CH_2$)-pyrazolyl.

$R^2$ and $R^5$

In some embodiments, $R^2$ and $R^5$ are not H, and $R^1$, $R^3$ and $R^4$ are H.

In these embodiments, $R^2$ may be selected from halo (such as Br or Cl), $(CH_2)_{n0}$—$C_{3-6}$ cycloalkyl, where n0=0 or 1 (such as cyclopropyl), $(CH_2)_{n1}$—$C_{1-3}$ alkoxy, where n1=0 or 1, optionally substituted by one or more fluoro groups (such as methoxy) and $C_{1-3}$ alkylester (such as $CO_2CH_3$). In some of these embodiments, $R^2$ may be selected from Br, Cl, cyclopropyl, methoxy and $CO_2CH_3$.

In some embodiments, $R^2$ may be $(CH_2)_{n3}$—$C_5$ heteroaryl, where n3=0-1, optionally substituted by methyl. In some of these embodiments, $R^2$ may be selected from pyrazol-1-yl, —($CH_2$)-pyrazol-1-yl, pyrazol-3-yl, 1-methylpyrazol-3-yl, pyrazol-4yl and 1-methylpyrazol-4-yl.

In these embodiments, $R^5$ may be selected from $C_{1-3}$ alkyl (such as ethyl) and $(CH_2)_{n1}$—$C_{1-3}$ alkoxy, where n1=0 or 1, optionally substituted by one or more fluoro groups (such as methoxy, $CH_2OCH_3$, isopropoxy, ethoxy and $OCF_3$). In some of these embodiments, $R^5$ may be selected from ethyl, methoxy, $CH_2OCH_3$, isopropoxy, ethoxy and $OCF_3$.

Of the above embodiments, compounds where $R^2$ is methoxy and $R^5$ is ethyl, isopropoxy and $CH_2OCH_3$ may show selective inhibition of HBO1.

Of the above embodiments, compounds where $R^5$ is methoxy and $R^2$ is $CH_2OCH_3$, cyclopropyl, Br, pyrazolyl, Cl and methoxy may show selective inhibition of KAT6A/6B.

$R^Y$

In some embodiments $R^Y$ is $(CH_2)_{n4}$-phenyl, where n4=0-2, where phenyl is optionally substituted by:
(a) $C_{1-4}$ alkyl, optionally substituted by one or more fluoro groups;
(b) $C_{1-4}$ alkoxy, optionally substituted by one or more fluoro groups;
(c) halo;
(d) cyano, nitro or amido;
(e) phenyl; or
(f) —$(CH_2)_{n5}$—, where n5 is 3 or 4.

In some of these embodiments, n4 is 0, such that $R^Y$ is optionally substituted phenyl. In other of these embodiments, n4 is 1, such that $R^Y$ is optionally substituted —$CH_2$-phenyl. In other of these embodiments, n4 is 2, such that $R^Y$ is optionally substituted —$C_2H_4$-phenyl.

In some of these embodiments, the phenyl group in $R^Y$ is unsubstituted. In other of these embodiments, the phenyl group in $R^Y$ is substituted by one substituent. In other of these embodiments, the phenyl group in $R^Y$ is substituted by two substituents.

If the phenyl group in $R^Y$ is substituted, the substituent(s) are selected from:
(a) $C_{1-4}$ alkyl, optionally substituted by one or more fluoro groups;
(b) $C_{1-4}$ alkoxy, optionally substituted by one or more fluoro groups;
(c) halo;
(d) cyano, nitro or amido;
(e) phenyl; and
(f) —$(CH_2)_{n5}$—, where n5 is 3 or 4.

In embodiments where the phenyl group in $R^Y$ is substituted by $C_{1-4}$ alkyl, optionally substituted by one or more fluoro groups, the $C_{1-4}$ alkyl may be unsubstituted by fluorine, i.e. be selected from methyl, ethyl, propyl and butyl. In other embodiments, the $C_{1-4}$ alkyl is substituted by one or more fluoro groups. In some of these embodiments, the $C_{1-4}$ alkyl is perfluorinated, for example, $CF_3$, $C_2F_5$ or $C_3F_7$. In some of these embodiments, the $C_{1-4}$ alkyl may be substituted by one, two, three, four, or five fluoro groups. In some embodiments, these groups may be substituted by one; one or two; or one, two or three fluoro groups.

In embodiments where the phenyl group in $R^Y$ is substituted by $C_{1-4}$ alkoxy, optionally substituted by one or more fluoro groups, the $C_{1-4}$ alkyloxy may be unsubstituted by fluorine, i.e. be selected from methoxy, ethoxy, propyloxy and butyloxy. In other embodiments, the $C_{1-4}$ alkyloxy is substituted by one or more fluoro groups. In some of these embodiments, the $C_{1-4}$ alkyloxy is perfluorinated, for example, $OCF_3$, $OC_2F_5$ or $OC_3F_7$. In some of these embodiments, the $C_{1-4}$ alkyl may be substituted by one, two, three, four, or five fluoro groups. In some embodiments, these groups may be substituted by one; one or two; or one, two or three fluoro groups.

In embodiments where the phenyl group in $R^Y$ is substituted by halo, the halo group may be selected from F, Cl, Br and I. In some of these embodiments, the halo group is F. In other of these embodiments, the halo group is Cl. In other of these embodiments, the halo group is Br. In other of these embodiments, the halo group is I.

In some embodiments where the phenyl group in $R^Y$ is substituted by cyano, nitro or amido, the substituent is cyano. In other embodiments, the substituent is nitro. In other embodiments, the substituent is amido.

In some embodiments the phenyl group in $R^Y$ is substituted by phenyl.

In embodiments where the phenyl group in $R^Y$ is substituted by —$(CH_2)_{n5}$—, n5 is 3 or 4. In some of these embodiments, n5 is 3, i.e. the phenyl group is fused with cyclopentene. In other of these embodiments, n5 is 4, i.e. the phenyl group is fused with cyclohexene.

In some embodiments $R^Y$ is pyridyl.

In some embodiments $R^Y$ is $C_{3-4}$ alkyl. In some these embodiments, $R^Y$ is propyl. In other of these embodiments, $R^Y$ is butyl.

In some embodiments $R^Y$ is $(CH_2)_{n6}$—$C_{3-6}$ cycloalkyl, where n6=0-2. In some embodiments when $R^Y$ is —$(CH_2)_{n6}$—$C_{3-6}$ cycloalkyl, and n6=0, then $R^Y$ may be selected from cyclopropyl, cyclobutyl, cyclopentyl and cyclohexyl. In some embodiments when $R^Y$ is $(CH_2)_{n6}$—$C_{3-6}$ cycloalkyl, and n6=1, then $R^Y$ may be selected from —$(CH_2)$-cyclopropyl, —$(CH_2)$-cyclobutyl, $(CH_2)$-cyclopentyl and $(CH_2)$-cyclohexyl. In some embodiments when $R^Y$ is $(CH_2)_{n6}$—$C_{3-6}$ cycloalkyl, and n6=2, then $R^Y$ may be selected from $(CH_2)_2$-cyclopropyl, $(CH_2)_2$-cyclobutyl, $(CH_2)_2$-cyclopentyl and $(CH_2)_2$-cyclohexyl.

In some embodiments $R^Y$ is $C_6$ heterocyclyl, optionally substituted by $C_{1-4}$ alkylester. In some of these embodiments $R^Y$ is tetrahydropyran-4-yl. In other of these embodiments $R^Y$ is 4-piperidyl. In some embodiments, $R^Y$ is 1-(2,2-dimethylpropanoyl)-4-piperidyl.

In some embodiments, $R^Y$ is $NHR^{YN}$ where $R^{YN}$ is selected from phenyl or cyclohexyl. In some of these embodiments $R^Y$ is —NH-phenyl. In some of these embodiments $R^Y$ is —NH— cyclohexyl.

In some embodiments, $R^Y$ is 2,6-dimethoxyphenyl.

In other embodiments, $R^Y$ is 2,6 dimethoxy, 4-phenylphenyl

In other embodiments, $R^Y$ is 2-methoxyphenyl.

In other embodiments, $R^Y$ is 2-methoxy, 5-ethylphenyl.

In other embodiments, $R^Y$ is $CH_2$phenyl

In other embodiments, $R^Y$ is $CH_2CH_2$phenyl.

In some embodiments, for compounds where $X^0=CR^C$, $X^1=O$, $X^2=N$, $X^3=CR^3$ and $X^4=CR^4$, and $R^1$, $R^2$, $R^3$ $R^4$, $R^5$, $R^C$ and $R^N$ are H, then $R^Y$ is not 4-methylphenyl or 3,4-dimethoxyphenyl.

In some embodiments, for compounds where $X^0=S$, $X^1=N$, $X^2=N$, $X^3=CR^3$ and $X^4=CR^4$, and $R^1$, $R^2$, $R^3$ $R^4$, $R^5$ and $R^N$ are H, then $R^Y$ is not 4-methylphenyl or 3,4-dimethoxyphenyl. In some embodiments, for compounds where $X^0=S$, $X^1=N$, $X^2=N$, $X^3=CR^3$ and $X^4=CR^4$, and $R^1$, $R^2$, $R^4$, $R^5$ and $R^N$ are H, and $R^3$ is methyl or chloro, then $R^Y$ is not 3-chlorophenyl or 3-methylphenyl.

In some embodiments, for compounds where $X^0=O$, $X^1=N$, $X^2=N$, $X^3=CR^3$ and $X^4=CR^4$, and $R^1$, $R^2$, $R^4$, $R^5$ and $R^N$ are H, and $R^3$ is $CF_3$, then $R^Y$ is not phenyl.

In some embodiments, for compounds where $X^0=O$, $X^1=N$, $X^2=N$, $X^3=N$ and $X^4=CR^4$, and $R^1$, $R^2$, $R^4$, $R^5$ and $R^N$ are H, then $R^Y$ is not phenyl, 4-chlorophenyl, 4-bromophenyl or 4-iodophenyl.

In some embodiments, for compounds where $X^0=S$, $X^1=N$, $X^2=N$, $X^3=CR^3$ and $X^4=CR^4$, and $R^1$, $R^2$, $R^4$, $R^5$ and $R^N$ are H, and $R^3$ is H or methyl, then $R^Y$ is not phenyl or 4-methylphenyl.

In some embodiments, for compounds where $X^0$=O, $X^1$=N, $X^2$=N, $X^3$=$CR^3$ and $X^4$=$CR^4$, and $R^1$, $R^2$, $R^3$ $R^4$, $R^5$ and $R^N$ are H, then $R^Y$ is not phenyl or 4-nitrophenyl.

Compounds of particular interest include those of the examples.

EXAMPLES

The following examples are provided solely to illustrate the present invention and are not intended to limit the scope of the invention, as described herein.

Acronyms

For convenience, many chemical moieties are represented using well known abbreviations, including but not limited to, methyl (Me), ethyl (Et), n-propyl (nPr), isopropyl (iPr), n-butyl (nBu), tert-butyl (tBu), phenyl (Ph), benzyl (Bn), methoxy (MeO), ethoxy (EtO), trimethylsilyl (TMS), and acetyl (Ac).

For convenience, many chemical compounds are represented using well known abbreviations, including but not limited to, $d^3$-methanol (MeOH), deuterated methanol ($d_4$-MeOD) ethanol (EtOH), isopropanol (i-PrOH), ether or diethyl ether ($Et_2O$), ethyl acetate (EtOAc), acetic acid (AcOH), acetonitrile (MeCN), dichloromethane (methylene chloride, DCM), trifluoroacetic acid (TFA), dimethylformamide (DMF), tetrahydrofuran (THF), dimethylsulfoxide (DMSO), deuterated chloroform ($CDCl_3$), diethylamine (DEA), deuterated dimethylsulfoxide (DMSO-$d_6$), N-ethyl-N'-(3-dimethylaminopropyl)carbodiimide hydrochloride (EDCl·HCl, EDCl), 1,1'-bis(diphenylphosphino)ferrocene (dppf), tert-butyloxycarbonyl (Boc, BOC), 2-(trimethylsilyl) ethoxymethyl (SEM), triethylamine ($Et_3N$ or TEA), 2-(1H-7-azabenzotriazol-1-yl)-1,1,3,3-tetramethyluronium hexafluorophosphate (HATU), 4-dimethylaminopyridine (DMAP), N,N-diisopropylethylamine (DIPEA or DIEA), 1,1'-bis(diphenylphosphino)ferrocene dichloropalladium (II) ($PdCl_2$(dppf)), trans-dichlorobis(triphenylphosphine) palladium(II) ($PdCl_2(PPh_3)_2$), tris(dibenzylideneacetone) dipalladium(0) ($Pd_2(dba)_3$), tetrakis(triphenylphosphine) palladium(0) ($Pd(PPh_3)_4$), 1,2-dichloroethane (DCE), benzyl (Bn) and 1-hydroxybenzotriazole (HOBt), N,N,N',N' Tetramethylethylenediamine (TMEDA), Lithium bis(trimethylsilyl)amide (LiHMDS), 2-(1H-Benzotriazole-1-yl)-1,1,3,3-tetramethyluronium hexafluorophosphate (HBTU), 2,4-dimethoxybenzyl (DMB).

In addition, TLC refers to thin layer chromatography, prep HPLC refers to preparative high-performance liquid chromatography, Prep. TLC refers to preparative thin layer chromatography, eq refers to equivalents, $R_t$ refers to retention time and con. refers to concentrated.

General Experimental Details

Unless otherwise stated the following generalisations apply. $^1$H NMR spectra were recorded on a Bruker Ultrashield Plus (400 MHz) or a Bruker AVANCE III (400 MHz). The multiplicity of a signal is designated by the following abbreviations: s, singlet; d, doublet; t, triplet; q, quartet; dd, doublet of doublets; dt, doublet of triplets; tt, triplet of triplets; br, broad; m, multiplet. All observed coupling constants, J, are reported in Hertz.

Exchangeable protons are not always observed.

Analytical LCMS data was generated using methods, including but not limited to, either an Agilent 6100 Series Single Quad LCMS, an Agilent 1260 Infinity Series UPLC/MS or an Agilent 1200 Series G6110A Quadrupole LCMS. Chlorine isotopes are reported as $^{35}$Cl, Bromine isotopes are reported as either $^{79}$Br or $^{81}$Br or both $^{79}$Br/$^{81}$Br. LC-MS equipment and conditions are as follows:

LCMS Method a (LCMS-A):
Equipment Information
LC model: Agilent 1200 (Pump type: Binary Pump, Detector type: DAD)
MS model: Agilent G6110A Quadrupole
Parameters of LCMS
LC: Column: Xbridge-C18, 2.5 μm, 2.1×30 mm
Column temperature: 30° C.
Acquisition of wavelength: 214 nm, 254 nm
Mobile phase: A: 0.07% HCOOH aqueous solution, B: MeOH
MS: Ion source: ES+ (or ES−) MS range: 50~900 m/z
Fragmentor: 60 Drying gas flow: 10 L/min
Nebulizer pressure: 35 psi Drying gas temperature: 350° C.
Vcap: 3.5 kV

| Gradient Table: | | | |
|---|---|---|---|
| Flow (mL/min) | T (min) | A (%) | B (%) |
| 0.5 | 0.0 | 70 | 30 30 |
| 0.5 | 0.2 | 70 | 30 |
| 0.5 | 1.8 | 5 | 95 |
| 0.5 | 2.4 | 5 | 95 |
| 0.5 | 2.6 | 70 | 30 |
| 0.5 | 3.5 | 70 | 30 35 |

Sample Preparation

The sample was dissolved in methanol, the concentration about 0.11~1 mg/mL, then filtered through syringe filter with 0.22 μm. (Injection volume: 1~10 μL)

LCMS Method B (LCMS-B):
Equipment Information
LC model: Agilent 1200 (Pump type: Binary Pump, Detector type: DAD)
MS model: Agilent G6110A Quadrupole
Parameters of LCMS
LC: Column: Xbridge-C18, 2.5 μm, 2.1×30 mm
Column temperature: 30° C.
Acquisition of wavelength: 214 nm, 254 nm
Mobile phase: A: 0.07% HCOOH aqueous solution, B: MeOH
MS: Ion source: ES+ (or ES−) MS range: 50~900 m/z
Fragmentor: 60 Drying gas flow: 10 L/min
Nebulizer pressure: 35 psi Drying gas temperature: 350° C.
Vcap: 3.5 kV

| Gradient Table: | | | |
|---|---|---|---|
| Flow (mL/min) | T (min) | A (%) | B (%) |
| 0.5 | 0.0 | 70 | 30 |
| 0.5 | 0.3 | 70 | 30 |
| 0.5 | 0.6 | 50 | 50 |
| 0.5 | 0.9 | 40 | 60 |
| 0.5 | 1.2 | 30 | 70 |
| 0.5 | 3.2 | 5 | 95 |
| 0.5 | 3.5 | 5 | 95 |
| 0.5 | 4.0 | 70 | 30 |
| 0.5 | 5.0 | 70 | 30 |

Sample Preparation

The sample was dissolved in methanol, the concentration about 0.11~1 mg/mL, then filtered through the syringe filter with 0.22 μm. (Injection volume: 1~10 μL)

LCMS Method C (LCMS-C):
Instrument: Agilent 6100 Series Single Quad LC/MS
Agilent 1200 Series HPLC
Pump: 1200 Series G1311A Quaternary pump
Autosampler: 1200 Series G1329A Thermostatted Autosampler
Detector: 1200 Series G1314B Variable Wavelength Detector
LC Conditions:
Reverse Phase HPLC analysis
Column: Luna C8 (2) 5 μm 50×4.6 mm 100 Å
Column temperature: 30° C.
Injection Volume: 5 μL
Solvent A: Water 0.1% Formic Acid
Solvent B: MeCN 0.1% Formic Acid
Gradient: 5-100% solvent B over 10 min
Detection: 254 nm or 214 nm
MS Conditions:
Ion Source: Quadrupole
Ion Mode: Multimode-ES
Drying gas temp: 300° C.
Vaporizer temperature: 200° C.
Capillary voltage (V): 2000 (positive)
Capillary voltage (V): 4000 (negative)
Scan Range: 100-1000
Step size: 0.1 sec
Acquisition time: 10 min
LCMS Method D (LCMS-D):
Instrument: Agilent 1260 Infinity Series UPLC/MS
Pump: 1260 Infinity G1312B Binary pump
Autosampler: 1260 Infinity G1367E 1260 HiP ALS
Detector: 1290 Infinity G4212A 1290 DAD
LC Conditions:
Reverse Phase HPLC analysis
Column: Poroshell 120 EC-C18 2.7 μm 50×3.0 mm
Column temperature: 35° C.
Injection Volume: 1 μL
Solvent A: Water 0.1% Formic Acid
Solvent B: MeCN 0.1% Formic Acid
Gradient: 5-100% solvent B over 3.8 min
Detection: monitored at 254 nm and 214 nm
MS Conditions:
Ion Source: Quadrupole
Ion Mode: API-ES
Drying gas temp: 350° C.
Capillary voltage (V): 3000 (positive)
Capillary voltage (V): 3000 (negative)
Scan Range: 100-1000
Step size: 0.1 sec
Acquisition time: 5 min
LCMS Method E (LCMS-E):
Instrument: Waters 2695 alliance
Pump: Quaternary Pump
Detector: 2996 Photodiode Array Detector
MS model: Micromass ZQ
LC Conditions:
Column: Xbridge-C18, 2.5 μm, 2.1×30 mm
Column temperature: 30° C.
Acquisition of wavelength: 214 nm, 254 nm
Mobile phase: A: 0.05% HCOOH aqueous solution, B: MeOH
Run time: 5 min
MS Conditions:
Ion source: ES+ (or ES−) MS range: 50-900 m/z
Capillary: 3.5 kV Cone: 35 V Extractor: 3 V
Drying gas flow: 350 L/hr cone: 50 L/hr
Desolvation temperature: 300° C.
Source temperature: 120° C.
Run time: 5 min Gradient Table:

| Flow (mL/min) | T (min) | A (%) | B (%) |
|---|---|---|---|
| 0.5 | 0.0 | 70 | 30 |
| 0.5 | 0.3 | 70 | 30 |
| 0.5 | 0.6 | 50 | 50 |
| 0.5 | 0.9 | 40 | 60 |
| 0.5 | 1.2 | 30 | 70 |
| 0.5 | 3.2 | 5 | 95 |
| 0.5 | 3.5 | 5 | 95 |
| 0.5 | 4.0 | 70 | 30 |
| 0.5 | 5.0 | 70 | 30 |

Sample Preparation
The sample was dissolved in methanol, the concentration about 0.11-1 mg/mL, then filtered through the syringe filter with 0.22 μm. (Injection volume: 1-10 μL)
Preparative HPLC
Instrument type: Varian 940-LC series;
Pump type: Quaternary Pump;
Detector type: Diode Array Detector
HPLC conditions: Waters Sunfire prep C18 OBD, 5 μm 19×100 mm column, eluting with a gradient of MeOH in water with 0.07% TFA at a flow rate of 15 mL/min. Acquisition wavelength 214 nm, 254 nm
Analytical thin-layer chromatography was performed on Merck silica gel 60 F254 aluminium-backed plates which were visualised using fluorescence quenching under UV light or a basic $KMnO_4$ dip or Ninhydrin dip.
Preparative thin-layer chromatography was performed using Tklst (China), grand grade: (HPTLC): 8±2 μm>80%; (TLC): 10-40 μm. Type: GF254. Compounds were visualised by UV (254 nm).
Flash chromatography was performed using a Biotage Isolera purification system using either Grace or RediSep® silica cartridges.
Column chromatography was performed using Tklst (China), grand grade, 100-200 meshes silica gel.
Microwave irradiation was achieved using a CEM Explorer SP Microwave Reactor. Where necessary, anhydrous solvents were purchased from Sigma-Aldrich or dried using conventional methods.
Preparative Mass-Directed HPLC
Instrument:
Waters ZQ 3100—Mass Detector
Waters 2545-Pump
Waters SFO System Fluidics Organizer
Waters 2996 Diode Array Detector
Waters 2767 Sample Manager
LC Conditions:
Reverse Phase HPLC analysis
Column: XBridge™ C18 5 μm 19×50 mm
Injection Volume 500 μL
Solvent A: Water 0.1% Formic Acid
Solvent B: Acetonitrile 0.1% Formic Acid
Gradient: 25-100% B over 10 min
Flow rate: 19 mL/min
Detection: 100-600 nm
MS Conditions:
Ion Source: Single-quadrupole
Ion Mode: ES positive
Source Temp: 150° C.
Desolvation Temp: 350° C.
Detection: Ion counting Capillary (KV)-3.00
Cone (V): 30
Extractor (V): 3
RF Lens (V): 0.1
can Range: 100-1000 Amu
Scan Time: 0.5 sec
Acquisition time: 10 min
Gas Flow
Desolvation L/hour-650
Cone L/hour-100

Microwave irradiation was achieved using a CEM Explorer SP Microwave Reactor.

Where necessary, anhydrous solvents were purchased from Sigma-Aldrich or dried using conventional methods.

Solutions of inorganic acids or bases were made up as aqueous solutions unless stated otherwise.

Additional sample extraction cartridges used are as follows:
Phase Separator:
Manufacturer: Biotage
Product: ISOLUTE® Phase Separator (3 mL unless otherwise stated)
Si-Amine Cartridges:
Manufacturer: Silicycle
Product: Si-amine 500 mg or 1 g Synthesis of Intermediates (i) 5-(3-Methoxyphenyl)isoxazol-3-amine I1

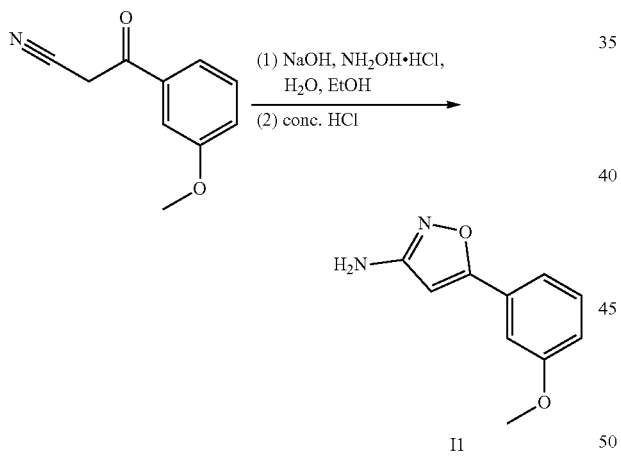

To a stirred solution of 3-(3-methoxyphenyl)-3-oxopropanenitrile (2.0 g, 11.4 mmol) and NaOH (500 mg, 12.5 mmol) in water (15 mL) and ethanol (15 mL) was added hydroxylamine hydrochloride (871 mg, 12.5 mmol) and the mixture was heated at 80° C. overnight. Concentrated HCl (1.4 mL, 12.5 mmol) was then added and the mixture was heated at 80° C. for a further 2 h. The mixture was basified to pH 10 with 2 M NaOH and extracted with EtOAc (50 mL×3). The combined organic extracts were washed with brine, dried over anhydrous Na$_2$SO$_4$, filtered and concentrated under reduced pressure. The residue was purified by column chromatography (petroleum ether/EtOAc=30/1 to 10/1 to 5/1) to give title compound I1 (650 mg, 31%) as a yellow solid. LCMS-B (ES-API): R$_t$0.71 min; m/z 191.0 [M+H]$^+$. $^1$H NMR (400 MHz, DMSO-d$_6$) δ 7.41-7.37 (m, 1H), 7.34-7.30 (m, 1H), 7.28-7.25 (m, 1H), 7.04-6.99 (m, 1H), 6.34 (s, 1H), 5.66 (s, 2H), 3.81 (s, 3H).

(ii) 5-(2-Methoxyphenyl)isoxazol-3-amine I2

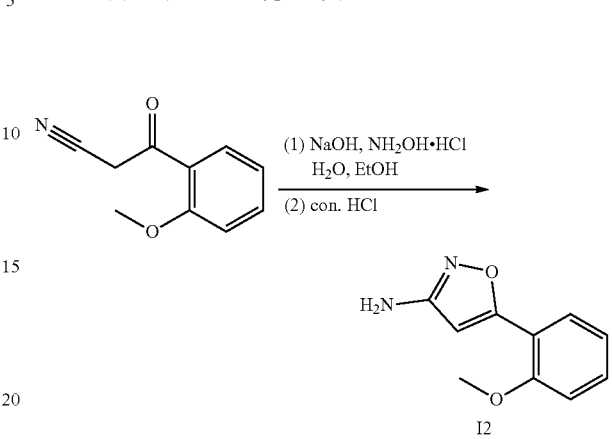

To a stirred solution of 3-(2-methoxyphenyl)-3-oxopropanenitrile (1.5 g, 8.56 mmol) and NaOH (377 mg, 9.42 mmol) in water (15 mL) and ethanol (15 mL) was added hydroxylamine hydrochloride (655 mg, 9.42 mmol) and the mixture was heated at 80° C. overnight. Concentrated HCl (0.7 mL, 8.56 mmol) was then added and the mixture was heated at 80° C. for a further 3 h. The mixture was basified to pH 10 with 2 M NaOH and extracted with EtOAc. The combined organic extracts were washed with brine, dried over anhydrous Na$_2$SO$_4$, filtered and concentrated under reduced pressure. The residue was purified by column chromatography (DCM/MeOH=500/1 to 200/1 to 100/1) to give title compound I2 (620 mg, 38%) as a yellow solid. LCMS-B (ES-API): R$_t$0.73 min; m/z 191.0 [M+H]$^+$. $^1$H NMR (400 MHz, DMSO-d$_6$) δ 7.74 (dd, J=7.8, 1.7 Hz, 1H), 7.48-7.40 (m, 1H), 7.19 (d, J=7.1 Hz, 1H), 7.10-7.03 (m, 1H), 6.29 (s, 1H), 5.60 (s, 2H), 3.92 (s, 3H).

(iii) 5-(2,5-Dimethoxyphenyl)isoxazol-3-amine I5

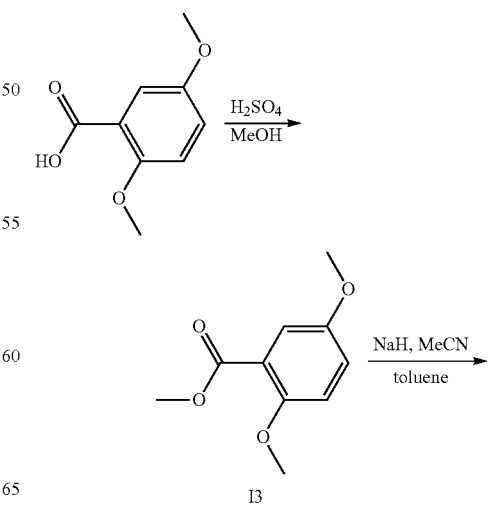

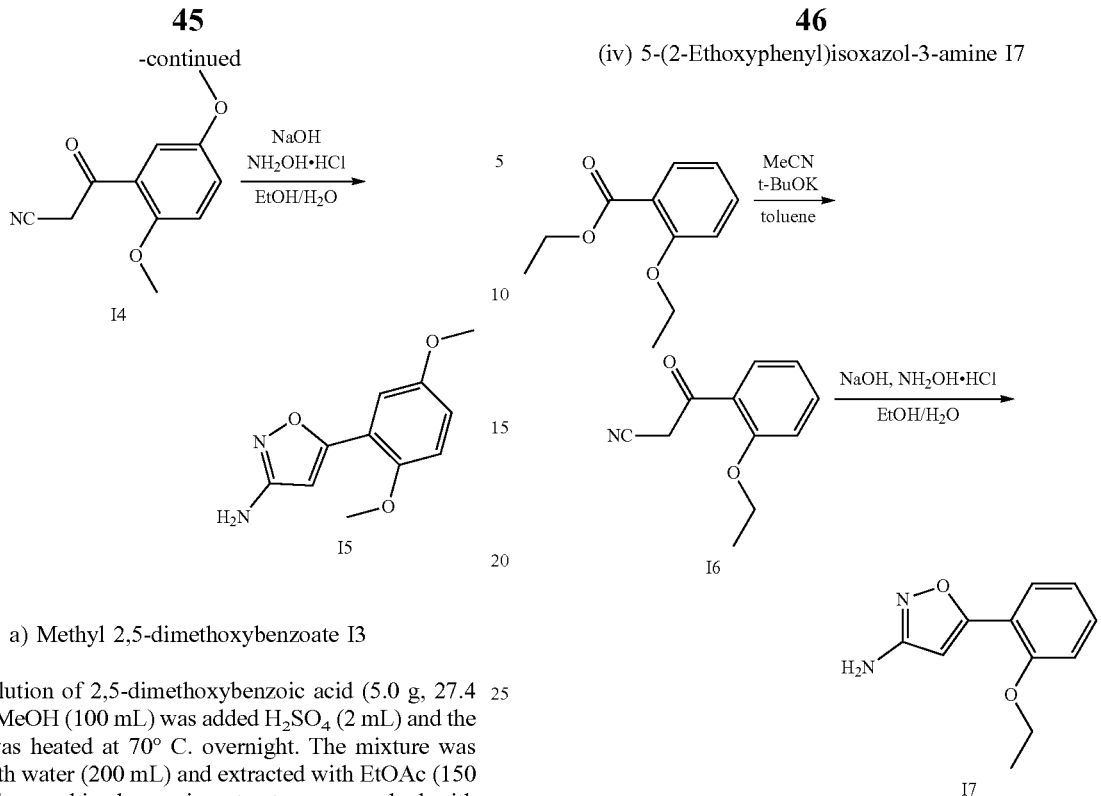

a) Methyl 2,5-dimethoxybenzoate I3

To a solution of 2,5-dimethoxybenzoic acid (5.0 g, 27.4 mmol) in MeOH (100 mL) was added $H_2SO_4$ (2 mL) and the mixture was heated at 70° C. overnight. The mixture was diluted with water (200 mL) and extracted with EtOAc (150 mL×3). The combined organic extracts were washed with brine, dried over anhydrous $Na_2SO_4$, filtered and concentrated under reduced pressure to give the title compound I3 (5.0 g, 93%) as a yellow oil. LCMS-A (ES-API): $R_t$ 2.24 min; m/z 197.1 [M+H]$^+$, 219.0 [M+Na]$^+$.

b) 3-(2,5-Dimethoxyphenyl)-3-oxopropanenitrile I4

To a solution of methyl 2,5-dimethoxybenzoate I3 (4.5 g, 22.9 mmol) and acetonitrile (1.41 g, 16.0 mmol) in toluene (150 mL) at 0° C. was added NaH (60% w/w dispersion in oil, 1.38 g, 34.4 mmol) and the mixture was stirred at 0° C. for 30 min then heated at 110° C. overnight. The reaction was quenched with water (400 mL) and the mixture was extracted with EtOAc (300 mL×3). The combined organic extracts were washed with brine, dried over anhydrous $Na_2SO_4$, filtered and concentrated under reduced pressure. The residue was purified by column chromatography (petroleum ether/EtOAc=30/1) to give the title compound I4 (1.9 g 40%) as a yellow solid. LCMS-A (ES-API): $R_t$ 1.15 min; m/z 206.1 [M+H]$^+$.

c) 5-(2,5-Dimethoxyphenyl)isoxazol-3-amine I5

3-(2,5-Dimethoxyphenyl)-3-oxopropanenitrile I4 (1.8 g, 8.78 mmol), NaOH (456 mg, 11.4 mmol), and $NH_2OH·HCl$ (793 mg, 11.4 mmol) were dissolved in ethanol (25 mL) and water (25 mL) and the mixture was heated at 80° C. overnight. The mixture was diluted with water (200 mL) and extracted with EtOAc (100 mL×3). The combined organic extracts were washed with brine, dried over anhydrous $Na_2SO_4$, filtered and concentrated under reduced pressure. The residue was purified by column chromatography (petroleum ether/EtOAc=5/1) to give the title compound I5 (600 mg 32%) as a yellow solid. LCMS-A (ES-API): $R_t$ 0.88 min; m/z 221.0 [M+H]$^+$. $^1$H NMR (400 MHz, DMSO-$d_6$) δ 7.25 (d, J=3.1 Hz, 1H), 7.14-7.09 (m, 1H), 7.04-6.99 (m, 1H), 6.30 (s, 1H), 5.63 (s, 2H), 3.86 (s, 3H), 3.76 (s, 3H).

(iv) 5-(2-Ethoxyphenyl)isoxazol-3-amine I7 a) 3-(2-Ethoxyphenyl)-3-oxopropanenitrile I6

To a solution of ethyl 2-ethoxybenzoate (5.0 g, 25.7 mmol) and acetonitrile (1.06 g, 25.7 mmol) in toluene (30 mL) at 0° C. was added potassium tert-butoxide (2.89 g, 25.7 mol) portion-wise and the mixture was stirred at room temperature for 1 h. Water (30 mL) was slowly added and the layers were separated. The organic layer was extracted with water (30 mL×3) and the combined aqueous layers were adjusted to pH 1 with concentrated HCl. The resulting precipitate was collected by filtration and the solid was purified by column chromatography (petroleum ether/EtOAc=50/1 to 20/1) to give the title compound I6 (800 mg, 16%) as a white solid. LCMS-A (ES-API): $R_t$ 1.67 min; m/z 190.1 [M+H]$^+$ b) 5-(2-Ethoxyphenyl)isoxazol-3-amine I7

To a stirred solution of 3-(2-ethoxyphenyl)-3-oxopropanenitrile I6 (800 mg, 4.23 mmol) and NaOH (186 mg, 4.65 mmol) in water (15 mL) and ethanol (15 mL) was added hydroxylamine hydrochloride (323 mg, 4.65 mmol) and the mixture was heated at 80° C. overnight. The mixture was diluted with water and extracted three times with EtOAc. The combined organic extracts were washed with brine, dried over anhydrous $Na_2SO_4$, filtered and concentrated under reduced pressure. The residue was purified by column chromatography (DCM/MeOH=100/0 to 100/1) followed by preparative HPLC to give the title compound I7 (40 mg, 5%) as a white solid. LCMS-A (ES-API): $R_t$ 1.44 min; m/z 205.0 [M+H]$^+$. $^1$H NMR (400 MHz, DMSO-$d_6$) δ 7.75 (d, J=8.0 Hz, 1H), 7.44-7.37 (m, 1H), 7.15 (d, J=8.4 Hz, 1H), 7.04 (t, J=7.6 Hz, 1H), 6.34 (s, 1H), 5.61 (s, 2H), 4.17 (q, J=6.9 Hz, 2H), 1.44 (t, J=6.9 Hz, 3H). 3-(2-Ethoxyphenyl)isoxazol-5-amine (80 mg, 10%) was also obtained as a white solid. LCMS-A (ES-API): $R_t$ 1.17 min; m/z 205.0 [M+H]$^+$. $^1$H NMR (400 MHz, DMSO-d$_6$) δ 7.68 (dd, J=7.7, 1.8 Hz, 1H), 7.41-7.34 (m, 1H), 7.13-7.07 (m, 1H), 7.00-6.94 (m, 1H), 6.60 (s, 2H), 5.45 (s, 1H), 4.09 (q, J=6.9 Hz, 2H), 1.37 (t, J=6.9 Hz, 3H).

(v) 5-(2,4-Dimethoxyphenyl)isoxazol-3-amine I8

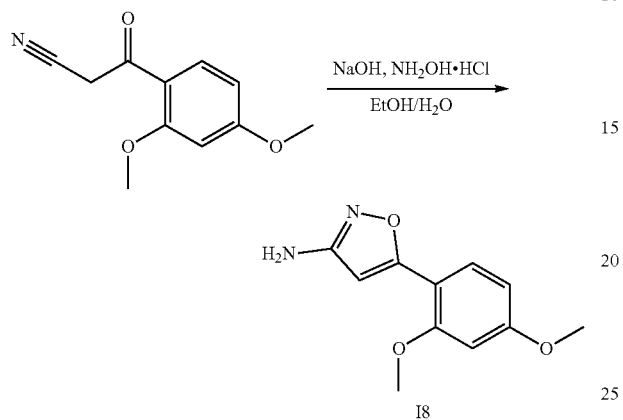

To a stirred solution of 3-(2,4-dimethoxyphenyl)-3-oxopropanenitrile (1.0 g, 4.87 mmol) and NaOH (220 mg, 4.53 mmol) in water (7.5 mL) and ethanol (7.5 mL) was added hydroxylamine hydrochloride (350 mg, 5.36 mmol) and the mixture was heated at 80° C. overnight. The mixture was diluted with water and extracted three times with EtOAc. The combined organic extracts were washed with brine, dried over anhydrous Na$_2$SO$_4$, filtered and concentrated under reduced pressure. The residue was purified by column chromatography (petroleum ether/EtOAc=5/1 to 2/1 to 1/1) to give the title compound I8 (580 mg, 54%) as a white solid. LCMS-B (ES-API): R$_t$ 2.14 min; m/z 221.0 [M+H]$^+$. $^1$H NMR (400 MHz, DMSO-d$_6$) δ 7.65 (d, J=8.6 Hz, 1H), 6.70 (d, J=2.4 Hz, 1H), 6.65 (dd, J=8.7, 2.4 Hz, 1H), 6.14 (s, 1H), 5.53 (s, 2H), 3.90 (s, 3H), 3.82 (s, 3H). 3-(2,4-Dimethoxyphenyl)isoxazol-5-amine (250 mg, 23%) was also obtained as a yellow oil. LCMS-B (ES-API): R$_t$ 1.70 min; m/z 221.0 [M+H]$^+$. $^1$H NMR (400 MHz, DMSO-d$_6$) δ 7.58 (d, J=8.5 Hz, 1H), 6.65 (d, J=2.4 Hz, 1H), 6.58 (dd, J=8.6, 2.4 Hz, 1H), 6.54 (s, 2H), 5.32 (s, 1H), 3.82 (s, 3H), 3.80 (s, 3H).

(vi)
5-(5-Cyclopropyl-2-methoxyphenyl)isoxazol-3-amine I11

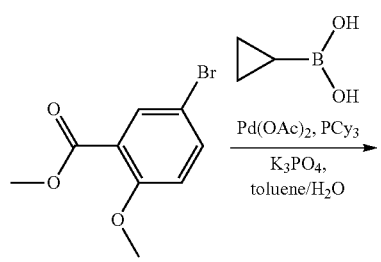

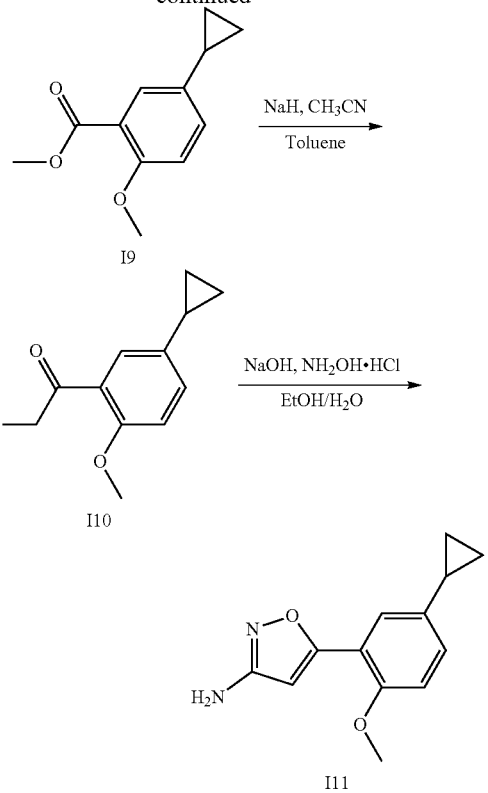

a) Methyl 5-cyclopropyl-2-methoxybenzoate I9

Methyl 5-bromo-2-methoxybenzoate (4.0 g, 16.3 mmol), cyclopropylboronic acid (2.9 g, 32.6 mmol), Pd(OAc)$_2$ (183 mg, 0.82 mmol), PCy$_3$ (457 mg, 1.63 mmol) and K$_3$PO$_4$ (10.4 g, 48.9 mmol) were dissolved in toluene (60 mL) and water (3 mL) under N$_2$ and the mixture was heated at 100° C. for 3 h. Water (150 mL) was added and the mixture was extracted with EtOAc (100 mL×3). The combined organic extracts were washed with brine, dried over anhydrous Na$_2$SO$_4$, filtered and concentrated under reduced pressure. The residue was purified by column chromatography (petroleum ether/EtOAc=100/1 to 20/1) to give the title compound I9 (2.3 g, 70%) as a yellow oil. LCMS-A (ES-API): R$_t$ 2.09 min; m/z 207.1 [M+H]$^+$.

b) 3-(5-Cyclopropyl-2-methoxyphenyl)-3-oxopropanenitrile I10

To a solution of methyl 5-cyclopropyl-2-methoxybenzoate I9 (2.20 g, 10.7 mmol) and acetonitrile (657 mg, 16.0 mmol) in toluene (40 mL) at 0° C. was added NaH (60% w/w dispersion in oil, 640 mg, 16.0 mmol) and the mixture stirred at 0° C. for 30 min then heated at 110° C. overnight. Water (100 mL) was added and the mixture was extracted with EtOAc (100 mL×3). The combined organic extracts were washed with brine, dried over anhydrous Na$_2$SO$_4$, filtered and concentrated under reduced pressure. The residue was purified by column chromatography (petroleum ether/EtOAc=30/1) to give the title compound I10 (1.3 g, 57%) as a yellow oil. LCMS-A (ES-API): R$_t$ 1.14 min; m/z 216.1 [M+H]$^+$.

c)
5-(5-Cyclopropyl-2-methoxyphenyl)isoxazol-3-amine I11

To a solution of 3-(5-cyclopropyl-2-methoxyphenyl)-3-oxopropanenitrile I10 (1.3 g, 6.04 mmol) and NaOH (314 mg, 7.85 mmol) in water (15 mL) and ethanol (15 mL) was added NH$_2$OH·HCl (545.6 mg, 7.85 mmol) and the mixture was heated at 80° C. overnight. Water (100 mL) was added and the mixture was extracted with EtOAc (100 mL×3). The combined organic extracts were washed with brine, dried over anhydrous Na$_2$SO$_4$, filtered and concentrated under reduced pressure. The residue was purified by column chromatography (petroleum ether/EtOAc=5/1) to give the title compound I11 (700 mg, 50%) as a yellow oil. LCMS-A (ES-API): R$_t$ 2.13 min; m/z 231.1 [M+H]$^+$. $^1$H NMR (400 MHz, DMSO-d$_6$) δ 7.43 (d, J=2.3 Hz, 1H), 7.16-7.11 (m, 1H), 7.08-7.04 (m, 1H), 6.26 (s, 1H), 5.59 (s, 2H), 3.87 (s, 3H), 1.98-1.90 (m, 1H), 0.95-0.88 (m, 2H), 0.65-0.60 (m, 2H).

(vii)
5-(5-Bromo-2-methoxyphenyl)isoxazol-3-amine I13

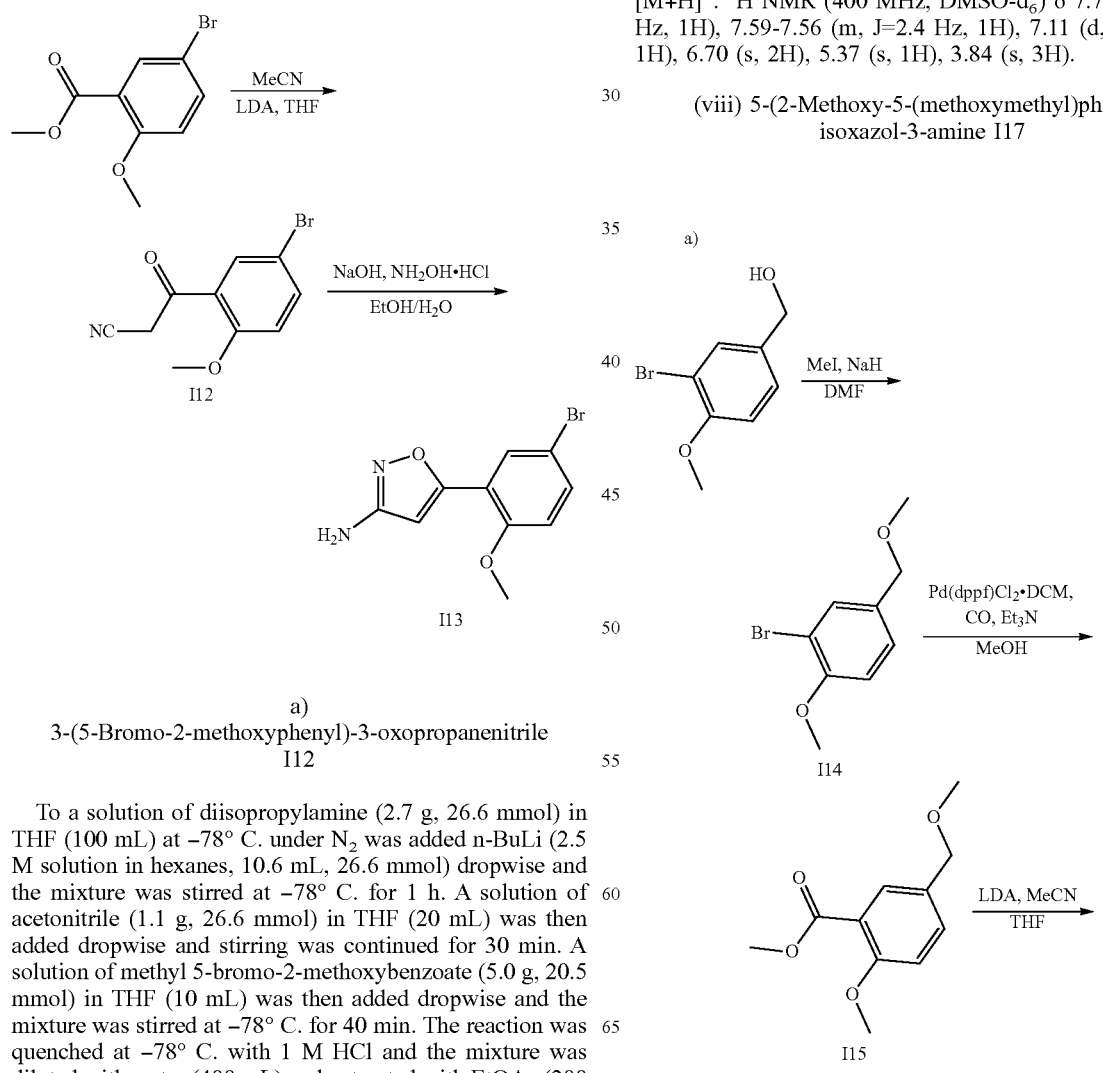

a)
3-(5-Bromo-2-methoxyphenyl)-3-oxopropanenitrile I12

To a solution of diisopropylamine (2.7 g, 26.6 mmol) in THF (100 mL) at −78° C. under N$_2$ was added n-BuLi (2.5 M solution in hexanes, 10.6 mL, 26.6 mmol) dropwise and the mixture was stirred at −78° C. for 1 h. A solution of acetonitrile (1.1 g, 26.6 mmol) in THF (20 mL) was then added dropwise and stirring was continued for 30 min. A solution of methyl 5-bromo-2-methoxybenzoate (5.0 g, 20.5 mmol) in THF (10 mL) was then added dropwise and the mixture was stirred at −78° C. for 40 min. The reaction was quenched at −78° C. with 1 M HCl and the mixture was diluted with water (400 mL) and extracted with EtOAc (200 mL×3). The combined organic extracts were washed with brine, dried over anhydrous Na$_2$SO$_4$, filtered and concentrated under reduced pressure to give the title compound I12 (5.0 g, 96% yield) as a yellow solid. LCMS-A (ES-API): R$_t$ 2.00 min; m/z 253.9/255.9 [M+H]$^+$.

b) 5-(5-Bromo-2-methoxyphenyl)isoxazol-3-amine I13

To a solution of 3-(5-bromo-2-methoxyphenyl)-3-oxopropanenitrile I12 (5.0 g, 19.7 mmol) and NaOH (1.02 g, 25.6 mmol) in water (75 mL) and ethanol (75 mL) was added NH$_2$OH·HCl (1.78 g, 25.6 mmol) and the mixture was heated at 80° C. overnight. Water (400 mL) was added and the mixture was extracted with EtOAc (200 mL×3). The combined organic extracts were washed with brine, dried over anhydrous Na$_2$SO$_4$, filtered and concentrated under reduced pressure. The residue was purified by column chromatography (petroleum ether/EtOAc=10/1) to give the title compound I13 (1.2 g, 22% yield) as a yellow solid. LCMS-A (ES-API): R$_t$ 1.81 min; m/z 268.9/270.9 [M+H]$^+$. $^1$H NMR (400 MHz, DMSO-d$_6$) δ 7.80 (d, J=2.4 Hz 1H), 7.62-7.59 (m, 1H), 7.17 (d, J=8.8 Hz, 1H), 6.33 (s, 1H), 5.67 (s, 2H), 3.92 (s, 3H). 3-(5-Bromo-2-methoxyphenyl)isoxazol-5-amine (1.4 g, 26% yield) was also obtained as a yellow solid. LCMS-A (ES-API): R$_t$ 2.0 min; m/z 268.9/270.9 [M+H]$^+$. $^1$H NMR (400 MHz, DMSO-d$_6$) δ 7.75 (d, J=2.8 Hz, 1H), 7.59-7.56 (m, J=2.4 Hz, 1H), 7.11 (d, J=8.8 Hz, 1H), 6.70 (s, 2H), 5.37 (s, 1H), 3.84 (s, 3H).

(viii) 5-(2-Methoxy-5-(methoxymethyl)phenyl)isoxazol-3-amine I17

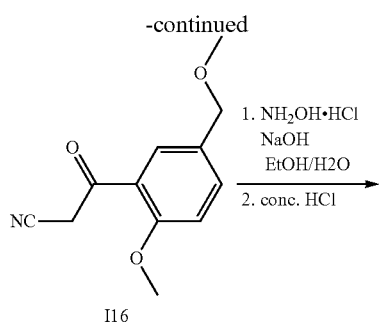

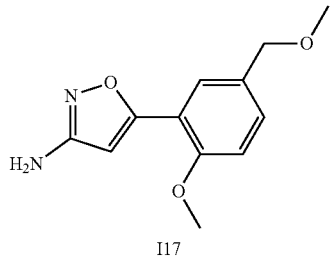

2-Bromo-1-methoxy-4-(methoxymethyl)benzene I14

To a solution of (3-bromo-4-methoxyphenyl)methanol (3.0 g, 13.8 mmol) and iodomethane (9.8 g, 69.1 mmol) in DMF (129 mL) at 0° C. was added NaH (60% w/w dispersion in oil, 1.1 g, 27.6 mmol) and the mixture was stirred at room temperature for 30 min. Water was added and the mixture was extracted with EtOAc (100 mL×3). The combined organic extracts were washed with brine, dried over anhydrous $Na_2SO_4$, filtered and concentrated under reduced pressure. The residue was purified by column chromatography (petroleum ether/EtOAc=20/1) to give the title compound I14 (2.3 g, 72% yield) as a yellow oil. LCMS-A (ES-API): $R_t$ 2.01 min; m/z 198.9/200.9 $[M-CH_3O]^+$. $^1H$ NMR (400 MHz, $CDCl_3$) δ 7.53 (d, J=2.1 Hz, 1H), 7.23 (dd, J=8.4, 2.1 Hz, 1H), 6.86 (d, J=8.4 Hz, 1H), 4.35 (s, 2H), 3.88 (s, 3H), 3.35 (s, 3H).

b) Methyl 2-methoxy-5-(methoxymethyl)benzoate I15

A mixture of 2-bromo-1-methoxy-4-(methoxymethyl)benzene 114 (1.5 g, 6.5 mmol), $Pd(dppf)Cl_2·DCM$ (265 mg, 0.325 mmol) and triethylamine (2.0 g, 19.5 mmol) in methanol (30 mL) was heated at 100° C. under a carbon monoxide atmosphere (0.2 MPa) overnight. The mixture was concentrated under reduced pressure and the residue was purified by column chromatography (petroleum ether/EtOAc=20/1 to 10/1) to give the title compound (1.1 g, 84% yield) as yellow oil. LCMS-A (ES-API): $R_t$ 0.79 min; m/z 233.0 $[M+Na]^+$.

c) 3-(2-Methoxy-5-(methoxymethyl)phenyl)-3-oxopropanenitrile I16

To a solution of diisopropylamine (870 mg, 8.6 mmol) in anhydrous THF (40 mL) at −78° C. under $N_2$ was added n-BuLi (2.5 M solution in hexanes, 3.4 mL, 8.6 mmol) dropwise and the mixture was stirred at −78° C. for 1 h. A solution of acetonitrile (350 mg, 8.6 mmol) in anhydrous THF (10 mL) was then added dropwise and stirring was continued at −78° C. for 30 min. A solution of methyl 2-methoxy-5-(methoxymethyl)benzoate I15 (1.2 g, 5.7 mmol) in anhydrous THF (10 mL) was then added dropwise and the mixture was stirred at −78° C. for 2 h. The reaction was quenched at −78° C. with 1 M HCl and the mixture was extracted with EtOAc (50 mL×3). The combined organic extracts were washed with brine, dried over anhydrous $Na_2SO_4$, filtered and concentrated under reduced pressure to give the title compound I16 (1.1 g, 91% yield) as a yellow solid, which was used in the next step without further purification. LCMS-A (ES-API): $R_t$ 0.83 min; m/z 220.0 $[M+H]^+$ 242.0 $[M+Na]^+$.

d) 5-(2-Methoxy-5-(methoxymethyl)phenyl)isoxazol-3-amine I17

To a solution of 3-(2-methoxy-5-(methoxymethyl)phenyl)-3-oxopropanenitrile I16 (1.5 g, 6.8 mmol) and NaOH (300 mg, 7.5 mmol) in ethanol (20 mL) and water (20 mL) was added $NH_2OH·HCl$ (522 mg, 7.5 mmol) and the mixture was heated at 80° C. overnight. The mixture was concentrated under reduced pressure the residue was purified by column chromatography (DCM/MeOH=200/1) to give an inseparable mixture of 5-(2-methoxy-5-(methoxymethyl) phenyl)isoxazol-3-amine and 3-(2-methoxy-5-(methoxymethyl)phenyl)isoxazol-5-amine, which required further purification. The procedure was repeated using 3-(2-methoxy-5-(methoxymethyl)phenyl)-3-oxopropanenitrile I16 (1.8 g, 8.2 mmol), $NH_2OH·HCl$ (628 mg, 9.0 mmol), NaOH (360 mg, 9.0 mmol) and ethanol/water (20 mL/20 mL) and the crude product was combined with the first batch and purified by column chromatography (DCM/MeOH=300/1 to 200/1) to give a mixture of 5-(2-methoxy-5-(methoxymethyl)phenyl)isoxazol-3-amine and 3-(2-methoxy-5-(methoxymethyl) phenyl)isoxazol-5-amine (3.0 g, 86%) as an orange liquid, which was dissolved in ethanol (40 mL) and water (20 mL). Concentrated aqueous HCl (2.0 mL) was added and the mixture was heated at 80° C. for 3 h, which resulted in decomposition of 3-(2-methoxy-5-(methoxymethyl)phenyl) isoxazol-5-amine. The mixture was neutralized with a saturated aqueous $NaHCO_3$ solution and extracted with EtOAc (100 mL×3). The combined organic extracts were washed with brine, dried over anhydrous $Na_2SO_4$, filtered and concentrated under reduced pressure. The residue was purified by column chromatography (DCM/MeOH=200/1) to give the title compound I17 (1.1 g, 31%) as an orange solid. LCMS-A (ES-API): $R_t$ 0.78 min, m/z 235.0 $[M+H]^+$. $^1H$ NMR (400 MHz, DMSO-$d_6$) δ 7.69 (d, J=2.0 Hz, 1H), 7.39-7.37 (m, 1H), 7.17 (d, J=8.4 Hz, 1H), 6.29 (s, 1H), 5.61 (s, 2H), 4.39 (s, 2H), 3.92 (s, 3H), 3.27 (s, 3H).

(ix) 2,6-Dimethoxybenzenesulfonyl Chloride I18

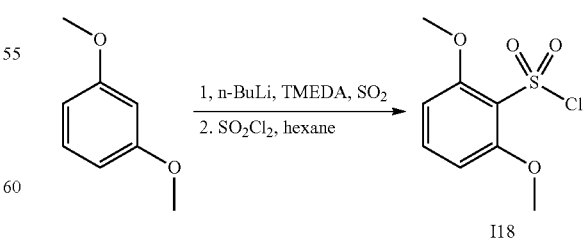

To a solution of 1,3-dimethoxybenzene (5.0 g, 36 mmol) and TMEDA (4.6 g, 39.8 mmol) in n-hexane (100 mL) at 0° C. under $N_2$ was added n-BuLi (2.5 M solution in hexanes, 16.0 mL, 39.8 mmol) dropwise while keeping the internal reaction temperature below 5° C. The mixture was stirred at 0° C. for 20 min then cooled to −78° C. and SO₂ gas was bubbled through the mixture for 20 min. The mixture was then allowed to warm slowly to 10° C. and the resulting precipitate was collected by filtration and washed with dry ether. The solid was suspended in n-hexane (100 mL), cooled to 0° C. and a solution of SO₂Cl₂ (4.9 g, 36 mmol) in n-hexane (20 mL) was added dropwise while keeping the internal temperature below 3° C. The mixture was then stirred at 0° C. for 1 h and the solids were collected by filtration and washed with cold/7-hexane. The solids were then partitioned between ether and water, the layers were separated and the aqueous layer was further extracted with ether. The combined organic extracts were dried over Na₂SO₄, filtered and concentrated under reduced pressure to give the title compound I18 (4.0 g, 47%) as a white solid. ¹H NMR (400 MHz, CDCl₃) δ 7.54 (t, J=8.4 Hz, 1H), 6.66 (d, J=8.4 Hz, 2H), 3.97 (s, 6H).

(x) 5-Ethyl-2-methoxybenzenesulfonyl Chloride I19

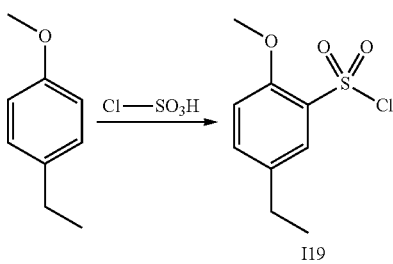

1-Ethyl-4-methoxybenzene (5.0 g, 37 mmol) was added dropwise to chlorosulfonic acid (20 mL) at 0° C. and the mixture was stirred at room temperature for 2 h then poured onto ice and extracted with EtOAc (50 mL×3). The combined organic extracts were dried over Na₂SO₄, filtered and concentrated under reduced pressure. The residue was purified by column chromatography (petroleum ether/EtOAc=100/1 to 30/1) to give the title compound I19 (4.6 g, 53%) as a white solid. LCMS-B (ES-API): R$_t$2.70 min; m/z 256.9 [M+Na]⁺.

(xi) 2,4-Dimethoxy-[1,1'-biphenyl]-3-sulfonyl Chloride I21

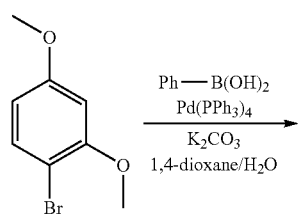

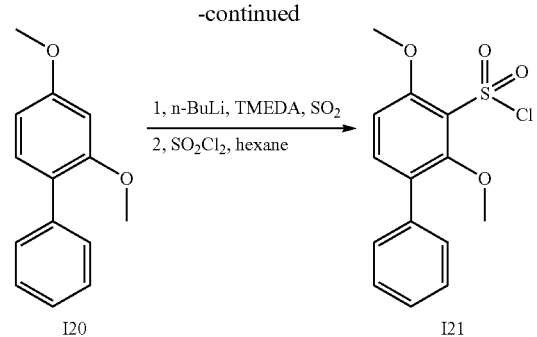

a) 2,4-Dimethoxy-1,1'-biphenyl I20

A suspension of 1-bromo-2,4-dimethoxybenzene (5.0 g, 23.0 mmol), phenylboronic acid (3.4 g, 27.6 mmol), Pd(PPh₃)₄ (1.3 g, 1.15 mmol) and potassium carbonate (7.3 g, 69.0 mmol) in 1,4-dioxane (30 mL) and water (6 mL) was heated at 90° C. under N₂ for 16 h. The mixture was filtered through a pad of Celite and washed with EtOAc. The filtrate was diluted with water and extracted with EtOAc (30 mL×3). The combined organic extracts were dried over Na₂SO₄, filtered and concentrated under reduced pressure. The residue was purified by column chromatography (petroleum ether/EtOAc=100/1 to 10/1) to give the title compound I20 (2.8 g, 57%) as a yellow oil. LCMS-B (ES-API): R$_t$2.46 min; m/z 215.0 [M+H]⁺.

b) 2,4-Dimethoxy-[1,1'-biphenyl]-3-sulfonyl Chloride I21

To a solution of 2,4-dimethoxy-1,1'-biphenyl I20 (1.0 g, 4.70 mmol) and TMEDA (601 mg, 5.20 mmol) in n-hexane (40 mL) at 0° C. under N₂ was added n-BuLi (2.5 M solution in hexanes, 2.1 mL, 5.20 mmol) dropwise while keeping the internal reaction temperature below 5° C. The mixture was stirred at 0° C. for 20 min then cooled to −70° C. and SO₂ gas was bubbled through the mixture for 20 min. The mixture was then allowed to warm slowly to 10° C. and the resulting precipitate was collected by filtration and washed with dry ether. The solid was suspended in n-hexane (40 mL), cooled to 0° C. and a solution of SO₂Cl₂ (634 mg, 4.7 mmol) in n-hexane (5 mL) was added dropwise while keeping the internal temperature below 3° C. The mixture was then stirred at 0° C. for 1 h and the solids were collected by filtration and washed with cold n-hexane. The solids were then partitioned between ether and water, the layers were separated and the aqueous layer was further extracted with ether. The combined organic extracts were dried over Na₂SO₄, filtered and concentrated under reduced pressure to give the title compound I21 (590 mg, 40%) as a white solid. ¹H NMR (400 MHz, DMSO-d₆) δ 7.48-7.35 (m, 4H), 7.34-7.21 (m, 2H), 6.89-6.85 (m, 1H), 3.76 (s, 3H), 3.29 (s, 3H).

(xii) 3,5-Dimethoxy-[1,1'-biphenyl]-4-sulfonyl Chloride I47

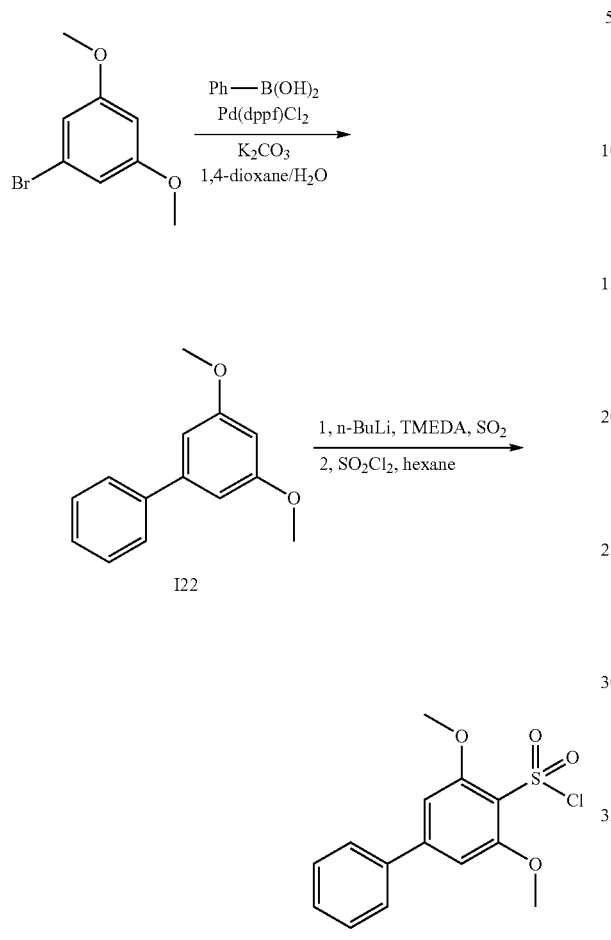

a) 3,5-Dimethoxy-1,1'-biphenyl I22

A suspension of 1-bromo-3,5-dimethoxybenzene (5.0 g, 23.0 mmol), phenylboronic acid (2.8 g, 23.0 mmol), Pd(dppf)Cl$_2$ (0.57 g, 0.69 mmol) and potassium carbonate (4.8 g, 34.6 mmol) in 1,4-dioxane (80 mL) and water (20 mL) was heated at 90° C. under N2 for 4 h. The mixture was diluted with water, extracted with EtOAc and the combined organic extracts were dried over Na$_2$SO$_4$, filtered and concentrated under reduced pressure. The residue was purified by column chromatography (petroleum ether/EtOAc=500/1 to 200/1 to 100/1) to give the title compound 3,5-dimethoxy-1,1'-biphenyl I22 (5.2 g, 100%) as a white solid. LCMS-A (ES-API): R$_t$ 2.47 min; m/z 215.0 [M+H]$^+$.

b) 3,5-Dimethoxy-[1,1'-biphenyl]-4-sulfonyl Chloride I47

I47 was prepared from 3,5-dimethoxy-1,1'-biphenyl I22 according to the procedure described for 2,4-dimethoxy-[1,1'-biphenyl]-3-sulfonyl chloride I21. $^1$H NMR (400 MHz, CDCl$_3$) δ 7.62-7.55 (m, 2H), 7.54-7.44 (m, 3H), 6.81 (s, 2H), 4.04 (s, 6H).

(xiii) 5-(2,5-Dimethoxyphenyl)isoxazol-3-amine I26

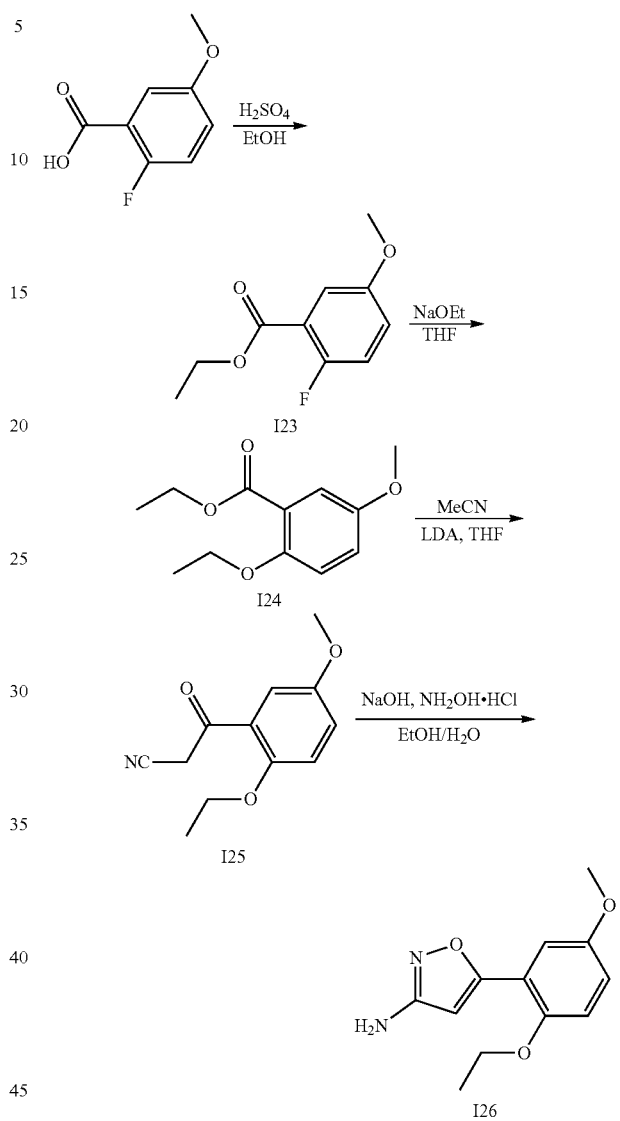

a) Ethyl 2-fluoro-5-methoxybenzoate I23

To a solution of 2-fluoro-5-methoxybenzoic acid (9.0 g, 53 mmol) in EtOH (80 mL) was added concentrated H$_2$SO$_4$ (30 drops) and the mixture was heated at 90° C. overnight. The mixture was concentrated under reduced pressure and the residue was purified by column chromatography (petroleum ether/EtOAc=20/1) to give the title compound I23 (9.0 g, 86%) as a colourless oil. LCMS-A (ES-API): R$_t$ 2.13 min; m/z 199.1 [M+H]$^+$.

b) Ethyl 2-ethoxy-5-methoxybenzoate I24

To a solution of ethyl 2-fluoro-5-methoxybenzoate I23 (2.0 g, 10 mmol) in THF (30 mL) was added NaOEt (2.0 g, 30 mmol) and the mixture was heated at 80° C. for 2 h. The mixture was diluted with EtOAc, washed with water, brine, dried over anhydrous Na$_2$SO$_4$, filtered and concentrated under reduced pressure. The residue was purified by column chromatography (petroleum ether/EtOAc=30/1) to give the title compound I24 (0.8 g, 35%) as a pale yellow oil. LCMS-A (ES-API): R$_t$ 2.19 min; m/z 225.1 [M+H]$^+$.

c) 3-(2-Ethoxy-5-methoxyphenyl)-3-oxopropanenitrile I25

To a solution of diisopropylamine (351 mg, 3.47 mmol) in THF (10 mL) at −78° C. under N$_2$ was added n-BuLi (2.5 M solution in hexanes, 1.4 mL, 3.47 mmol) dropwise and the mixture was stirred at −78° C. for 1 h. A solution of acetonitrile (142 mg, 3.47 mmol) in THF (1 mL) was then added dropwise and stirring was continued for 30 min. A solution of ethyl 2-ethoxy-5-methoxybenzoate I24 (600 mg, 2.67 mmol) in THF (1 mL) was then added dropwise and the mixture was stirred at 0° C. for 1 h. The reaction was quenched with a saturated aqueous NH$_4$Cl solution, diluted with EtOAc and the mixture was washed with water, brine, dried over anhydrous Na$_2$SO$_4$, filtered and concentrated under reduced pressure. The residue was purified by column chromatography (petroleum ether/EtOAc=5/1) to give the title compound I25 (420 mg, 72%) as a yellow solid. LCMS-A (ES-API): R$_t$ 1.96 min; m/z 220.1 [M+H]$^+$.

d) 5-(2-Ethoxy-5-methoxyphenyl)isoxazol-3-amine I26

To a solution of 3-(2-ethoxy-5-methoxyphenyl)-3-oxopropanenitrile I25 (100 mg, 0.46 mmol) and NH$_2$OH·HCl (42 mg, 0.6 mmol) in ethanol (3 mL) was added a solution of NaOH (24 mg, 0.6 mmol) in water (3 mL) and the mixture was heated at 90° C. overnight. The reaction was repeated using 3-(2-ethoxy-5-methoxyphenyl)-3-oxopropanenitrile I25 (300 mg, 1.37 mmol), NH$_2$OH·HCl (123 mg, 1.78 mmol), NaOH (71 mg, 1.78 mmol) and EtOH/water (5 mL/5 mL). The two reaction mixtures were then combined, diluted with EtOAc, washed with water, brine, dried over anhydrous Na$_2$SO$_4$, filtered and concentrated under reduced pressure. The residue was purified by column chromatography (petroleum ether/EtOAc=3/1) to give the title compound I26 (130 mg, 30%) as a yellow solid. LCMS-A (ES-API): R$_t$ 3.25 min; m/z 235.1 [M+H]$^+$. $^1$H NMR (400 MHz, DMSO-d$_6$) δ 7.25 (d, J=3.2 Hz, 1H), 7.14-7.09 (m, 1H), 6.98-6.97 (m, 1H), 6.66 (s, 1H), 5.67 (s, 2H), 4.03 (q, J=7.2 Hz, 2H) 3.70 (s, 3H), 1.34 (t, J=6.8 Hz, 3H).

(xiv) 5-(2-Isopropoxy-5-methoxyphenyl)isoxazol-3-amine I29

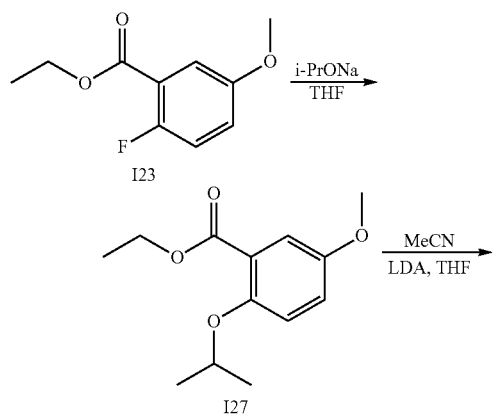

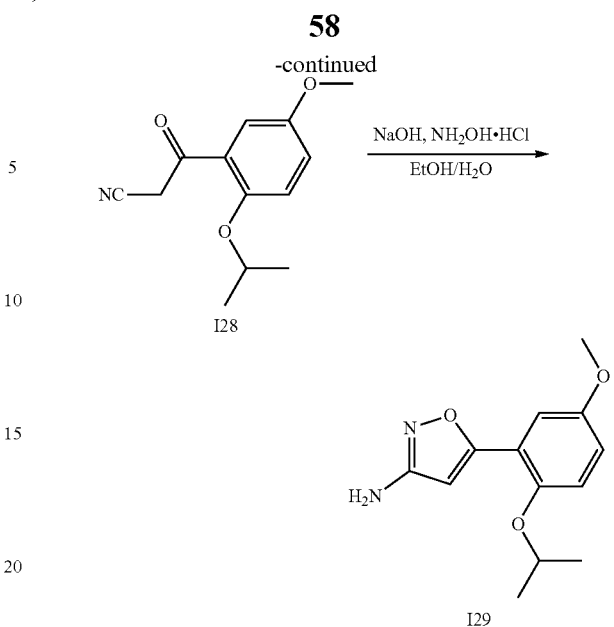

a) Ethyl 2-isopropoxy-5-methoxybenzoate I27

To a solution of ethyl 2-fluoro-5-methoxybenzoate I23 (1.0 g, 5.0 mmol) in THF (25 mL) was added sodium propan-2-olate (1.2 g, 15.0 mmol) and the mixture was heated at 80° C. for 1 h. The reaction was repeated on ethyl 2-fluoro-5-methoxybenzoate I23 (1.0 g, 5.0 mmol) and the reaction mixtures were combined, diluted with EtOAc, washed with water, brine, dried over anhydrous Na$_2$SO$_4$, filtered and concentrated under reduced pressure. The residue was purified by column chromatography (petroleum ether/EtOAc=20/1) to give the title compound I27 (0.6 g, 25%) as a yellow solid. LCMS-A (ES-API): R$_t$ 2.3 min; m/z 239.1 [M+H]$^+$.

3-(2-Isopropoxy-5-methoxyphenyl)-3-oxopropanenitrile I28

To a solution of diisopropylamine (332 mg, 3.28 mmol) in THF (10 mL) at −78° C. under N$_2$ was added n-BuLi (2.5 M solution in hexanes, 1.3 mL, 3.28 mmol) dropwise and the mixture was stirred at −78° C. for 1 h. A solution of acetonitrile (135 mg, 3.28 mmol) in THF (1 mL) was then added dropwise and stirring was continued for 30 min. A solution of ethyl 2-isopropoxy-5-methoxybenzoate I27 (600 mg, 2.52 mmol) in THF (1 mL) was then added dropwise and the mixture was stirred at 0° C. for 1 h. The reaction was quenched with a saturated aqueous NH$_4$Cl solution, diluted with EtOAc and the mixture was washed with water, brine, dried over anhydrous Na$_2$SO$_4$, filtered and concentrated under reduced pressure. The residue was purified by column chromatography (petroleum ether/EtOAc=5/1) to give the title compound I28 (200 mg, 35%) as a yellow solid. LCMS-A (ES-API): R$_t$ 2.09 min; m/z 234.1 [M+H]$^+$.

c) 5-(2-Isopropoxy-5-methoxyphenyl)isoxazol-3-amine I29

To a solution of 3-(2-isopropoxy-5-methoxyphenyl)-3-oxopropanenitrile I28 (180 mg, 0.76 mmol) and NH$_2$OH·HCl (70 mg, 1.0 mmol) in ethanol (5 mL) was added a solution of NaOH (40 mg, 1.0 mmol) in water (5 mL) and the mixture was heated at 80° C. overnight. The mixture was diluted with EtOAc and washed with water, brine, dried over anhydrous Na$_2$SO$_4$, filtered and concentrated under reduced pressure. The residue was purified by column chromatography (DCM/MeOH=50/1) to give the title compound I29 (80 mg, 42%) as a yellow solid. LCMS-A (ES-API): R$_t$ 1.99 min; m/z 249.1 [M+H]$^+$. $^1$H NMR (400 MHz, DMSO-d$_6$) δ 7.25 (d, J=3.2 Hz, 1H), 7.14-7.12 (m, 1H), 7.00-6.97 (m, 1H), 6.38 (s, 1H), 5.62 (s, 2H), 4.72-4.66 (m, 1H) 3.76 (s, 3H), 1.37 (d, J=6.0 Hz, 6H).

(xv) 5-(2-(Trifluoromethoxy)phenyl)isoxazol-3-amine I30

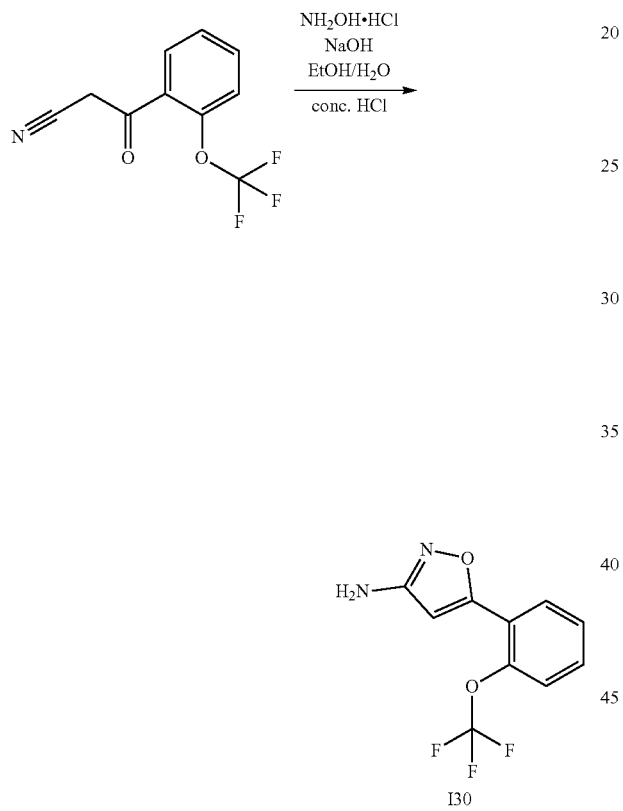

To a solution of 3-oxo-3-(2-(trifluoromethoxy)phenyl) propanenitrile (500 mg, 2.18 mmol) in ethanol (10 mL) and water (10 mL) was added NaOH (96 mg, 2.40 mmol) and NH$_2$OH·HCl (167 mg, 2.40 mmol) and the mixture was heated at 70° C. overnight. Concentrated HCl (0.27 mL, 2.40 mmol) was then added and the mixture was heated at 80° C. for 2 h. The mixture was adjusted to pH 10 with 2 NaOH and extracted with EtOAc (30 mL×3). The combined organic extracts were washed with brine, dried over anhydrous Na$_2$SO$_4$, filtered and concentrated under reduced pressure. The residue was purified by column chromatography (DCM/MeOH=100/0 to 100/1) to give the title compound I30 (205 mg, 38%) as a yellow solid. LCMS-A (ES-API): R$_t$ 2.90 min; m/z 245.0 [M+H]$^+$. $^1$H NMR (400 MHz, DMSO-d$_6$) δ 7.97-7.90 (m, 1H), 7.65-7.51 (m, 3H), 6.26 (s, 1H), 5.78 (s, 2H).

(xvi) 5-(5-(Cyclohexylmethyl)-2-methoxyphenyl) isoxazol-3-amine I33 and 3-(5-(cyclohexylmethyl)-2-methoxyphenyl)isoxazol-5-amine I34

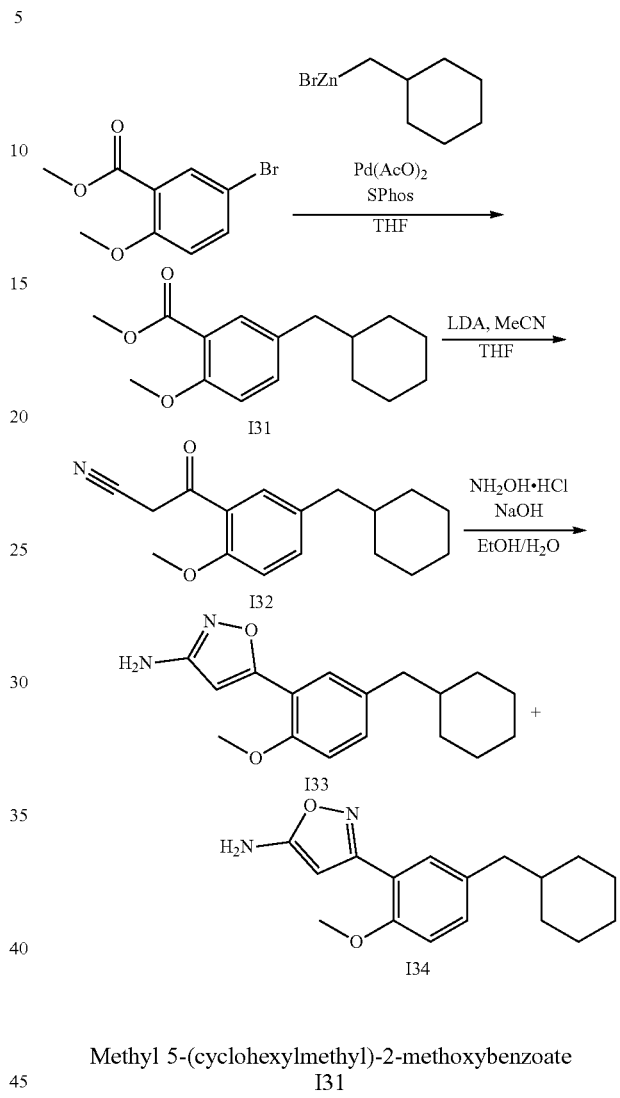

Methyl 5-(cyclohexylmethyl)-2-methoxybenzoate I31

To a solution of methyl 5-bromo-2-methoxybenzoate (500 mg, 2.04 mmol), Pd(OAc)$_2$ (9 mg, 0.04 mmol) and SPhos (19 mg, 0.04 mmol) in THF (20 mL) was added (cyclohexylmethyl)zinc(II) bromide (0.5 M solution in THF, 4.9 mL, 2.45 mmol) and the mixture was stirred at room temperature for 2 h. The reaction was quenched with a saturated aqueous NH$_4$Cl solution (10 mL) then diluted with water and extracted with EtOAc. The organic extract was washed with brine, dried over anhydrous Na$_2$SO$_4$, filtered and concentrated under reduced pressure. The residue was purified by column chromatography (petroleum ether/ EtOAc=50/1) to give the title compound I31 (284 mg, 53%) as a yellow oil. LCMS-A (ES-API): R$_t$ 2.71 min; m/z 263.0 [M+H]$^+$.

b) 3-(5-(Cyclohexylmethyl)-2-methoxyphenyl)-3-oxopropanenitrile I32

To a solution of diisopropylamine (732 mg, 7.23 mmol) in anhydrous THF (25 mL) at −78° C. under N$_2$ was added n-butyllithium (2.5 M solution in hexanes, 3 mL, 7.23 mmol) dropwise and the mixture was stirred at −78° C. for 1 h. A solution of acetonitrile (297 mg, 7.23 mmol) in anhydrous THF (5 mL) was then added dropwise and stirring was continued at −78° C. for 30 min. A solution of methyl 5-(cyclohexylmethyl)-2-methoxybenzoate I31 (1.46 g, 5.56 mmol) in anhydrous THF (5 mL) was then added dropwise and the mixture was stirred at −78° C. for 40 min. The reaction was quenched at −78° C. with 1 M HCl and the mixture was extracted with EtOAc. The organic extracts were washed with brine, dried over anhydrous $Na_2SO_4$, filtered and concentrated. The residue was purified by column chromatography (petroleum ether/EtOAc=40/1) to give the title compound I32 (707 mg, 47%) as a white solid. LCMS-A (ES-API): $R_t$2.72 min; m/z 272.1 [M+H]$^+$.

c) 5-(5-(Cyclohexylmethyl)-2-methoxyphenyl)isoxazol-3-amine I33 and 3-(5-(cyclohexylmethyl)-2-methoxyphenyl)isoxazol-5-amine I34

To a solution of 3-(5-(cyclohexylmethyl)-2-methoxyphenyl)-3-oxopropanenitrile I32 (540 mg, 2.0 mmol) and NaOH (88 mg, 2.19 mmol) in water (10 mL) and ethanol (10 mL) was added $NH_2OH·HCl$ (152 mg, 2.19 mmol) and the mixture was heated at 80° C. overnight. The mixture was partitioned between water and EtOAc, the layers were separated and the organic layer was washed with water, brine, dried over anhydrous $Na_2SO_4$, filtered and concentrated under reduced pressure. The residue was purified by column chromatography (petroleum ether/EtOAc=8/1) to give 5-(5-(cyclohexylmethyl)-2-methoxyphenyl)isoxazol-3-amine I33 (85 mg, 12%) as a yellow solid. LCMS-A (ES-API): 2.61 min; m/z 287.1 [M+H]$^+$. $^1$H NMR (400 MHz, DMSO-d$_6$) δ 7.50 (d, J=2.2 Hz, 1H), 7.20 (dd, J=8.5, 2.3 Hz, 1H), 7.10-7.06 (m, 1H), 6.26 (s, 1H), 5.62 (s, 2H), 3.88 (s, 3H), 2.45 (d, J=7.0 Hz, 2H), 1.68-1.57 (m, 5H), 1.49-1.42 (m, 1H), 1.18-1.08 (m, 3H), 0.96-0.85 (m, 2H). 3-(5-(Cyclohexylmethyl)-2-methoxyphenyl)isoxazol-5-amine I34 (190 mg, 26%) was also obtained as a yellow solid. LCMS-A (ES-API): $R_t$2.53; m/z 287.1 [M+H]$^+$. $^1$H NMR (400 MHz, DMSO-d$_6$) δ 7.42 (d, J=2.3 Hz, 1H), 7.17 (dd, J=8.4, 2.3 Hz, 1H), 7.04-7.00 (m, 1H), 6.59 (s, 2H), 5.36 (s, 1H), 3.79 (s, 3H), 2.41 (d, J=7.0 Hz, 2H), 1.68-1.55 (m, 5H), 1.48-1.40 (m, 1H), 1.19-1.08 (m, 3H), 0.96-0.84 (m, 2H).

(xvii)
5-(4-Chloro-2-methoxyphenyl)isoxazol-3-amine I36

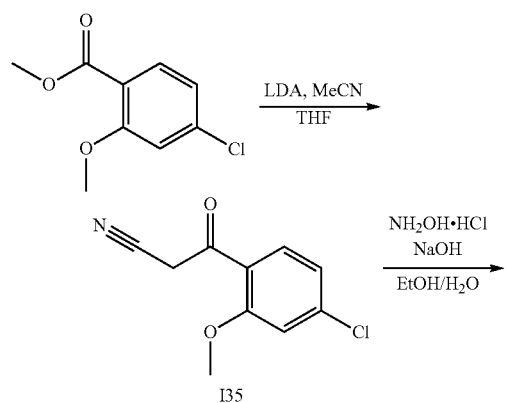

a)
3-(4-Chloro-2-methoxyphenyl)-3-oxopropanenitrile I35

To a solution of diisopropylamine (656 mg, 6.78 mmol) in anhydrous THF (15 mL) at −78° C. under $N_2$ was added n-butyllithium (2.5 M solution in hexanes, 2.6 mL, 6.78 mmol) dropwise and the mixture was stirred at −78° C. for 1 h. A solution of acetonitrile (266 mg, 6.78 mmol) in anhydrous THF (5 mL) was then added dropwise and stirring was continued at −78° C. for 30 min. A solution of methyl 4-chloro-2-methoxybenzoate (1.0 g, 4.98 mmol) in anhydrous THF (5 mL) was then added and the mixture was stirred at −78° C. for 40 min. The reaction was quenched at −78° C. with 1 M HCl and the mixture was extracted with EtOAc. The organic extracts were washed with brine, dried over anhydrous $Na_2SO_4$, filtered and concentrated to give the title compound I35 (750 mg, 72%) as a yellow solid. LCMS-A (ES-API): $R_t$1.91 min; m/z 210.0 [M+H]$^+$.

b) 5-(4-Chloro-2-methoxyphenyl)isoxazol-3-amine I36

To a solution of 3-(4-chloro-2-methoxyphenyl)-3-oxopropanenitrile I35 (350 mg, 1.69 mmol) and NaOH (75 mg, 1.86 mmol) in water (10 mL) and ethanol (10 mL) was added $NH_2OH·HCl$ (130 mg, 1.86 mmol) and the mixture was heated at 80° C. overnight. Concentrated HCl (0.5 mL) was then added and the mixture was stirred at 80° C. for 2.5 h. The mixture was adjusted to pH 10 with 2 M NaOH and extracted with EtOAc. The organic extracts were washed with brine, dried over anhydrous $Na_2SO_4$, filtered and concentrated under reduced pressure The residue was purified by column chromatography (petroleum ether/EtOAc=8/1) to give the title compound I36 (130 mg, 35%) as a yellow solid. LCMS-A (ES-API): $R_t$ 1.84 min; m/z 225.0 [M+H]$^+$. $^1$H NMR (400 MHz, DMSO-d$_6$) δ 7.73 (d, J=8.4 Hz, 1H), 7.28 (d, J=2.0 Hz, 1H), 7.13 (dd, J=8.4, 2.0 Hz, 1H), 6.28 (s, 1H), 5.64 (s, 2H), 3.95 (s, 3H).

(xviii)
5-(5-Chloro-2-methoxyphenyl)isoxazol-3-amine I38

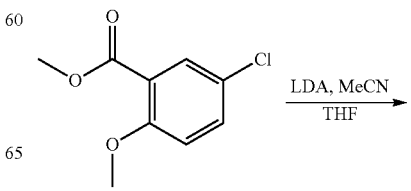

-continued

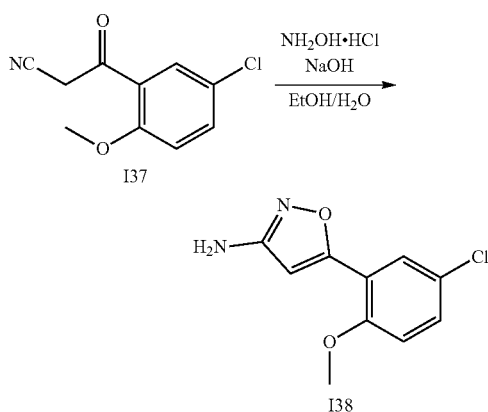

a)
3-(5-Chloro-2-methoxyphenyl)-3-oxopropanenitrile I37

To a solution of diisopropylamine (3.29 g, 32.5 mmol) in anhydrous THF (100 mL) at −78° C. under $N_2$ was added n-butyllithium (2.5 M solution in hexanes, 13.0 mL, 32.5 mmol) dropwise and the mixture was stirred at −78° C. for 1 h. A solution of acetonitrile (1.33 g, 32.5 mmol) in anhydrous THF (20 mL) was then added dropwise and stirring was continued at −78° C. for 30 min. A solution of methyl 5-chloro-2-methoxybenzoate (5.0 g, 25.0 mmol) in anhydrous THF (10 mL) was then added and the mixture was stirred at −78° C. for 40 min. The reaction was quenched at −78° C. with 1 M HCl and the mixture was extracted with EtOAc (100 mL×3). The combined organic extracts were washed with brine, dried over anhydrous $Na_2SO_4$, filtered and concentrated to give the title compound I37 (4.9 g, 94%) as an orange solid, which was used in the next step without further purification. LCMS-A (ES-API): $R_t$ 2.10 min; m/z 209.9 [M+H]$^+$, 231.9 [M+Na]$^+$.

b) 5-(5-Chloro-2-methoxyphenyl)isoxazol-3-amine I38

To a solution of 3-(5-chloro-2-methoxyphenyl)-3-oxopropanenitrile I37 (2.0 g, 9.6 mmol) and NaOH (420 mg, 10.5 mmol) in water (20 mL) and ethanol (20 mL) was added $NH_2OH·HCl$ (730 mg, 10.5 mmol) and the mixture was heated at 80° C. overnight. Water (40 mL) was added and the mixture was extracted with EtOAc (50 mL×3). The combined organic extracts were washed with brine, dried over anhydrous $Na_2SO_4$, filtered and concentrated under reduced pressure The residue was purified by column chromatography (DCM/MeOH=400/1) to give the title compound I38 (66 mg, 3%) as a white solid. LCMS-A (ES-API): $R_t$ 1.59 min; m/z 224.9 [M+H]$^+$. $^1$H NMR (400 MHz, DMSO-$d_6$) δ 7.69 (d, J=2.7 Hz, 1H), 7.53-7.46 (m, 1H), 7.25-7.20 (m, 1H), 6.34 (s, 1H), 5.67 (s, 2H), 3.93 (s, 3H). 3-(5-Chloro-2-methoxyphenyl)isoxazol-5-amine (158 mg, 7%) was also obtained as a white solid. LCMS-A (ES-API): $R_t$ 1.43 min; m/z 224.9 [M+H]$^+$. $^1$H NMR (400 MHz, DMSO-$d_6$) δ 7.63 (d, J=2.8 Hz, 1H), 7.46 (dd, J=8.9, 2.8 Hz, 1H), 7.17 (d, J=8.9 Hz, 1H), 6.70 (s, 2H), 5.39 (s, 1H), 3.84 (s, 3H).

(xix) 5-(2-Methoxy-5-(oxazol-2-yl)phenyl)isoxazol-3-amine I42

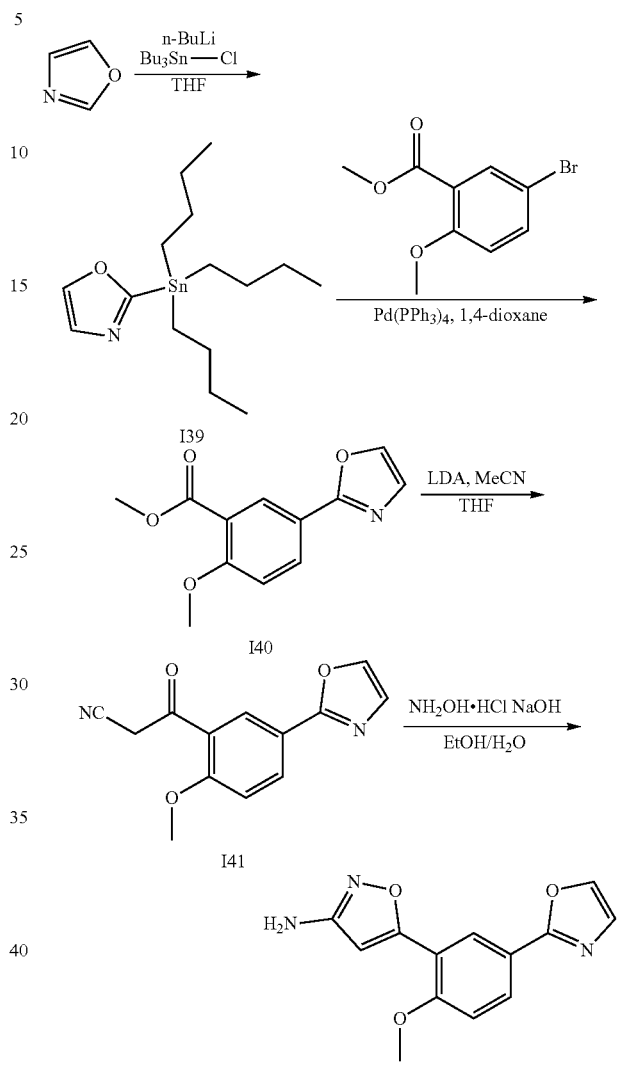

a) 2-(Tributylstannyl)oxazole I39

To a solution of oxazole (500 mg, 7.25 mmol) in THF (15 mL) at −78° C. under $N_2$ was added n-BuLi (2.5 M solution in hexanes, 2.9 mL, 7.32 mmol) dropwise and the mixture was stirred at −78° C. for 30 min. Tributylchlorostannane (1.96 mL, 7.25 mmol) was then added and the mixture was allowed to warm to room temperature and stirred for 1 h. The solvent was removed under reduced pressure and residue was taken up in hexanes (50 mL). The resulting precipitate was removed by filtration and the filtrate was concentrated under reduced pressure to give the title compound I39 (2.0 g, 77%) as colourless oil. $^1$H NMR (400 MHz, DMSO-$d_6$) δ 8.20 (s, 1H), 7.20 (s, 1H), 1.59-1.49 (m, 6H), 1.31-1.26 (m, 6H), 1.16-1.10 (m, 6H), 0.83 (t, J=7.3 Hz, 9H).

b) Methyl 2-methoxy-5-(oxazol-2-yl)benzoate I40

To a solution of methyl 5-bromo-2-methoxybenzoate (2.0 g, 8.2 mmol) in 1,4-dioxane (25 mL) was added 2-(tributylstannyl)oxazole I39 (4.4 g, 12.3 mmol) and Pd(PPh$_3$)$_4$ (947 mg, 0.8 mmol) and the mixture was heated at 120° C. for 3 h. The solvent was removed under reduced pressure and the residue was purified by column chromatography (petroleum ether/EtOAc=10/1) to give the title compound I40 (550 mg, 29%) as a yellow solid. LCMS-A (ES-API): R$_t$ 0.99 min; m/z 234.0 [M+H]$^+$.

c) 3-(2-Methoxy-5-(oxazol-2-yl)phenyl)-3-oxopropanenitrile I41

To a solution of diisopropylamine (310 mg, 3.1 mmol) in THF (20 mL) at −78° C. under N$_2$ was added n-BuLi (2.5 M solution in hexanes, 1.24 mL, 3.1 mmol) dropwise and the mixture was stirred at −78° C. for 1 h. A solution of acetonitrile (126 mg, 3.1 mmol) in THF (5 mL) was then added dropwise and stirring was continued at −78° C. for 30 min. A solution of methyl 2-methoxy-5-(oxazol-2-yl)benzoate I40 (550 mg, 2.4 mmol) in THF (5 mL) was then added and the mixture was stirred at −78° C. for 40 min. The reaction was quenched at −78° C. with 1 M HCl and the mixture was diluted with water and extracted with EtOAc (150 mL×3). The combined organic extracts were washed with brine, dried over anhydrous Na$_2$SO$_4$, filtered and concentrated under reduced pressure to give the title compound I41 (530 mg, 92%) as an orange solid. LCMS-A (ES-API): R$_t$ 0.86 min; m/z 243.0 [M+H]$^+$.

d) 5-(2-Methoxy-5-(oxazol-2-yl)phenyl)isoxazol-3-amine I42

To a solution of 3-(2-methoxy-5-(oxazol-2-yl)phenyl)-3-oxopropanenitrile I41 (530 mg, 2.19 mmol) and NaOH (114 mg, 2.85 mmol) in ethanol (20 mL) and water (20 mL) was added NH$_2$OH·HCl (198 mg, 2.85 mmol) and the mixture was heated at 80° C. overnight. Water was added and the mixture was extracted with EtOAc (150 mL×3). The combined organic extracts were washed with brine, dried over anhydrous Na$_2$SO$_4$, filtered and concentrated under reduced pressure. The residue was purified by column chromatography (petroleum ether/EtOAc=5/1) to give the title compound I42 (130 mg, 23%) as a yellow solid. LCMS-A (ES-API): R$_t$ 0.74 min; m/z 258.1 [M+H]$^+$. $^1$H NMR (400 MHz, DMSO-d$_6$) δ 8.32 (d, J=2.2 Hz, 1H), 8.20 (s, 1H), 8.04 (dd, J=8.8, 2.3 Hz, 1H), 7.36 (d, J=8.4 Hz, 1H), 7.37 (s, 1H), 6.37 (s, 1H), 5.68 (s, 2H), 4.01 (s, 3H).

(xx) 5-(2-Ethyl-5-methoxyphenyl)isoxazol-3-amine I46

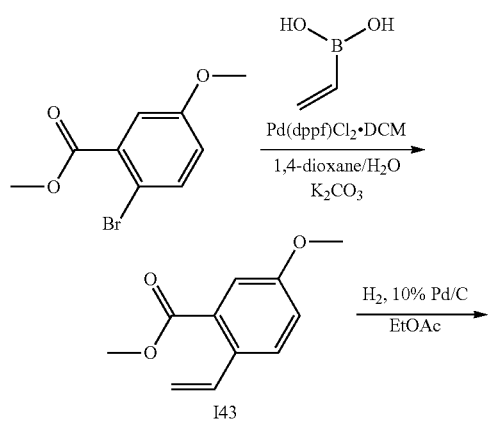

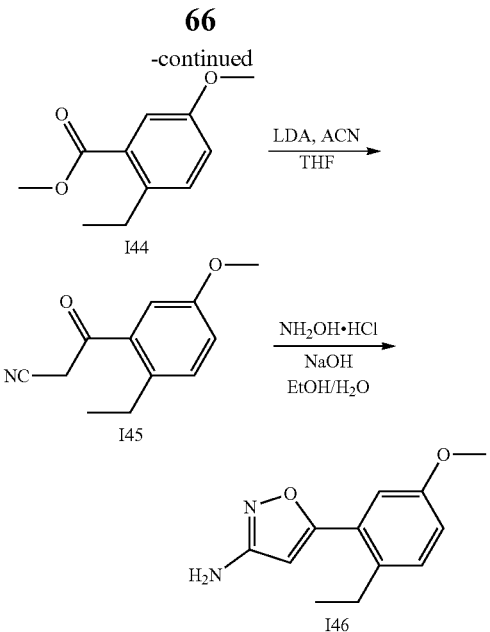

a) Methyl 5-methoxy-2-vinylbenzoate I43

A mixture of methyl 2-bromo-5-methoxybenzoate (3.0 g, 12.2 mmol), vinylboronic acid (2.26 g, 14.7 mmol), K$_2$CO$_3$ (5.08 g, 36.72 mmol) and Pd(dppf)Cl$_2$·DCM (500 mg, 0.61 mmol) in 1,4-dioxane/H$_2$O (40 mL/10 mL) was heated at 90° C. under N2 overnight. The mixture was filtered through a pad of Celite and washed with EtOAc. The filtrate was diluted with water, the layers were separated and the aqueous layer was extracted with EtOAc. The combined organic layers were washed with brine, dried over anhydrous Na$_2$SO$_4$, filtered and concentrated under reduced pressure. The residue was purified by column chromatography (petroleum ether) to give the title product I43 (1.9 g, 81%) as a yellow oil. LCMS-A (ES-API): R$_t$ 2.28 min; m/z 193.0 [M+H]$^+$.

b) Methyl 2-ethyl-5-methoxybenzoate I44

To a solution of methyl 5-methoxy-2-vinylbenzoate I43 (1.9 g, 9.89 mmol) in EtOAc (20 mL) was added 10% Pd/C (190 mg) and the mixture was stirred at room temperature under a H$_2$ atmosphere overnight. The catalyst was removed by filtration and the filtrate was concentrated under reduced pressure. The residue was purified by column chromatography (petroleum ether/EtOAc=50/1 to 20/1) to give the title compound I44 (1.31 g, 63%) as a yellow oil. LCMS-A (ES-API): R$_t$ 2.45 min; m/z 195.0 [M+H]$^+$.

c) 3-(2-Ethyl-5-methoxyphenyl)-3-oxopropanenitrile I45

To a solution of diisopropylamine (799 mg, 7.90 mmol) in THF (25 mL) at −78° C. under N2 was added n-BuLi (2.5 M solution in hexanes 3.16 mL, 7.90 mmol) dropwise and the mixture was stirred at −78° C. for 1 h. A solution of acetonitrile (324 mg, 7.90 mmol) in THF (5 mL) was then added dropwise and stirring was continued for 30 min. A solution of methyl 2-ethyl-5-methoxybenzoate I44 (1.18 g, 6.08 mmol) in THF (3 mL) was then added and the mixture was stirred at −78° C. for 40 min. The reaction was diluted with water and the mixture was extracted with EtOAc. The organic extract was washed with brine, dried over anhydrous Na$_2$SO$_4$, filtered and concentrated under reduced pressure. The residue was purified by column chromatography (petroleum ether/EtOAc=30/1 to 5/1) to give the title compound I45 (829 mg, 67%) as a yellow oil, which was used directly in the next step.

d) 5-(2-Ethyl-5-methoxyphenyl)isoxazol-3-amine I46

To a solution of 3-(2-ethyl-5-methoxyphenyl)-3-oxopropanenitrile I45 (829 mg, 4.08 mmol) and NaOH (180 mg, 4.49 mmol) in water (10 mL) and ethanol (10 mL) was added NH$_2$OH·HCl (312 mg, 4.49 mmol) and the mixture was heated at 80° C. overnight. The mixture was diluted with water and extracted with EtOAc. The combined organic extracts were washed with brine, dried over anhydrous Na$_2$SO$_4$, filtered and concentrated under reduced pressure. The residue was purified by column chromatography (petroleum ether/EtOAc=20/1 to 5/1) to give the title product I46 (250 mg, 28%) as a white solid. LCMS-A (ES-API): R$_t$ 2.13 min; m/z 219.0 [M+H]$^+$. $^1$H NMR (400 MHz, DMSO-d$_6$) δ 7.29 (d, J=4.2 Hz, 1H), 7.07 (d, J=1.4 Hz, 1H), 7.01-6.98 (m, 1H), 6.08 (s, 1H), 5.64 (s, 2H), 3.78 (s, 3H), 2.72 (q, J=7.4 Hz, 2H), 1.14 (t, J=7.4 Hz, 3H).

(xxi) (3-Methoxyphenyl)methanesulfonyl Chloride I48

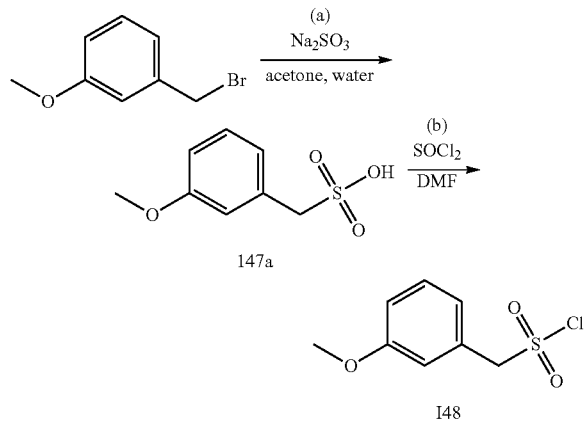

a) (3-Methoxyphenyl)methanesulfonic Acid I47a

A suspension of 1-(bromomethyl)-3-methoxybenzene (2.0 g, 9.95 mmol) and sodium sulfite (1.3 g, 10.6 mmol) in water (40 mL) and acetone (12 mL) was heated at 90° C. for 16 h. The mixture was allowed to cool to room temperature, toluene was added and the mixture was concentrated under reduced pressure to give the title compound (2.0 g, 100%) as a white solid, which was used in the next step without further purification. LCMS-A (ES-API): R$_t$ 0.62 min; m/z 200.9 [M−H]$^-$.

b) (3-Methoxyphenyl)methanesulfonyl Chloride I48

To a stirred solution of (3-methoxyphenyl)methanesulfonic acid I47a (636 mg, 3.15 mmol) in DCM (25 mL) was added DMF (5 drops) and the mixture was cooled to −20° C. Oxalyl chloride (2.7 mL, 31.4 mmol) was added and the mixture was stirred at −20° C. for 30 min, then allowed to warm to room temperature and stirred for 2 h. DCM (20 mL) was added and the mixture was washed with water and brine. The organic layer was dried over Na$_2$SO$_4$, filtered and concentrated to give the title compound (450 mg, 65%) as a yellow oil, which was used in the next step without further purification. LCMS-A (ES-API): R$_t$ 0.95 min; m/z 237.8 [M+Na]$^+$ (LCMS sample treated with MeNH$_2$ to give 1-(3-methoxyphenyl)-N-methylmethanesulfonamide, exact mass: 215.06).

(xxii) Phenylsulfamoyl Chloride I50

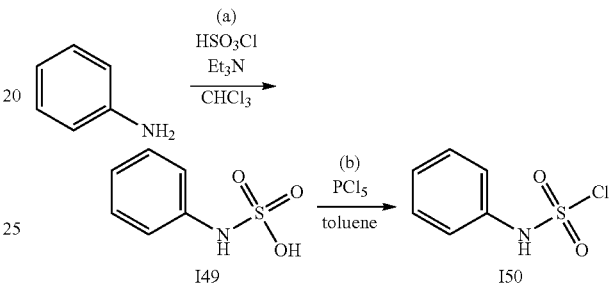

a) Phenylsulfamic Acid I49

To a solution of aniline (2.0 g, 21.5 mmol) and Et$_3$N (19.6 g, 194 mmol) in chloroform (40 mL) at 0° C. was added chlorosulfonic acid (2.5 g, 21.5 mmol) dropwise and the mixture was stirred at 0° C. for 2 h. The mixture was concentrated under reduced pressure and the residue was dissolved in a 1 M aqueous NaOH solution (75 mL) and concentrated under reduced pressure. The residue was suspended in boiling ethanol, filtered and washed with ethanol. The filter cake was dried under reduced pressure to give the title compound (3.0 g, 81%) as a white solid. LCMS-A (ES-API): R$_t$ 0.30 min; m/z 172.1 [M−H]$^-$.

b) Phenylsulfamoyl Chloride I50

To a solution of phenylsulfamic acid I49 (2.0 g, 11.5 mmol) in toluene (30 mL) was added PCl$_5$ (4.8 g, 23.5 mmol) and the mixture was heated at reflux under N$_2$ for 2 h, then was allowed to cool to room temperature and was filtered. The filtrate was concentrated under reduced pressure to give the title compound (1.3 g, 59%) as a yellow oil, which was used in the next step without further purification. LCMS-A (ES-API): R$_t$ 3.05 min; m/z 188.0 [M+MeOH—Cl]$^+$.

(xxiii) 2-Cyclohexylethane-1-sulfonyl Chloride I52

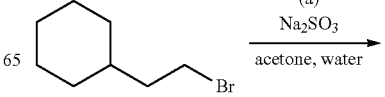

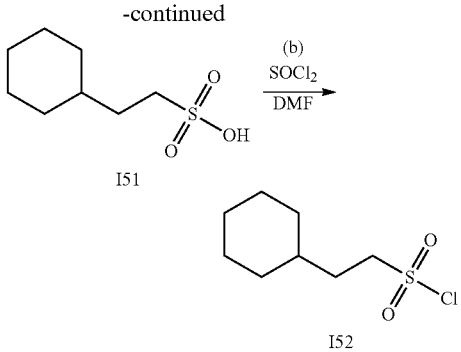

a) 2-Cyclohexylethane-1-sulfonic Acid I51

A suspension of (2-bromoethyl)cyclohexane (3.0 g, 16.0 mmol) and sodium sulfite (2.13 g, 17.0 mmol) in water (60 mL) and acetone (18 mL) was heated at 90° C. for 16 h. The mixture was allowed to cool to room temperature, toluene was added and the mixture was concentrated under reduced pressure to give the title compound (3.0 g, 100%) as a white solid, which was used in the next step without further purification.

b) 2-Cyclohexylethane-1-sulfonyl Chloride I52

To a stirred solution of 2-cyclohexylethane-1-sulfonic acid I51 (605 mg, 3.15 mmol) in DCM (25 mL) was added DMF (5 drops) and the mixture was cooled to −20° C. Oxalyl chloride (2.7 mL, 31.4 mmol) was added and the mixture was stirred at −20° C. for 30 min, then allowed to warm to room temperature and stirred for 2 h. DCM (20 mL) was added and the mixture was washed with water and brine. The organic layer was dried over Na$_2$SO$_4$, filtered and concentrated under reduced pressure to give the title compound (270 mg, 45%) as a yellow oil, which was used in the next step without further purification.

(xxiv) Cyclohexylmethanesulfonyl Chloride I54

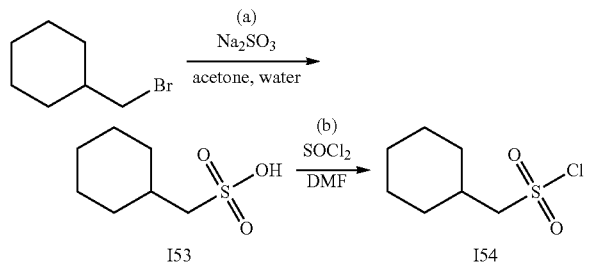

a) Cyclohexylmethanesulfonic Acid I53

A suspension of (bromomethyl)cyclohexane (5.0 g, 28.1 mmol) and sodium sulfite (3.8 g, 30.0 mmol) in water (80 mL) and acetone (30 mL) was heated at 90° C. for 16 h. The mixture was allowed to cool to room temperature, toluene was added and the mixture was concentrated under reduced pressure to give the title compound (4.95 g, 99%) as a white solid, which was used in the next step without further purification. LCMS-A (ES-API): R$_t$ 0.36 min; m/z 177.0 [M−H]$^-$.

b) Cyclohexylmethanesulfonyl Chloride I54

To a stirred solution of cyclohexylmethanesulfonic acid I53 (1.5 g, 8.4 mmol) in DCM (45 mL) was added DMF (12 drops) and the mixture was cooled to −20° C. Oxalyl chloride (10.7 g, 84.2 mmol) was added and the mixture was stirred at −20° C. for 30 min, then allowed to warm to room temperature and stirred for 2 h. DCM (20 mL) was added and the mixture was washed with water and brine. The organic layer was dried over Na$_2$SO$_4$, filtered and concentrated under reduced pressure to give the title compound (300 mg, 19%) as a yellow oil, which was used in the next step without further purification.

(xxv) 5-(2-Methoxy-5-(trifluoromethyl)phenyl)-1,3,4-thiadiazol-2-amine I57

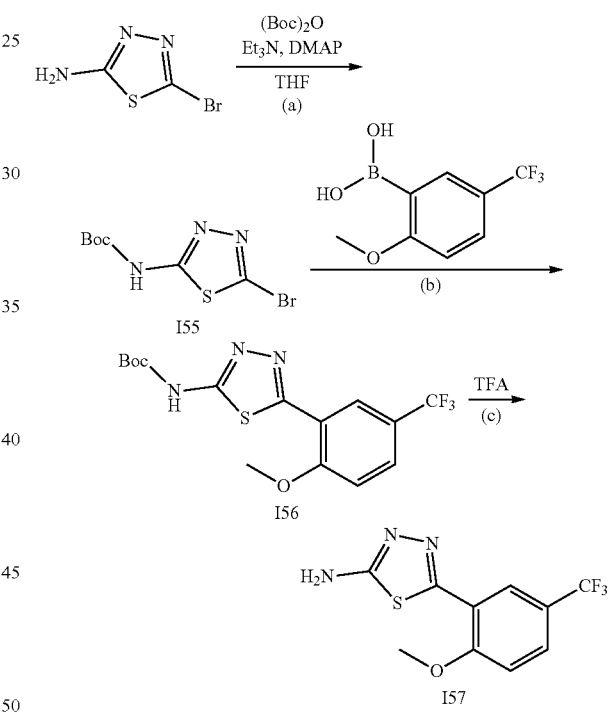

a) tert-Butyl (5-bromo-1,3,4-thiadiazol-2-yl)carbamate I55

To a solution of 5-bromo-1,3,4-thiadiazol-2-amine (4.0 g, 22 mmol) in THF (50 mL) was added di-tert-butyl dicarbonate (5.2 g, 24 mmol), Et$_3$N (4.5 g, 44 mmol) and DMAP (538 mg, 4.4 mmol) and the mixture was stirred at room temperature overnight. Water was added and the mixture was extracted with EtOAc (50 mL×3). The combined organic layers were washed with brine, dried over Na$_2$SO$_4$, filtered and concentrated under reduced pressure. The residue was purified by column chromatography (MeOH/DCM=1/100) to give the title compound (3.4 g, 55%) as a light yellow solid. LCMS-A (ES-API): R$_t$ 1.22 min; m/z 279.9, 281.9 [M+H]$^+$.

b) tert-Butyl (5-(2-methoxy-5-(trifluoromethyl)phenyl)-1,3,4-thiadiazol-2-yl)carbamate I56

A mixture of tert-butyl (5-bromo-1,3,4-thiadiazol-2-yl)carbamate I55 (300 mg, 1.07 mmol), (2-methoxy-5-(trifluoromethyl)phenyl)boronic acid (282 mg, 1.28 mmol), Pd(dppf)Cl$_2$·DCM (87 mg, 0.107 mmol) and Na$_2$CO$_3$ (340 mg, 3.21 mmol) in DME (8 mL) and water (12 mL) was heated at reflux under N$_2$ for 16 h. The solvent was removed under reduced pressure and the residue was purified by column chromatography (MeOH/DCM=1/200 to 1/100) then triturated with MeOH (60 mL) to give the title compound (190 mg, 47%) as a white solid. LCMS-A (ES-API): R$_t$2.63 min; m/z 376.0 [M+H]$^+$, 319.9 [M-t-Bu+2H]$^+$.

c) 5-(2-Methoxy-5-(trifluoromethyl)phenyl)-1,3,4-thiadiazol-2-amine I57

To a stirred solution of tert-butyl (5-(2-methoxy-5-(trifluoromethyl)phenyl)-1,3,4-thiadiazol-2-yl)carbamate I56 (95 mg, 0.25 mmol) in DCM (3 mL) was added TFA (0.8 mL) and the mixture was stirred at room temperature for 5 h then concentrated under reduced pressure. The residue was diluted with DCM (30 mL), washed with saturated aqueous NaHCO$_3$ solution (30 mL×2) and the organic layer was dried over Na$_2$SO$_4$, filtered and concentrated under reduced pressure to give the title compound (60 mg, 86%) as a white solid. LCMS-A (ES-API): R$_t$1.75 min; m/z 275.9 [M+H]$^+$.
$^1$H NMR (400 MHz, DMSO-d$_6$) δ 8.36 (d, J=2.3 Hz, 1H), 7.81 (dd, J=8.8, 2.4 Hz, 1H), 7.60 (br s, 2H), 7.42 (d, J=8.8 Hz, 1H), 4.03 (s, 3H).

(xxvi) 5-(5-((1H-Pyrazol-1-yl)methyl)-2-methoxyphenyl)isoxazol-3-amine I62

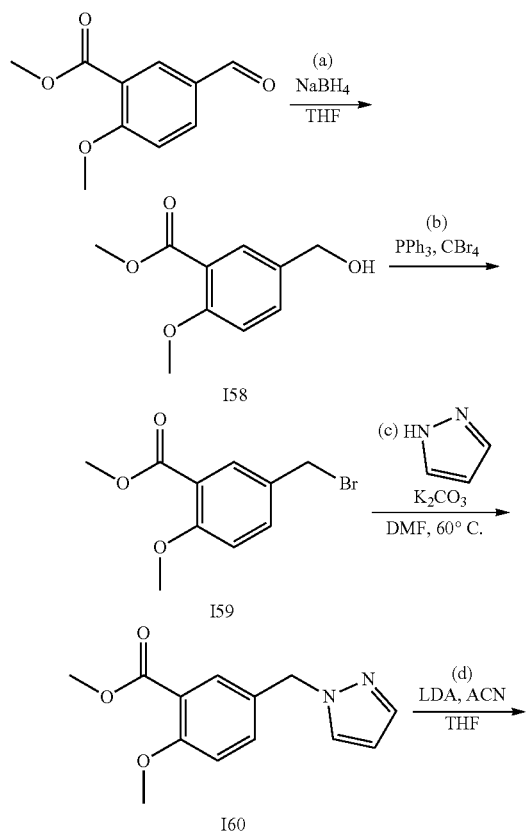

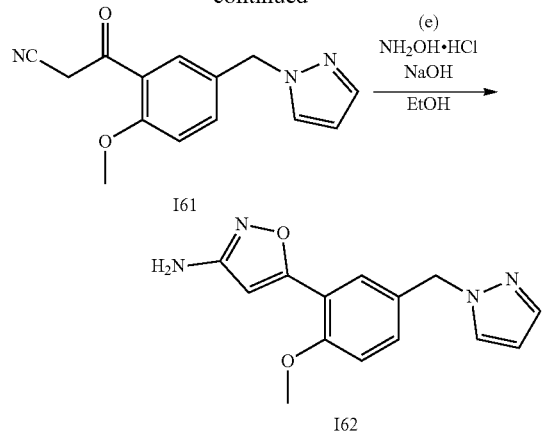

a) Methyl 5-(hydroxymethyl)-2-methoxybenzoate I58

To a solution of methyl 5-formyl-2-methoxybenzoate (4.6 g, 23.7 mmol) in THF (230 mL) was added NaBH$_4$ (1.1 g, 28.4 mmol) and the mixture was stirred at room temperature for 2 h. The reaction was quenched with 1 M aqueous HCl then diluted with water and extracted with DCM. The organic extracts were washed with brine, dried over Na$_2$SO$_4$, filtered and concentrated under reduced pressure. The residue was purified by column chromatography (Pet. Ether/DCM=1/2) to give the title compound (3.2 g, 68%) as a yellow oil. LCMS-E (ES-API): R$_t$ 0.77 min; m/z 197.0 [M+H]$^+$.

b) Methyl 5-(bromomethyl)-2-methoxybenzoate I59

To a solution of methyl 5-(hydroxymethyl)-2-methoxybenzoate I58 (2.8 g, 14.3 mmol) in DCM (108 mL) was added PPh$_3$ (5.6 g, 21.4 mmol) and CBr$_4$ (7.1 g, 21.4 mmol) and the mixture was heated at 40° C. for 90 min. Water was added and the mixture was extracted with DCM. The organic extracts were washed with brine, dried over Na$_2$SO$_4$, filtered and concentrated under reduced pressure. The residue was purified by column chromatography (Pet. Ether/EtOAc=10/1) to give the title compound (2.2 g, 60%) as a yellow solid. LCMS-A (ES-API): R$_t$ 2.14 min; m/z 258.9/260.9 [M+H]$^+$.

c) Methyl 5-((1H-pyrazol-1-yl)methyl)-2-methoxybenzoate I60

To a solution of 1H-pyrazole (867 mg, 12.7 mmol) and K$_2$CO$_3$ (2.4 g, 17.0 mmol) in DMF (179 mL) was added a solution of methyl 5-(bromomethyl)-2-methoxybenzoate I59 (2.2 g, 8.5 mmol) in DMF (27 mL) and the mixture was heated at 60° C. overnight. Water was added and the mixture was extracted with EtOAc. The organic extracts were washed with brine, dried over Na$_2$SO$_4$, filtered and concentrated under reduced pressure. The residue was purified by column chromatography (Pet. Ether/EtOAc=8/1) to give the title compound (887 mg, 42%) as a white solid. LCMS-A (ES-API): R$_t$ 0.70 min; m/z 247.0 [M+H]$^+$.

d) 3-(5-((1H-Pyrazol-1-yl)methyl)-2-methoxyphenyl)-3-oxopropanenitrile I61

To a solution of diisopropylamine (428 mg, 4.2 mmol) in THF (33 mL) at −78° C. under N$_2$ was added n-BuLi (2.5 M solution in hexanes, 1.7 mL, 4.2 mmol) dropwise and the mixture was stirred at −78° C. for 1 h. A solution of acetonitrile (173 mg, 4.2 mmol) in THF (4 mL) was then added dropwise and stirring was continued at −78° C. for 30 min. A solution of methyl 5-((1H-pyrazol-1-yl)methyl)-2-methoxybenzoate I60 (800 mg, 3.3 mmol) in THF (4 mL) was then added and the mixture was stirred at −78° C. for 40 min. The reaction was quenched at −78° C. with 1 M aqueous HCl and the mixture was diluted with water and extracted with EtOAc (150 mL×3). The combined organic extracts were washed with brine, dried over $Na_2SO_4$, filtered and concentrated under reduced pressure to give the title compound (690 mg, 86%) as an orange solid. LCMS-A (ES-API): $R_t$ 0.74 min; m/z 256.0 $[M+H]^+$.

e) 5-(5-((1H-Pyrazol-1-yl)methyl)-2-methoxyphenyl)isoxazol-3-amine I62

To a solution of 3-(5-((1H-pyrazol-1-yl)methyl)-2-methoxyphenyl)-3-oxopropanenitrile I61 (690 mg, 2.7 mmol) and NaOH (120 mg, 3.0 mmol) in ethanol (3.6 mL) and water (3.6 mL) was added $NH_2OH \cdot HCl$ (209 mg, 3.0 mmol) and the mixture was heated at 80° C. overnight. Concentrated aqueous HCl (1.5 mL) was then added and the mixture was heated at 80° C. for a further 2 h. Water was added and the mixture was extracted with EtOAc. The combined organic extracts were washed with brine, dried over $Na_2SO_4$, filtered and concentrated under reduced pressure. The residue was purified by column chromatography (Pet. Ether/EtOAc=6/1) to give the title compound (57 mg, 8%) as a yellow solid. LCMS-A (ES-API): $R_t$ 0.62 min; m/z 271.0 $[M+H]^+$. $^1$H NMR (400 MHz, DMSO-$d_6$) δ 7.83 (d, J=2.3 Hz, 1H), 7.65 (d, J=2.3 Hz, 1H), 7.45 (d, J=1.8 Hz, 1H), 7.33 (dd, J=8.6, 2.3 Hz, 1H), 7.15 (d, J=8.7 Hz, 1H), 6.27 (s, 1H), 6.26 (t, J=2.0 Hz, 1H), 5.60 (s, 2H), 5.32 (s, 2H), 3.90 (s, 3H).

(xxvii) 5-(2-Methoxy-5-(1H-pyrazol-1-yl)phenyl)isoxazol-3-amine I65

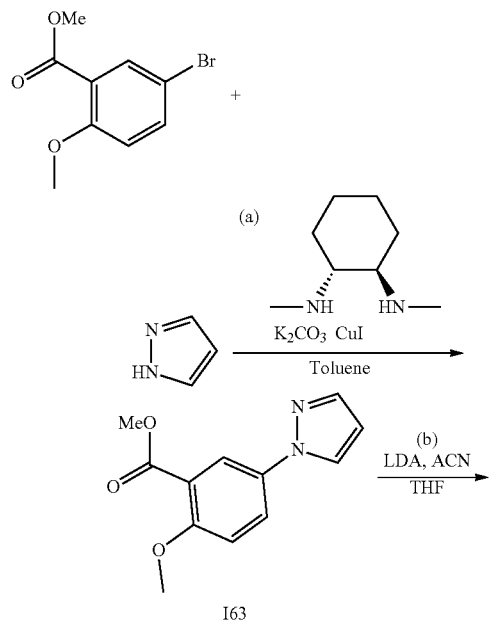

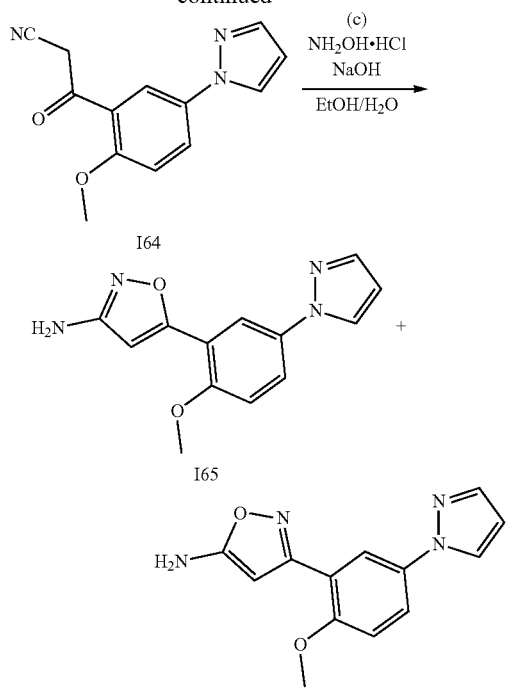

a) Methyl 2-methoxy-5-(1H-pyrazol-1-yl)benzoate I63

To a solution of methyl 5-bromo-2-methoxybenzoate (500 mg, 2.07 mmol) and 1H-pyrazole (282 mg, 4.14 mmol) in toluene (4 mL) was added CuI (20 mg, 0.104 mmol), $K_2CO_3$ (602 mg, 4.36 mmol) and (1R,2R)—N1,N2-dimethylcyclohexane-1,2-diamine (59 mg, 0.415 mmol) and the mixture was heated at 140° C. for 2 h under microwave irradiation. Water was added and the mixture was extracted with EtOAc (100 mL×3). The combined organic layers were washed with brine, dried over $Na_2SO_4$, filtered and concentrated under reduced pressure. The residue was purified by column chromatography (Pet. Ether/EtOAc=10/1) to give the title compound (280 mg, 56%) as a yellow oil. LCMS-A (ES-API): $R_t$ 1.07 min; m/z 233.0 $[M+H]^+$.

b) 3-(2-Methoxy-5-(1H-pyrazol-1-yl)phenyl)-3-oxopropanenitrile I64

To a solution of diisopropylamine (0.68 g, 6.7 mmol) in THF (30 mL) at −78° C. under $N_2$ was added n-BuLi (2.5 M solution in hexanes, 2.7 mL, 6.7 mmol) dropwise and the mixture was stirred at −78° C. for 1 h. A solution of acetonitrile (0.275 g, 6.7 mmol) in THF (10 mL) was then added dropwise and stirring was continued for 30 min. A solution of methyl 2-methoxy-5-(1H-pyrazol-1-yl)benzoate I63 (1.2 g, 5.2 mmol) in THF (10 mL) was then added dropwise and the mixture was stirred at −78° C. for 40 min. The reaction was quenched at −78° C. with 1 M aqueous HCl and the mixture was diluted with water (400 mL) and extracted with EtOAc (200 mL×3). The combined organic extracts were washed with brine, dried over $Na_2SO_4$, filtered and concentrated under reduced pressure. The residue was purified by column chromatography (Pet. Ether/EtOAc=5/1) to give the title compound (0.96 g, 77%) as a yellow solid. LCMS-E (ES-API): $R_t$ 3.52 min; m/z 242.0 $[M+H]^+$.

c) 5-(2-Methoxy-5-(1H-pyrazol-1-yl)phenyl)isoxazol-3-amine I65

To a solution of 3-(2-methoxy-5-(1H-pyrazol-1-yl)phenyl)-3-oxopropanenitrile I64 (960 mg, 4.0 mmol) and NaOH (208 mg, 5.2 mmol) in water (25 mL) and ethanol (25 mL) was added NH$_2$OH·HCl (360 mg, 5.2 mmol) and the mixture was heated at 80° C. overnight. Water (100 mL) was added and the mixture was extracted with EtOAc (200 mL×3). The combined organic extracts were washed with brine, dried over Na$_2$SO$_4$, filtered and concentrated under reduced pressure. The residue was purified by column chromatography (Pet. Ether/EtOAc=10/1 to 5/1) to give the title compound (280 mg, 28%) as a yellow solid. LCMS-A (ES-API): R$_t$ 1.60 min; m/z 256.9 [M+H]$^+$. $^1$H NMR (400 MHz, DMSO-d$_6$) δ 8.53 (d, J=2.4 Hz, 1H), 8.17 (d, J=2.8 Hz, 1H), 7.91-7.88 (m, 1H), 7.73 (d, J=1.6 Hz, 1H), 7.33 (d, J=8.8 Hz, 1H), 6.53 (t, J=2.0 Hz, 1H), 6.38 (s, 1H), 5.68 (s, 2H), 3.97 (s, 3H).

3-(2-Methoxy-5-(1H-pyrazol-1-yl)phenyl)isoxazol-5-amine (230 mg, 25%) was also obtained as a yellow solid. LCMS-B (ES-API): R$_t$ 3.15 min; m/z 257.1 [M+H]$^+$. $^1$H NMR (400 MHz, DMSO-d$_6$) δ 8.46 (d, J=2.4 Hz, 1H), 8.09 (d, J=2.8 Hz, 1H), 7.86 (dd, J=9.0, 2.9 Hz, 1H), 7.71 (d, J=1.7 Hz, 1H), 7.26 (d, J=9.0 Hz, 1H), 6.71 (s, 2H), 6.51 (t, J=2.5, 1.8

(xxviii) 5-(2-Bromo-6-methoxyphenyl)isoxazol-3-amine I68

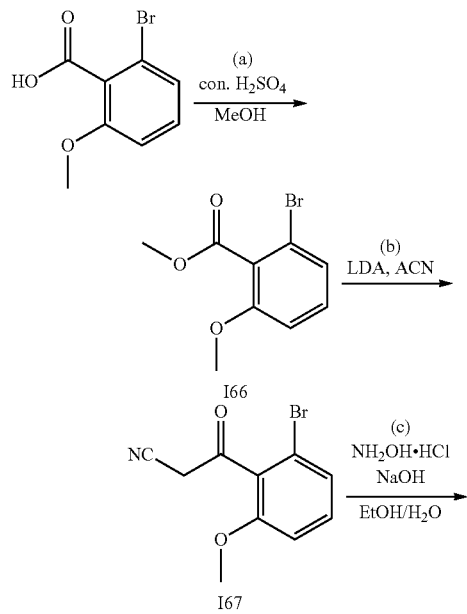

a) Methyl 2-bromo-6-methoxybenzoate I66

To a solution of 2-bromo-6-methoxybenzoic acid (4.7 g, 20.3 mmol) in methanol (100 mL) was added concentrated H$_2$SO$_4$ (15 mL) and the mixture was heated at 70° C. for 3 days. The mixture was diluted with water and extracted with EtOAc (300 mL×3). The combined organic extracts were washed with brine, dried over Na$_2$SO$_4$, filtered and concentrated under reduced pressure to give the title compound (2.36 g, 48%) as a yellow oil. LCMS-A (ES-API): R$_t$ 2.10 min; m/z 244.9/246.9 [M+H]$^+$.

b) 3-(2-Bromo-6-methoxyphenyl)-3-oxopropanenitrile I67

To a solution of diisopropylamine (536 mg, 5.3 mmol) in dry THF (40 mL) at −78° C. under N$_2$ was added n-BuLi (2.5 M solution in hexanes, 2.1 mL, 5.3 mmol) dropwise and the mixture was stirred at −78° C. for 1 h. A solution of acetonitrile (218 mg, 5.30 mmol) in THF (5 mL) was then added dropwise and stirring was continued for 30 min. A solution of methyl 2-bromo-6-methoxybenzoate I66 (1.0 g, 4.08 mmol) in THF (5 mL) was then added rapidly and the mixture was stirred at −78° C. for 40 min. The mixture was adjusted to pH 5 at −78° C. by addition of 1 M aqueous HCl and extracted with EtOAc (40 mL×3). The combined organic extracts were washed with brine, dried over Na$_2$SO$_4$, filtered and concentrated under reduced pressure to give the title compound (1.0 g, 99%) as a yellow solid, which was used directly in the next step.

c) 5-(2-Bromo-6-methoxyphenyl)isoxazol-3-amine I68

To a solution of 3-(2-bromo-6-methoxyphenyl)-3-oxopropanenitrile I67 (1.0 g, 3.95 mmol) and NaOH (174 mg, 4.35 mmol) in water (15 mL) and ethanol (15 mL) was added NH$_2$OH·HCl (302 mg, 4.35 mmol) and the mixture was heated at 80° C. overnight. The mixture was diluted with water and extracted with EtOAc. The organic layer was washed with water, brine, dried over Na$_2$SO$_4$, filtered and concentrated under reduced pressure. The residue was purified by column chromatography (Pet. Ether/EtOAc=10/1 to 3/1) to give the title compound (130 mg, 12%) as a yellow oil. LCMS-A (ES-API): R$_t$ 1.35 min; m/z 268.9, 270.9 [M+H]$^+$. $^1$H NMR (400 MHz, DMSO-d$_6$) δ 7.41 (t, J=8.2 Hz, 1H), 7.34-7.29 (m, 1H), 7.19-7.13 (m, 1H), 5.92 (s, 1H), 5.61 (s, 2H), 3.76 (s, 3H).

(xxix) 5-(3,5-Dimethoxyphenyl)-1,3,4-thiadiazol-2-amine I70

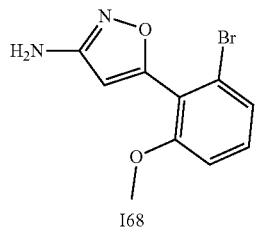

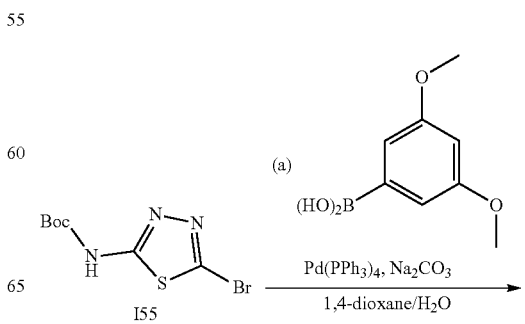

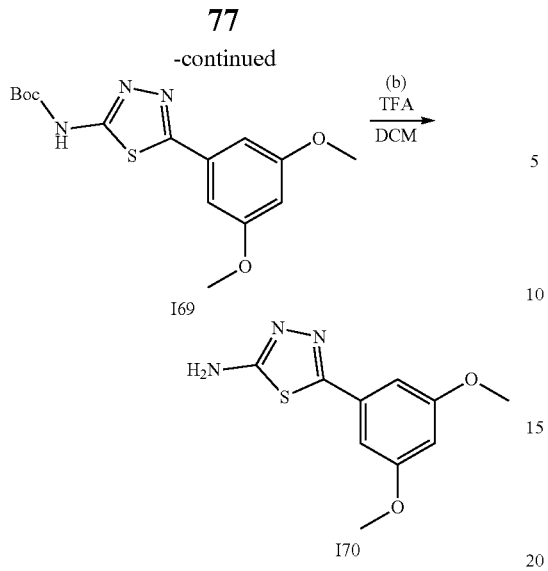

a) tert-Butyl (5-(3,5-dimethoxyphenyl)-1,3,4-thiadiazol-2-yl)carbamate I69

To a solution of tert-butyl (5-bromo-1,3,4-thiadiazol-2-yl)carbamate I55 (400 mg, 1.43 mmol) and (3,5-dimethoxyphenyl)boronic acid (520 mg, 2.86 mmol) in 1,4-dioxane (25 mL) and water (5 mL) under N2 was added Pd(PPh$_3$)$_4$ (166 mg, 0.14 mmol) and Na$_2$CO$_3$ (455 mg, 4.29 mmol) and the mixture was heated at 100° C. overnight. Water was added and the mixture was extracted with EtOAc. The combined organic extracts were washed with brine, dried over Na$_2$SO$_4$, filtered and concentrated under reduced pressure. The residue was purified by column chromatography (Pet. Ether/EtOAc=5/1) to give the title compound (200 mg, 42%) as a white solid. LCMS-E (ES-API): R$_t$ 3.05 min; m/z 338.2 [M+H]$^+$.

b) 5-(3,5-Dimethoxyphenyl)-1,3,4-thiadiazol-2-amine I70

A mixture of tert-butyl (5-(3,5-dimethoxyphenyl)-1,3,4-thiadiazol-2-yl)carbamate I69 (200 mg, 0.59 mmol) in TFA (201 mg, 1.77 mmol) was stirred at room temperature overnight then concentrated under reduced pressure to give the title compound (100 mg, 72%) as a colourless oil, which was used directly in the next step.

(xxx) 5-(2-(Methoxymethyl)phenyl)-1,3,4-oxadiazol-2-amine I74

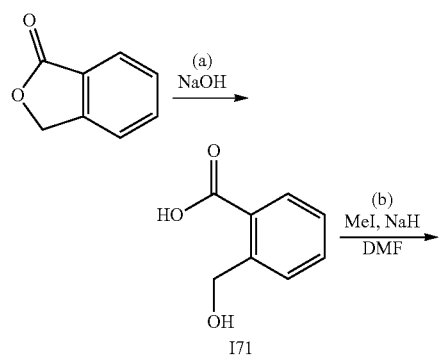

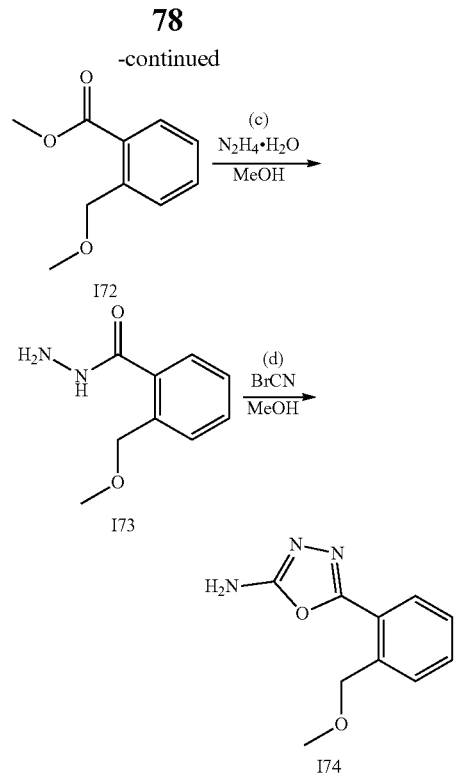

a) 2-(Hydroxymethyl)benzoic acid I71

To a solution of NaOH (2.25 g, 56.0 mmol) in H$_2$O (50 mL) was added isobenzofuran-1(3H)-one (5.0 g, 37.3 mmol) and the mixture was heated at reflux for 3 h, then allowed to cool to room temperature. Concentrated aqueous HCl was added to the mixture until a precipitate formed, which was collected by filtration to give the title compound (2.7 g, 48%) as a white solid which was used directly in the next step.

b) Methyl 2-(methoxymethyl)benzoate I72

To a solution of 2-(hydroxymethyl)benzoic acid I71 (2.5 g, 16.4 mmol) and iodomethane (4.7 g, 32.9 mmol) in DMF (100 mL) at 0° C. was added NaH (60% w/w in oil, 984 mg, 24.6 mmol) and the mixture was stirred at room temperature for 30 min. Water was added and the mixture was extracted with EtOAc. The combined organic extracts were washed with brine, dried over Na$_2$SO$_4$, filtered and concentrated under reduced pressure. The residue was purified by column chromatography (Pet. Ether/EtOAc=20/1) to give the title compound (880 mg, 33%) as a yellow oil. LCMS-A (ES-API): R$_t$ 1.60 min; m/z 181.0 [M+H]$^+$.

c) 2-(Methoxymethyl)benzohydrazide I73

To a solution of methyl 2-(methoxymethyl)benzoate I72 (850 mg, 4.7 mmol) in MeOH (15 mL) was added hydrazine hydrate (1.5 g, 30 mmol) and the mixture was heated at 120° C. in a sealed tube overnight. Water was added and the mixture was extracted with EtOAc. The organic extracts were washed with brine, dried over Na$_2$SO$_4$, filtered and concentrated under reduced pressure. The residue was purified by column chromatography (Pet. Ether/EtOAc=5/1) to give the title compound (600 mg, 71%) as a white solid. LCMS-A (ES-API): R$_t$ 0.31 min; m/z 181.0 [M+H]$^+$.

d) 5-(2-(Methoxymethyl)phenyl)-1,3,4-oxadiazol-2-amine I74

To a solution of 2-(methoxymethyl)benzohydrazide I73 (450 mg, 2.50 mmol) in MeOH (10 mL) was added BrCN (291 mg, 2.75 mmol) and the mixture was heated at 80° C. in a sealed tube overnight. Water was added and the mixture was extracted with EtOAc. The organic extracts were washed with brine, dried over $Na_2SO_4$, filtered and concentrated under reduced pressure. The residue was purified by column chromatography (Pet. Ether/EtOAc=3/1) to give the title compound (100 mg, 20%) as a yellow solid. LCMS-E (ES-API): $R_t$ 0.82 min; m/z 205.96 $[M+H]^+$. $^1$H NMR (400 MHz, DMSO-$d_6$) δ 7.73 (dd, J=7.7, 1.4 Hz, 1H), 7.62 (d, J=7.5 Hz, 1H), 7.55-7.48 (m, 1H), 7.47-7.41 (m, 1H), 7.24 (s, 2H), 4.77 (s, 2H), 3.40 (s, 3H).

(xxxi) 5-(5-Chloro-2-isopropoxyphenyl)-1,3,4-thiadiazol-2-amine I76 compound (190 mg, 24%) as a yellow solid. LCMS-A (ES-API): $R_t$ 2.67 min; m/z 370.0 $[M+H]^+$.

b) 5-(5-Chloro-2-isopropoxyphenyl)-1,3,4-thiadiazol-2-amine I76

To a solution of tert-butyl (5-(5-chloro-2-isopropoxyphenyl)-1,3,4-thiadiazol-2-yl)carbamate I75 (100 mg, 0.27 mmol) in DCM (9 mL) was added TFA (3 mL) and the mixture was stirred at room temperature overnight. The mixture was concentrated under reduced pressure, the residue was diluted with EtOAc and washed with a saturated aqueous $NaHCO_3$ solution and brine. The organic layer was dried over $Na_2SO_4$, filtered and concentrated under reduced pressure to give the title compound (75 mg, 100%) as a white solid. LCMS-A (ES-API): $R_t$ 2.19 min; m/z 269.9 $[M+H]^+$.

(xxxii) 5-(5-Methoxy-2-(methoxymethyl)phenyl)-1,3,4-thiadiazol-2-amine I80

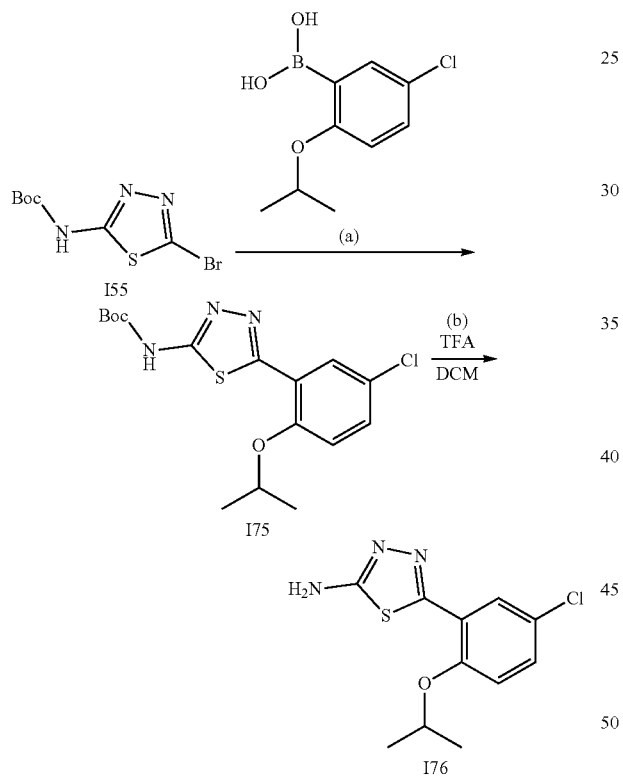

a) tert-Butyl (5-(5-chloro-2-isopropoxyphenyl)-1,3,4-thiadiazol-2-yl)carbamate I75

A mixture of tert-butyl (5-bromo-1,3,4-thiadiazol-2-yl)carbamate I55 (500 mg, 1.79 mmol), (5-chloro-2-isopropoxyphenyl)boronic acid (422 mg, 1.97 mmol), $Pd(PPh_3)_4$ (104 mg, 0.09 mmol) and $Na_2CO_3$ (379 mg, 3.58 mmol) in 1,4-dioxane (10 mL) and water (2 mL) was heated at reflux overnight under $N_2$. The mixture was diluted with EtOAc and washed with water and brine. The organic layer was dried over $Na_2SO_4$, filtered and concentrated under reduced pressure. The residue was purified by column chromatography (Pet. Ether/EtOAc=3/1) to give the title a) 2-Bromo-4-methoxy-1-(methoxymethyl)benzene I77

To a solution of (2-bromo-4-methoxyphenyl)methanol (1.8 g, 8.29 mmol) in THF (25 mL) at 0° C. was added NaH (60% w/w in oil, 398 mg, 9.95 mmol) and the mixture was stirred for 15 min. Iodomethane (1.3 g, 9.12 mmol) was added and the mixture was allowed to warm to room temperature and stirred for 2 h. The reaction was quenched with water (1 mL) and the mixture was diluted with EtOAc and washed with water and brine. The organic layer was dried over $Na_2SO_4$, filtered and concentrated under reduced pressure. The residue was purified by column chromatography (Pet. Ether/EtOAc=10/1) to give the title compound (1.6 g, 84%) as a light yellow solid. $^1$H NMR (400 MHz, $CDCl_3$) δ 7.37 (d, J=8.4 Hz, 1H), 7.14 (d, J=2.4 Hz, 1H), 6.58 (dd, J=8.8, 2.4 Hz, 1H), 4.50 (s, 2H), 3.82 (s, 3H), 3.45 (s, 3H).

b) 2-(5-Methoxy-2-(methoxymethyl)phenyl)-4,4,5,5-tetramethyl-1,3,2-dioxaborolane I78

To a solution of 2-bromo-4-methoxy-1-(methoxymethyl)benzene I77 (1.6 g, 6.92 mmol) in 1,4-dioxane (25 mL) was added 4,4,4',4',5,5,5',5'-octamethyl-2,2'-bi(1,3,2-dioxaborolane) (2.6 g, 10.4 mmol), potassium acetate (2.0 g, 20.8 mmol) and $Pd(dppf)Cl_2$ (260 mg, 0.35 mmol) and the mixture was heated at 100° C. overnight. The mixture was diluted with ethyl acetate and washed with water and brine. The organic layer was dried over $Na_2SO_4$, filtered and concentrated under reduced pressure. The residue was purified by column chromatography (Pet. Ether/EtOAc=10/1) to give the title compound (1.5 g, 79%) as a yellow solid. $^1$H NMR (400 MHz, $CDCl_3$) δ 7.33-7.29 (m, 2H), 6.94 (dd, J=8.4, 2.9 Hz, 1H), 4.62 (s, 2H), 3.82 (s, 3H), 3.37 (s, 3H), 1.35 (s, 12H).

c) tert-Butyl (5-(5-methoxy-2-(methoxymethyl)phenyl)-1,3,4-thiadiazol-2-yl) carbamate I79

A mixture of tert-butyl (5-bromo-1,3,4-thiadiazol-2-yl)carbamate I55 (500 mg, 1.79 mmol), 2-(5-methoxy-2-(methoxymethyl)phenyl)-4,4,5,5-tetramethyl-1,3,2-dioxaborolane I78 (498 mg, 1.79 mmol), $Pd(PPh_3)_4$ (104 mg, 0.09 mmol) and $Na_2CO_3$ (379 mg, 3.58 mmol) in 1,4-dioxane (10 mL) and water (2 mL) was heated at 100° C. overnight under $N_2$. LCMS analysis showed 20% conversion to the title compound.
A mixture of 2-(5-methoxy-2-(methoxymethyl)phenyl)-4,4,5,5-tetramethyl-1,3,2-dioxaborolane I78 (120 mg, 0.43 mmol), tert-butyl (5-bromo-1,3,4-thiadiazol-2-yl)carbamate I55 (100 mg, 0.36 mmol), $Pd(dppf)Cl_2 \cdot DCM$ (15 mg, 0.018 mmol) and $Na_2CO_3$ (76 mg, 0.72 mmol) in 1,2-dimethoxyethane (5 mL) and water (1 mL) was heated at reflux overnight under $N_2$. LCMS analysis showed 50% conversion to the title compound. This reaction was scaled up accordingly using tert-butyl (5-bromo-1,3,4-thiadiazol-2-yl)carbamate I55 (300 mg, 1.07 mmol).
The three reactions were combined, diluted with EtOAc and washed with water and brine. The organic layer was dried over $Na_2SO_4$, filtered and concentrated under reduced pressure. The residue was purified by column chromatography (Pet. Ether/EtOAc=3/1) to give the title compound (230 mg, 20%) as a yellow solid. LCMS-A (ES-API): $R_t$ 2.32 min; m/z 352.0 $[M+H]^+$.

d) 5-(5-Methoxy-2-(methoxymethyl)phenyl)-1,3,4-thiadiazol-2-amine I80 tert-Butyl (5-(5-methoxy-2-(methoxymethyl)phenyl)-1,3,4-thiadiazol-2-yl)carbamate I79 (120 mg, 0.34 mmol) was dissolved in a 4 M solution of HCl in 1,4-dioxane (10 mL) and the mixture was stirred at room temperature for 48 h, then concentrated under reduced pressure. The residue was diluted with EtOAc and washed with a saturated aqueous $NaHCO_3$ solution and brine. The organic layer was dried over $Na_2SO_4$, filtered and concentrated under reduced pressure to give the title compound (90 mg, 100%) as a yellow solid. LCMS-A (ES-API): $R_t$ 0.39 min; m/z 274.0 $[M+Na]^+$.

(xxxiii) 5-(2-Chloro-5-methoxyphenyl)-1,3,4-thiadiazol-2-amine I82

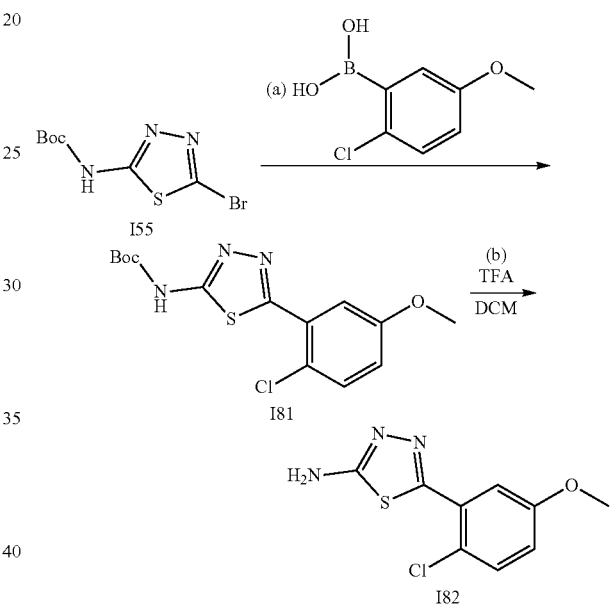

a) tert-Butyl (5-(5-chloro-2-isopropoxyphenyl)-1,3,4-thiadiazol-2-yl)carbamate I81

A mixture of tert-butyl (5-bromo-1,3,4-thiadiazol-2-yl)carbamate I55 (100 mg, 0.36 mmol), (2-chloro-5-methoxyphenyl)boronic acid (75 mg, 0.40 mmol), $Pd(PPh_3)_4$ (21 mg, 0.018 mmol) and $Na_2CO_3$ (76 mg, 0.72 mmol) in 1,4-dioxane (5 mL) and water (1 mL) was heated at 100° C. overnight under $N_2$. This reaction was scaled up accordingly with tert-butyl (5-bromo-1,3,4-thiadiazol-2-yl)carbamate I55 (500 mg, 1.79 mmol) and the two reaction mixtures were combined, diluted with EtOAc and washed with water and brine. The organic layer was dried over $Na_2SO_4$, filtered and concentrated under reduced pressure. The residue was purified by column chromatography (Pet. Ether/EtOAc=40/1) to give the title compound (260 mg, 35%) as a yellow solid. LCMS-E (ES-API): $R_t$ 3.90 min; m/z 341.7 $[M+H]^+$.

b) 5-(2-Chloro-5-methoxyphenyl)-1,3,4-thiadiazol-2-amine I82 To a solution of tert-butyl (5-(2-chloro-5-methoxyphenyl)-1,3,4-thiadiazol-2-yl)carbamate 181 (150 mg, 0.44 mmol) in DCM (3 mL) was added TFA (1 mL) and the mixture was stirred at room temperature overnight. The mixture was concentrated under reduced pressure, the residue was diluted with EtOAc and washed with a saturated aqueous NaHCO$_3$ solution and brine. The organic layer was dried over Na$_2$SO$_4$, filtered and concentrated under reduced pressure to give the title compound (110 mg, 100%) as a yellow solid. LCMS-E (ES-API): R$_t$0.69 min; m/z 241.9 [M+H]$^+$.

(xxxiv) 5-(5-((1H-Pyrazol-1-yl)methyl)-2-methoxyphenyl)-1,3,4-thiadiazol-2-amine I87

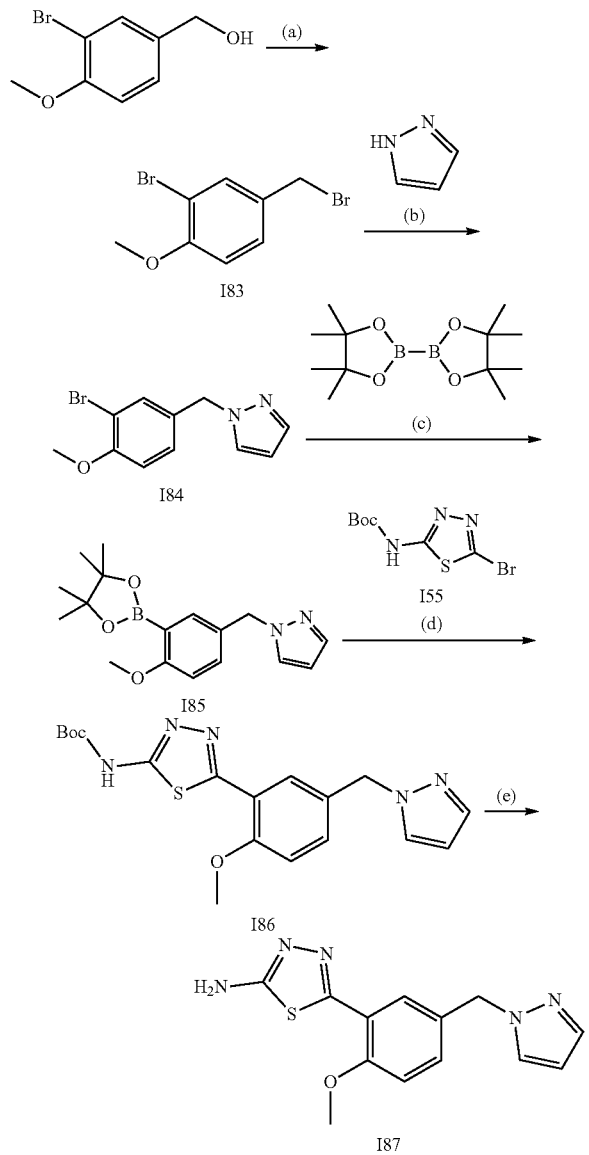

a) 2-Bromo-4-(bromomethyl)-1-methoxybenzene I83

To a solution of (3-bromo-4-methoxyphenyl)methanol (1.0 g, 4.61 mmol) in DCM (15 mL) was added PPh$_3$ (1.8 g, 6.92 mmol) and CBr$_4$ (2.3 g, 6.92 mmol) and the mixture was heated at reflux for 1 h. The mixture was concentrated under reduced pressure and the residue was purified by column chromatography (Pet. Ether/EtOAc=20/1) to give the title compound (0.9 g, 69%) as a yellow solid. $^1$H NMR (400 MHz, CDCl$_3$) δ 7.62 (d, J=1.6 Hz, 1H), 7.34 (dd, J=8.4, 2.4 Hz, 1H), 6.88 (d, J=8.4 Hz, 1H), 4.46 (s, 2H), 3.92 (s, 3H).

b) 1-(3-Bromo-4-methoxybenzyl)-1H-pyrazole I84

To a solution of 1H-pyrazole (584 mg, 8.56 mmol) in THF (35 mL) at 0° C. was added NaH (60% w/w in oil, 342 mg, 8.56 mmol) and the mixture was stirred for 10 min. 2-Bromo-4-(bromomethyl)-1-methoxybenzene I83 (800 mg, 2.86 mmol) was then added and the mixture was allowed to warm to room temperature and was stirred for 3 h. The reaction was quenched with water and the mixture was diluted with EtOAc and washed with water and brine. The organic layer was dried over Na$_2$SO$_4$, filtered and concentrated under reduced pressure. The residue was purified by column chromatography (Pet. Ether/EtOAc=5/1) to give the title compound (700 mg, 82%) as a yellow oil. LCMS-E (ES-API): R$_t$ 2.52 min; m/z 267.0 [M+H]$^+$.

c) 1-(4-Methoxy-3-(4,4,5,5-tetramethyl-1,3,2-dioxaborolan-2-yl)benzyl)-1H-pyrazole I85

To a solution of 1-(3-bromo-4-methoxybenzyl)-1H-pyrazole I84 (100 mg, 0.37 mmol) in 1,4-dioxane (5 mL) was added 4,4,4',4',5,5,5',5'-octamethyl-2,2'-bi(1,3,2-dioxaborolane) (142 mg, 0.56 mmol), potassium acetate (73 mg, 0.74 mmol) and Pd(dppf)Cl$_2$·DCM (16 mg, 0.019 mmol) and the mixture was heated at 100° C. overnight. This reaction was scaled up accordingly using 1-(3-bromo-4-methoxybenzyl)-1H-pyrazole I84 (600 mg, 2.25 mmol) and the two reaction mixtures were combined, diluted with EtOAc and washed with water and brine. The organic layer was dried over Na$_2$SO$_4$, filtered and concentrated under reduced pressure. The residue was purified by column chromatography (Pet. Ether/EtOAc=5/1) to give the title compound (400 mg, 49%) as a yellow oil. LCMS-E (ES-API): R$_t$ 2.72 min; m/z 315.2 [M+H]$^+$.

d) tert-Butyl (5-(5-((1H-pyrazol-1-yl)methyl)-2-methoxyphenyl)-1,3,4-thiadiazol-2-yl) carbamate I86

A mixture of 1-(4-methoxy-3-(4,4,5,5-tetramethyl-1,3,2-dioxaborolan-2-yl)benzyl)-1H-pyrazole I85 (100 mg, 0.32 mmol), tert-butyl (5-bromo-1,3,4-thiadiazol-2-yl)carbamate I55 (90 mg, 0.32 mmol), Pd(dppf)Cl$_2$·DCM (13 mg, 0.016 mmol) and Na$_2$CO$_3$ (68 mg, 0.64 mmol) in 1,2-dimethoxyethane (10 mL) and water (2 mL) was heated at 100° C. overnight under N$_2$. This reaction was scaled up accordingly using 1-(4-methoxy-3-(4,4,5,5-tetramethyl-1,3,2-dioxaborolan-2-yl)benzyl)-1H-pyrazole I85 (300 mg, 0.95 mmol) and the two reaction mixtures were combined, diluted with EtOAc and washed with water and brine. The organic layer was dried over Na$_2$SO$_4$, filtered and concentrated under reduced pressure. The residue was purified by column chromatography (Pet. Ether/EtOAc=1/1) to give the title compound (150 mg, 30%) as an off-white solid. LCMS-A (ES-API): R$_t$2.34 min; m/z 388.0.

e) 5-(5-((1H-Pyrazol-1-yl)methyl)-2-methoxyphenyl)-1,3,4-thiadiazol-2-amine I87 tert-Butyl (5-(5-((1H-pyrazol-1-yl)methyl)-2-methoxyphenyl)-1,3,4-thiadiazol-2-yl)carbamate I86 (50 mg, 0.13 mmol) was dissolved in a 4 M solution of HCl in 1,4- dioxane (10 mL) and the mixture was stirred at room temperature for 4 h then concentrated under reduced pressure. The residue was diluted with EtOAc and washed with a saturated aqueous NaHCO$_3$ solution and brine. The organic layer was dried over Na$_2$SO$_4$, filtered and concentrated under reduced pressure to give the title compound (45 mg, 100%) as an off-white solid. LCMS-E (ES-API): R$_t$ 0.94 min; m/z 288.1 [M+H]$^+$.

(xxxv) 5-(2-((1H-Pyrazol-1-yl)methyl)phenyl)-1,3,4-thiadiazol-2-amine I90

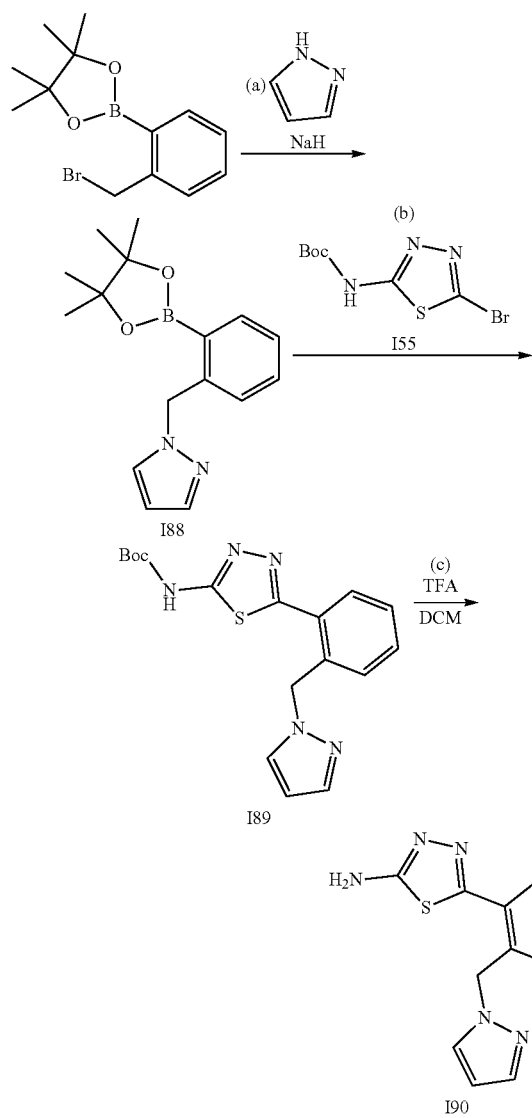

a) (1-(2-(4,4,5,5-Tetramethyl-1,3,2-dioxaborolan-2-yl)benzyl)-1H-pyrazole I88

To a solution of 1H-pyrazole (550 mg, 8.07 mmol) in THF (20 mL) at 0° C. was added NaH (60% w/w dispersion in oil, 323 mg, 8.07 mmol) and the mixture was stirred for 10 min. 2-(2-(Bromomethyl)phenyl)-4,4,5,5-tetramethyl-1,3,2-dioxaborolane (800 mg, 2.69 mmol) was added and the mixture was allowed to warm to room temperature and stirred for 3 h. The reaction was quenched with water and the mixture was diluted with EtOAc and washed with water and brine. The organic layer was dried over Na$_2$SO$_4$, filtered and concentrated under reduced pressure. The residue was purified by column chromatography (Pet. Ether/EtOAc=10/1) to give the title compound (400 mg, 52%) as a yellow solid. LCMS-E (ES-API): R$_t$ 3.25 min; m/z 285.1 [M+H]$^+$.

b) tert-Butyl (5-(2-((1H-pyrazol-1-yl)methyl)phenyl)-1,3,4-thiadiazol-2-yl)carbamate I89

A mixture of tert-butyl (5-bromo-1,3,4-thiadiazol-2-yl)carbamate I55 (200 mg, 0.71 mmol), 1-(2-(4,4,5,5-tetramethyl-1,3,2-dioxaborolan-2-yl)benzyl)-1H-pyrazole I88 (202 mg, 0.71 mmol), Pd(PPh$_3$)$_4$ (46 mg, 0.04 mmol) and Na$_2$CO$_3$ (151 mg, 1.42 mmol) in 1,4-dioxane (20 mL) and water (4 mL) was heated at 100° C. overnight under N$_2$. The mixture was diluted with EtOAc, washed with water and brine and the organic layer was dried over Na$_2$SO$_4$, filtered and concentrated under reduced pressure. The residue was purified by column chromatography (Pet. Ether/EtOAc=1/1) to give the title compound (70 mg, 22%) as a yellow solid. LCMS-E (ES-API): R$_t$ 2.85 min; m/z 358.0 [M+H]$^+$.

c) 5-(2-((1H-Pyrazol-1-yl)methyl)phenyl)-1,3,4-thiadiazol-2-amine I90

To a solution of tert-butyl (5-(2-((1H-pyrazol-1-yl)methyl)phenyl)-1,3,4-thiadiazol-2-yl) carbamate I89 (30 mg, 0.08 mmol) in DCM (5 mL) was added TFA (1 mL) and the mixture was stirred at room temperature overnight. The mixture was concentrated under reduced pressure, the residue was diluted with EtOAc and washed with a saturated aqueous NaHCO$_3$ solution and brine. The organic layer was dried over Na$_2$SO$_4$, filtered and concentrated under reduced pressure to give the title compound (20 mg, 90%) as a yellow solid. LCMS-E (ES-API): R$_t$ 0.85 min; m/z 258.1 [M+H]$^+$.

(xxxvi) 5-(2-Methoxypyridin-3-yl)-1,3,4-thiadiazol-2-amine I92

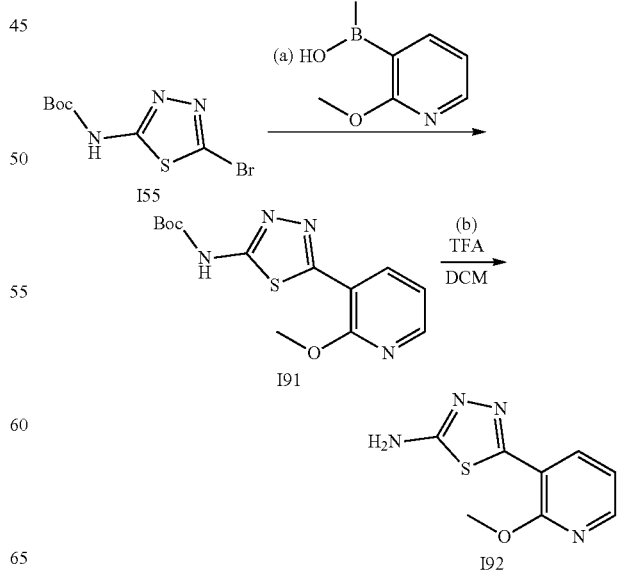

a) tert-Butyl (5-(2-methoxypyridin-3-yl)-1,3,4-thiadiazol-2-yl)carbamate I91

A mixture of tert-butyl (5-bromo-1,3,4-thiadiazol-2-yl)carbamate I55 (100 mg, 0.36 mmol), (2-methoxypyridin-3-yl)boronic acid (61 mg, 1.1 mmol), Pd(PPh$_3$)$_4$ (21 mg, 0.018 mmol) and K$_2$CO$_3$ (99 mg, 0.72 mmol) in 1,4-dioxane (5 mL) and water (1 mL) was heated at reflux under N$_2$ overnight.

A mixture of tert-butyl (5-bromo-1,3,4-thiadiazol-2-yl)carbamate I55 (600 mg, 2.16 mmol), (2-methoxypyridin-3-yl)boronic acid (367 mg, 2.4 mmol), Pd(PPh$_3$)$_4$ (125 mg, 0.11 mmol) and K$_2$CO$_3$ (596 mg, 4.32 mmol) in 1,4-dioxane (10 mL) and water (2 mL) was heated at reflux under N$_2$ overnight.

The two mixtures were combined, diluted with EtOAc and washed with water and brine. The organic layer was dried over Na$_2$SO$_4$, filtered and concentrated under reduced pressure. The residue was purified by column chromatography (Pet. Ether/EtOAc=4/1) to give the title compound (260 mg, 34%) as a yellow solid. LCMS-A (ES-API): R$_t$ 2.23 min; m/z 309.0 [M+H]$^+$.

b) 5-(2-Methoxypyridin-3-yl)-1,3,4-thiadiazol-2-amine I92

To a solution of tert-butyl (5-(2-methoxypyridin-3-yl)-1,3,4-thiadiazol-2-yl)carbamate I91 (100 mg, 0.32 mmol) in DCM (9 mL) was added TFA (3 mL) and the mixture was stirred at room temperature overnight. The mixture was concentrated under reduced pressure, the residue was diluted with EtOAc and washed with a saturated aqueous NaHCO$_3$ solution and brine. The organic layer was dried over Na$_2$SO$_4$, filtered and concentrated under reduced pressure to give the title compound (70 mg, 100%) as a white solid. LCMS-A (ES-API): R$_t$ 0.36 min; m/z 209.0 [M+H]$^+$.

(xxxvii) 5-(2-Ethoxy-5-methoxyphenyl)-1,2,4-oxadiazol-3-amine I100

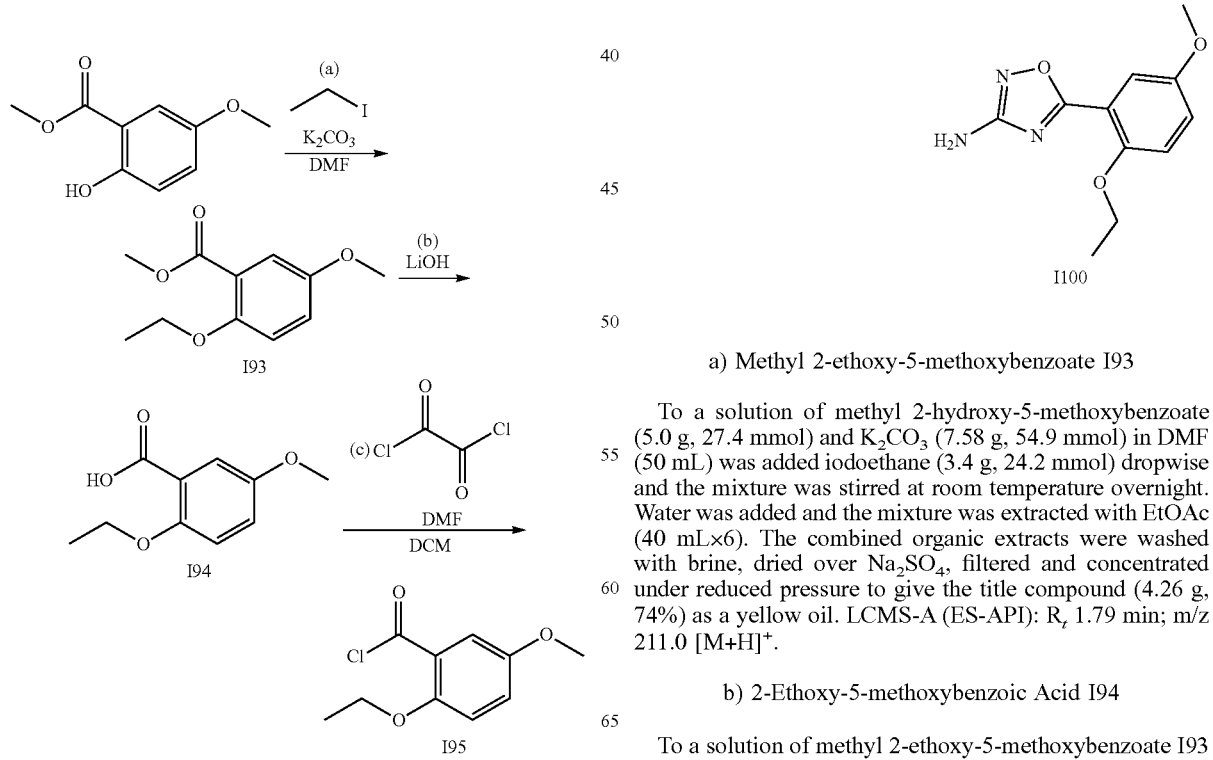

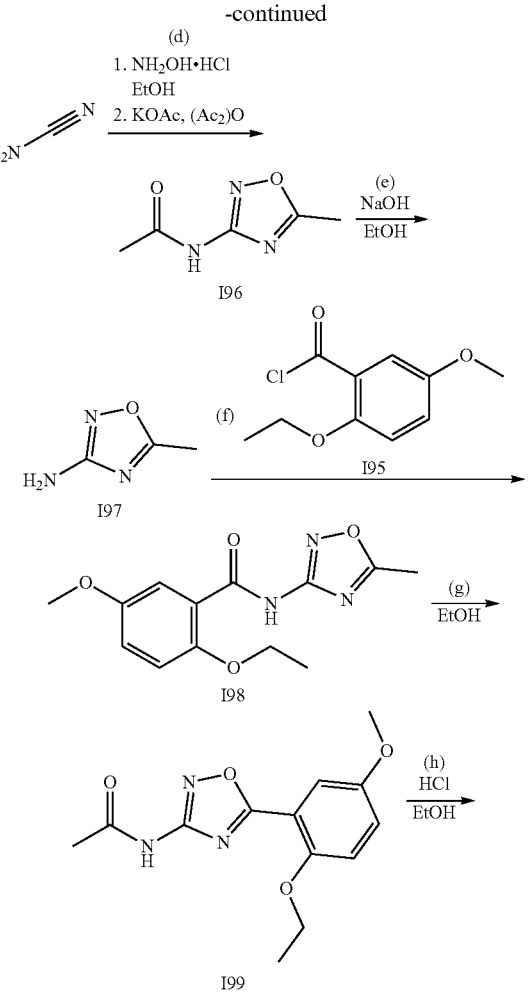

a) Methyl 2-ethoxy-5-methoxybenzoate I93

To a solution of methyl 2-hydroxy-5-methoxybenzoate (5.0 g, 27.4 mmol) and K$_2$CO$_3$ (7.58 g, 54.9 mmol) in DMF (50 mL) was added iodoethane (3.4 g, 24.2 mmol) dropwise and the mixture was stirred at room temperature overnight. Water was added and the mixture was extracted with EtOAc (40 mL×6). The combined organic extracts were washed with brine, dried over Na$_2$SO$_4$, filtered and concentrated under reduced pressure to give the title compound (4.26 g, 74%) as a yellow oil. LCMS-A (ES-API): R$_t$ 1.79 min; m/z 211.0 [M+H]$^+$.

b) 2-Ethoxy-5-methoxybenzoic Acid I94

To a solution of methyl 2-ethoxy-5-methoxybenzoate I93 (4.26 g, 20.3 mmol) in THF (50 mL) was added a solution of lithium hydroxide monohydrate (1.77 g, 40.6 mmol) in water (10 mL) dropwise and the mixture was stirred at room temperature overnight. Most of the THF was removed under reduced pressure and the aqueous residue was adjusted to pH 5-6 with aqueous HCl. The resulting precipitate was collected by filtration and dried to give the title compound (3.4 g, 85%) as a white solid. LCMS-A (ES-API): $R_t$ 0.78 min; m/z 197.0 [M+H]$^+$.

c) 2-Ethoxy-5-methoxybenzoyl Chloride I95

To a solution of 2-ethoxy-5-methoxybenzoic acid I94 (950 mg, 4.8 mmol) and DMF (1 drop) in DCM (20 mL) at 0° C. under $N_2$ was added a solution of oxalyl chloride (615 mg, 4.8 mmol) in DCM (3 mL) dropwise and the mixture was allowed to warm to room temperature and stirred for 2 h. The mixture was concentrated under reduced pressure to give the title compound (995 mg, 97%) as a yellow oil, which was used directly in the next step.

d) N-(5-Methyl-1,2,4-oxadiazol-3-yl)acetamide I96

A mixture of cyanamide (9.5 g, 0.22 mol) and $NH_2OH \cdot HCl$ (14.7 g, 0.22 mol) in dry EtOH (100 mL) was heated at reflux for 8 h and the solvent was then removed under reduced pressure. Potassium acetate (30 g, 0.31 mol) and $Ac_2O$ (50 mL) were added and the mixture was heated at reflux for 30 min then poured onto ice (300 g). The mixture was made strongly basic with NaOH (45 g) and then heated at 80° C. for 45 min. After cooling to room temperature, the mixture was extracted with EtOAc (100 mL×6) and the combined organic extracts were washed with brine, dried over $Na_2SO_4$, filtered and concentrated under reduced pressure to give the title compound (acetate hydrolysis did not occur) (5.2 g, 17%). LCMS-A (ES-API): $R_t$ 0.274 min; m/z 164.0 [M+Na]$^+$.

e) 5-Methyl-1,2,4-oxadiazol-3-amine I97

A mixture of N-(5-methyl-1,2,4-oxadiazol-3-yl)acetamide I96 (5.2 g, 31.9 mmol) and NaOH (2.7 g, 63.8 mmol) in EtOH (50 mL) was heated at 80° C. for 45 min then allowed to cool to room temperature and extracted with diethyl ether (50 mL×6). The combined organic extracts were washed with brine, dried over $Na_2SO_4$, filtered and concentrated under reduced pressure to give the title compound (2.53 g, 80%) as a white solid. LCMS-A (ES-API): $R_t$ 0.36 min; m/z 100.0 [M+H]$^+$.

f) 2-Ethoxy-5-methoxy-N-(5-methyl-1,2,4-oxadiazol-3-yl)benzamide I98

To a solution of 5-methyl-1,2,4-oxadiazol-3-amine I97 (450 mg, 4.5 mmol) in pyridine (25 mL) at 0° C. under $N_2$ was slowly added 2-ethoxy-5-methoxybenzoyl chloride I95 (972 mg, 4.5 mmol) and the mixture was stirred at room temperature overnight. Water was added and the mixture was adjusted to pH 4-5 with 1 M aqueous HCl and extracted with EtOAc (150 mL×3). The combined organic layers were washed with brine, dried over $Na_2SO_4$, filtered and concentrated under reduced pressure. The residue was purified by column chromatography (Pet. Ether/EtOAc=3/1) to give the title compound (400 mg, 30%) as a white solid. LCMS-A (ES-API): $R_t$ 1.56 min; m/z 278.0 [M+H]$^+$. $^1$H NMR (400 MHz, DMSO-$d_6$) δ 10.9 (s, 1H), 7.27 (d, J=2.8 Hz, 1H), 7.15-7.12 (m, 2H), 4.15 (q, J=6.9 Hz, 2H), 3.76 (s, 3H), 2.56 (s, 3H), 1.37 (t, J=6.9 Hz, 3H).

g) N-(5-(2-Ethoxy-5-methoxyphenyl)-1,2,4-oxadiazol-3-yl)acetamide I99

A solution of 2-ethoxy-5-methoxy-N-(5-methyl-1,2,4-oxadiazol-3-yl)benzamide I98 (400 mg, 1.4 mmol) in EtOH (20 mL) was heated at reflux overnight. The solvent was removed under reduced pressure and the residue was purified by column chromatography (DCM/MeOH=400/1) to give the title compound (200 mg, 50%) as a white solid. LCMS-A (ES-API): $R_t$ 1.0 min; m/z 278.0 [M+H]$^+$.

h) 5-(2-Ethoxy-5-methoxyphenyl)-1,2,4-oxadiazol-3-amine I100

A mixture of N-(5-(2-ethoxy-5-methoxyphenyl)-1,2,4-oxadiazol-3-yl)acetamide I99 (170 mg, 0.614 mmol) and concentrated aqueous HCl (2 mL) in EtOH (15 mL) was heated at reflux overnight. The mixture was concentrated under reduced pressure and the residue was purified by column chromatography (Pet. Ether/EtOAc=5/1) to give the title compound (70 mg, 49%) as a white solid. LCMS-A (ES-API): $R_t$ 1.05 min; m/z 236.0 [M+H]$^+$.

(xxxviii) 5-(2-Ethylphenyl)-1,3,4-thiadiazol-2-amine I102

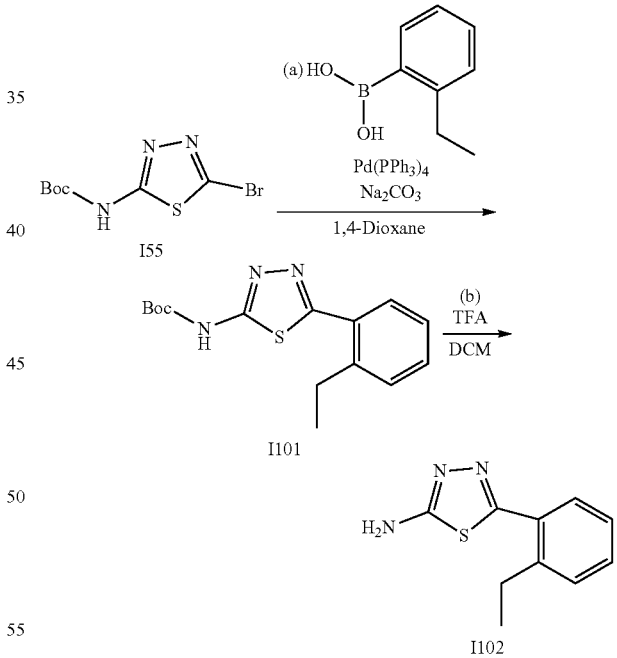

a) tert-Butyl (5-(2-ethylphenyl)-1,3,4-thiadiazol-2-yl)carbamate I101

To a solution of tert-butyl (5-bromo-1,3,4-thiadiazol-2-yl)carbamate I55 (400 mg, 1.43 mmol), (2-ethylphenyl)boronic acid (429 mg, 2.86 mmol) and $Na_2CO_3$ (454 mg, 4.28 mmol) in 1,4-dioxane (48 mL) and $H_2O$ (12 mL) was added Pd(PPh$_3$)$_4$ (83 mg, 0.072 mmol) and the mixture was heated at reflux overnight. The mixture was diluted with water and extracted with EtOAc. The combined organic layers were washed with water, brine, dried over $Na_2SO_4$, filtered and concentrated under reduced pressure. The residue was purified by column chromatography (Pet. Ether/EtOAc=6/1) to give the title compound (436 mg, 100%) as a yellow oil. LCMS-A (ES-API): $R_t$2.59 min; m/z 306.2 $[M+H]^+$.

b) 5-(2-Ethylphenyl)-1,3,4-thiadiazol-2-amine I102

To a solution of tert-butyl (5-(2-ethylphenyl)-1,3,4-thiadiazol-2-yl)carbamate I101 (436 mg, 1.43 mmol) in DCM (30 mL) was added TFA (10 mL) and the mixture was stirred at room temperature overnight. The mixture was concentrated under reduced pressure and the residue was purified by column chromatography (Pet. Ether/EtOAc=8/1) to give the title compound (190 mg, 65%) as a white solid. LCMS-A (ES-API): $R_t$0.67 min; m/z 206.0 $[M+H]^+$. $^1$H NMR (400 MHz, DMSO-$d_6$) δ 7.45 (d, J=7.3 Hz, 1H), 7.42-7.35 (m, 2H), 7.32 (s, 2H), 7.31-7.26 (m, 1H), 2.85 (q, J=7.5 Hz, 2H), 1.13 (t, J=7.5 Hz, 3H).

(xxxix) 5-(2-Methoxy-5-(trifluoromethyl)phenyl)isoxazol-3-amine I105

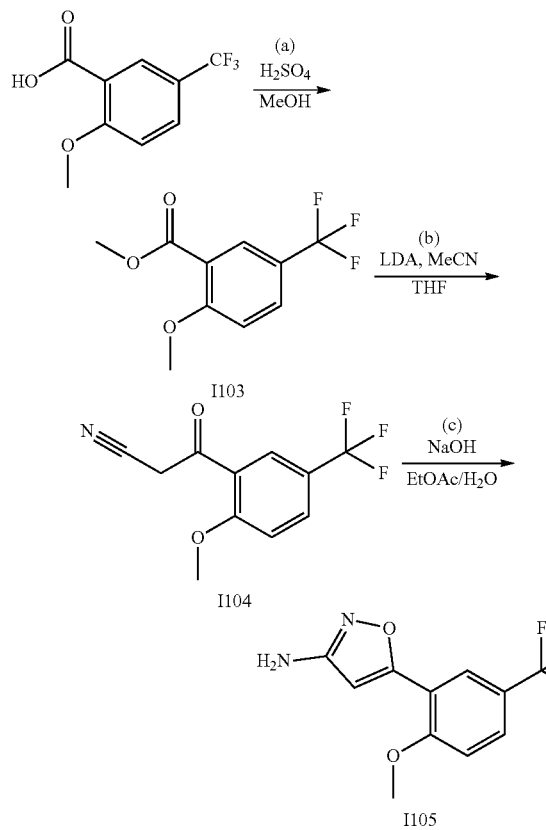

a) Methyl 2-methoxy-5-(trifluoromethyl)benzoate I103

To a solution of 2-methoxy-5-(trifluoromethyl) benzoic acid (2.0 g, 9.09 mmol) in methanol (100 mL) was added concentrated $H_2SO_4$ (2 mL) and the mixture was heated at 70° C. overnight. The mixture was then concentrated under reduced pressure to give the title compound (1.3 g, 62%) as a yellow oil. LCMS-A (ES-API): $R_t$2.26 min; m/z 235.0 $[M+H]^+$. Product was used without further purification.

b) 3-(2-Methoxy-5-(trifluoromethyl)phenyl)-3-oxopropanenitrile I104

To a solution of diisopropylamine (730 mg, 7.22 mmol) in anhydrous THF (25 mL) at −78° C. under $N_2$ was added n-butyllithium (2.5 M solution in hexanes, 3.0 mL, 7.22 mmol) dropwise and the mixture was stirred at −78° C. for 1 h. A solution of acetonitrile (300 mg, 7.22 mmol) in anhydrous THF (5 mL) was then added dropwise and the resulting mixture was stirred at −78° C. for 30 min. A solution of methyl 2-methoxy-5-(trifluoromethyl)benzoate I103 (1.3 g, 5.55 mmol) in anhydrous THF (3 mL) was added rapidly and the mixture was stirred at −78° C. for 40 min. The mixture was diluted with water, extracted with EtOAc and the combined organic extracts were washed with brine, dried over $Na_2SO_4$, filtered and concentrated under reduced pressure. The residue was purified by column chromatography (Pet. ether/EtOAc=10/1 to 5/1) to give the title compound (1.3 g, 90%) as a yellow oil, which was used directly in the next step.

c) 5-(2-Methoxy-5-(trifluoromethyl)phenyl)isoxazol-3-amine I105

To a solution of 3-(2-methoxy-5-(trifluoromethyl)phenyl)-3-oxopropanenitrile I104 (1.3 g, 5.35 mmol) and NaOH (235 mg, 5.88 mmol) in water (15 mL) and ethanol (15 mL) was added hydroxylamine hydrochloride (409 mg, 5.88 mmol) and the mixture was heated at 80° C. overnight. The mixture was diluted with water, extracted with EtOAc and the combined organic extracts were washed with brine, dried over anhydrous $Na_2SO_4$, filtered and concentrated under reduced pressure. The residue was purified by column chromatography (Pet. Ether/EtOAc=20/1 to 5/1) to give the title compound (250 mg, 18%) as a white solid. LCMS-A (ES-API): $R_t$2.20 min; m/z 259.0 $[M+H]^+$. $^1$H NMR (400 MHz, DMSO-$d_6$) δ 7.98 (d, J=2.4 Hz, 1H), 7.82 (dd, J=8.8, 2.4 Hz, 1H), 7.40 (d, J=8.8 Hz, 1H), 6.39 (s, 1H), 5.71 (s, 2H), 4.02 (s, 3H).

Additional Intermediates

| | |
|---|---|
| I106 | Phenylmethanesulfonyl chloride |
| I107 | Benzenesulfonyl chloride |
| I108 | ((2-Chloroethyl)sulfonyl)benzene |
| I109 | 5-(2-Methoxyphenyl)-1,3,4-thiadiazol-2-amine |

Examples 1-23 (Table A)

General Method AA:

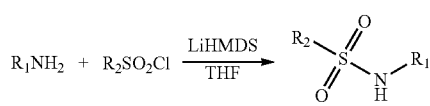

To a solution of the amine (1.0 eq) in anhydrous THF (10 mL) at −78° C. under $N_2$ was added LiHMDS (1 M solution in THF, 1.8-5.0 eq) dropwise and the mixture was stirred at −78° C. for 2 h unless specified otherwise. A solution of sulfonyl chloride (1.5 eq, unless specified otherwise) in anhydrous THF (2.0 mL) was then added dropwise and the mixture was allowed to warm to room temperature and stirred overnight. Where specified in Table A, the reaction was quenched with 1 M HCl. Water was added and the mixture was extracted with EtOAc. The combined organic extracts were washed with brine, dried over anhydrous $Na_2SO_4$, filtered and concentrated under reduced pressure. The residue was purified by column chromatography, preparative TLC, prep HPLC and/or recrystallization to give the desired compound.

General Method AB:

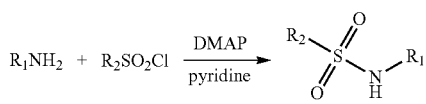

To a solution of the amine (1.0 eq) in pyridine (4 mL) under $N_2$ was added the sulfonyl chloride (1.5 eq) and DMAP (0.2 eq) and the mixture was heated at 90° C. overnight. The reaction was quenched with 1 M HCl, water was then added and the mixture was extracted with EtOAc. The combined organic extracts were washed with brine, anhydrous $Na_2SO_4$, filtered and concentrated under reduced pressure. The residue was purified by preparative TLC to give the desired compound.

The following examples were synthesized according to general method AA or AB using the appropriate amine $R_1NH_2$ and sulfonyl chloride $R_2SO_2Cl$ intermediate.

TABLE A

| Example | Starting materials | Name and structure | Analytical data | Method | Notes |
|---|---|---|---|---|---|
| 1 | I18 & I13 | 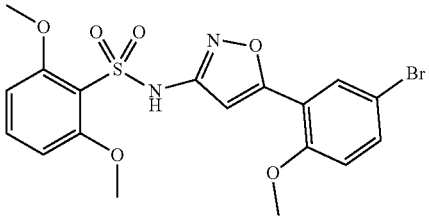 [SMILES: COc1ccc(Br)cc1-c1cc(NS(=O)(=O)c2c(OC)cccc2OC)no1]<br>N-(5-(5-Bromo-2-methoxyphenyl)isoxazol-3-yl)-2,6-dimethoxybenzenesulfonamide | LCMS-A (ES-API): $R_t$ 2.34 min; m/z 468.8/470.8 [M + H]$^+$; $^1$H NMR (400 MHz, DMSO-$d_6$) δ 11.2 (s, 1H), 7.83 (d, J = 2.0 Hz, 1H), 7.66-7.63 (m, 1H), 7.49 (t, J = 8.4 Hz, 1H), 7.18 (t, J = 9.2 Hz 1H), 6.77 (d, J = 8.4 Hz, 2H), 6.72 (s, 1H), 3.91 (s, 3H), 3.72 (s, 6H). | AA | 5.0 eq LiHMDS used; Column chromatography (petroleum ether/EtOAc 5/1) |
| 2 | I106 & I2 | 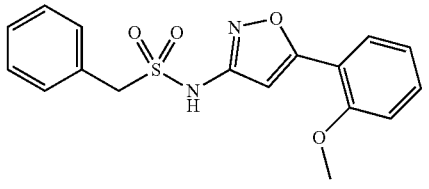 [SMILES: COc1ccccc1-c1cc(NS(=O)(=O)Cc2ccccc2)no1]<br>N-(5-(2-Methoxyphenyl)isoxazol-3-yl)-1-phenylmethanesulfonamide | LCMS-A (ES-API): $R_t$ 2.35 min, m/z 345.0 [M + H]$^+$; $^1$H NMR (400 MHz, DMSO-$d_6$) δ 11.0 (s, 1H), 7.82 (dd, J = 7.8, 1.4 Hz, 1H), 7.56-7.47 (m, 1H), 7.41-7.30 (m, 5H), 7.23 (d, J = 8.4 Hz, 1H), 7.11 (t, J = 7.5 Hz, 1H), 6.49 (s, 1H), 4.67 (s, 2H), 3.92 (s, 3H). | AB | Prep. TLC (CHCl$_3$/MeOH 100/1) |
| 3 | I107 & I2 | 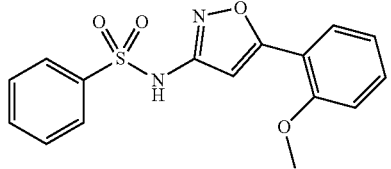 [SMILES: COc1ccccc1-c1cc(NS(=O)(=O)c2ccccc2)no1]<br>N-(5-(2-Methoxyphenyl)isoxazol-3-yl)benzenesulfonamide | LCMS-A (ES-API): $R_t$ 2.20 min, m/z 330.9 [M + H]$^+$; $^1$H NMR (400 MHz, DMSO-d6) δ 11.6 (s, 1H), 7.90 (d, J = 7.7 Hz, 2H), 7.78-7.73 (m, 1H), 7.72-7.58 (m, 3H), 7.53-7.46 (m, 1H), 7.21 (d, J = 8.5 Hz, 1H), 7.08 (t, J = 7.6 Hz, 1H), 6.70 (s, 1H), 3.94 (s, 3H). | AA | 3.0 eq LiHMDS used; Quenched with 1 M HCl before workup; Purified by prep HPLC |

TABLE A-continued

| Example | Starting materials | Name and structure | Analytical data | Method | Notes |
|---|---|---|---|---|---|
| 4 | I108 & I2 | 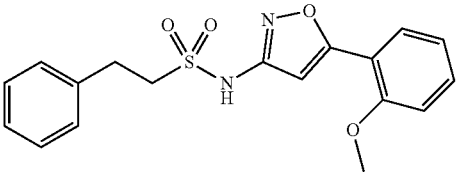 [SMILES: COc1ccccc1-c1cc(NS(=O)(=O)CCc2ccccc2)no1]<br>N-(5-(2-Methoxyphenyl)isoxazol-3-yl)-2-phenylethane-1-sulfonamide | LCMS-A (ES-API): $R_t$ 2.32 min, m/z 380.9 [M + Na]$^+$; $^1$H NMR (400 MHz, DMSO-$d_6$) δ 11.2 (s, 1H), 7.82 (dd, J = 7.8, 1.5 Hz, 1H), 7.54-7.48 (m, 1H), 7.32-7.17 (m, 6H), 7.11 (t, J = 7.5 Hz, 1H), 6.71 (s, 1H), 3.94 (s, 3H), 3.67-3.58 (m, 2H), 3.08-2.99 (m, 2H). | AA | 3.0 eq LiHMDS used; Quenched with 1 M HCl before workup; Prep. TLC (DCM/ MeOH 100/1) |
| 5 | I18 & I7 | 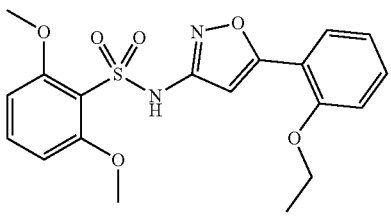 [SMILES: CCOc1ccccc1-c1cc(NS(=O)(=O)c2c(OC)cccc2OC)no1]<br>N-(5-(2-Ethoxyphenyl)isoxazol-3-yl)-2,6-dimethoxybenzenesulfonamide | LCMS-A (ES-API): $R_t$ 2.19 min, m/z 404.9 [M + H]$^+$; $^1$H NMR (400 MHz, DMSO-$d_6$) δ 11.1 (s, 1H), 7.75 (dd, J = 7.8, 1.7 Hz, 1H), 7.52-7.40 (m, 2H), 7.15 (d, J = 8.4 Hz, 1H), 7.09-7.02 (m, 1H), 6.78 (s, 1H), 6.75 (s, 2H), 4.14 (q, J = 6.9 Hz, 2H), 3.81 (s, 6H), 1.35 (t, J = 6.9 Hz, 3H). | AA | 3.0 eq LiHMDS used; Prep. TLC (DCM/ MeOH 100/1) |
| 6 | I47 & I5 | 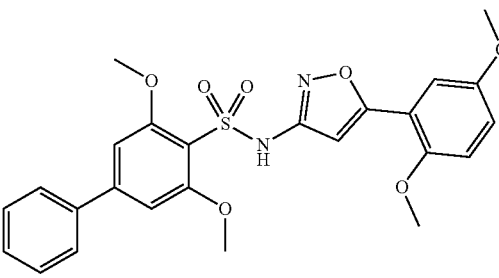<br>N-(5-(2,5-Dimethoxyphenyl)isoxazol-3-yl)-3,5-dimethoxy-[1,1'-biphenyl]-4-sulfonamide | LCMS-A (ES-API): $R_t$ 2.41 min, m/z 497.1 [M + H]$^+$; $^1$H NMR (400 MHz, DMSO-$d_6$) δ 11.2 (s, 1H), 7.77 (d, J = 7.2 Hz, 2H), 7.43-7.50 (m, 3H), 7.26 (d, J = 2.8 Hz, 1H), 7.15 (d, J = 9.2 Hz, 1H), 7.07 (t, J = 2.8 Hz, 1H), 6.99 (s, 2H), 6.76 (s, 1H), 3.94 (s, 6H), 3.85 (s, 3H), 3.75 (s, 3H). | AA | 3.0 eq LiHMDS used; Recrystallized from petroleum ether |
| 7 | I18 & I5 | 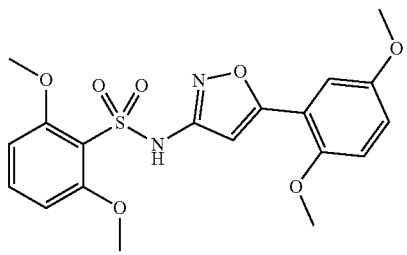 [SMILES: COc1ccc(OC)c(-c2cc(NS(=O)(=O)c3c(OC)cccc3OC)no2)c1]<br>N-(5-(2,5-Dimethoxyphenyl)isoxazol-3-yl)-2,6-dimethoxybenzenesulfonamide | LCMS-A (ES-API): $R_t$ 2.34 min, m/z 421.1 [M + H]$^+$; $^1$H NMR (400 MHz, DMSO-$d_6$) δ 11.1 (s, 1H), 7.49 (t, J = 8.5 Hz, 1H), 7.25 (d, J = 3.0 Hz, 1H), 7.14 (d, J = 9.1 Hz, 1H), 7.05 (dd, J = 9.1, 3.1 Hz, 1H), 6.77 (d, J = 8.5 Hz, 2H), 6.70 (s, 1H), 3.84 (s, 3H), 3.83 (s, 6H), 3.75 (s, 3H). | AA | 3.0 eq LiHMDS used; Recrystallized from petroleum ether |

TABLE A-continued

| Example | Starting materials | Name and structure | Analytical data | Method | Notes |
|---|---|---|---|---|---|
| 8 | I18 & I11 | 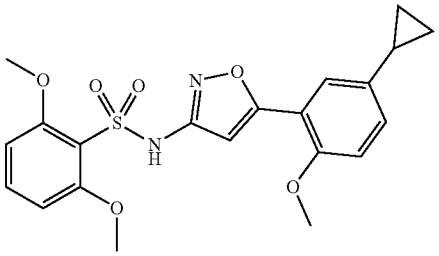 [SMILES: COc1ccc(C2CC2)cc1-c1cc(NS(=O)(=O)c2c(OC)cccc2OC)no1]<br>N-(5-(5-Cyclopropyl-2-methoxyphenyl)isoxazol-3-yl)-2,6-dimethoxybenzenesulfonamide | LCMS-A (ES-API): $R_t$ 2.36 min; m/z 431.0 [M + H]$^+$; $^1$H NMR (400 MHz, DMSO-d$_6$) δ 11.1 (s, 1H), 7.48 (t, J = 8.5 Hz, 1H), 7.44 (d, J = 2.2 Hz, 1H), 7.16 (dd, J = 8.7, 2.2 Hz, 1H), 7.07 (d, J = 8.7 Hz, 1H), 6.77 (d, J = 8.5 Hz, 2H), 6.66 (s, 1H), 3.85 (s, 3H), 3.82 (s, 6H), 1.97-1.90 (m, 1H), 0.95-0.87 (m, 2H), 0.67-0.58 (m, 2H). | AA | 3.0 eq LiHMDS used; Recrystallized from petroleum ether |
| 9 | I18 & I1 | 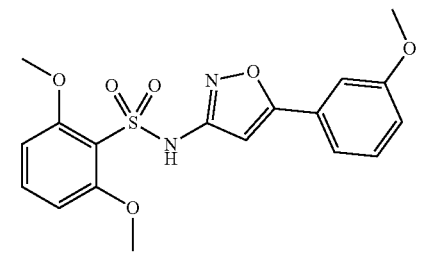 [SMILES: COc1cccc(-c2cc(NS(=O)(=O)c3c(OC)cccc3OC)no2)c1]<br>2,6-Dimethoxy-N-(5-(3-methoxyphenyl)isoxazol-3-yl)benzenesulfonamide | LCMS-A (ES-API): $R_t$ 2.10 min, m/z 391.0 [M + H]$^+$, 413.0 [M + Na]$^+$; $^1$H NMR (400 MHz, DMSO-d$_6$) δ 11.1 (s, 1H), 7.48 (t, J = 8.5 Hz, 1H), 7.41 (t, J = 7.9 Hz, 1H), 7.37-7.33 (m, 1H), 7.31-7.28 (m, 1H), 7.07-7.02 (m, 1H), 6.77 (s, 1H), 6.76 (d, J = 8.8 Hz, 2H), 3.81 (s, 3H), 3.80 (s, 6H). | AA | 3.0 eq LiHMDS used; Prep. TLC (DCM/MeOH, 100/1) |
| 10 | I21 & I2 | 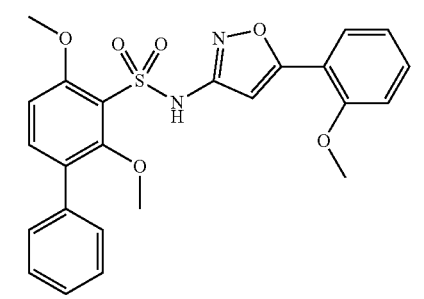 [SMILES: COc1ccccc1-c1cc(NS(=O)(=O)c2c(OC)ccc(-c3ccccc3)c2OC)no1]<br>2,4-Dimethoxy-N-(5-(2-methoxyphenyl)isoxazol-3-yl)-[1,1'-biphenyl]-3-sulfonamide | LCMS-A (ES-API): $R_t$ 2.48 min, m/z 467.0 [M + H]$^+$, 489.0 [M + Na]$^+$; $^1$H NMR (400 MHz, DMSO-d$_6$) δ 11.3 (s, 1H), 7.81-7.74 (m, 1H), 7.57-7.42 (m, 6H), 7.40-7.34 (m, 1H), 7.20 (d, J = 8.3 Hz, 1H), 7.12-7.02 (m, 2H), 6.78 (s, 1H), 3.88 (s, 3H), 3.87 (s, 3H), 3.38 (s, 3H). | AA | 3.0 eq LiHMDS used; Prep. TLC (DCM/MeOH, 100/1) |
| 11 | I47 & I2 | 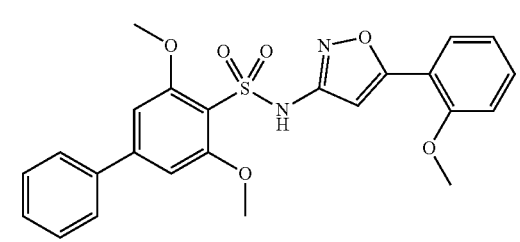 [SMILES: COc1ccccc1-c1cc(NS(=O)(=O)c2c(OC)cc(-c3ccccc3)cc2OC)no1]<br>3,5-Dimethoxy-N-(5-(2-methoxyphenyl)isoxazol-3-yl)-[1,1'-biphenyl]-4-sulfonamide | LCMS-A (ES-API): $R_t$ 2.42 min, m/z 467.0 [M + H]$^+$; $^1$H NMR (400 MHz, DMSO-d$_6$) δ 11.2 (s, 1H), 7.82-7.72 (m, 3H), 7.53-7.38 (m, 4H), 7.20 (d, J = 8.4 Hz, 1H), 7.06 (t, J = 7.5 Hz, 1H), 6.99 (s, 2H), 6.74 (s, 1H), 3.94 (s, 6H), 3.91 (s, 3H). | AA | 3.0 eq LiHMDS used; 1.8 eq sulfonyl chloride used; Recrystallized from petroleum ether |

TABLE A-continued

| Example | Starting materials | Name and structure | Analytical data | Method | Notes |
|---|---|---|---|---|---|
| 12 | I19 & I8 | 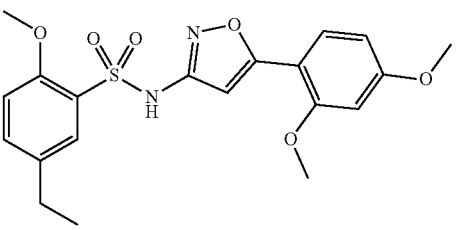 [SMILES: CCc1ccc(OC)c(S(=O)(=O)Nc2cc(-c3ccc(OC)cc3OC)on2)c1]<br>N-(5-(2,4-Dimethoxyphenyl)isoxazol-3-yl)-5-ethyl-2-methoxybenzenesulfonamide | LCMS-B (ES-API): $R_t$ 2.82 min, m/z 419.0 [M + H]$^+$; $^1$H NMR (400 MHz, DMSO-d$_6$) δ 11.2 (s, 1H), 7.69-7.65 (m, 2H), 7.46 (dd, J = 8.5, 2.3 Hz, 1H), 7.13 (d, J = 8.5 Hz, 1H), 6.71 (d, J = 2.3 Hz, 1H), 6.65 (dd, J = 8.7, 2.4 Hz, 1H), 6.50 (s, 1H), 3.90 (s, 3H), 3.82 (s, 3H), 3.79 (s, 3H), 2.61 (q, J = 7.6 Hz, 2H), 1.15 (t, J = 7.6 Hz, 3H). | AA | 3.0 eq LiHMDS used; 3.0 eq sulfonyl chloride used; Prep. TLC (DCM/MeOH, 80/1) |
| 13 | I19 & I1 | 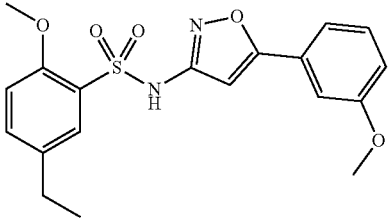 [SMILES: CCc1ccc(OC)c(S(=O)(=O)Nc2cc(-c3cccc(OC)c3)on2)c1]<br>5-Ethyl-2-methoxy-N-(5-(3-methoxyphenyl)isoxazol-3-yl)benzenesulfonamide | LCMS-B (ES-API): $R_t$ 2.87 min, m/z 389.0 [M + H]$^+$; $^1$H NMR (400 MHz, DMSO-d$_6$) δ 11.3 (s, 1H), 7.72 (s, 1H), 7.53-7.28 (m, 4H), 7.12 (d, J = 8.4 Hz, 1H), 7.07 (d, J = 5.6 Hz, 1H), 6.85 (s, 1H), 3.81 (s, 3H), 3.78 (s, 3H), 2.61 (q, J = 7.6 Hz, 2H), 1.15 (t, J = 7.6 Hz, 3H). | AA | 2.0 eq LiHMDS used and stirred at -78° C. for 30 min before adding sulfonyl chloride; Prep. TLC (DCM/MeOH, 60/1) |
| 14 | I18 & I29 | 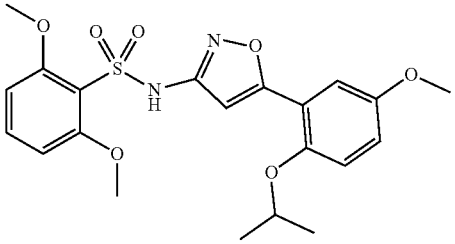 [SMILES: COc1ccc(OC(C)C)c(-c2cc(NS(=O)(=O)c3c(OC)cccc3OC)no2)c1]<br>N-(5-(2-Isopropoxy-5-methoxyphenyl)isoxazol-3-yl)-2,6-dimethoxybenzenesulfonamide | LCMS-A (ES-API): $R_t$ 2.39 min; m/z 449.0 [M + H]$^+$; $^1$H NMR (400 MHz, CDCl3) δ 7.95 (s, 1H), 7.43-7.33 (m, 2H), 7.10 (s, 1H), 6.93-6.87 (m, 2H), 6.61 (d, J = 8.5 Hz, 2H), 4.60-4.51 (m, 1H), 3.94 (s, 6H), 3.79 (s, 3H), 1.36 (d, J = 6.0 Hz, 6H). | AA | 3.0 eq LiHMDS used; Column chromatography (DCM/MeOH = 50/1) and recrystallization from petroleum ether/EtOAc = 3/1 |
| 15 | I18 & I38 | 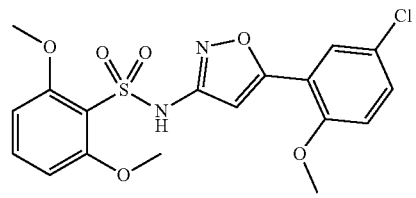 [SMILES: COc1ccc(Cl)cc1-c1cc(NS(=O)(=O)c2c(OC)cccc2OC)no1]<br>N-(5-(5-Chloro-2-methoxyphenyl)isoxazol-3-yl)-2,6-dimethoxybenzenesulfonamide | LCMS-A (ES-API): $R_t$ 2.28 min; m/z 424.9 [M + H]$^+$; $^1$H NMR (400 MHz, DMSO-d$_6$) δ 11.2 (s, 1H), 7.72 (d, J = 2.7 Hz, 1H), 7.56-7.45 (m, 2H), 7.24 (d, J = 9.0 Hz, 1H), 6.81-6.71 (m, 3H), 3.91 (s, 3H), 3.82 (s, 6H). | AA | 5 eq LiHMDS used; Prep. TLC (petroleum ether/EtOAc = 3/1) |
| 16 | I18 & I26 | 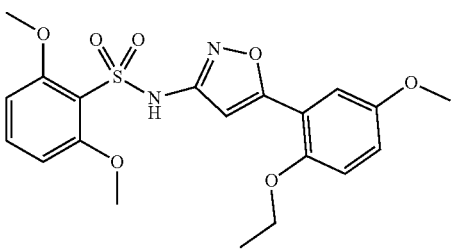 [SMILES: CCOc1ccc(OC)cc1-c1cc(NS(=O)(=O)c2c(OC)cccc2OC)no1] | LCMS-A (ES-API): $R_t$ 2.23 min, m/z 435.0 [M + H]$^+$; $^1$H NMR (400 MHz, DMSO-d$_6$) δ 11.1 (s, 1H), 7.48 (t, J = 8.5 Hz, 1H), 7.24 (d, J = 3.1 Hz, 1H), 7.12-7.08 (m, 1H), 7.06-7.00 (m, 1H), 6.79-6.74 (m, 3H), 4.07 (q, J = 6.9 Hz, 2H), 3.80 (s, 6H), 3.75 (s, 3H), 1.31 (t, J = 6.9 Hz, 3H). | AA | 3.0 eq LiHMDS used; Purified by prep HPLC |

TABLE A-continued

| Example | Starting materials | Name and structure | Analytical data | Method | Notes |
|---|---|---|---|---|---|
| 17 | I18 & I109 | N-(5-(2-Ethoxy-5-methoxyphenyl)isoxazol-3-yl)-2,6-dimethoxybenzenesulfonamide | LCMS-A (ES-API): $R_t$ 1.83 min, m/z 407.9 [M + H]$^+$; $^1$H NMR (400 MHz, DMSO-d$_6$) δ 14.1 (s, 1H), 8.03-7.96 (m, 1H), 7.58-7.50 (m, 1H), 7.44 (t, J = 8.4 Hz, 1H), 7.31-7.25 (m, 1H), 7.16-7.09 (m, 1H), 6.74 (d, J = 8.5 Hz, 2H), 3.97 (s, 3H), 3.71 (s, 6H). | AB | Prep TLC (petroleum ether/ EtOAc = 10/1) |
| | | 2,6-Dimethoxy-N-(5-(2-methoxyphenyl)-1,3,4-thiadiazol-2-yl)benzenesulfonamide | | | |
| 18 | I18 & I42 | 2,6-Dimethoxy-N-(5-(2-methoxy-5-(oxazol-2-yl)phenyl)isoxazol-3-yl)benzenesulfonamide | LCMS-A (ES-API): $R_t$ 2.01 min, m/z 457.9 [M + H]$^+$; $^1$H NMR (400 MHz, DMSO-d$_6$) δ 11.2 (s, 1H), 8.31 (d, J = 2.2 Hz, 1H), 8.21 (s, 1H), 8.05 (dd, J = 8.8, 2.3 Hz, 1H), 7.47 (t, J = 8.7 Hz, 1H), 7.41-7.34 (m, 2H), 6.82-6.72 (m, 3H), 3.98 (s, 3H), 3.82 (s, 6H). | AA | 3.0 eq LiHMDS used; Quenched with 1 M HCl before workup; Prep. TLC (CHCl$_3$/ MeOH = 100/1) |
| 19 | I18 & I33 | N-(5-(5-(Cyclohexylmethyl)-2-methoxyphenyl)isoxazol-3-yl)-2,6-dimethoxybenzenesulfonamide | LCMS-A (ES-API): $R_t$ 2.77 min, m/z 487.0 [M + H]$^+$; $^1$H NMR (400 MHz, DMSO-d$_6$) δ 11.1 (s, 1H), 7.52-7.44 (m, 2H), 7.24 (dd, J = 8.5, 2.2 Hz, 1H), 7.09 (d, J = 8.6 Hz, 1H), 6.77 (d, J = 8.5 Hz, 2H), 6.67 (s, 1H), 3.86 (s, 3H), 3.83 (s, 6H), 2.44 (d, J = 7.0 Hz, 2H), 1.67-1.53 (m, 5H), 1.48-1.40 (m, 1H), 1.17-1.08 (m, 3H), 0.95-0.83 (m, 2H). | AA | 4 eq LiHMDS used; Prep. TLC (DCM/ MeOH = 75/1) |
| 20 | I18 & I34 | N-(3-(5-(Cyclohexylmethyl)-2-methoxyphenyl)isoxazol-5-yl)-2,6-dimethoxybenzenesulfonamide | LCMS-A (ES-API): $R_t$ 2.71 min, m/z 487.0 [M + H]$^+$; $^1$H NMR (400 MHz, DMSO-d$_6$) δ 11.8 (s, 1H), 7.52 (t, J = 8.5 Hz, 1H), 7.42 (d, J = 2.3 Hz, 1H), 7.24-7.17 (m, 1H), 7.07-7.00 (m, 1H), 6.80 (d, J = 8.5 Hz, 2H), 6.04 (s, 1H), 3.83 (s, 6H), 3.76 (s, 3H), 2.40 (d, J = 7.0 Hz, 2H), 1.70-1.51 (m, 5H), 1.49-1.36 (m, 1H), 1.19-1.07 (m, 3H), 0.96-0.81 (m, 2H). | AA | 4 eq LiHMDS used; Prep. TLC (DCM/ MeOH = 75/1) |

TABLE A-continued

| Example | Starting materials | Name and structure | Analytical data | Method | Notes |
|---|---|---|---|---|---|
| 21 | I18 & I36 | 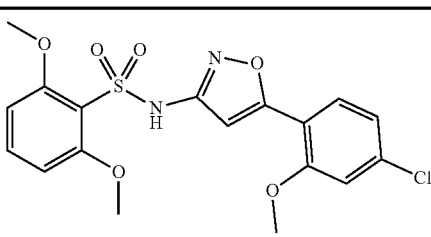<br>N-(5-(4-Chloro-2-methoxyphenyl)isoxazol-3-yl)-2,6-dimethoxybenzenesulfonamide | LCMS-A (ES-API): $R_t$ 2.29 min, m/z 424.9 [M + H]$^+$; $^1$H NMR (400 MHz, DMSO-$d_6$) δ 11.1 (s, 1H), 7.75 (d, J = 8.4 Hz, 1H), 7.49 (t, J = 8.5 Hz, 1H), 7.31 (d, J = 2.0 Hz, 1H), 7.14 (dd, J = 8.4, 2.0 Hz, 1H), 6.77 (d, J = 8.5 Hz, 2H), 6.68 (s, 1H), 3.93 (s, 3H), 3.82 (s, 6H). | AA | 4 eq LiHMDS used; Prep. TLC (DCM/MeOH = 100/1) |
| 22 | I18 & I30 | 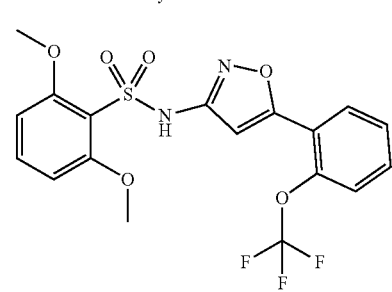<br>2,6-Dimethoxy-N-(5-(2-(trifluoromethoxy)phenyl)isoxazol-3-yl)benzenesulfonamide | LCMS-A (ES-API): $R_t$ 2.30 min; m/z 444.9 [M + H]$^+$; $^1$H NMR (400 MHz, MeOD) δ 7.91 (dd, J = 7.8, 1.8 Hz, 1H), 7.60-7.54 (m, 1H), 7.51-7.43 (m, 3H), 6.77-6.73 (m, 3H), 3.89 (s, 6H). | AA | 3.0 eq LiHMDS used; Purified by prep HPLC |
| 23 | I18 & I45 | 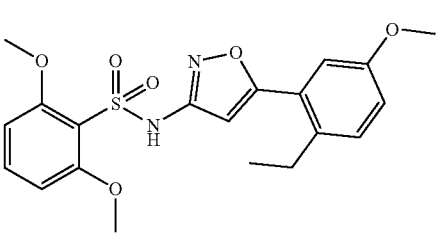 [SMILES: CCc1ccc(OC)cc1-c1cc(NS(=O)(=O)c2c(OC)cccc2OC)no1]<br>N-(5-(2-Ethyl-5-methoxyphenyl)isoxazol-3-yl)-2,6-dimethoxybenzenesulfonamide | LCMS-A (ES-API): $R_t$ 2.40 min, m/z 419.0 [M + H]$^+$; $^1$H NMR (400 MHz, DMSO-$d_6$) δ 11.2 (s, 1H), 7.52 (t, J = 8.0 Hz, 1H), 7.29 (d, J = 8.4 Hz, 1H), 7.04-7.00 (m, 2H), 6.79 (d, J = 8.4 Hz, 2H), 6.46 (s, 1H), 3.81 (s, 6H), 3.76 (s, 3H), 2.59 (q, J = 7.2 Hz, 2H), 1.04 (t, J = 7.2 Hz, 3H) | AA | 3.0 eq LiHMDS used; Prep. TLC (petroleum ether/EtOAc = 10/1) |

Examples 24-42 (Table B)

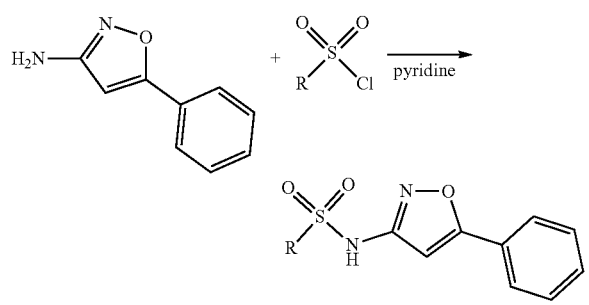

General Procedure BA:

5-Phenylisoxazol-3-amine (0.050 g, 0.312 mmol) and the appropriate sulfonyl chloride (1 eq) in pyridine (0.125 μL) were irradiated in a microwave reactor at 110° C. for 2 h. The reaction was cooled and concentrated to dryness. The material was partitioned between 1 M HCl (2 mL) and EtOAc (2 mL), then the layers were separated. The organic layer was washed with 1 M HCl (1 mL), brine (1 mL) and dried (Na$_2$SO$_4$). The crude material was taken up in minimal EtOAc and allowed to stand for 2 h at 0° C. The resulting precipitate was collected and air-dried to give the desired product.

General Procedure BB:

A mixture of 5-phenylisoxazol-3-amine (0.050 g, 0.312 mmol), the appropriate sulfonyl chloride (2 eq) and pyridine (1 mL) was stirred at room temperature for 16 h. The mixtures were diluted with DCM (1 mL) and washed with 1 M HCl (2 mL). The aqueous layer was removed and the organic layer was dried to give the crude residue. The product was purified by HPLC to give the title compound.

General Method BC:

Sulfonyl chlorides (0.62 mmol) were added to a solution of 5-phenylisoxazol-3-amine (50 mg, 0.31 mmol) in pyridine (1 mL). The reaction mixture was stirred at room temperature overnight. 2 N HCl (10 mL) and EtOAc were added. The layers were separated and the aqueous layer was extracted with EtOAc (2×10 mL). The combined organic layers were washed with brine, dried ($Na_2SO_4$) and concentrated. Purification via preparative mass-directed HPLC obtained the desired product.

General Method BD:

5-Phenylisoxazol-3-amine (50 mg, 0.312 mmol), the appropriate sulfonyl chloride (0.624 mmol, 2 eq) and pyridine (1 mL) were stirred at room temperature for 3 days. The mixtures were diluted with DCM (1 mL) and washed with 1 M HCl (2 mL). The aqueous layer was removed and the organic layer was dried to give the crude residues. The crude product was purified by HPLC to give the title compound.

General Method BE:

5-Phenylisoxazole-3-amine (50 mg, 0.312 mmol), the appropriate sulfonyl chloride (0.624 mmol, 2 eq) and pyridine (1 mL) were combined. The reaction mixtures were stirred at room temperature for 1 day. The mixtures were diluted with DCM (1 mL) and washed with 1 M HCl (2 mL). The aqueous layer was removed and the organic layer was dried to give the crude residue. The crude material was purified by flash chromatography, gradient eluting with 100% dichloromethane to 30% MeOH/dichloromethane, to give the title compound.

General Method BF:

The compounds were prepared as per general method BE and then further purified by HPLC to give the title compound.

The following examples in Table B were synthesized according to general method BA, BB, BC BD, BE or BF using the appropriate sulfonyl chloride $RSO_2Cl$ intermediate.

TABLE B

| Example | Structure | Name | LCMS | Method |
| --- | --- | --- | --- | --- |
| 24 | 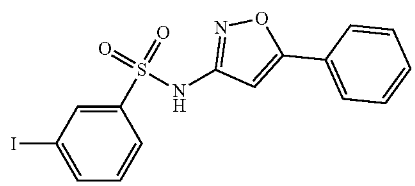 [SMILES: O=S(=O)(Nc1cc(-c2ccccc2)on1)c1cccc(I)c1] | 3-iodo-N-(5-phenylisoxazol-3-yl)benzenesulfonamide | LCMS: $R_t$ 3.484 min; m/z 426.7 $[M + H]^+$ | BA |
| 25 | 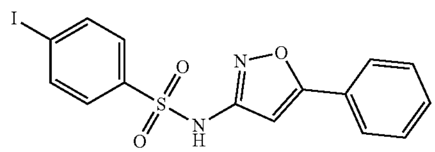 [SMILES: O=S(=O)(Nc1cc(-c2ccccc2)on1)c1ccc(I)cc1] | 4-iodo-N-(5-phenylisoxazol-3-yl)benzenesulfonamide | LCMS: $R_t$ 3.611 min; m/z 426.7 $[M + H]^+$ | BA |
| 26 | 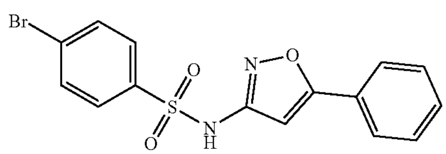 [SMILES: O=S(=O)(Nc1cc(-c2ccccc2)on1)c1ccc(Br)cc1] | 4-bromo-N-(5-phenylisoxazol-3-yl)benzenesulfonamide | LCMS: $R_t$ 3.594 min; m/z 380.7 $[M + H]^+$ | BA |
| 27 | 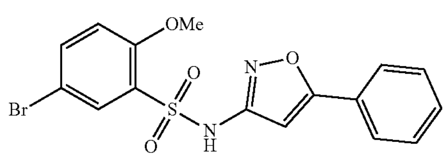 [SMILES: COc1ccc(Br)cc1S(=O)(=O)Nc1cc(-c2ccccc2)on1] | 5-bromo-2-methoxy-N-(5-phenylisoxazol-3-yl)benzenesulfonamide | LCMS: $R_t$ 5.57 min, m/z = 409.1 $[M + H]^+$ | BB |
| 28 | 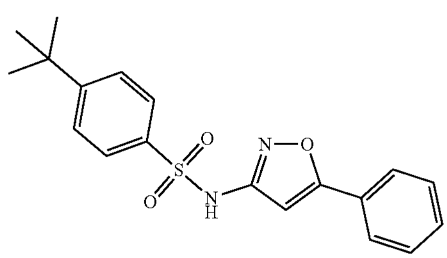 [SMILES: CC(C)(C)c1ccc(S(=O)(=O)Nc2cc(-c3ccccc3)on2)cc1] | 4-(tert-butyl)-N-(5-phenylisoxazol-3-yl)benzenesulfonamide | LCMS: $R_t$ 5.82 min, m/z 357.4 $[M + H]^+$. | BB |
| 29 | 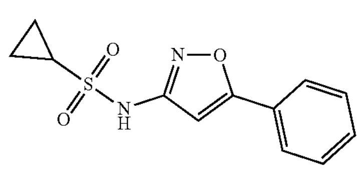 [SMILES: O=S(=O)(Nc1cc(-c2ccccc2)on1)C1CC1] | N-(5-phenylisoxazol-3-yl)cyclopropanesulfonamide | LCMS: $R_t$ 5.06 min, m/z 265.7 $[M + H]^+$. | BC |

TABLE B-continued

| Example | Structure | Name | LCMS | Method |
|---|---|---|---|---|
| 30 | 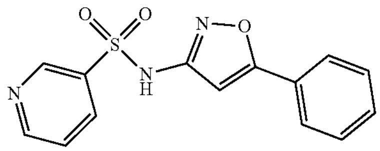 [SMILES: O=S(=O)(Nc1cc(-c2ccccc2)on1)c1cccnc1] | N-(5-phenylisoxazol-3-yl)pyridine-3-sulfonamide | LCMS: $R_t$ 5.00 min, m/z 302.5 [M + H]$^+$. | BC |
| 31 | 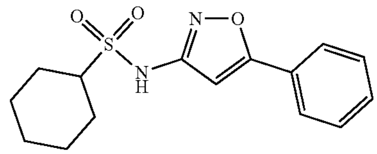 [SMILES: O=S(=O)(Nc1cc(-c2ccccc2)on1)C1CCCCC1] | N-(5-phenylisoxazol-3-yl)cyclohexanesulfonamide | LCMS: $R_t$ 6.47 min, m/z 305.1 [M − H]$^-$. | BC |
| 32 | 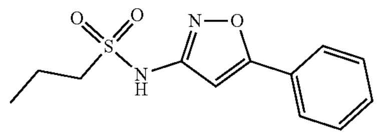 [SMILES: CCCS(=O)(=O)Nc1cc(-c2ccccc2)on1] | N-(5-phenylisoxazol-3-yl)propane-1-sulfonamide | LCMS: $R_t$ 5.19 min, m/z 267.2 [M + H]$^+$. | BC |
| 33 | 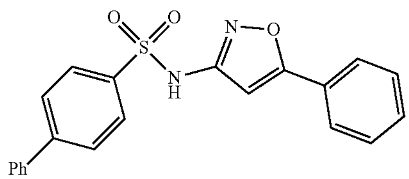 [SMILES: O=S(=O)(Nc1cc(-c2ccccc2)on1)c1ccc(-c2ccccc2)cc1] | N-(5-phenylisoxazol-3-yl)-[1,1'-biphenyl]-4-sulfonamide | LCMS: $R_t$ 6.95 min, m/z 377.28 [M + H]$^+$. | BD |
| 34 | 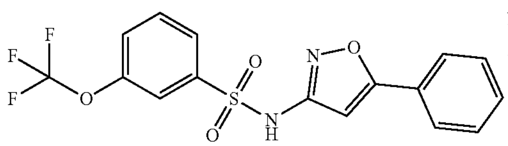 | N-(5-phenylisoxazol-3-yl)-3-(trifluoromethoxy)benzenesulfonamide | LCMS: $R_t$ 5.64 min, m/z 385.5 [M + H]$^+$. | BD |
| 35 | 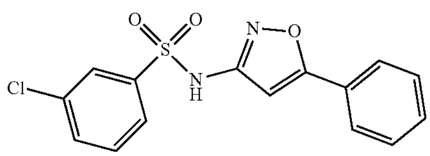 [SMILES: O=S(=O)(Nc1cc(-c2ccccc2)on1)c1cccc(Cl)c1] | 3-chloro-N-(5-phenylisoxazol-3-yl)benzenesulfonamide | LCMS: $R_t$ 5.48 min, m/z 335.4 [M + H]$^+$. | BD |
| 36 | 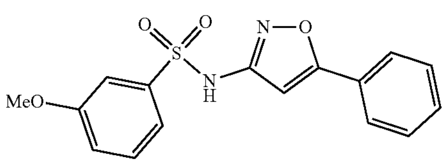 [SMILES: COc1cccc(S(=O)(=O)Nc2cc(-c3ccccc3)on2)c1] | 3-methoxy-N-(5-phenylisoxazol-3-yl)benzenesulfonamide | LCMS: $R_t$ 5.42 min, m/z 331.5 [M + H]$^+$. | BD |
| 37 | 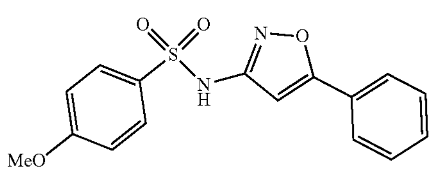 [SMILES: COc1ccc(S(=O)(=O)Nc2cc(-c3ccccc3)on2)cc1] | 4-methoxy-N-(5-phenylisoxazol-3-yl)benzenesulfonamide | LCMS: $R_t$ 5.35 min, m/z 331.3 [M + H]$^+$. | BD |
| 38 | 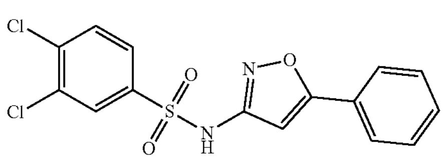 [SMILES: O=S(=O)(Nc1cc(-c2ccccc2)on1)c1ccc(Cl)c(Cl)c1] | 3,4-dichloro-N-(5-phenylisoxazol-3-yl)benzenesulfonamide | LCMS: $R_t$ 6.93 min, m/z 369.15 [M + H]$^+$. | BF |

TABLE B-continued

| Example | Structure | Name | LCMS | Method |
|---|---|---|---|---|
| 39 | 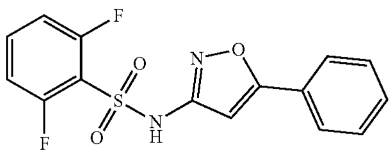 [SMILES: O=S(=O)(Nc1cc(-c2ccccc2)on1)c1c(F)cccc1F] | 2,6-difluoro-N-(5-phenylisoxazol-3-yl)benzenesulfonamide | LCMS: R$_t$ 6.15 min, m/z 337.14 [M + H]$^+$. | BF |
| 40 | 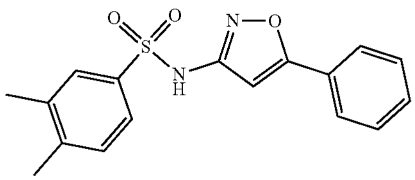 [SMILES: Cc1ccc(S(=O)(=O)Nc2cc(-c3ccccc3)on2)cc1C] | 3,4-dimethyl-N-(5-phenylisoxazol-3-yl)benzenesulfonamide | LCMS: R$_t$ 6.60 min, m/z 329.21 [M + H]$^+$. | BE |
| 41 | 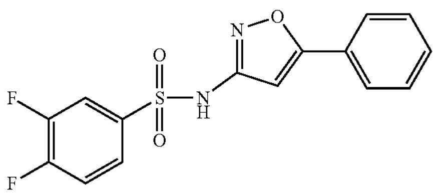 [SMILES: O=S(=O)(Nc1cc(-c2ccccc2)on1)c1ccc(F)c(F)c1] | 3,4-difluoro-N-(5-phenylisoxazol-3-yl)benzenesulfonamide | LCMS: R$_t$ 6.47 min, m/z 337.14 [M + H]$^+$. | BE |
| 42 | 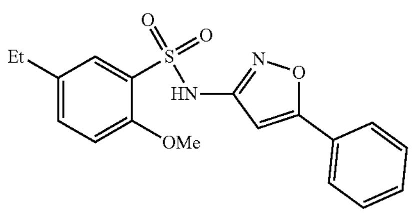 [SMILES: CCc1ccc(OC)c(S(=O)(=O)Nc2cc(-c3ccccc3)on2)c1] | 5-ethyl-2-methoxy-N-(5-phenylisoxazol-3-yl)benzenesulfonamide | LCMS: R$_t$ 5.63 min, m/z 358.8 [M + H]$^+$. | BB |
| 76 | 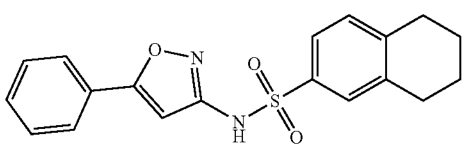 [SMILES: O=S(=O)(Nc1cc(-c2ccccc2)on1)c1ccc2c(c1)CCCC2] | N-(5-phenylisoxazol-3-yl)-5,6,7,8-tetrahydronaphthalene-2-sulfonamide | LCMS R$_t$ 5.77 min, m/z = 355.8 [M + H]$^+$ | BD |

Compounds in Table C were synthesized following analogous methods to general method BD:

TABLE C

| Example | Structure | Name | LCMS |
|---|---|---|---|
| 43 | 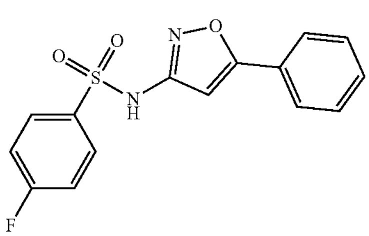 [SMILES: O=S(=O)(Nc1cc(-c2ccccc2)on1)c1ccc(F)cc1] | 4-fluoro-N-(5-phenylisoxazol-3-yl)benzenesulfonamide | LCMS: R$_t$ 6.28 min, m/z 319.25 [M + H]$^+$. |
| 44 | 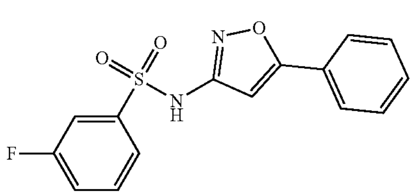 | 3-fluoro-N-(5-phenylisoxazol-3-yl)benzenesulfonamide | LCMS: R$_t$ 6.28 min, m/z 319.25 [M + H]$^+$. |

TABLE C-continued

| Example | Structure | Name | LCMS |
|---|---|---|---|
| 45 | 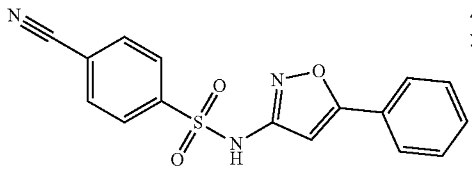 [SMILES: N#Cc1ccc(S(=O)(=O)Nc2cc(-c3ccccc3)on2)cc1] | 4-cyano-N-(5-phenylisoxazol-3-yl)benzenesulfonamide | LCMS: R$_t$ 6.06 min, m/z 326.24 [M + H]$^+$. |
| 46 | 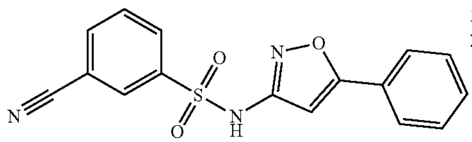 [SMILES: N#Cc1cccc(S(=O)(=O)Nc2cc(-c3ccccc3)on2)c1] | 3-cyano-N-(5-phenylisoxazol-3-yl)benzenesulfonamide | LCMS: R$_t$ 6.05 min, m/z 326.24 [M + H]$^+$. |
| 47 | 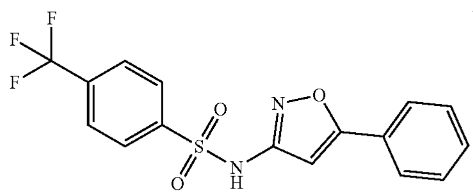 [SMILES: O=S(=O)(Nc1cc(-c2ccccc2)on1)c1ccc(C(F)(F)F)cc1] | N-(5-phenylisoxazol-3-yl)-4-(trifluoromethyl)benzenesulfonamide | LCMS: R$_t$ 6.73 min, m/z 369.15 [M + H]$^+$. |
| 48 | 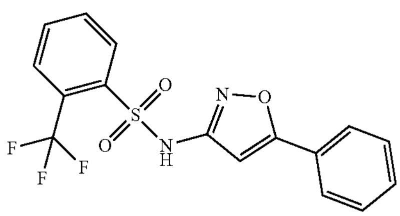 [SMILES: O=S(=O)(Nc1cc(-c2ccccc2)on1)c1ccccc1C(F)(F)F] | N-(5-phenylisoxazol-3-yl)-2-(trifluoromethyl)benzenesulfonamide | LCMS: R$_t$ 5.56 min, m/z 369.7 [M + H]$^+$. |
| 49 | 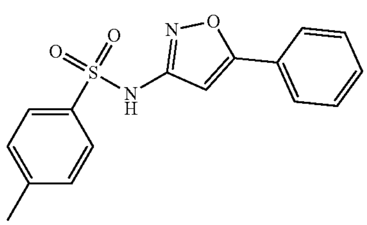 [SMILES: Cc1ccc(S(=O)(=O)Nc2cc(-c3ccccc3)on2)cc1] | 4-methyl-N-(5-phenylisoxazol-3-yl)benzenesulfonamide | LCMS: R$_t$ 5.52 min, m/z 315.4 [M + H]$^+$. |
| 50 | 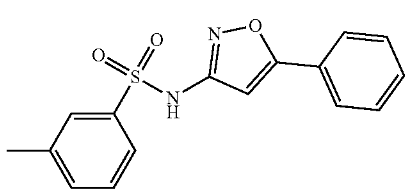 [SMILES: Cc1cccc(S(=O)(=O)Nc2cc(-c3ccccc3)on2)c1] | 3-methyl-N-(5-phenylisoxazol-3-yl)benzenesulfonamide | LCMS: R$_t$ 5.51 min, m/z 315.0 [M + H]$^+$. |
| 51 | 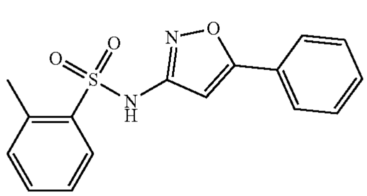 [SMILES: Cc1ccccc1S(=O)(=O)Nc1cc(-c2ccccc2)on1] | 2-methyl-N-(5-phenylisoxazol-3-yl)benzenesulfonamide | LCMS: R$_t$ 5.46 min, m/z 315.1 [M + H]$^+$. |

General Method D:

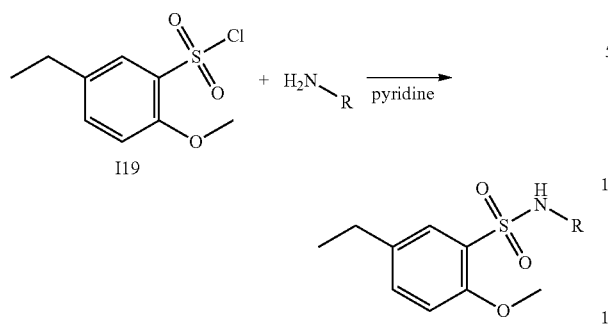

A suspension of 5-ethyl-2-methoxybenzene-1-sulfonyl chloride I19 (150 mg, 0.639 mmol) and the appropriate amine (0.639 mmol) in pyridine (2 mL) was irradiated in the microwave at 110° C. for 2 hours. Water (20 mL) was added and the resultant solid removed by filtration and air-dried to yield the product.

Compounds in Table D were synthesized following analogous methods to general method D:

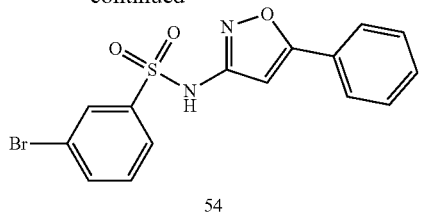

5-Phenylisoxazol-3-amine (0.050 g, 0.312 mmol) and 3-bromo-1-sulfonyl chloride (0.080 g, 0.312 mmol) in pyridine (0.125 mL) were irradiated in a microwave reactor at 110° C. for 3 h. The reaction was cooled and concentrated to dryness. The material was partitioned between 1 M HCl (2 mL) and EtOAc (2 mL), then the layers were separated. The organic layer was washed again with 1 M HCl (1 mL), then brine (1 mL), dried ($Na_2SO_4$) and concentrated in vacuo. The crude material was taken up in minimal EtOAc and hexane was slowly added until precipitation began. The mixture was allowed to stand for 2 h at 0° C. The resulting precipitate was collected and air-dried. Three rounds of precipitation from EtOAc/hexane gave the desired product

TABLE D

| Example | Structure | Name | LCMS |
|---|---|---|---|
| 52 | 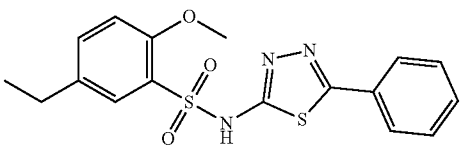 [SMILES: CCc1ccc(OC)c(S(=O)(=O)Nc2nnc(-c3ccccc3)s2)c1] | 5-ethyl-2-methoxy-N-(5-phenyl-1,3,4-thiadiazol-2-yl)benzenesulfonamide | LCMS $R_t$: 6.393 min; m/z 376.0 $[M + H]^+$. |
| 53 | 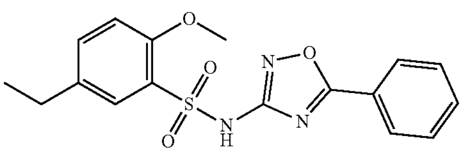 [SMILES: CCc1ccc(OC)c(S(=O)(=O)Nc2noc(-c3ccccc3)n2)c1] | 5-ethyl-2-methoxy-N-(5-phenyl-1,2,4-oxadiazol-3-yl)benzenesulfonamide | LCMS $R_t$: 6.447 min; m/z 360.0 $[M + H]^+$. |

Example 54: 3-Bromo-N-(5-phenylisoxazol-3-yl)benzenesulfonamide, 54

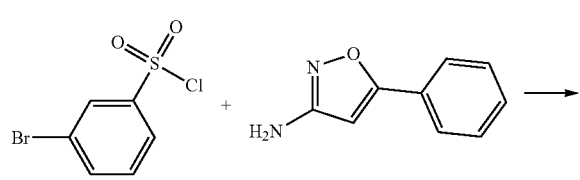

54 (0.042 g, 35% yield) as a >98% pure white solid by LCMS. LCMS: $R_t$ 3.585 min; m/z 380.7 $[M+H]^+$.

Example 55: 2,6-Dimethoxy-N-[5-(2-methoxyphenyl)isoxazol-3-yl]-N-methyl-4-phenyl-benzenesulfonamide, 55

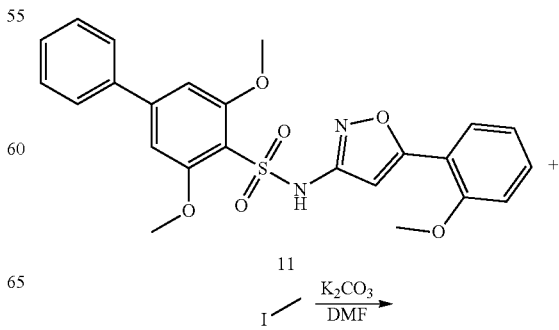

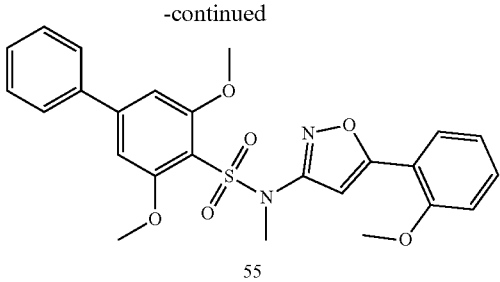

55

To a solution of 2,6-dimethoxy-N-[5-(2-methoxyphenyl)isoxazol-3-yl]-4-phenyl-benzenesulfonamide 11 (0.0170 g, 0.0364 mmol) in anhydrous DMF (1 mL) was added iodomethane (0.00746 mL, 0.120 mmol) and potassium carbonate (0.020 g, 0.15 mmol). The mixture was stirred at room temperature for 4 h, poured into water and extracted with ethyl acetate (3×15 mL). The organic phase was washed with brine and evaporated in vacuo to give the desired product (15 mg, 87% yield) as a yellow oil. $^1$H NMR (400 MHz, Chloroform-d) δ 7.90 (dd, J=7.8, 1.7 Hz, 1H), 7.57-7.51 (m, 2H), 7.49-7.35 (m, 4H), 7.17 (s, 1H), 7.04 (td, J=7.6, 1.1 Hz, 1H), 6.98 (dd, J=8.4, 1.0 Hz, 1H), 6.75 (s, 2H), 3.92 (s, 3H), 3.88 (s, 6H), 3.46 (s, 3H). Purity 95%. LCMS: $R_t$ 6.417 min, m/z 480.7 [M+H]$^+$, 502.7 [M+Na]$^+$.

Example 56: 2,6-Dimethoxy-N-(5-(2-methoxyphenyl)isoxazol-3-yl)benzenesulfonamide, 56

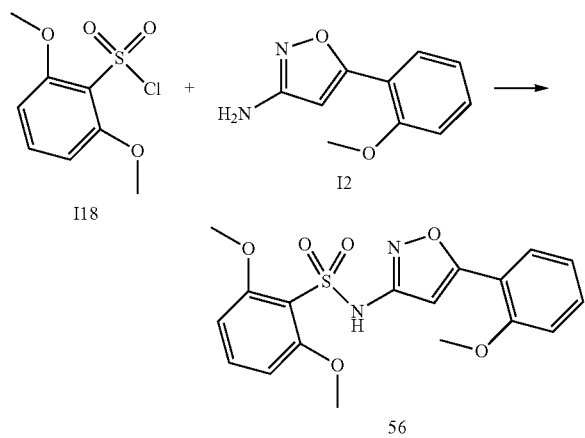

A solution of 2,6-dimethoxybenzenesulfonyl chloride I18 (0.0592 g, 0.250 mmol) and 5-(2-methoxyphenyl)-1,2-oxazol-3-amine I2 (0.0476 g, 0.250 mmol) in pyridine (0.500 mL) was irradiated in the microwave at 130° C. for 2 h. The reaction was cooled to room temperature then diluted with EtOAc (10 mL). The organics were washed with 1 M HCl (10 mL) and the aqueous layer back extracted twice with EtOAc (2×10 mL). The combined organic layers were dried in vacuo and the crude material was purified by solid phase extraction (500 mg, Si-amine cartridge, 3 void volumes of MeOH followed by 3 void volumes of methanolic HCl). The acidic eluate was concentrated in vacuo and the residue wet loaded onto silica gel and purified by column chromatography (4 g, SiO$_2$ cartridge 0-50% EtOAc in petroleum benzine 40-60° C.) to give the title compound 56 (4.40 mg, 4.5% yield) as a white solid. $^1$H NMR (400 MHz, CDCl$_3$) δ 8.00 (s, 1H), 7.83 (dd, J=1.74, 7.79 Hz, 1H), 7.42-7.34 (m, 2H), 7.05-6.94 (m, 3H), 6.61 (d, J=8.50 Hz, 2H), 3.95 (s, 6H), 3.93 (s, 3H). LCMS: $R_t$ 5.70 min, m/z 390.8 [M+H]$^+$, 412.7 [M+Na]$^+$.

Example 57: 2,4-Dimethoxy-N-(5-(2-methoxyphenyl)isoxazol-3-yl)benzenesulfonamide, 57

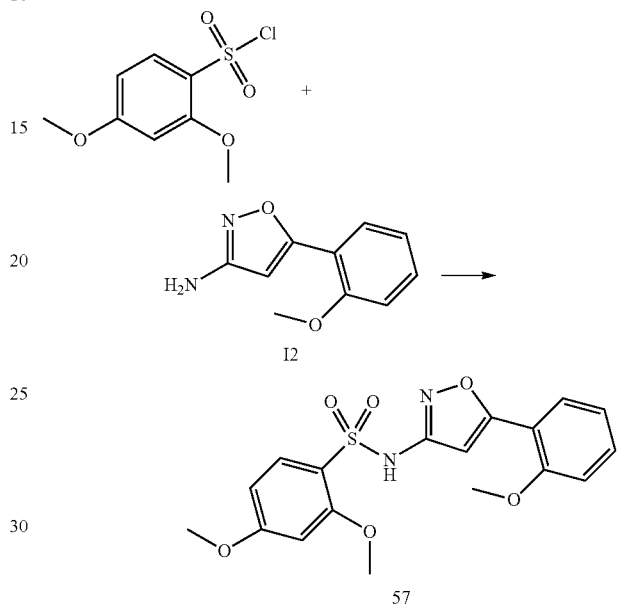

A solution of 2,4-dimethoxybenzene-1-sulfonyl chloride (0.12 g, 0.53 mmol) and 5-(2-methoxyphenyl)isoxazol-3-amine I2 (0.10 g, 0.53 mmol) in pyridine (0.600 mL) was irradiated in the microwave at 130° C. for 2 h. The reaction was cooled to room temperature then diluted with EtOAc (10 mL). The organics were washed with 1 M HCl (10 mL) and the aqueous layer back extracted twice with EtOAc (2×10 mL). The combined organic layers were dried in vacuo and the residue wet-loaded onto silica gel and the product purified by column chromatography (24 g, SiO$_2$ cartridge 0-30% EtOAc in petroleum benzine 40-60° C.) to give the desired product 57 (0.192 g, 94% yield) as a white solid. $^1$H NMR (400 MHz, CDCl$_3$) δ 7.85-7.79 (m, 2H), 7.58 (s, 1H), 7.43-7.36 (m, 1H), 7.03-6.96 (m, 2H), 6.89 (s, 1H), 6.51-6.44 (m, 2H), 3.98 (s, 3H), 3.95 (s, 3H), 3.82 (s, 3H). Purity >85% as judged by $^1$H-NMR. LCMS: $R_t$ 5.86 min, m/z 390.8 [M+H]$^+$.

Example 58: 5-Ethyl-2-methoxy-N-(5-(2-methoxyphenyl)isoxazol-3-yl)benzenesulfonamide, 58

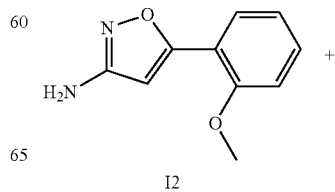

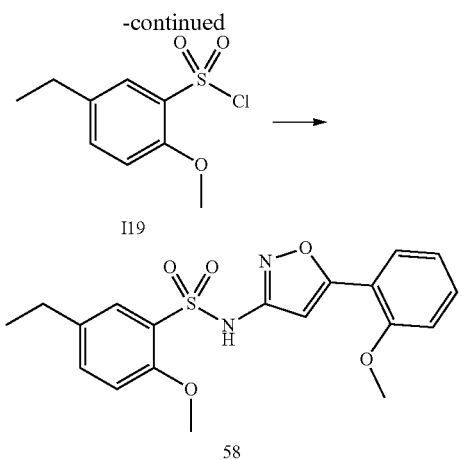

A solution of 5-(2-methoxyphenyl)isoxazol-3-amine I2 (100 mg, 0.526 mmol) and the 5-ethyl-2-methoxybenzenesulfonyl chloride I19 (123 mg, 0.526 mmol) in pyridine (2 mL) was irradiated in the microwave for 2 h at 100° C. Upon cooling, the reaction mixture was diluted with water (100 mL) and the resultant precipitate removed by filtration. The solid was washed with water (50 mL), petroleum benzine 40-60° C. (50 mL) and air dried to yield the product 58 as a white solid (97 mg, 47%). $^1$H NMR (400 MHz, DMSO-d$^6$) δ=11.32 (s, 1H), 7.76 (dd, J=7.8, 1.7, 1H), 7.70 (d, J=2.3, 1H), 7.53-7.45 (m, 2H), 7.21 (d, J=7.9, 1H), 7.14 (d, J=8.5, 1H), 7.11-7.04 (m, 1H), 6.66 (s, 1H), 3.92 (s, 3H), 3.80 (s, 3H), 2.62 (q, J=7.6, 2H), 1.16 (t, J=7.6, 3H). LCMS: R$_t$ 6.554 min, m/z 389.1 [M+H]$^+$.

Example 59: 5-Ethyl-N-(5-(2-fluorophenyl)isoxazol-3-yl)-2-methoxybenzenesulfonamide, 59

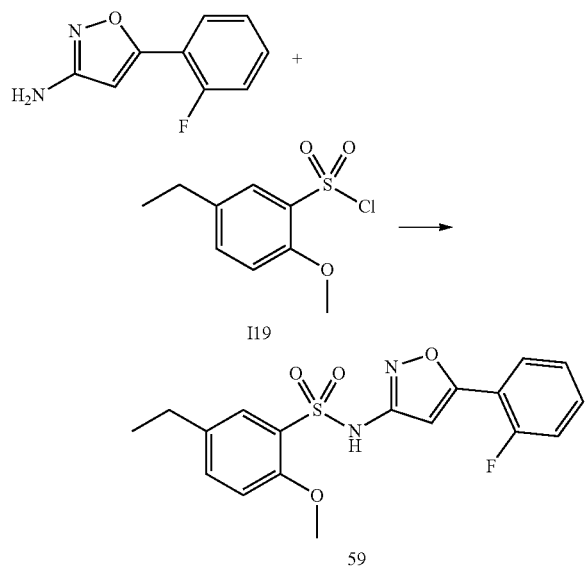

A solution of 5-ethyl-2-methoxybenzene-1-sulfonyl chloride I19 (263 mg, 1.12 mmol) and 5-(2-fluorophenyl)isoxazol-3-amine (200 mg, 1.12 mmol) in pyridine (2.0 mL) was irradiated in the microwave at 100° C. for 2 hours. Upon cooling the reaction mixture was added to water (50 mL) and the resultant green solid removed by filtration, the solid was dissolved in a minimum amount of acetone (4 mL) before petroleum spirits 40-60° C. (70 mL) was added causing dark blue droplets of oil to form. The mother liquor was decanted off and evaporated to yield a tan solid. The solid was dissolved in acetone (2 mL) then petroleum spirits 40-60° C. (50 mL) was added causing a precipitate to form. The solid was removed by filtration and air dried to yield the product as a tan solid (23 mg, 5%). $^1$H NMR (400 MHz, DMSO-d$^6$) δ=11.46 (s, 1H), 7.87 (td, J=7.7, 1.7, 1H), 7.69 (d, J=2.3, 1H), 7.66-7.55 (m, 1H), 7.52-7.33 (m, 3H), 7.15 (d, J=8.5, 1H), 6.65 (d, J=3.5, 1H), 3.79 (s, 3H), 2.62 (q, J=7.6, 2H), 1.15 (t, J=7.6, 3H). LCMS: R$_t$ 3.787 min, m/z=377.2 [M+H]$^+$.

Example 60: N-(5-(2-Fluorophenyl)isoxazol-3-yl)-5,6,7,8-tetrahydronaphthalene-2-sulfonamide, 60

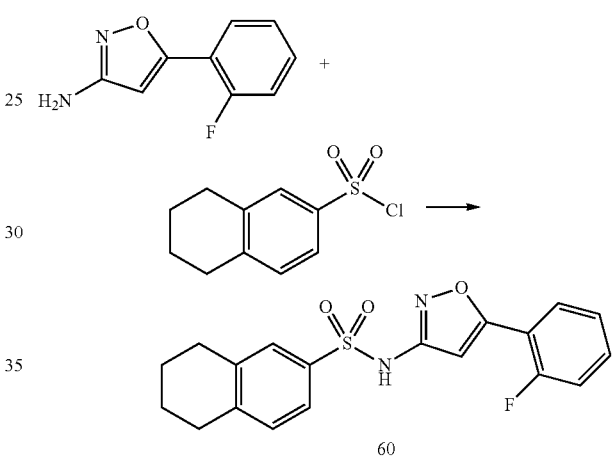

A solution of 5-(2-fluorophenyl)isoxazol-3-amine (250 mg, 1.40 mmol) and 5,6,7,8-tetrahydronaphthalene-2-sulfonyl chloride (324 mg 1.40 mmol) in pyridine (2 mL) was irradiated in the microwave for 2 hours at 100° C. Upon cooling the reaction mixture was added to water (50 mL) and the resultant precipitate removed by filtration, washed with petroleum benzine 40-60° C. (100 mL) and air dried to yield the title compound as a tan solid (226 mg, 43%). LCMS: R$_t$ 3.978 min; m/z 371.1 [M−H]$^−$. $^1$H NMR (400 MHz, DMSO-d$^6$) δ=7.93-7.85 (m, 1H), 7.65-7.56 (m, 3H), 7.50-7.35 (m, 2H), 7.28 (d, J=8.0, 1H), 6.70 (d, J=3.3, 1H), 2.87-2.69 (m, 4H), 1.72 (s, 4H).

Example 61: N-(4-Chloro-5-phenylisoxazol-3-yl)-3,4-dimethylbenzenesulfonamide, 61

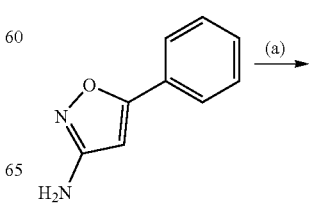

119

-continued

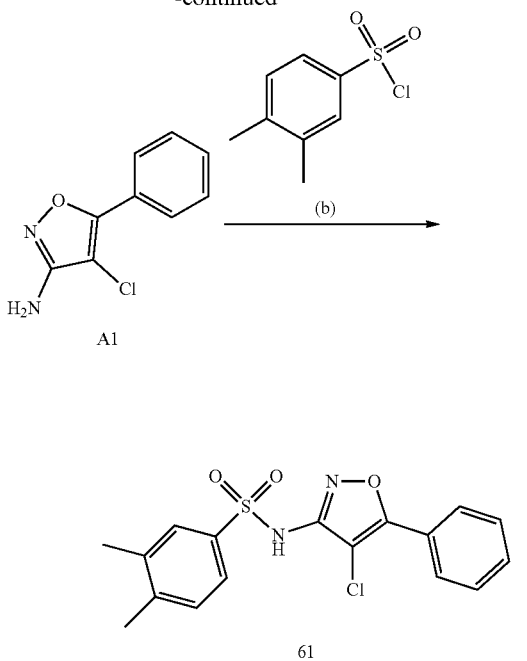

61 a) 4-Chloro-5-phenylisoxazol-3-amine, A1

N-Chlorosuccinimide (0.60 g, 4.5 mmol) was added to a solution of 5-phenyl-1,2-oxazole-3-amine (0.36 g, 2.3 mmol) in DCM (8 mL) at 0° C. The reaction mixture was allowed to warm up to room temperature and stirred at room temperature overnight. Acetonitrile (3 mL) was added to allow remaining solids to dissolve. An additional amount of N-chlorosuccinimide (0.60 g) was added at 0° C. and the reaction mixture was allowed to warm up to room temperature and stirred for 24 h. The reaction mixture was cooled to 0° C. and an extra amount of N-chlorosuccinimide (0.60 g) was added. The reaction mixture was allowed to warm up to room temperature and stirred for 48 h. Water (20 mL) was added followed by DCM (20 mL). The layers were separated and the aqueous layer was extracted with DCM (2×20 mL). The combined organic layers were washed with brine, dried (Na$_2$SO$_4$) and concentrated. Purification by combiflash (0-100% EtOAc/cyclohexane) obtained the desired product A1 (0.21 g, 48%) as an off-white solid. LCMS: R$_t$ 5.07 min, m/z 195.5 [M+H]$^+$.

b) N-(4-Chloro-5-phenylisoxazol-3-yl)-3,4-dimethylbenzenesulfonamide, 61

3,4-Dimethylbenzylsulfonylchloride (0.11 g, 0.53 mmol) was added to a solution of A1 (0.052 g, 0.27 mmol) in pyridine (1 mL). The reaction mixture was stirred at room temperature overnight. The reaction mixture was partitioned between 2 N HCl (5 mL) and EtOAc (10 mL). The aqueous layer was extracted with EtOAc (2×10 mL). The combined organic layers were washed with brine, dried (Na$_2$SO$_4$) and concentrated. Purification by combiflash (0-100% EtOAc/cyclohexane) obtained the desired product 61 (15 mg, 15%) as an off-white solid. LCMS: R$_t$ 5.73 min, m/z 363.7 [M+H]$^+$.

120

Example 62: N-(5-(4-Bromophenyl)isoxazol-3-yl)benzenesulfonamide, 62

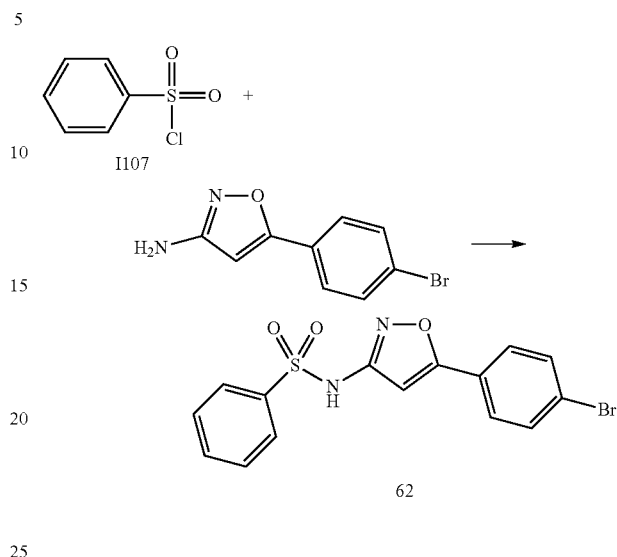

62

Benzenesulfonyl chloride I107 (0.040 mL, 0.314 mmol), 5-(4-bromophenyl)isoxazol-3-amine (0.050 g, 0.209 mmol) and pyridine (1 mL) were mixed at room temperature and stirred for 16 h. The solvent was removed in vacuo to afford a crude residue. This was dissolved in DCM (2 mL) and 1 M HCl (2 mL) and filtered through a phase separation cartridge. The crude material was purified by flash chromatography gradient eluting with 100% dichloromethane to 20% MeOH/dichloromethane to give the desired product 62 (13 mg, 14% yield). LCMS: R$_t$ 5.66 min, m/z=377.5 [M−H]$^-$.

Example 63: N-(5-phenylisoxazol-3-yl)benzenesulfonamide, 63

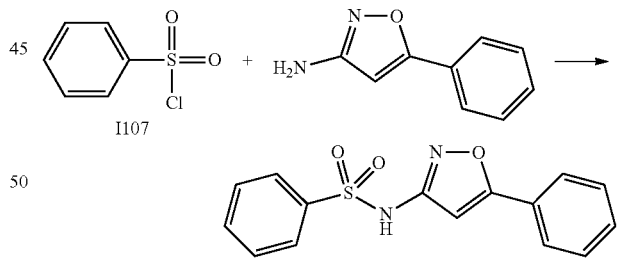

62

3-Amino-5-phenylisoxazole (0.051 g, 0.320 mmol), pyridine (1 mL) and benzenesulfonyl chloride I107 (0.094 mL, 0.736 mmol) were mixed at room temperature and stirred for 16 h. The solvent was removed in vacuo to afford a crude residue. This was dissolved in DCM (2 mL) and 1 M HCl (2 mL) and filtered through a phase separation cartridge. All crudes were purified by flash chromatography gradient eluting with 100% dichloromethane to 20% MeOH/dichloromethane to give the title compound 63 (38 mg, 40% yield). LCMS: R$_t$ 5.36 min, m/z=301.5 [M+H]$^+$.

Example 64: 2-Fluoro-N-(5-phenylisoxazol-3-yl)benzenesulfonamide, 64

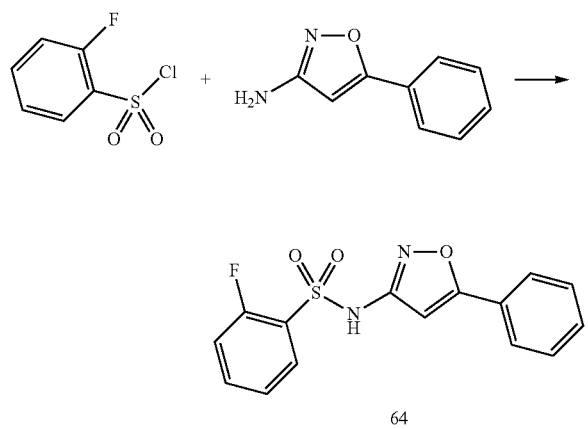

2-Fluorobenzenesulfonyl chloride (0.050 mL, 0.375 mmol), pyridine (1 mL), and 5-phenylisoxazol-3-amine (0.030 g, 0.187 mmol) were mixed at room temperature and stirred for 16 h. Water was added and the precipitate was collected by filtration. The product was recrystallized to give the desired product 64 (58 mg, 97% yield). $^1$H NMR (300 MHz, Methanol-d$_4$) δ 8.02-7.95 (m, 1H), 7.74-7.68 (m, 2H), 7.67-7.59 (m, 1H), 7.47-7.39 (m, 3H), 7.36-7.21 (m, 2H), 6.62 (s, 1H).

Example 65: 2-Phenyl-N-(5-phenylisoxazol-3-yl)ethane-1-sulfonamide, 65

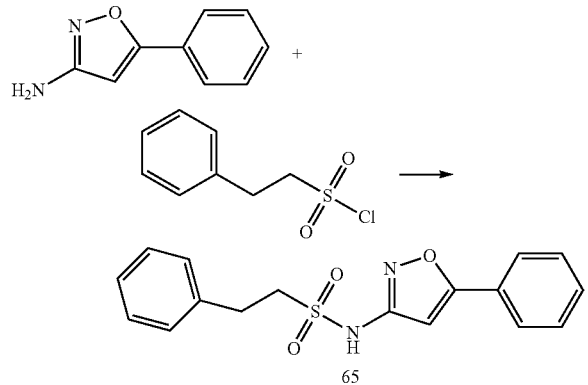

2-Phenylethanesulfonylchloride (0.17 g, 0.81 mmol) was added to a solution of 5-phenyl-1,2-oxazole-3-amine (0.065 g, 0.41 mmol) in pyridine (1 mL). The reaction mixture was stirred at room temperature overnight. The reaction mixture was partitioned between 2 N HCl (5 mL) and EtOAc (10 mL). The aqueous layer was extracted with EtOAc (2×10 mL). The combined organic layers were washed with brine, dried (Na$_2$SO$_4$) and concentrated. Purification by combiflash (0-100% EtOAc/cyclohexane) obtained the desired product 65 (2 mg, 2%) as an off white solid. LCMS: R$_t$ 5.54 min, m/z 329.3 [M+H]$^+$.

Example 66: 2-Fluoro-N-(5-(4-fluoro-[1,1'-biphenyl]-3-yl)-1,3,4-thiadiazol-2-yl)benzenesulfonamide, 66

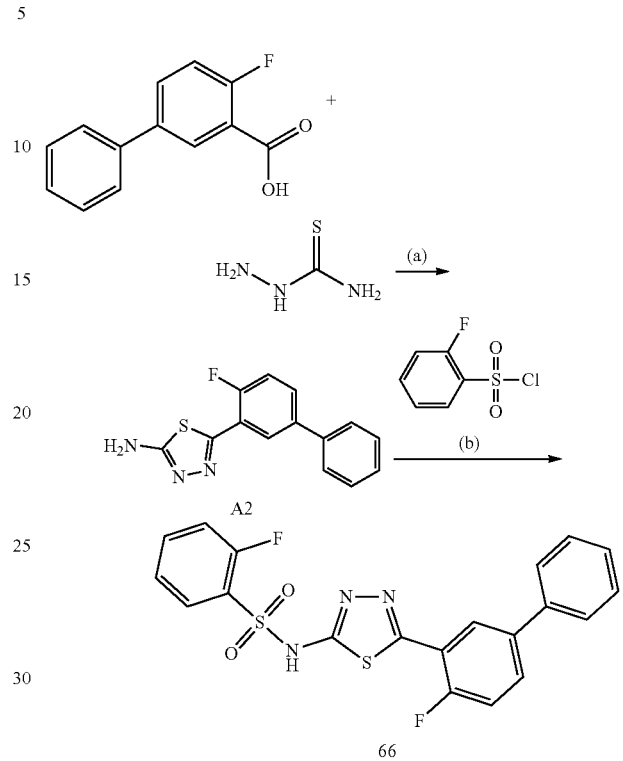

a) 5-(4-fluoro-[1,1'-biphenyl]-3-yl)-1,3,4-thiadiazol-2-amine, A2

A mixture of 2-fluoro-5-phenylbenzoic acid (0.100 g, 0.463 mmol) and thiosemicarbazide (0.46 g, 0.500 mmol) was stirred in POCl$_3$ (1 mL) and heated to 75° C. for 1 h. Water (2 mL) was slowly added to the reaction and the mixture was heated to reflux for 2 h. After cooling, the reaction was cooled with ice/water and the pH was adjusted to 8 with 15 M KOH. The solid that crashed out was filtered and dried to in vacuo to afford an off-white solid (0.200 g). The solid was recrystallised from hot ethanol affording the desired product A2 as an off white solid (0.125 g, 92% yield). LCMS: R$_t$ 5.21 min, m/z=272.3 [M+H]$^+$.

b) 2-Fluoro-N-(5-(4-fluoro-[1,1'-biphenyl]-3-yl)-1,3,4-thiadiazol-2-yl)benzenesulfonamide, 66

To a solution of A2 (0.035 g, 0.129 mmol) in dry pyridine (1 mL) at 0° C. was added 2-fluorobenzenesulfonyl chloride (0.020 mL, 0.155 mmol). The mixture was stirred at room temperature for 4 days. Another 1.2 eq of 2-fluorobenzenesulfonyl chloride (0.020 mL) was added and the mixture was stirred for a further 16 h while heating to 50° C. The solvent was removed in vacuo. Toluene (1 mL) was added and the solvent was removed in vacuo to afford a crude residue as an orange solid (0.085 g). The crude was purified by preparative TLC eluting with 1% MeOH/dichloromethane affording a clear smear (0.022 g). This was further purified by HPLC collecting the desired product 66 as a pale yellow solid (0.0059 g, 11% yield). LCMS: R$_t$ 8.07 min, m/z 430.14 [M+H]$^+$.

Example 67: N-(5-(4-Fluoro-[1,1'-biphenyl]-3-yl)-1,3,4-thiadiazol-2-yl)benzenesulfonamide, 67

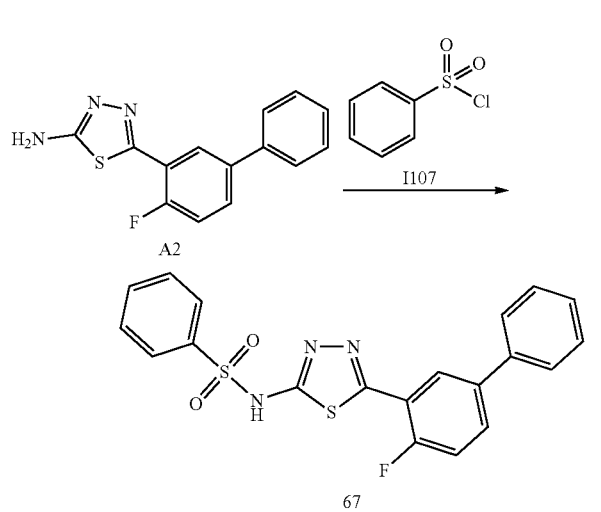

To a solution of A2 (0.050 g, 0.184 mmol) in dry pyridine (1 mL) at 0° C. was added benzenesulfonyl chloride I107 (0.028 mL, 0.221 mmol). The mixture was stirred at room temperature for 16 h. Another 1.2 eq of benzenesulfonyl chloride I107 (0.028 mL) was added and the mixture was stirred for a further 16 h. The solvent was removed in vacuo. Toluene (1 mL) was added and the solvent was removed in vacuo to afford a crude residue as an orange solid (0.065 g). This was purified twice by flash chromatography gradient eluting with 100% dichloromethane to 10% MeOH/dichloromethane then gradient eluting with 100% dichloromethane to 5% MeOH/dichloromethane affording the title product 67 as a white paste (0.012 g, 16% yield). LCMS: $R_t$ 5.82 min, m/z 412.0 [M+H]⁺.

Example 68: 2-Fluoro-N-(5-phenyl-1,2,4-oxadiazol-3-yl)benzenesulfonamide, 68

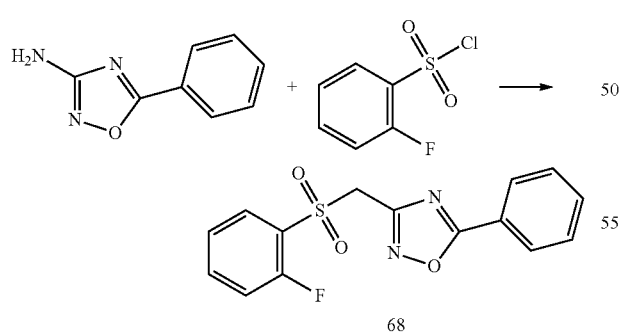

2-Fluorobenzenesulfonyl chloride (0.045 mL, 0.340 mmol), (0.030 g, 0.170 mmol) and pyridine (1 mL) were mixed at room temperature and stirred for 16 h. Water was added and the precipitate filtered. The solid was further purified by HPLC to give the title compound 68 (9.0 mg, 15% yield). LCMS $R_t$ 6.73 min, m/z=320.20 [M+H]⁺.

Example 69: Methyl 3-(3-((2,6-dimethoxyphenyl)sulfonamido)isoxazol-5-yl)-4-methoxybenzoate, 69

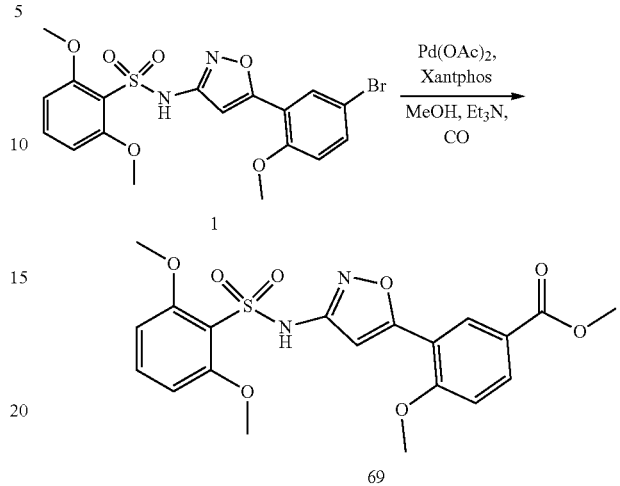

A mixture of N-(5-(5-bromo-2-methoxyphenyl)isoxazol-3-yl)-2,6-dimethoxybenzenesulfonamide 1 (100 mg, 0.212 mmol), Pd(OAc)₂ (1.4 mg, 3.9 umol), Xantphos (11 mg, 0.19 mmol) and Et₃N (107 mg, 1.2 mmol) in MeOH (15 mL) was heated at 100° C. under a CO atmosphere (1 atm) overnight. The catalyst was removed by filtration, washed with MeOH and the filtrate was concentrated under reduced pressure. The residue was purified by prep. TLC (DCM/MeOH=50/1) to give the title compound 69 (20 mg, 21%) as a white solid. LCMS-A (ES-API): $R_t$ 2.08 min; m/z 448.9 [M+H]⁺. ¹H NMR (400 MHz, CDCl₃) δ 8.53 (d, J=2.2 Hz, 1H), 8.08 (dd, J=8.8, 2.2 Hz, 1H), 7.94 (s, 1H), 7.40 (t, J=8.5 Hz, 1H), 7.05-6.98 (m, 2H), 6.62 (d, J=8.6 Hz, 2H), 4.00 (s, 3H), 3.96 (s, 6H), 3.90 (s, 3H).

Example 70: N-(5-(2,5-Dimethoxyphenyl)-1,3,4-thiadiazol-2-yl)-2,6-dimethoxybenzenesulfonamide, 70

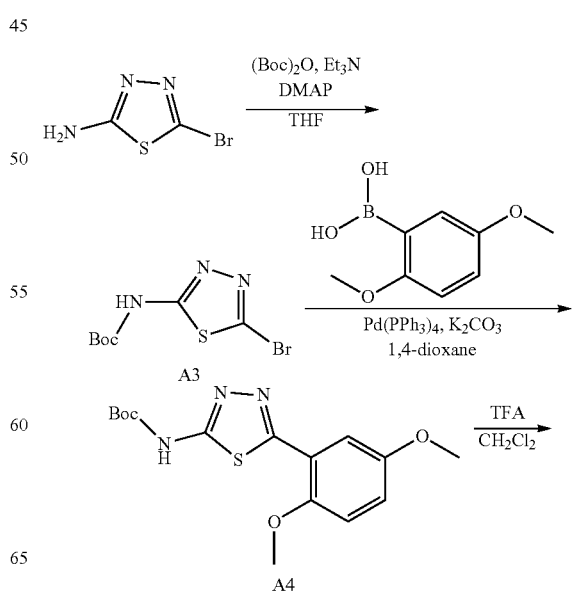

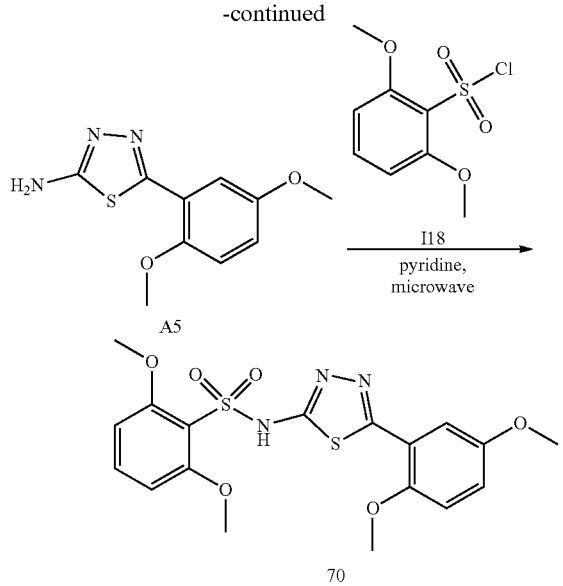

a) tert-Butyl (5-bromo-1,3,4-thiadiazol-2-yl)carbamate, A3

To a solution of 5-bromo-1,3,4-thiadiazol-2-amine (1.0 g, 5.56 mmol) in THF (15 mL) was added di-tert-butyl dicarbonate (1.3 g, 6.12 mmol), Et$_3$N (1.1 g, 11.1 mmol) and DMAP (136 mg, 1.11 mmol) and mixture was stirred at room temperature overnight. The mixture was partitioned between water and EtOAc, the layers were separated and the organic layer was washed with brine, dried over anhydrous Na$_2$SO$_4$, filtered and concentrated under reduced pressure. The residue was purified by column chromatography (DCM/MeOH=100/1) to give the title compound A3 (0.8 g, 50%) as a yellow solid. LCMS (ES-API): R$_t$ 2.10 min; m/z 279.9/281.8 [M+H]$^+$.

b) tert-Butyl (5-(2,5-dimethoxyphenyl)-1,3,4-thiadiazol-2-yl)carbamate, A4

To a solution of tert-butyl (5-bromo-1,3,4-thiadiazol-2-yl)carbamate A3 (100 mg, 0.36 mmol) in 1,4-dioxane (5 mL) was added (2,5-dimethoxyphenyl)boronic acid (73 mg, 0.40 mmol), Pd(PPh$_3$)$_4$ and a solution of K$_2$CO$_3$ (100 mg, 0.72 mmol) in water (1 mL) and the mixture was heated at 100° C. overnight. To a second solution of tert-butyl (5-bromo-1,3,4-thiadiazol-2-yl)carbamate A3 (600 mg, 2.14 mmol) in 1,4-dioxane (10 mL) was added (2,5-dimethoxyphenyl)boronic acid (428 mg, 2.35 mmol), Pd(PPh$_3$)$_4$ (124 mg, 0.107 mmol) and a solution of K$_2$CO$_3$ (590 mg, 4.28 mmol) in water (2 mL) and the mixture was heated at 100° C. overnight. The two reaction mixtures were combined and partitioned between water and EtOAc. The layers were separated and the organic layer was washed with brine, dried over anhydrous Na$_2$SO$_4$, filtered and concentrated under reduced pressure. The residue was purified by column chromatography (DCM/MeOH=40/1) to give the title compound A4 (350 mg, 42%) as a yellow solid. LCMS (ES-API): R$_t$ 2.39 min; m/z 338.0 [M+H]$^+$.

c) 5-(2,5-Dimethoxyphenyl)-1,3,4-thiadiazol-2-amine, A5

To a solution of tert-butyl (5-(2,5-dimethoxyphenyl)-1,3,4-thiadiazol-2-yl)carbamate A4 (100 mg, 0.3 mmol) in DCM (5 mL) was added TFA (1.5 mL) and the mixture was stirred at room temperature overnight. The mixture was concentrated under reduced pressure and the residue was diluted with a saturated aqueous NaHCO$_3$ solution and extracted with EtOAc. The organic extract was dried over anhydrous Na$_2$SO$_4$, filtered and concentrated under reduced pressure to give the title compound A5 (80 mg, >100%) as a yellow solid, which was used directly in the next step without further purification. LCMS (ES-API): R$_t$ 0.54 min; m/z 238.0 [M+H]$^+$.

d) N-(5-(2,5-Dimethoxyphenyl)-1,3,4-thiadiazol-2-yl)-2,6-dimethoxybenzenesulfonamide, 70

To a solution of 5-(2,5-dimethoxyphenyl)-1,3,4-thiadiazol-2-amine A5 (80 mg, assumed 0.3 mmol) in pyridine (3 mL) was added 2,6-dimethoxybenzenesulfonyl chloride I18 (107 mg, 0.45 mmol) and the mixture was heated at 120° C. under microwave irradiation for 2 h. The mixture was concentrated under reduced pressure and the residue was partitioned between water and EtOAc. The layers were separated and the organic layer was washed with brine, dried over anhydrous Na$_2$SO$_4$, filtered and concentrated under reduced pressure. The residue was purified by column chromatography (DCM/MeOH=20/1) to give the title compound 70 (20 mg, 15% over two steps) as a yellow solid. R$_t$ 2.02 min; m/z 437.9 [M+H]$^+$. $^1$H NMR (400 MHz, CDCl$_3$) δ 7.64 (d, J=3.2 Hz, 1H), 7.35 (t, J=8.4 Hz, 1H), 7.03-7.01 (m, 1H), 6.96-6.94 (m, 1H), 6.60 (d, J=8.4 Hz, 2H), 3.93 (s, 3H), 3.85 (s, 6H), 3.83 (s, 3H).

Example 71: 2,6-Dimethoxy-N-(5-(5-methoxy-2-(methoxymethyl)phenyl)isoxazol-3-yl)benzenesulfonamide, 71

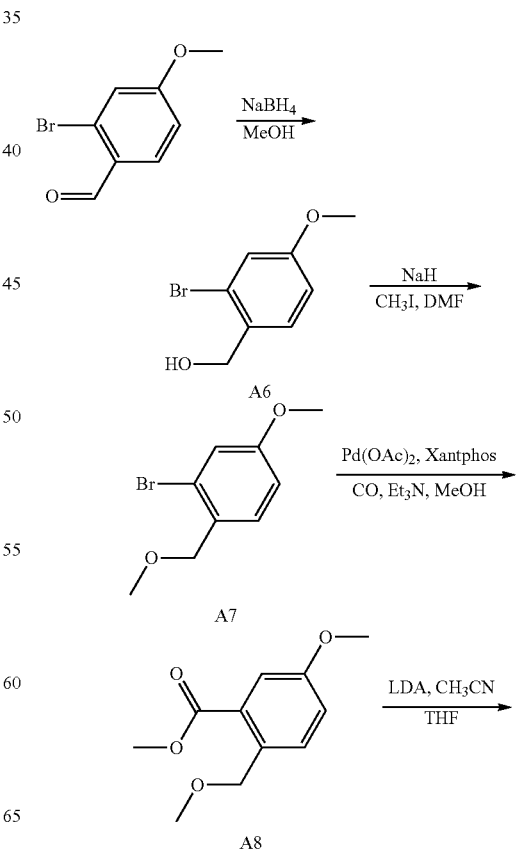

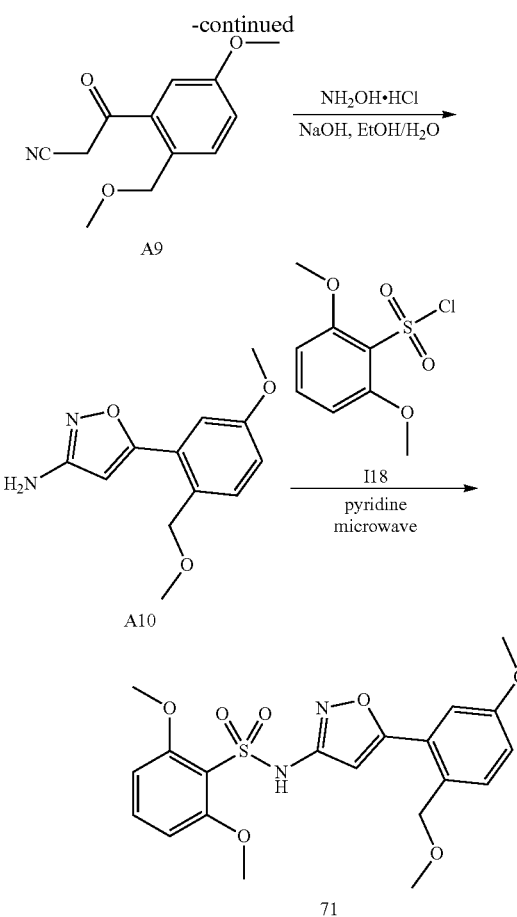

a) (2-Bromo-4-methoxyphenyl)methanol, A6

To a solution of 2-bromo-4-methoxybenzaldehyde (5.0 g, 23 mmol) in MeOH (30 mL) was added NaBH$_4$ (1.1 g, 28 mmol) and the mixture was stirred at room temperature for 2 h. The reaction was quenched with water (1 mL) and the mixture was partitioned between water and EtOAc. The layers were separated and the organic layer was washed with brine, dried over anhydrous Na$_2$SO$_4$, filtered and concentrated under reduced pressure. The residue was purified by column chromatography (petroleum ether/EtOAc=5/1) to give the title compound A6 (4.2 g, 84%) as a colourless oil. LCMS-A (ES-API): R$_t$ 0.85 min; m/z 238.9 [M+Na]$^+$. $^1$H NMR (400 MHz, CDCl$_3$) δ 7.38 (d, J=8.4 Hz, 1H), 7.13 (d, J=2.8 Hz, 1H), 6.89-6.87 (m, 1H), 4.70 (s, 2H), 3.82 (s, 3H).

b) 2-Bromo-4-methoxy-1-(methoxymethyl)benzene, A7

To a solution of (2-bromo-4-methoxyphenyl)methanol A6 (200 mg, 0.92 mmol) in DMF (5 mL) at 0° C. was added NaH (60% dispersion in oil, 40 mg, 1.01 mmol) and the mixture was stirred for 15 min. Methyl iodide (143 mg, 1.01 mmol) was added and the mixture was allowed to warm to room temperature and stirred for 1 h. The reaction was quenched with water (1 mL). The following procedure was performed twice: To a solution of (2-bromo-4-methoxyphenyl)methanol A6 (2.0 g, 9.21 mmol) in DMF (20 mL) at 0° C. was added NaH (60% dispersion in oil, 400 mg, 10.1 mmol) and the mixture was stirred for 15 min. Methyl iodide (1.4 g, 10.1 mmol) was added and the mixture was allowed to warm to room temperature and stirred for 1 h. The three reaction mixtures were combined and partitioned between water and EtOAc. The layers were separated and the organic layer was washed with brine, dried over anhydrous Na$_2$SO$_4$, filtered and concentrated under reduced pressure. The residue was purified by column chromatography (petroleum ether/EtOAc=10/1) to give the title compound A7 (1.8 g, 43% yield) as a light yellow oil. LCMS-A (ES-API): R$_t$ 2.18 min; m/z 231.1 [M+H]$^+$.

c) Methyl 5-methoxy-2-(methoxymethyl)benzoate, A8

To a solution of 2-bromo-4-methoxy-1-(methoxymethyl)benzene A7 (600 mg, 2.6 mmol) in MeOH (15 mL) was added Pd(OAc)$_2$ (58 mg, 0.26 mmol), Et$_3$N (789 g, 7.8 mmol) and Xantphos (150 mg, 0.26 mmol) and the mixture was heated at 90° C. under a CO atmosphere (1 atm) for 48 h. The reaction was performed two more times as follows:

1. To a solution of 2-bromo-4-methoxy-1-(methoxymethyl)benzene A7 (1.1 g, 4.76 mmol) in MeOH (15 mL) was added Pd(OAc)$_2$ (108 mg, 0.48 mmol), Et$_3$N (1.4 g, 14.3 mmol) and Xantphos (278 mg, 0.48 mmol) and the mixture was heated at 90° C. under a CO atmosphere (1 atm) overnight.

2. To a solution of 2-bromo-4-methoxy-1-(methoxymethyl)benzene A7 (1.3 g, 5.63 mmol) in MeOH (20 mL) was added Pd(OAc)$_2$ (126 mg, 0.56 mmol), Et$_3$N (1.7 g, 16.9 mmol) and Xantphos (307 mg, 0.56 mmol) and the mixture was heated at 90° C. under a CO atmosphere (1 atm) for 48 h. The three reaction mixtures were combined and partitioned between water and EtOAc. The layers were separated and the organic layer was washed with brine, dried over anhydrous Na$_2$SO$_4$, filtered and concentrated under reduced pressure. The residue was purified by column chromatography (petroleum ether/EtOAc=20/1) to give the title compound A8 (600 mg, 22%) as a yellow oil. LCMS-A (ES-API): R$_t$ 2.18 min; m/z 233.0 [M+Na]$^+$.

d) 3-(5-Methoxy-2-(methoxymethyl)phenyl)-3-oxopropanenitrile, A9

To a solution of diisopropylamine (63 mg, 0.62 mmol) in THF (10 mL) at −78° C. under N2 was added n-BuLi (2.5 M solution in hexanes, 0.25 mL, 0.62 mmol) dropwise and the mixture was stirred at −78° C. for 0.5 h. A solution of acetonitrile (25 mg, 0.62 mmol) in THF (1 mL) was added dropwise and stirring was continued for 30 min. A solution of methyl 5-methoxy-2-(methoxymethyl)benzoate A8 (100 mg, 0.48 mmol) in THF (1 mL) was then added dropwise and the mixture was stirred at −78° C. for 1 h. The reaction was quenched with a saturated aqueous NH$_4$Cl solution. The procedure was repeated using methyl 5-methoxy-2-(methoxymethyl)benzoate A8 (500 mg, 2.38 mmol) and the two reaction mixtures were combined and partitioned between water and EtOAc. The layers were separated and the organic layer was washed with brine, dried over anhydrous Na$_2$SO$_4$, filtered and concentrated under reduced pressure. The residue was purified by column chromatography (petroleum ether/EtOAc=4/1) to give the title compound A9 (480 mg, 77%) as a yellow solid. LCMS-A (ES-API): R$_t$ 1.04 min; m/z 220.1 [M+H]$^+$.

e) 5-(5-Methoxy-2-(methoxymethyl)phenyl)isoxazol-3-amine, A10

To a solution of 3-(5-methoxy-2-(methoxymethyl)phenyl)-3-oxopropanenitrile A9 (100 mg, 0.46 mmol) in ethanol (5 mL) was added a solution of NaOH (24 mg, 0.60 mmol) in H$_2$O (5 mL) followed by NH$_2$OH·HCl (42 mg, 0.6 mmol) and the mixture was heated at 80° C. overnight. The procedure was repeated as follows: To a solution of 3-(5-methoxy-2-(methoxymethyl)phenyl)-3-oxopropanenitrile A9 (300 mg, 1.37 mmol) in ethanol (5 mL) was added a solution of NaOH (71 mg, 1.78 mmol) in H$_2$O (5 mL) followed by NH$_2$OH·HCl (124 mg, 1.78 mmol) and the mixture was heated at 80° C. overnight. The two reaction mixtures were combined and partitioned between water and EtOAc. The layers were separated and the organic layer was washed with brine, dried over anhydrous Na$_2$SO$_4$, filtered and concentrated under reduced pressure. The residue was purified by column chromatography (DCM/MeOH=20/1) to give the title compound A10 (60 mg, 14%) as a yellow solid. LCMS-A (ES-API): R$_t$ 0.70 min; m/z 235.0 [M+H]$^+$.

f) 2,6-Dimethoxy-N-(5-(5-methoxy-2-(methoxymethyl)phenyl)isoxazol-3-yl)benzenesulfonamide, 71

To a solution of 5-(5-methoxy-2-(methoxymethyl)phenyl)isoxazol-3-amine A10 (60 mg, 0.26 mmol) in pyridine (3 mL) was added 2,6-dimethoxybenzenesulfonyl chloride I18 (92 mg, 0.39 mmol) and the mixture was heated at 120° C. for 2 h under microwave irradiation. The mixture was concentrated under reduced pressure and the residue was purified by column chromatography (DCM/MeOH=50/1) to give the title compound 71 (15 mg, 14%) as a yellow solid. LCMS-A (ES-API): R$_t$ 2.19 min; m/z 435.0 [M+H]$^+$. $^1$H NMR (400 MHz, CDCl$_3$) δ 7.96 (s, 1H), 7.43-7.39 (m, 2H), 7.20 (d, J=2.8 Hz, 1H), 6.98 (dd, J=8.4, 2.4 Hz, 1H), 6.81 (s, 1H), 6.62 (d, J=8.8 Hz, 2H), 4.40 (s, 2H), 3.96 (s, 6H), 3.82 (s, 3H), 3.39 (s, 3H).

Example 72: 2,6-Dimethoxy-N-(5-(2-methoxy-5-(1H-pyrazol-5-yl)phenyl)isoxazol-3-yl)benzenesulfonamide, 72

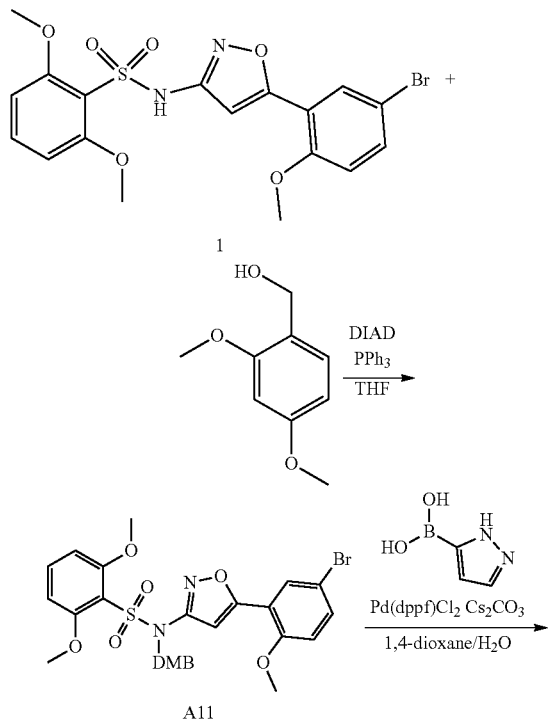

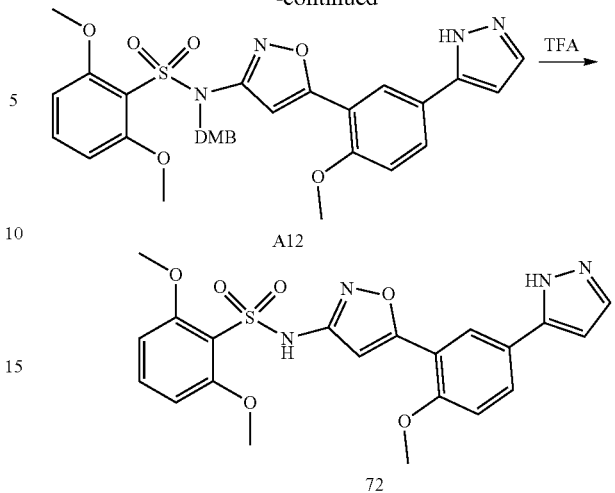

a) N-(5-(5-Bromo-2-methoxyphenyl)isoxazol-3-yl)-N-(2,4-dimethoxybenzyl)-2,6-dimethoxybenzenesulfonamide, A11

To a solution of N-(5-(5-bromo-2-methoxyphenyl)isoxazol-3-yl)-2,6-dimethoxybenzenesulfonamide 1 (300 mg, 639 mmol), (2,4-dimethoxyphenyl)methanol (430 mg, 2.6 mmol) and PPh$_3$ (502 mg, 1.9 mmol) in THF (15 mL) at 0° C. was added a solution of DIAD (258 mg, 1.3 mmol) in THF (5 mL) dropwise and the mixture was allowed to warm to room temperature and stirred overnight. Water was added and the mixture was extracted with EtOAc (200 mL×3). The combined organic extracts were washed with brine, dried over anhydrous Na$_2$SO$_4$, filtered and concentrated under reduced pressure. The residue was purified by column chromatography (petroleum ether/EtOAc=3/1) then rinsed with MeOH to give the title compound A11 (70 mg, 18%) as a white solid. LCMS-A (ES-API): R$_t$ 2.53 min; m/z 619.0 [M+H]$^+$.

b) N-(2,4-Dimethoxybenzyl)-2,6-dimethoxy-N-(5-(2-methoxy-5-(1H-pyrazol-5-yl)phenyl)isoxazol-3-yl)benzenesulfonamide, A12

A mixture of N-(5-(5-bromo-2-methoxyphenyl)isoxazol-3-yl)-N-(2,4-dimethoxybenzyl)-2,6-dimethoxybenzenesulfonamide A11 (65 mg, 0.105 mmol), (1H-pyrazol-5-yl)boronic acid (17.7 mg, 0.158 mmol), Pd(dppf)Cl$_2$ (3.9 mg, 0.005 mmol) and Cs$_2$CO$_3$ (103 mg, 0.103 mmol) in 1,4-dioxane (10 mL) and water (2 mL) was heated at 100° C. under N$_2$ overnight. Water was added and the mixture was extracted with EtOAc (200 mL×3). The combined organic extracts were washed with water, brine, dried over anhydrous Na$_2$SO$_4$, filtered and concentrated under reduced pressure. The residue was purified by prep-TLC (petroleum ether/EtOAc=1/1) to give the title compound A12 (35 mg, 55% yield) as a white solid. LCMS-A (ES-API): R$_t$ 2.43 min; m/z 607.0 [M+H]$^+$.

c) 2,6-Dimethoxy-N-(5-(2-methoxy-5-(1H-pyrazol-5-yl)phenyl)isoxazol-3-yl)benzenesulfonamide, 72

A solution of N-(2,4-dimethoxybenzyl)-2,6-dimethoxy-N-(5-(2-methoxy-5-(1H-pyrazol-5-yl)phenyl)isoxazol-3-yl)benzenesulfonamide A12 (35 mg, 0.16 mmol) in TFA (5 mL) was stirred at room temperature overnight then concentrated under reduced pressure. The residue was purified by prep-TLC (DCM/MeOH=100/1) to give the title compound 72 (8 mg, 31%) as a white solid. LCMS-A (ES-API): R$_t$ 1.63 min; m/z 457.0 [M+H]$^+$. $^1$H NMR (400 MHz, DMSO-d$_6$) δ 12.9 (br s, 1H), 11.0 (brs, 1H), 8.17 (s, 1H), 7.89 (d, J=8.4 Hz, 1H), 7.76 (br s, 1H), 7.50 (t, J=8.4 Hz, 1H), 7.25 (d, J=8.4 Hz, 1H), 6.78 (d, J=8.4 Hz, 2H), 6.72 (d, J=6.4 Hz, 2H), 3.93 (s, 3H), 3.83 (s, 6H).

Example 73: 2,6-Dimethoxy-N-(5-(2-methoxy-5-(methoxymethyl)phenyl)isoxazol-3-yl)benzenesulfonamide, 73

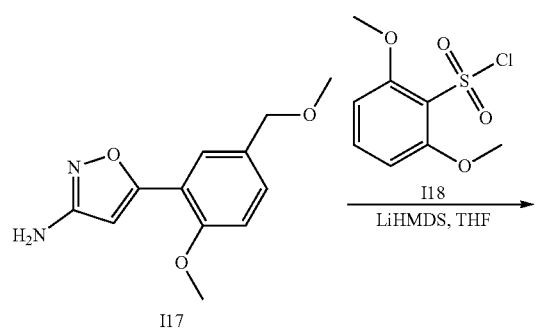

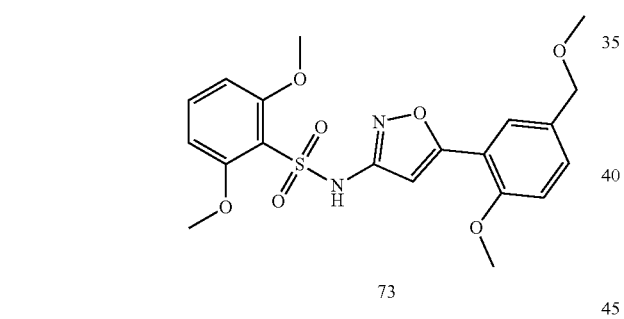

To a solution of 5-(2-methoxy-5-(methoxymethyl)phenyl)isoxazol-3-amine I17 (1.0 g, 4.27 mmol) in dry THF (40 mL) at −78° C. under N$_2$ was added LiHMDS (1.0 M solution in THF, 12.8 mL, 12.8 mmol) dropwise and the mixture was stirred at −78° C. for 1 h. A solution of 2,6-dimethoxybenzenesulfonyl chloride I18 (1.52 g, 6.41 mmol) in anhydrous THF (2 mL) was then added dropwise and the mixture was allowed to warm to room temperature and stirred overnight. The mixture was acidified to pH 4-5 with 1 M aqueous HCl and extracted with EtOAc. The combined organic extracts were washed with water, brine, dried over anhydrous Na$_2$SO$_4$, filtered and concentrated under reduced pressure. The residue was purified by column chromatography (DCM/MeOH=200/1) to give the title compound 73 (800 mg, 43% yield) as a white solid. LCMS-A (ES-API): R$_t$ 2.15 min; m/z, 435.0 [M+H]$^+$; $^1$H NMR (400 MHz, DMSO-d$_6$) δ 11.1 (s, 1H), 7.70 (d, J=2.2 Hz, 1H), 7.49 (t, J=8.5 Hz, 1H), 7.41 (dd, J=8.6, 2.2 Hz, 1H), 7.18 (d, J=8.6 Hz, 1H), 6.77 (d, J=8.5 Hz, 2H), 6.69 (s, 1H), 4.38 (s, 2H), 3.90 (s, 3H), 3.83 (s, 6H), 3.26 (s, 3H).

Example 74: N-(3-(2-bromophenyl)isoxazol-5-yl)-5-ethyl-2-methoxybenzenesulfonamide, 74

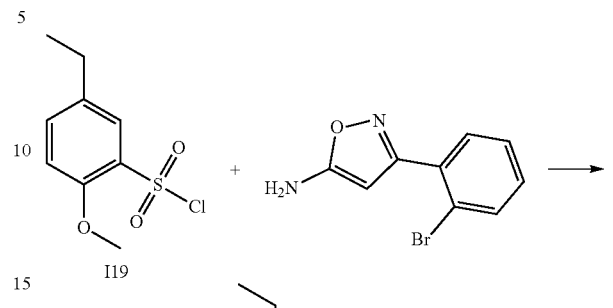

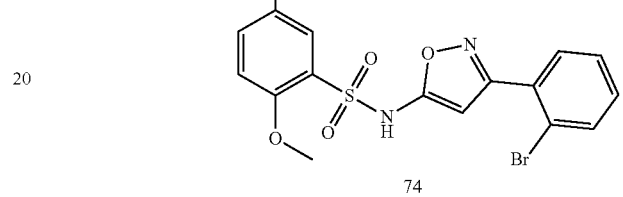

A mixture of 5-ethyl-2-methoxylbenzenesulfonyl chloride I19 (0.098 g, 0.418 mmol), pyridine (1 mL) and 3-(2-bromophenyl)-1,2-oxazol-5-amine (0.050 g, 0.209 mmol) was stirred at room temperature for 16 h. The mixtures were diluted with DCM (1 mL) and washed with 1 M HCl (2 mL). The aqueous layer was removed and the organic layer was dried to give the crude residue. The product was purified by HPLC to give the title compound 74 (12 mg, 13% yield). LCMS R$_t$ 5.75 min, m/z=436.9/438.8 [M+H]$^+$.

Example 75: N-(3-(3-bromophenyl)isoxazol-5-yl)-5-ethyl-2-methoxybenzenesulfonamide, 75

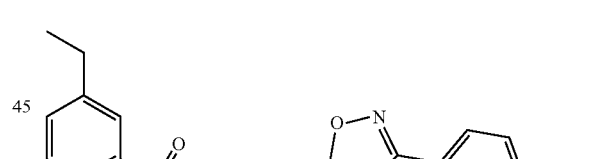

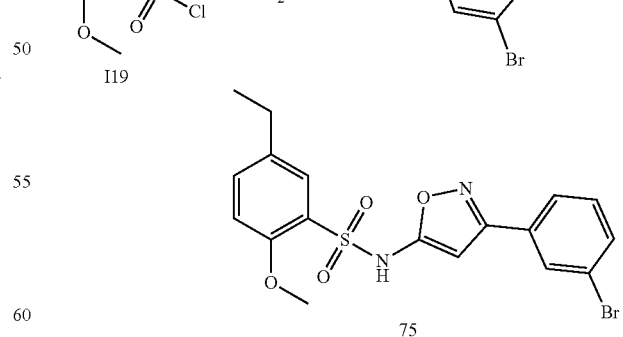

A mixture of 5-ethyl-2-methoxylbenzenesulfonyl chloride I19 (0.098 g, 0.418 mmol), pyridine (1 mL) and 3-(3-bromophenyl)isoxazol-5-amine (0.050 g, 0.209 mmol) was stirred at room temperature for 16 h. The mixtures were diluted with DCM (1 mL) and washed with 1 M HCl (2 mL).

The aqueous layer was removed and the organic layer was dried to give the crude residue. The product was purified by HPLC to give the title compound (12 mg, 13% yield). LCMS $R_t$ 5.91 min, m/z=438.8 [M+H]$^+$.

Example 77: N-(3-(3-benzylphenyl)isoxazol-5-yl)-3,4-dimethylbenzenesulfonamide, 77

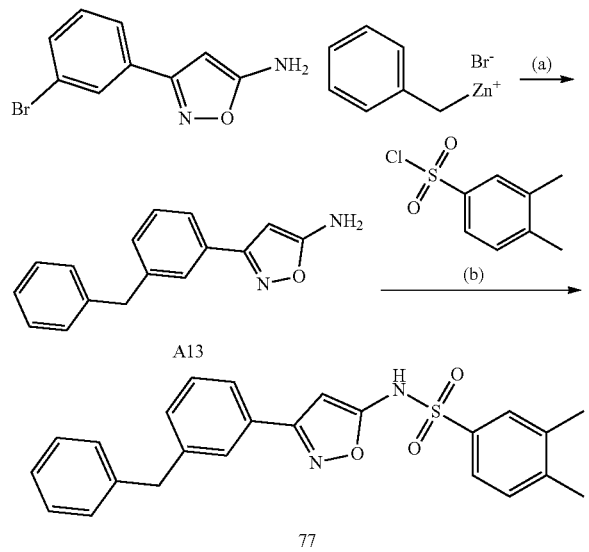

a) 3-(3-Benzylphenyl)isoxazol-5-amine, A13

Benzylzinc bromide (0.502 mL, 0.5 M in THF, 0.251 mmol) was added to a solution of 3-(3-bromo-phenyl)-isoxazol-5-ylamine (0.050 g, 0.209 mmol), Pd(OAc)$_2$ (0.001 g, 0.004 mmol), S-Phos (0.002 g, 0.004 mmol) in THF (2 mL). The mixture was stirred for 16 h at room temperature. Additional benzylzinc bromide (0.502 mL, 0.5 M in THF, 0.251 mmol), Pd(OAc)$_2$ (0.003 g, 0.012 mmol) and S-Phos (0.009 g, 0.024 mmol) were added and the mixture continued stirring for 16 h. The mixture was quenched with saturated NH$_4$Cl (3 mL) and diluted in EtOAc (5 mL). The organic layer was isolated and washed with water (2×5 mL). The organic layer was dried (magnesium sulfate), filtered and reduced in vacuo to afford A13 as a brown oil (0.052 g, 99% crude yield). The product was used without further purification. LCMS $R_t$ 5.42 min, m/z=251.5 [M+H]$^+$.

b) N-(3-(3-benzylphenyl)isoxazol-5-yl)-3,4-dimethylbenzenesulfonamide, 77

A mixture of 3-(3-benzylphenyl)isoxazol-5-amine A13 (0.169 g, 0.675 mmol), 3,4-dimethylbenzenesulfonyl chloride (0.104 g, 0.506 mmol) and pyridine (1 mL) was stirred at room temperature for 16 h. The mixtures were diluted with DCM (1 mL) and washed with 1M HCl (2 mL). The aqueous layer was removed and the organic layer was dried to give the crude residue. The product was purified by HPLC to give the title compound 77 (1.3 mg, 1%). LCMS $R_t$ 6.36 min, m/z=419.8 [M+H]$^+$.

Example 78: 3,4-dimethyl-N-(3-(3-phenethylphenyl)isoxazol-5-yl)benzenesulfonamide, 78

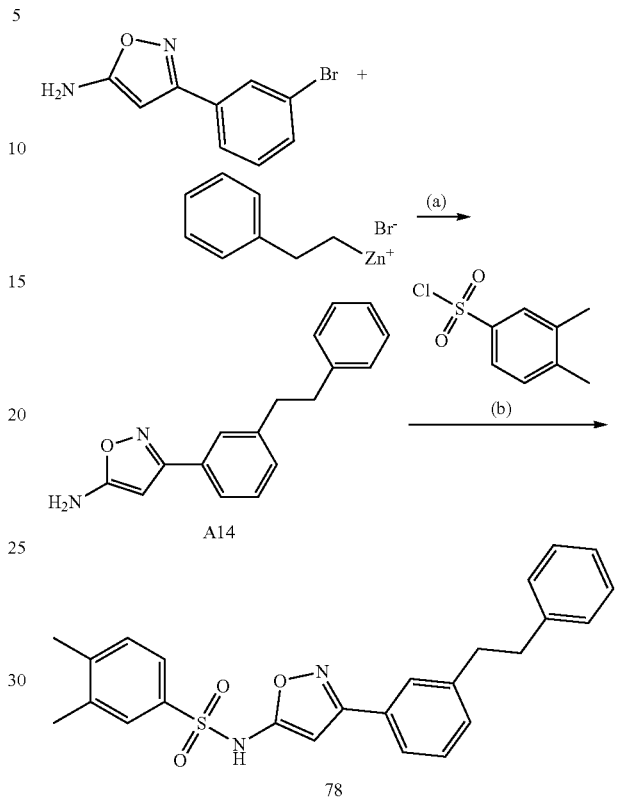

a) 3-(3-Phenethylphenyl)isoxazol-5-amine, A14

Phenethylzinc bromide (0.502 mL, 0.5 M in THF, 0.251 mmol) was added to a solution of 3-(3-bromophenyl)-isoxazol-5-ylamine (0.050 g, 0.209 mmol), Pd(OAc)$_2$ (0.001 g, 0.004 mmol), S-Phos (0.002 g, 0.008 mmol) in THF (2 mL). The mixture was stirred for 16 h at room temperature. Phenethylzinc bromide (0.502 mL, 0.5 M in THF, 0.251 mmol), Pd(OAc)$_2$ (0.003 g, 0.012 mmol) and S-Phos (0.009 g, 0.024 mmol) were added and the reaction continued stirring for another 16 h. The mixture was quenched with saturated NH$_4$Cl (3 mL) and diluted in EtOAc (5 mL). The organic layer was isolated and washed with water (2×5 mL). The organic layer was dried (magnesium sulfate), filtered and reduced in vacuo to afford A14 as a brown oil (0.046 g, 83% crude yield). A14 was used without further purification. LCMS $R_t$ 5.60 min, m/z=265.7 [M+H]$^+$.

b) 3,4-Dimethyl-N-(3-(3-phenethylphenyl)isoxazol-5-yl)benzenesulfonamide, 78

A mixture of 3-(3-benzylphenyl)isoxazol-5-amine A14 (0.092 g, 0.348 mmol) (0.050 g, 0.312 mmol), 3,4-dimethylbenzenesulfonyl chloride (0.096 g, 0.47 mmol) and pyridine (1 mL) was stirred at room temperature for 16 h. The mixture was diluted with DCM (1 mL) and washed with 1M HCl (2 mL). The aqueous layer was removed and the organic layer was dried to give the crude residue. The product was purified by HPLC to give the title compound 78 (17 mg, 11% yield).) LCMS $R_t$ 6.51 min, m/z=433.4 [M+H]$^+$.

Example 79: N-(3-(2-bromophenyl)isoxazol-5-yl)benzenesulfonamide, 79

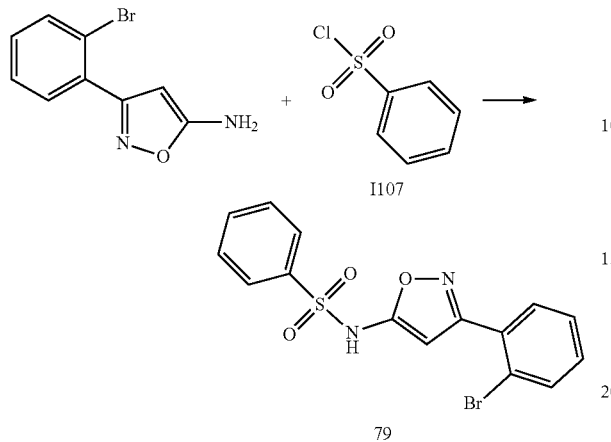

A mixture of 3-(2-bromophenyl)isoxazol-5-amine (0.050 g, 0.209 mmol), benzenesulfonyl chloride I107 (0.040 mL, 0.314 mmol) and pyridine (1 mL) was stirred at room temperature for 16 h. The solvent was removed in vacuo to afford the crude residue. This was dissolved in DCM (2 mL) and 1M HCl (2 mL) and filtered through a phase separation cartridge. The crude was purified by flash chromatography gradient eluting with 100% dichloromethane to 20% MeOH/dichloromethane to give the title compound 79 (21 mg, 27% yield) LCMS $R_t$ 5.85 min, m/z=378.9 [M+H]$^+$.

Example 80: N-(3-(3-bromophenyl)isoxazol-5-yl)benzenesulfonamide, 80

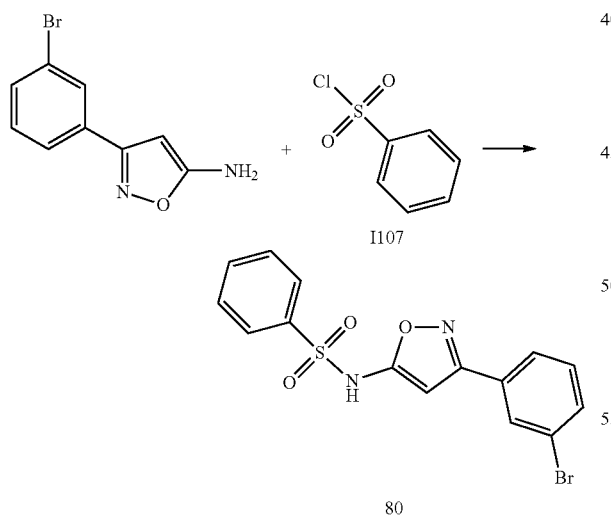

A mixture of 3-(3-bromophenyl)isoxazol-5-amine (0.050 g, 0.209 mmol), benzenesulfonyl chloride I107 (0.040 mL, 0.314 mmol) and pyridine (1 mL) was stirred at room temperature for 16 h. The solvent was removed in vacuo to afford a crude residue. This was dissolved in DCM (2 mL) and 1M HCl (2 mL) and filtered through a phase separation cartridge. The crude product was purified by flash chromatography gradient eluting with 100% dichloromethane to 20% MeOH/dichloromethane to give the title compound (66 mg, 84% yield) LCMS $R_t$ 6.13 min, m/z=381.4 [M+H]$^+$.

Example 81: 1-phenyl-N-(5-phenylisoxazol-3-yl)methanesulfonamide, 81

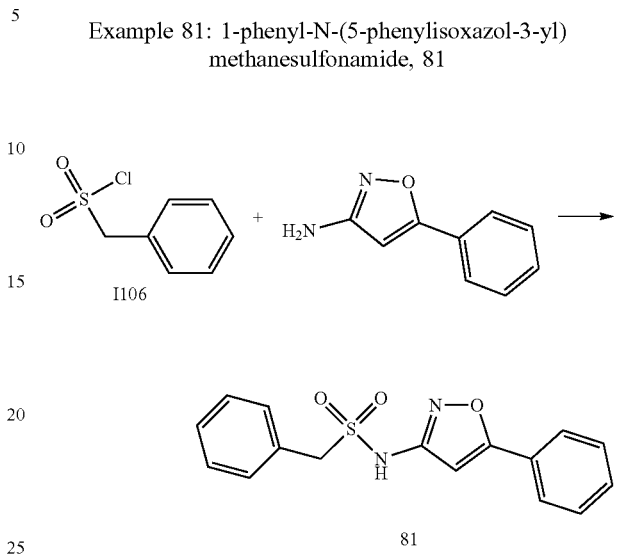

3-Amino-5-phenylisoxazole (0.051 g, 0.320 mmol), pyridine (1 mL) and phenylmethanesulfonyl chloride I106 (0.140 g, 0.736 mmol) were mixed at room temperature and stirred for 16 h. The solvent was removed in vacuo to afford a crude residue. The residue was dissolved in DCM (2 mL) and 1M HCl (2 mL) and filtered through a phase separation cartridge. The crude was purified by flash chromatography, gradient eluting with 100% dichloromethane to 20% MeOH/dichloromethane, to give the title compound 81 (86 mg, 86% yield). LCMS: $R_t$ 5.38 min, m/z=315.4 [M+H]$^+$.

Example 82: 2-fluoro-N-(3-phenylisoxazol-5-yl)benzenesulfonamide, 82

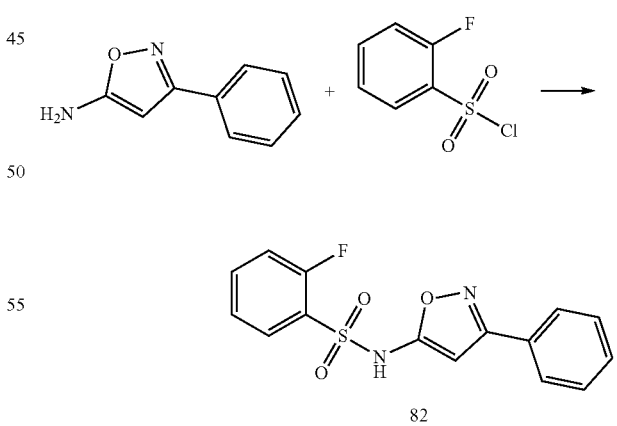

2-Fluorobenzenesulfonyl chloride (0.050 mL, 0.375 mmol), 3-phenylisoxazol-5-amine (0.030 g, 0.187 mmol) and pyridine (1 mL) were mixed at room temperature and stirred for 16 h. Water was added and the resultant precipitate was filtered to give the title compound 82 (32 mg, 53% yield). LCMS: $R_t$ 6.88 min, m/z=318.0 [M+H]$^+$.

Example 83: methyl 5-((3,4-dimethylphenyl)sulfonamido)-3-(4-methoxyphenyl)isoxazole-4-carboxylate, 83

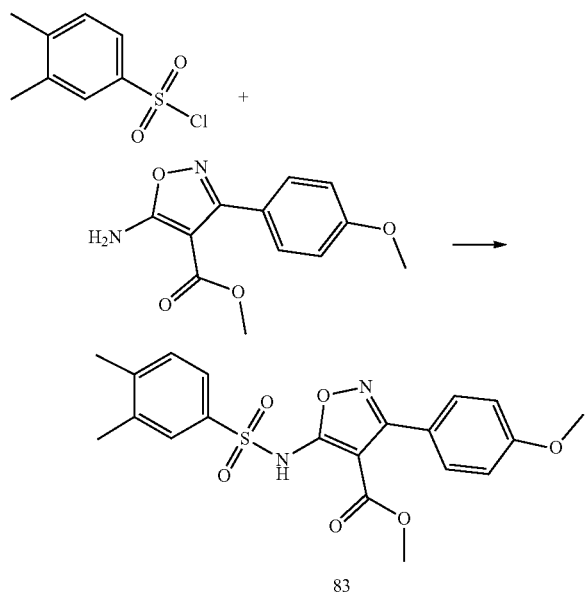

To a solution of methyl 5-amino-3-(4-methoxyphenyl)isoxazole-4-carboxylate (0.057 g, 0.230 mmol) in dry THF (2 mL) at 0° C. was added NaH (0.011 g, 0.459 mmol) and the mixture was stirred for 10 min while warming to room temperature. The temperature was again cooled to 0° C. and 3,4-dimethylbenzenesulfonyl chloride (0.094 g, 0.459 mmol) was added and the reaction was stirred for 16 h while warming to room temperature. The solvent was removed and the residue suspended in MeOH, filtered and reduced to give an orange/white solid (0.201 g). A fraction of the solid was purified by HPLC to give the title compound 83 as a clear oil (0.004 g, 4% yield). LCMS: $R_t$ 6.60 min, m/z=417.22 [M+H]$^+$.

Example 84: 2,6-Dimethoxy-N-(5-(4-methoxy-[1,1'-biphenyl]-3-yl)isoxazol-3-yl)benzenesulfonamide, 84

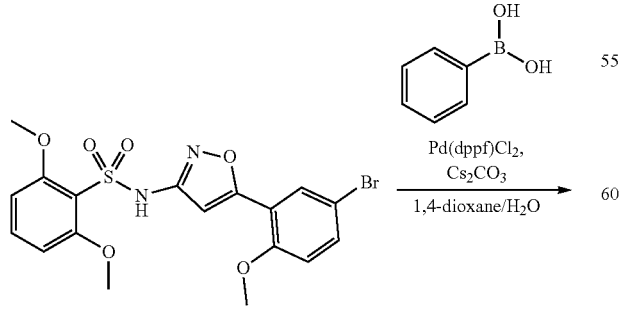

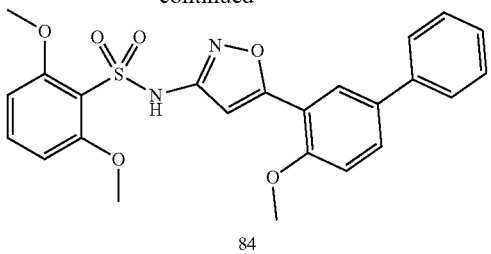

To a solution of N-(5-(5-bromo-2-methoxyphenyl)isoxazol-3-yl)-2,6-dimethoxybenzenesulfonamide 1 (50 mg, 0.106 mmol) and phenylboronic acid (20 mg, 0.160 mmol) in 1,4-dioxane (5 mL) and H$_2$O (1 mL) was added CS$_2$CO$_3$ (104 mg, 0.319 mmol) and Pd(dppf)Cl$_2$ (4 mg, 0.005 mmol) and the mixture was heated at 100° C. overnight. The mixture was diluted with water and washed with EtOAc (30 mL×2). The aqueous layer was then adjusted to pH 4-5 with 1 M aqueous HCl and extracted with EtOAc (50 mL×2). The combined organic extracts were dried over anhydrous Na$_2$SO$_4$, filtered and concentrated under reduced pressure. The residue was purified by silica gel chromatography (Pet. ether/EtOAc=5/1) to give the title compound (40 mg, 81%) as a white solid. LCMS (ES-API): $R_t$ 2.41 min; m/z 467.0 [M+H]$^+$. $^1$H NMR (400 MHz, DMSO-d$_6$) δ 11.1 (s, 1H), 7.98 (d, J=2.0 Hz, 1H), 7.79-7.76 (m, 1H), 7.67 (d, J=7.2 Hz, 2H), 7.51-7.47 (m, 3H), 7.36-7.29 (m, 2H), 6.79-6.74 (m, 3H), 3.95 (s, 3H), 3.84 (s, 6H).

Example 85: 5-Ethyl-2-methoxy-N-(3-(pyridin-4-yl)isoxazol-5-yl)benzenesulfonamide, 85

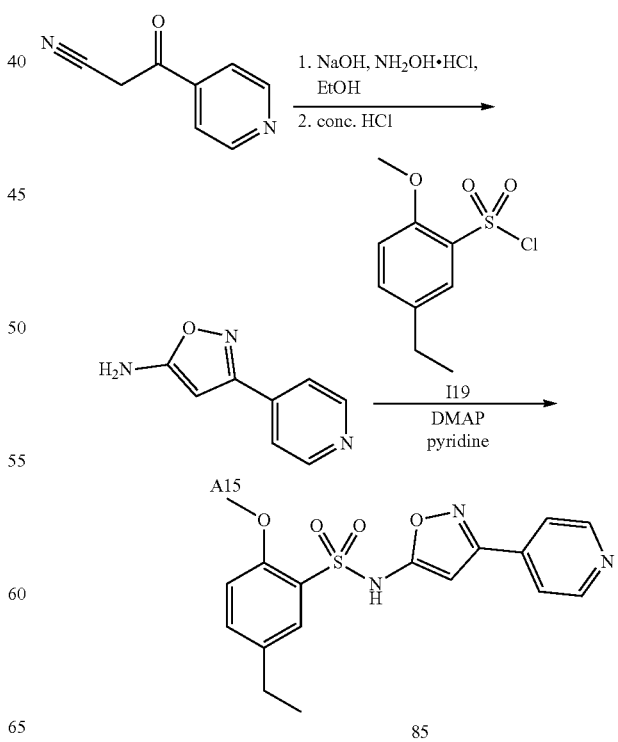

a) 3-(Pyridin-4-yl)isoxazol-5-amine, A15

To a solution of 3-oxo-3-(pyridin-4-yl)propanenitrile (1.5 g, 10.3 mmol) and NaOH (452 mg, 11.3 mmol) in water (15 mL) and ethanol (15 mL) was added hydroxylamine hydrochloride (787 mg, 11.3 mmol) and the mixture was heated at 80° C. overnight. Concentrated aqueous HCl (1.3 mL, 11.3 mmol) was then added and the mixture was heated at 80° C. for a further 2 h. The mixture was adjusted to pH 10 with 2 M aqueous NaOH and extracted with EtOAc (50 mL×3). The combined organic extracts were washed with brine, dried over anhydrous Na$_2$SO$_4$, filtered and concentrated under reduced pressure. The residue was purified by column chromatography (DCM/MeOH=100/1 to 60/1) to give the title compound (200 mg, 13%) as a white solid. LCMS-B (ES-API): R$_t$ 0.26 min; m/z 162.1 [M+H]$^+$. $^1$H NMR (400 MHz, DMSO-d$_6$) δ 8.68-8.63 (m, 2H), 7.72-7.67 (m, 2H), 6.94 (s, 2H), 5.52 (s, 1H).

b) 5-Ethyl-2-methoxy-N-(3-(pyridin-4-yl)isoxazol-5-yl)benzenesulfonamide, 85

To a solution of 3-(pyridin-4-yl)isoxazol-5-amine A15 (50 mg, 0.31 mmol) in pyridine (2 mL) was added 5-ethyl-2-methoxybenzenesulfonyl chloride I19 (109 mg, 0.46 mmol) and DMAP (4 mg, 0.031 mmol) and the mixture was heated at 90° C. overnight. Water (20 mL) was added and the mixture and adjusted to pH 5-6 with 2 M aqueous HCl and extracted with EtOAc (30 mL×3). The combined organic extracts were washed with brine, dried over Na$_2$SO$_4$, filtered and concentrated under reduced pressure. The residue was purified by prep. TLC (DCM/MeOH=80/1) to give the title compound (15 mg, 13%) as a yellow solid. LCMS-B (ES-API): R$_t$ 2.11 min; m/z 360.0 [M+H]$^+$. $^1$H NMR (400 MHz, DMSO-d$_6$) δ 8.69 (d, J=6.0 Hz, 2H), 7.78 (d, J=6.4 Hz, 2H), 7.71 (d, J=2.3 Hz, 1H), 7.47 (dd, J=8.5, 2.3 Hz, 1H), 7.14 (d, J=8.5 Hz, 1H), 6.35 (s, 1H), 3.79 (s, 3H), 2.60 (q, J=7.6 Hz, 2H), 1.14 (t, J=7.6 Hz, 3H).

Example 86: 5-Ethyl-2-methoxy-N-(3-(3-methoxyphenyl)isoxazol-5-yl)benzenesulfonamide, 86

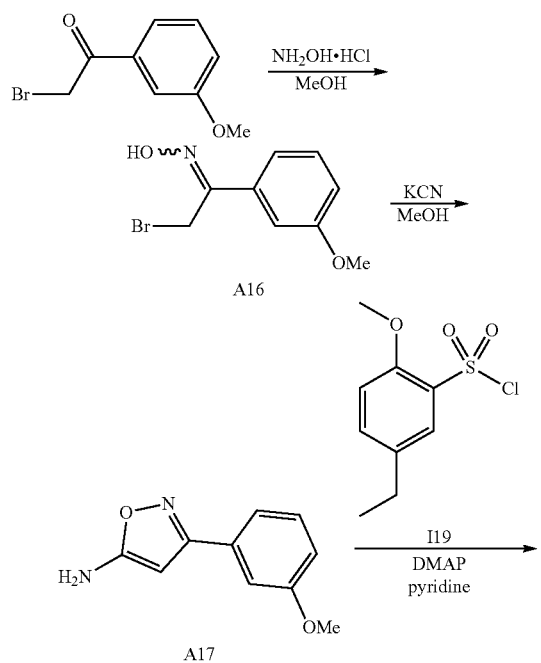

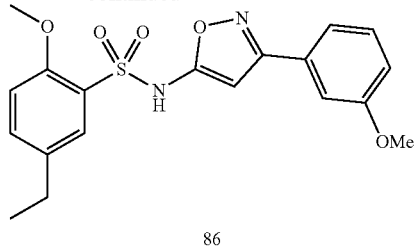

86 a) 2-Bromo-1-(3-methoxyphenyl)ethan-1-one oxime, A16

To a suspension of 2-bromo-1-(3-methoxyphenyl)ethan-1-one (5.0 g, 21.8 mmol) in MeOH (40 mL) and water (6 mL) at 0° C. was added hydroxylamine hydrochloride (4.5 g, 65.4 mmol) and the mixture was stirred at room temperature overnight. The mixture was diluted with water and extracted with EtOAc (60 mL×3). The combined organic extracts were washed with brine, dried over Na$_2$SO$_4$, filtered and concentrated under reduced pressure to give the title compound (5.2 g, 98%) as grey solid. $^1$H NMR analysis showed an unassigned 3:7 mixture of oxime isomers. LCMS-B (ES-API): R$_t$ 2.41 min; m/z 243.9/245.9 [M+H]$^+$. $^1$H NMR (400 MHz, DMSO-d$_6$) δ 12.1 (br s, 0.3H), 12.0 (br s, 0.7H), 7.35 (t, J=7.9 Hz, 1H), 7.31-7.23 (m, 2H), 7.03-6.97 (m, 1H), 4.71 (s, 1.4H), 4.55 (s, 0.6H), 3.79 (s, 3H).

b) 3-(3-Methoxyphenyl)isoxazol-5-amine, A17

To a stirred suspension of KCN (960 mg, 14.7 mmol) in MeOH (60 mL) was added a solution of oxime A16 (3.0 g, 12.3 mmol) in MeOH (15 mL) and the mixture was stirred at room temperature for 20 min. The mixture was diluted with water, extracted with EtOAc (40 mL×3) and the combined organic extracts were washed with brine, dried over anhydrous Na$_2$SO$_4$, filtered and concentrated under reduced pressure. The residue was purified by silica gel chromatography (Pet. ether/EtOAc=20/1 to 10/1 to 6/1) to give the title compound (1.2 g, 47%) as a yellow solid. LCMS-B (ES-API): R$_t$ 1.78 min; m/z 191.0 [M+H]$^+$. $^1$H NMR (400 MHz, DMSO-d$_6$) δ 7.36 (t, J=7.9 Hz, 1H), 7.30-7.27 (m, 1H), 7.25-7.23 (m, 1H), 7.02-6.98 (m, 1H), 6.75 (s, 2H), 5.40 (s, 1H), 3.80 (s, 3H).

c) 5-Ethyl-2-methoxy-N-(3-(3-methoxyphenyl)isoxazol-5-yl)benzenesulfonamide, 86

To a solution of 3-(3-methoxyphenyl)isoxazol-5-amine A17 (250 mg, 1.31 mmol) in pyridine (20 mL) was added 5-ethyl-2-methoxybenzenesulfonyl chloride I19 (461 mg, 1.97 mmol) and DMAP (16 mg, 0.131 mmol) and the mixture was heated at 90° C. overnight. The mixture was diluted with water, adjusted to pH 5 with 1 M aqueous HCl and extracted with EtOAc (40 mL×3). The combined organic extracts were washed with brine, dried over anhydrous Na$_2$SO$_4$, filtered and concentrated under reduced pressure. The residue was purified by silica gel chromatography (Pet. ether/EtOAc=10/1 to 6/1 to 3/1) to give the title compound (90 mg, 17%) as a white solid. LCMS-B (ES-API): R$_t$ 2.82 min; m/z 389.0 [M+H]$^+$. $^1$H NMR (400 MHz, DMSO-d$_6$) δ 7.72 (d, J=2.3 Hz, 1H), 7.49 (dd, J=8.5, 2.3 Hz, 1H), 7.40-7.31 (m, 2H), 7.30-7.27 (m, 1H), 7.16 (d, J=8.6

Hz, 1H), 7.06-7.01 (m, 1H), 6.28 (s, 1H), 3.82 (s, 3H), 3.79 (s, 3H), 2.60 (q, J=7.5 Hz, 2H), 1.14 (t, J=7.5 Hz, 3H).

Example 87: N-(5-(5-Cyano-2-methoxyphenyl)isoxazol-3-yl)-2,6-dimethoxybenzenesulfonamide, 87

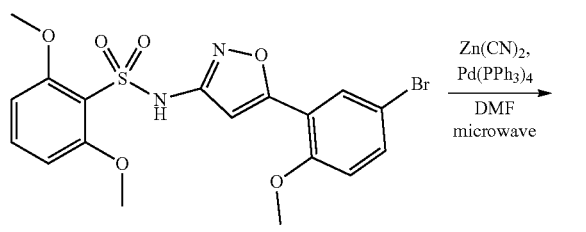

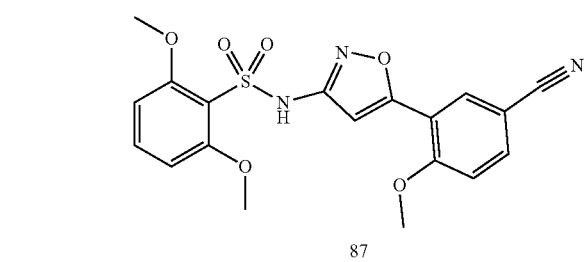

87

To a solution of N-(5-(5-bromo-2-methoxyphenyl)isoxazol-3-yl)-2,6-dimethoxybenzenesulfonamide 1 (50 mg, 0.106 mmol) in DMF (3 mL) was added Zn(CN)$_2$ (13.5 mg, 0.128 mmol) and Pd(PPh$_3$)$_4$ (6.2 mg, 0.005 mmol) and the mixture was heated at 130° C. for 2 h under microwave irradiation. The mixture was diluted with water, extracted with EtOAc (50 mL×3) and the combined organic extracts were dried over anhydrous Na$_2$SO$_4$, filtered and concentrated under reduced pressure. The residue was purified by prep. TLC (DCM/MeOH=70/1) to give the title compound (15 mg, 34%) as a white solid. LCMS-B (ES-API): R$_t$ 1.90 min; m/z 416.0 [M+H]$^+$. $^1$H NMR (400 MHz, CDCl$_3$) δ 8.12 (d, J=2.0 Hz, 1H), 7.68 (dd, J=8.8, 2.0 Hz, 1H), 7.41 (t, J=8.4 Hz, 1H), 7.06 (d, J=8.8 Hz, 1H), 7.04 (s, 1H), 6.63 (d, J=8.8 Hz, 2H), 4.02 (s, 3H), 3.96 (s, 6H).

Example 88: 2,6-Dimethoxy-N-(5-(2-(trifluoromethyl)phenyl)isoxazol-3-yl)benzenesulfonamide, 88

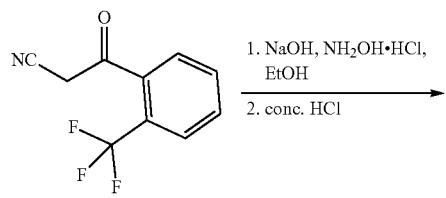

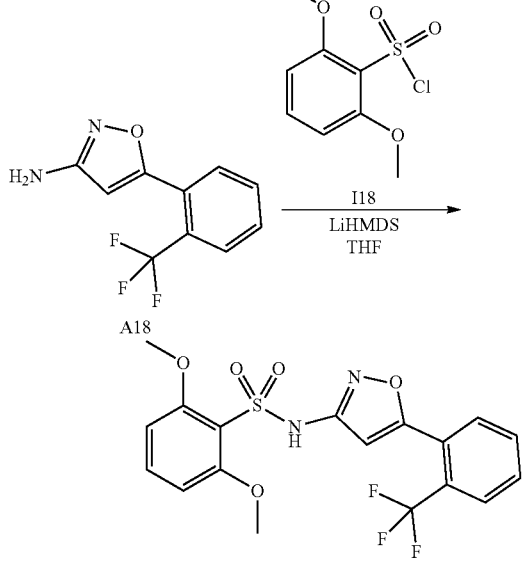

a) 5-(2-(Trifluoromethyl)phenyl)isoxazol-3-amine, A18

To a solution of 3-oxo-3-(2-(trifluoromethyl)phenyl)propanenitrile (500 mg, 2.35 mmol) and NaOH (103 mg, 2.58 mmol) in H$_2$O (8 mL) and EtOH (8 mL) was added hydroxylamine hydrochloride (179 mg, 2.58 mmol) and the mixture was heated at 80° C. overnight. Concentrated aqueous HCl (0.5 mL, 3 mmol) was then added and the mixture was heated at 80° C. for a further 2.5 h. The mixture was adjusted to pH 10 with 2 M aqueous NaOH and extracted with EtOAc. The combined organic extracts were washed with brine, dried over anhydrous Na$_2$SO$_4$, filtered and concentrated under reduced pressure. The residue was purified by silica gel chromatography (DCM/MeOH=200/1) to give the title compound (170 mg, 32%) as a yellow oil. LCMS-A (ES-API): R$_t$ 1.33 min; m/z 229.0 [M+H]$^+$. $^1$H NMR (400 MHz, DMSO-d$_6$) δ 7.91 (d, J=7.6 Hz, 1H), 7.80-7.72 (m, 3H), 6.14 (s, 1H), 5.72 (s, 2H).

b) 2,6-Dimethoxy-N-(5-(2-(trifluoromethyl)phenyl)isoxazol-3-yl)benzenesulfonamide, 88

To a solution of 5-(2-(trifluoromethyl)phenyl)isoxazol-3-amine A18 (60 mg, 0.263 mmol) in anhydrous THF (12 mL) at −78° C. under N$_2$ was added LiHMDS (1 M solution in THF, 1.1 mL, 1.05 mmol) dropwise and the mixture was stirred at −78° C. for 2 h. A solution of 2,6-dimethoxybenzenesulfonyl chloride I18 (94 mg, 0.394 mmol) in anhydrous THF (2 mL) was then added dropwise and the mixture was allowed to warm to room temperature and stirred overnight. The mixture was diluted with water, extracted with EtOAc and the combined organic extracts were washed with water, brine, dried over anhydrous Na$_2$SO$_4$, filtered and concentrated under reduced pressure. The residue was purified by prep. TLC (DCM/MeOH=20/1) to give the title compound (31 mg, 28%) as a white solid. LCMS-A (ES-API): R$_t$ 2.27 min; m/z 428.9 [M+H]$^+$. $^1$H NMR (400 MHz, DMSO-d$_6$) δ 7.93 (d, J=8.0 Hz, 1H), 7.80-7.77 (m, 3H), 7.50 (t, J=8.6 Hz, 1H), 7.03 (s, 1H), 6.78 (d, J=8.4 Hz, 2H), 6.56 (s, 1H), 3.79 (s, 6H).

Other Compounds
The following compounds were obtained commercially:

| Example | Structure |
|---|---|
| 89 | 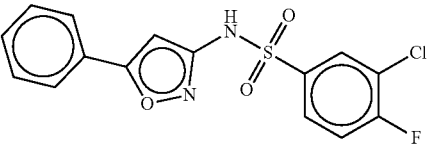 |
| 90 | 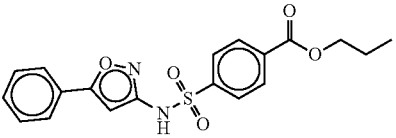 |
| 91 | 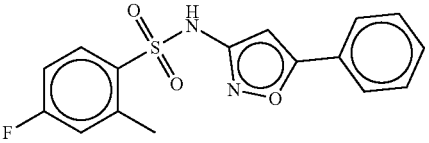 |
| 92 | 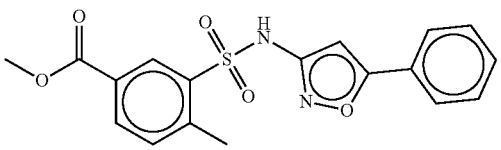 |

Examples 93-115 (Table E)

General Method EA

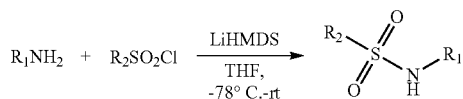

To a solution of the amine (1.0 eq) in anhydrous THF (10 mL) at −78° C. under $N_2$ was added LiHMDS (1 M solution in THF, 3.0 eq) dropwise and the mixture was stirred at −78° C. for 2 h. A solution of the sulfonyl chloride (1.5 eq) in anhydrous THF (2.0 mL) was then added dropwise and the mixture was allowed to warm to room temperature and was stirred overnight. Water was added and the mixture was extracted with EtOAc. The combined organic extracts were washed with brine, dried over anhydrous $Na_2SO_4$, filtered and concentrated under reduced pressure. The residue was purified by column chromatography, prep. TLC or recrystallisation to give the desired compound.

General Method EB:

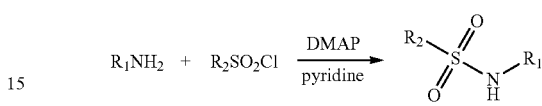

To a solution of the amine (1.0 eq) in pyridine (4 mL) under $N_2$ was added the sulfonyl chloride (1.5 eq) and DMAP (0.2 eq) and the mixture was heated at 90° C. overnight. The reaction was quenched with 1 M aqueous HCl, water was then added and the mixture was extracted with EtOAc. The combined organic extracts were washed with brine, dried over anhydrous $Na_2SO_4$, filtered and concentrated under reduced pressure. The residue was purified by preparative TLC to give the desired compound.

General Method EC:

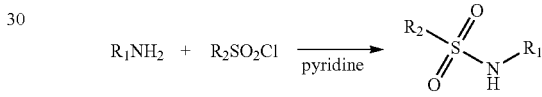

To a solution of the amine (1.0 eq) in pyridine (2 mL) was added the sulfonyl chloride (2.0 eq) and the mixture was heated at 120° C. under microwave irradiation for 2 h. The reaction was quenched with 1 M aqueous HCl, water was then added and the mixture was extracted with EtOAc. The combined organic extracts were washed with brine, dried over anhydrous $Na_2SO_4$, filtered and concentrated under reduced pressure. The residue was purified by preparative TLC to give the desired compound.

The following examples were synthesised according to general method EA, EB or EC using the appropriate amine $R_1NH_2$ and sulfonyl chloride $R_2SO_2Cl$ intermediate.

| Example | Starting materials | Name and structure | Analytical data | Method | Notes |
|---|---|---|---|---|---|
| 93 | I18 & 5-phenylisoxazol-3-amine | 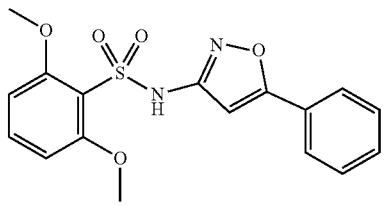 [SMILES: COc1cccc(OC)c1S(=O)(=O)Nc1cc(-c2ccccc2)on1]<br>2,6-Dimethoxy-N-(5-phenylisoxazol-3-yl)benzenesulfonamide | LCMS-E (ES-API): $R_t$ 2.60 min; m/z 361.0 [M + H]$^+$, $^1$H NMR (400 MHz, DMSO-$d_6$) δ 11.1 (br s, 1H), 7.73-7.71 (m, 2H), 7.52-7.38 (m, 4H), 6.72 (d, J = 8.4 Hz, 2H), 6.70 (s, 1H), 3.78 (s, 6H). | EC | Prep. TLC (EtOAc/DCM = 1/3) |

-continued

| Example | Starting materials | Name and structure | Analytical data | Method | Notes |
|---|---|---|---|---|---|
| 94 | I18 & I87 | 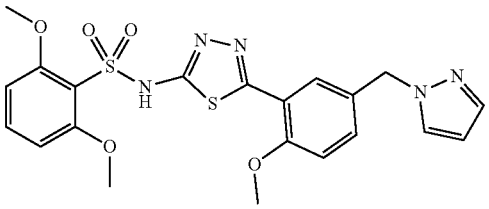 [SMILES: COc1ccc(Cn2cccn2)cc1-c1nnc(NS(=O)(=O)c2c(OC)cccc2OC)s1]<br>N-(5-(5-((1H-Pyrazol-1-yl)methyl)-2-methoxyphenyl)-1,3,4-thiadiazol-2-yl)-2,6-dimethoxybenzenesulfonamide | LCMS-E (ES-API): $R_t$ 1.57 min; m/z 488.1 [M + H]$^+$, $^1$H NMR (400 MHz, d$_4$-MeOD) δ 7.98 (d, J = 2.3 Hz, 1H), 7.73 (s, 1H), 7.52 (d, J = 1.9 Hz, 1H), 7.44 (t, J = 8.5 Hz, 1H), 7.39 (dd, J = 8.7, 2.3 Hz, 1H), 7.18 (d, J = 8.6 Hz, 1H), 6.74 (d, J = 8.4 Hz, 2H), 6.33 (t, J = 2.2 Hz, 1H), 5.36 (s, 2H), 4.00 (s, 3H), 3.79 (s, 6H). | EC | 1.5 eq sulfonyl chloride used; Prep. TLC (DCM/MeOH = 20/1) |
| 95 | I18 & I74 | 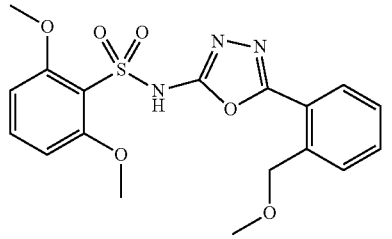 [SMILES: COCc1ccccc1-c1nnc(NS(=O)(=O)c2c(OC)cccc2OC)o1]<br>2,6-Dimethoxy-N-(5-(2-(methoxymethyl)phenyl)-1,3,4-oxadiazol-2-yl)benzenesulfonamide | LCMS-A (ES-API): $R_t$ 3.35 min; m/z 406.0 [M + H]$^+$, $^1$H NMR (400 MHz, DMSO-d$_6$) δ 7.75 (d, J = 7.8 Hz, 1H), 7.68-7.59 (m, 2H), 7.51-7.42 (m, 2H), 6.76 (d, J = 8.4 Hz, 2H), 4.69 (s, 2H), 3.73 (s, 6H), 3.33 (s, 3H). | EA | Prep. TLC (DCM/MeOH = 20/1) |
| 96 | I18 & I80 | 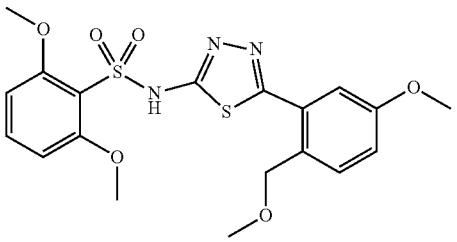 [SMILES: COCc1ccc(OC)cc1-c1nnc(NS(=O)(=O)c2c(OC)cccc2OC)s1]<br>2,6-Dimethoxy-N-(5-(5-methoxy-2-(methoxymethyl)phenyl)-1,3,4-thiadiazol-2-yl)benzenesulfonamide | LCMS-A (ES-API): $R_t$ 2.03 min; m/z 451.9 [M + H]$^+$, $^1$H NMR (400 MHz, d$_4$-MeOD) δ 7.49-7.43 (m, 2H), 7.19 (d, J = 2.7 Hz, 1H), 7.10 (dd, J = 8.5, 2.7 Hz, 1H), 6.76 (d, J = 8.80 Hz, 2H), 4.59 (s, 2H), 3.86 (s, 3H), 3.82 (s, 6H), 3.34 (s, 3H). | EC | 1.5 eq sulfonyl chloride used; Prep. TLC (DCM/MeOH = 15/1) |
| 97 | 2,6-Difluoro benzene sulfonyl chloride & I2 | 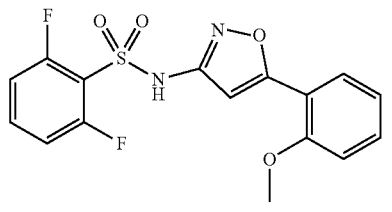 [SMILES: COc1ccccc1-c1cc(NS(=O)(=O)c2c(F)cccc2F)no1]<br>2,6-Difluoro-N-(5-(2-methoxyphenyl)isoxazol-3-yl)benzenesulfonamide | LCMS-E (ES-API): $R_t$ 2.84 min; m/z 366.8 [M + H]$^+$, $^1$H NMR (400 MHz, DMSO-d$_6$) δ 11.6 (br s, 1H), 7.82-7.72 (m, 2H), 7.53-7.46 (m, 1H), 7.33 (t, J = 9.3 Hz, 2H), 7.21 (d, J = 8.4 Hz, 1H), 7.08 (t, J = 7.5 Hz, 1H), 6.69 (s, 1H), 3.92 (s, 3H). | EC | 1.2 eq sulfonyl chloride used; Column chromatography (Pet. Ether/EtOAc = 10/1 to 5/1) |

-continued

| Example | Starting materials | Name and structure | Analytical data | Method | Notes |
|---|---|---|---|---|---|
| 98 | I18 & I62 | N-(5-(5-((1H-Pyrazol-1-yl)methyl)-2-methoxyphenyl)isoxazol-3-yl)-2,6-dimethoxybenzenesulfonamide | LCMS-A (ES-API): R$_t$ 2.14 min; m/z 471.0 [M + H]$^+$, $^1$H NMR (400 MHz, DMSO-d$_6$) δ 7.81 (d, J = 2.2 Hz, 1H), 7.64 (s, 1H), 7.47-7.42 (m, 2H), 7.34 (d, J = 8.9 Hz, 1H), 7.15 (d, J = 8.6 Hz, 1H), 6.74 (d, J = 8.5 Hz, 2H), 6.67 (s, 1H), 6.24 (t, J = 2.1 Hz, 1H), 5.31 (s, 2H), 3.87 (s, 3H), 3.79 (s, 6H). | EC | 3.5 eq sulfonyl chloride used; Prep. TLC (Pet. Ether/ EtOAc = 1/1) |
| 99 | I18 & I70 | N-(5-(3,5-Dimethoxyphenyl)-1,3,4-thiadiazol-2-yl)-2,6-dimethoxybenzenesulfonamide | LCMS-A (ES-API): R$_t$ 2.23 min; m/z 437.9 [M + H]$^+$, $^1$H NMR (400 MHz, DMSO-d$_6$) δ 14.1 (br s, 1H), 7.45 (t, J = 8.4 Hz, 1H), 6.94 (d, J = 2.3 Hz, 2H), 6.75 (d, J = 8.5 Hz, 2H), 6.68 (t, J = 2.3 Hz, 1H), 3.82 (s, 6H), 3.71 (s, 6H). | EC | Prep. TLC (DCM/ MeOH = 30/1) |
| 100 | I18 & I57 | 2,6-Dimethoxy-N-(5-(2-methoxy-5-(trifluoromethyl)phenyl)-1,3,4-thiadiazol-2-yl)benzenesulfonamide | LCMS-A (ES-API): R$_t$ 2.37 min; m/z 475.9 [M + H]$^+$, $^1$H NMR (400 MHz, DMSO-d$_6$) δ 14.2 (br s, 1H), 8.25 (d, J = 2.4 Hz, 1H), 7.90 (dd, J = 9.0, 2.4 Hz, 1H), 7.48 (d, J = 8.8 Hz, 1H), 7.44 (t, J = 8.4 Hz, 1H), 6.74 (d, J = 8.4 Hz, 2H), 4.06 (s, 3H), 3.71 (s, 6H). | EC | 1.0 mL pyridine used; Prep. TLC (Pet. Ether/ EtOAc = 1/1) |
| 101 | I18 & I90 | N-(5-(2-((1H-Pyrazol-1-yl)methyl)phenyl)-1,3,4-thiadiazol-2-yl)-2,6-dimethoxybenzenesulfonamide | LCMS-A (ES-API): R$_t$ 1.90 min; m/z 458.0 [M + H]$^+$, $^1$H NMR (400 MHz, d$_4$-MeOD) δ 7.72-7.68 (m, 1H), 7.64 (d, J = 2.4 Hz, 1H), 7.53 (d, J = 1.9 Hz, 1H), 7.52-7.45 (m, 3H), 7.00-6.95 (m, 1H), 6.77 (d, J = 8.4 Hz, 2H), 6.33 (t, J = 2.1 Hz, 1H), 5.73 (s, 2H), 3.82 (s, 6H). | EC | 1.5 eq sulfonyl chloride used; Purified by prep. HPLC |

-continued

| Example | Starting materials | Name and structure | Analytical data | Method | Notes |
|---|---|---|---|---|---|
| 102 | Cyclo-hexane-sulfonyl chloride & I2 | 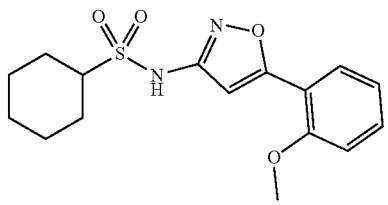 [SMILES: COc1ccccc1-c1cc(NS(=O)(=O)C2CCCCC2)no1]<br>N-(5-(2-Methoxyphenyl)isoxazol-3-yl)cyclohexanesulfonamide | LCMS-A (ES-API): $R_t$ 2.41 min; m/z 337.0 [M + H]$^+$,<br>$^1$H NMR (400 MHz, DMSO-d$_6$) δ 10.9 (br s, 1H), 7.82 (dd, J = 7.8, 1.8 Hz, 1H), 7.55-7.47 (m, 1H), 7.23 (d, J = 8.4 Hz, 1H), 7.11 (t, J = 7.6 Hz, 1H), 6.72 (s, 1H), 3.94 (s, 3H), 3.28-3.20 (m, 1H), 2.08-2.05 (m, 2H), 1.84-1.73 (m, 2H), 1.62-1.59 (m, 1H), 1.49-1.36 (m, 2H), 1.33-1.24 (m, 2H), 1.19-1.08 (m, 1H). | EA | Purified by prep. HPLC |
| 103 | I48 & I2 | 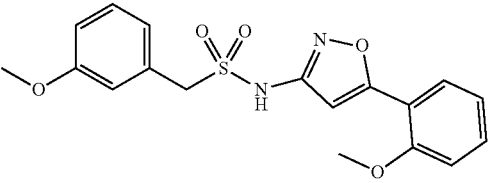 [SMILES: COc1cccc(CS(=O)(=O)Nc2cc(-c3ccccc3OC)on2)c1]<br>1-(3-Methoxyphenyl)-N-(5-(2-methoxyphenyl)isoxazol-3-yl)methanesulfonamide | LCMS-A (ES-API): $R_t$ 2.34 min; m/z 375.0 [M + H]$^+$,<br>$^1$H NMR (400 MHz, DMSO-d$_6$) δ 11.0 (br s, 1H), 7.82 (dd, J = 7.7, 1.7 Hz, 1H), 7.55-7.48 (m, 1H), 7.31-7.25 (m, 1H), 7.23 (d, J = 8.3 Hz, 1H), 7.11 (t, J = 7.6, 1.0 Hz, 1H), 6.94-6.88 (m, 2H), 6.88 (s, 1H), 6.50 (s, 1H), 4.63 (s, 2H), 3.92 (s, 3H), 3.69 (s, 3H). | EC | 1.5 eq sulfonyl chloride used; 1.0 mL pyridine used; Prep. TLC (Pet. Ether/EtOAc = 2/1) |
| 104 | I18 & I102 | 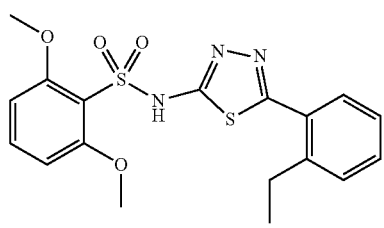 [SMILES: CCc1ccccc1-c1nnc(NS(=O)(=O)c2c(OC)cccc2OC)s1]<br>N-(5-(2-Methylphenyl)-1,3,4-thiadiazol-2-yl)-2,6-dimethoxybenzenesulfonamide | LCMS-B (ES-API): $R_t$ 2.61 min; m/z 406.0 [M + H]$^+$,<br>$^1$H NMR (400 MHz, DMSO-d$_6$) δ 14.2 (br s, 1H), 7.56 (dd, J = 7.6, 1.3 Hz, 1H), 7.52-7.42 (m, 3H), 7.39-7.34 (m, 1H), 6.76 (d, J = 8.4 Hz, 2H), 3.73 (s, 6H), 2.85 (q, J = 7.5 Hz, 2H), 1.16 (t, J = 7.5 Hz, 3H). | EC | 1.0 mL pyridine used; Prep. TLC (DCM/MeOH = 50/1) |
| 105 | I18 & I65 | 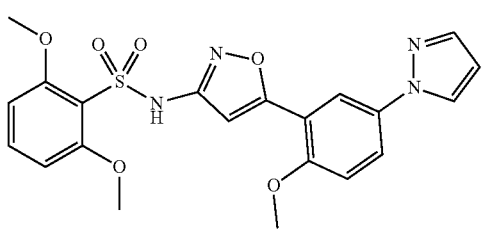 [SMILES: COc1ccc(-n2cccn2)cc1-c1cc(NS(=O)(=O)c2c(OC)cccc2OC)no1]<br>2,6-Dimethoxy-N-(5-(2-methoxy-5-(1H-pyrazol-1-yl)phenyl)isoxazol-3-yl)benzenesulfonamide | LCMS-B (ES-API): $R_t$ 2.47 min; m/z 457.0 [M + H]$^+$,<br>$^1$H NMR (400 MHz, DMSO-d$_6$) δ 11.2 (br s, 1H), 8.53 (d, J = 2.6 Hz, 1H), 8.18 (d, J = 2.8 Hz, 1H), 7.93 (dd, J = 9.1, 2.8 Hz, 1H), 7.73 (s, 1H), 7.49 (t, J = 8.5 Hz, 1H), 7.33 (d, J = 9.1 Hz, 1H), 6.79-6.77 (m, 3H), 6.52 (t, J = 2.1 Hz, 1H), 3.95 (s, 3H), 3.84 (s, 6H). | EC | Prep. TLC (DCM/MeOH = 50/1) |

| Example | Starting materials | Name and structure | Analytical data | Method | Notes |
|---|---|---|---|---|---|
| 106 | I18 & I105 | 2,6-Dimethoxy-N-(5-(2-methoxy-5-(trifluoromethyl)phenyl)isoxazol-3-yl)benzenesulfonamide | LCMS-A (ES-API): $R_t$ 2.43 min; m/z 458.9 [M + H]$^+$, $^1$H NMR (400 MHz, DMSO-d$_6$) δ 11.2 (br s, 1H), 7.99 (d, J = 2.4 Hz, 1H), 7.85 (dd, J = 9.0, 2.4 Hz, 1H), 7.49 (t, J = 8.5 Hz, 1H), 7.42 (d, J = 8.9 Hz, 1H), 6.77 (d, J = 8.4 Hz, 2H), 6.78 (s, 1H), 4.00 (s, 3H), 3.82 (s, 6H). | EC | 1.5 eq sulfonyl chloride used; 1.0 mL pyridine used; No HCl used in workup; Prep. TLC (Pet. + Ether/ EtOAc = 3/1) |
| 107 | 2-Phenyl-ethane-1-sulfonyl chloride & I17 | N-(5-(2-Methoxy-5-(methoxymethyl)phenyl)isoxazol-3-yl)-2-phenylethane-1-sulfonamide | LCMS-A (ES-API): $R_t$ 2.46 min; m/z 403.0 [M + H]$^+$, $^1$H NMR (400 MHz, DMSO-d$_6$) δ 7.69 (d, J = 2.2 Hz, 1H), 7.37 (dd, J = 8.5, 2.3 Hz, 1H), 7.29-7.24 (m, 2H), 7.22-7.13 (m, 4H), 6.56 (s, 1H), 4.39 (s, 2H), 3.90 (s, 3H), 3.27 (s, 3H), 3.25-3.21 (m, 2H), 2.98-2.91 (m, 2H). | EC | 1.0 mL pyridine used; Prep. TLC (Pet. Ether/ EtOAc = 3/1) |
| 108 | I18 & I68 | N-(5-(2-Bromo-6-methoxyphenyl)isoxazol-3-yl)-2,6-dimethoxybenzenesulfonamide | LCMS-A (ES-API): $R_t$ 2.32 min; m/z 468.8/470.8 [M + H]$^+$, $^1$H NMR (400 MHz, DMSO-d$_6$) δ 11.2 (br s, 1H), 7.41 (t, J = 8.2 Hz, 2H), 7.30 (d, J = 8.0 Hz, 1H), 7.16 (d, J = 8.5 Hz, 1H), 6.73 (d, J = 8.4 Hz, 2H), 6.31 (s, 1H), 3.76 (s, 6H), 3.72 (s, 3H). | EC | 1.2 eq sulfonyl chloride used; 3.0 mL pyridine used; No HCl used in workup; Prep. TLC (Pet. Ether/ EtOAc = 1/1) |
| 109 | I18 & I100 | N-(5-(2-Ethoxy-5-methoxyphenyl)-1,2,4-oxadiazol-3-yl)-2,6-dimethoxybenzenesulfonamide | LCMS-A (ES-API): $R_t$ 2.24 min; m/z 436.0 [M + H]$^+$, $^1$H NMR (400 MHz, DMSO-d$_6$) δ 11.7 (s, 1H), 7.50 (t, J = 8.5 Hz, 1H), 7.29 (dd, J = 2.6, 1.0 Hz, 1H), 7.23-7.16 (m, 2H), 6.78 (d, J = 8.4 Hz, 2H), 4.08 (q, J = 6.9 Hz, 2H), 3.79 (s, 6H), 3.75 (s, 3H), 1.29 (t, J = 7.0 Hz, 3H). | EC | 1.2 eq sulfonyl chloride and 0.2 eq DMAP used; 1.5 mL pyridine used; Prep. TLC (DCM/ MeOH = 30/1) |

-continued

| Example | Starting materials | Name and structure | Analytical data | Method | Notes |
|---|---|---|---|---|---|
| 110 | I18 & I82 | 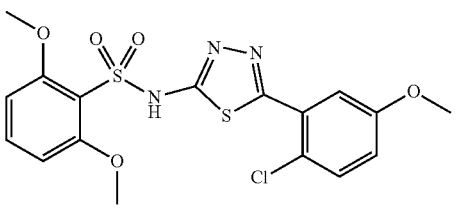 [SMILES: COc1ccc(Cl)c(-c2nnc(NS(=O)(=O)c3c(OC)cccc3OC)s2)c1]<br>N-(5-(2-Chloro-5-methoxyphenyl)-1,3,4-thiadiazol-2-yl)-2,6-dimethoxybenzenesulfonamide | LCMS-A (ES-API): $R_t$ 2.27 min; m/z 441.9 $[M + H]^+$,<br>$^1$H NMR (400 MHz, CDCl$_3$) δ 7.49 (d, J = 3.0 Hz, 1H), 7.40 (t, J = 8.0 Hz, 1H), 7.39 (d, J = 8.0 Hz, 1H), 6.99 (dd, J = 8.9, 2.8 Hz, 1H), 6.61 (d, J = 8.4 Hz, 2H), 3.89 (s, 6H), 3.85 (s, 3H). | EC | 1.5 eq sulfonyl chloride used; Concentrated and purified by Prep. TLC (DCM/MeOH = 15/1) |
| 111 | I18 & I76 | 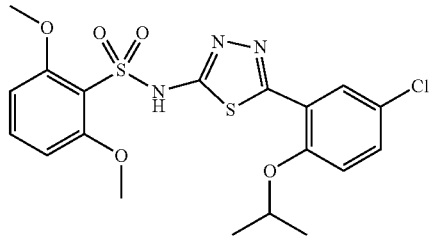 [SMILES: COc1cccc(OC)c1S(=O)(=O)Nc1nnc(-c2cc(Cl)ccc2OC(C)C)s1]<br>N-(5-(5-Chloro-2-isopropoxyphenyl)-1,3,4-thiadiazol-2-yl)-2,6-dimethoxybenzenesulfonamide | LCMS-A (ES-API): $R_t$ 2.42 min; m/z 469.9 $[M + H]^+$,<br>$^1$H NMR (400 MHz, CDCl$_3$) δ 8.11 (d, J = 2.6 Hz, 1H), 7.40-7.35 (m, 2H), 6.94 (d, J = 8.9 Hz, 1H), 6.62 (d, J = 8.1 Hz, 2H), 4.79-4.70 (m, 1H), 3.88 (s, 6H), 1.46 (d, J = 5.9 Hz, 6H). | EC | 1.5 eq sulfonyl chloride used; 3.0 mL pyridine used; No HCl used in workup; Prep. TLC (DCM/MeOH = 15/1) |
| 112 | I106 & I17 | 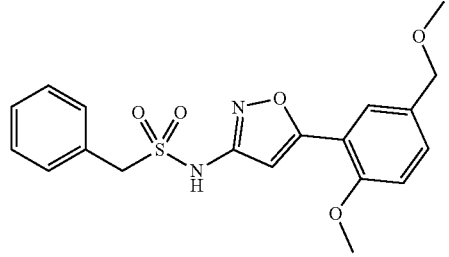 [SMILES: COCc1ccc(OC)c(-c2cc(NS(=O)(=O)Cc3ccccc3)no2)c1]<br>N-(5-(2-Methoxy-5-(methoxymethyl)phenyl)isoxazol-3-yl)-1-phenylmethanesulfonamide | LCMS-A (ES-API): $R_t$ 2.33 min; m/z 389.0 $[M + H]^+$,<br>$^1$H NMR (400 MHz, DMSO-d$_6$) δ 11.1 (br s, 1H), 7.76 (d, J = 2.2 Hz, 1H), 7.45 (dd, J = 8.6, 2.2 Hz, 1H), 7.41-7.30 (m, 5H), 7.21 (d, J = 8.5 Hz, 1H), 6.49 (s, 1H), 4.66 (s, 2H), 4.42 (s, 2H), 3.93 (s, 3H), 3.29 (s, 3H). | EB | Prep. TLC (Pet. Ether/EtOAc = 2/1) |
| 113 | I18 & I92 | 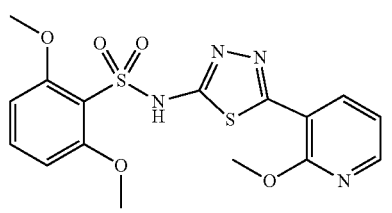 [SMILES: COc1cccc(OC)c1S(=O)(=O)Nc1nnc(-c2cccnc2OC)s1]<br>2,6-Dimethoxy-N-(5-(2-methoxypyridin-3-yl)-1,3,4-thiadiazol-2-yl)benzenesulfonamide | LCMS-A (ES-API): $R_t$ 1.51 min; m/z 408.9 $[M + H]^+$,<br>$^1$H NMR (400 MHz, DMSO-d$_6$) δ 14.2 (br s, 1H), 8.38 (d, J = 6.2 Hz, 2H), 7.45 (t, J = 8.4 Hz, 1H), 7.25-7.19 (m, 1H), 6.76 (d, J = 8.4 Hz, 2H), 4.06 (s, 3H), 3.71 (s, 6H). | EC | 1.5 eq sulfonyl chloride used; 3.0 mL pyridine used; No HCl used in workup; Column chromatography (DCM/MeOH = 50/1) |

| Example | Starting materials | Name and structure | Analytical data | Method | Notes |
|---|---|---|---|---|---|
| 114 | I52 & I2 | 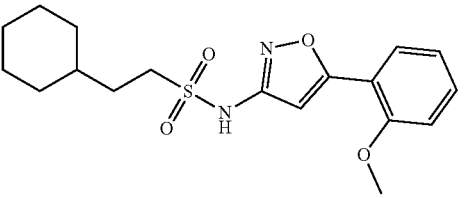 [SMILES: COc1ccccc1-c1cc(NS(=O)(=O)CCC2CCCCC2)no1]<br>2-Cyclohexyl-N-(5-(2-methoxyphenyl)isoxazol-3-yl)ethane-1-sulfonamide | LCMS-E (ES-API): $R_t$ 3.40 min; m/z 365.1 [M + H]$^+$, $^1$H NMR (400 MHz, DMSO-$d_6$) δ 7.75-7.73 (m, 1H), 7.47-7.38 (m, 1H), 7.17 (d, J = 8.5 Hz, 1H), 7.06 (t, J = 7.6 Hz, 1H), 6.54-6.53 (m, 1H), 3.90 (s, 3H), 3.01-2.89 (m, 2H), 1.67-1.50 (m, 7H), 1.34-1.05 (m, 4H), 0.89-0.77 (m, 2H). | EA | 4.2 eq sulfonyl chloride used; Column chromatography (Pet. Ether/EtOAc = 3/1) |
| 115 | I54 & I2 | 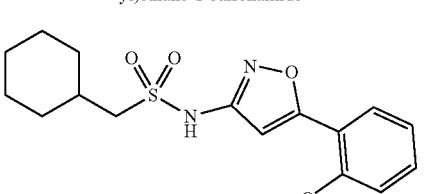<br>1-Cyclohexyl-N-(5-(2-methoxyphenyl)isoxazol-3-yl)methanesulfonamide | LCMS-E (ES-API): $R_t$ 3.24 min; m/z 351.9 [M + H]$^+$, $^1$H NMR (400 MHz, DMSO-$d_6$) δ 7.78 (dd, J = 7.8, 1.7 Hz, 1H), 7.50-7.43 (m, 1H), 7.21 (d, J = 8.3 Hz, 1H), 7.09 (t, J = 7.5 Hz, 1H), 6.61 (s, 1H), 3.92 (s, 3H), 3.02 (d, J = 5.5 Hz, 2H), 2.05-1.94 (m, 1H), 1.91-1.80 (m, 3H), 1.68-1.52 (m, 3H), 1.37-1.27 (m, 1H), 1.15-0.99 (m, 3H). | EA | Prep. TLC (Pet. Ether/EtOAc = 3/1) |

Example 116: N-Phenyl((5-(2-methoxyphenyl)-1,2-oxazol-3-yl)amino)sulfonamide, I16

Example 117: N-Cyclohexyl((5-(2-methoxyphenyl)-1,2-oxazol-3-yl)amino)sulfonamide, 117

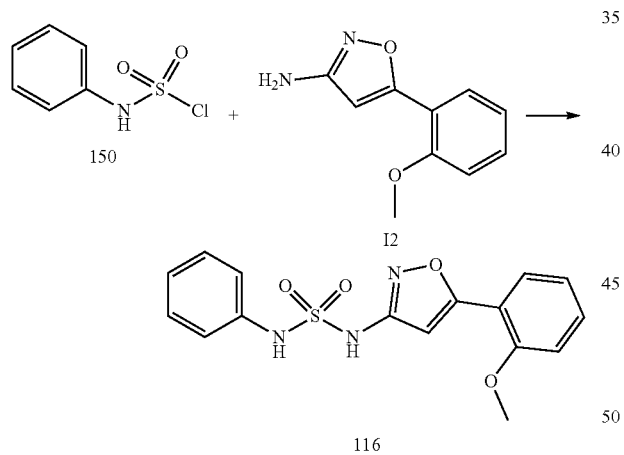

A mixture of 5-(2-methoxyphenyl)isoxazol-3-amine I2 (40 mg, 0.21 mmol) and phenylsulfamoyl chloride I50 (200 mg, 1.05 mmol) in toluene (6 mL) was heated at 60° C. for 2 h. The mixture was adjusted to pH 5 with 1 M aqueous HCl and extracted with EtOAc (20 mL×3). The combined organic extracts were washed with brine, dried over Na$_2$SO$_4$, filtered and concentrated under reduced pressure. The residue was purified by prep. TLC (DCM/MeOH=30/1) to give the title compound (18 mg, 25%) as a white solid. LCMS-A (ES-API): $R_t$ 3.79 min; m/z 346.0 [M+H]$^+$. $^1$H NMR (400 MHz, DMSO-$d_6$) δ 11.4 (br s, 1H), 10.5 (br s, 1H), 7.76 (d, J=7.8 Hz, 1H), 7.49 (t, J=7.9 Hz, 1H), 7.35-7.14 (m, 5H), 7.15-6.93 (m, 2H), 6.77 (s, 1H), 3.94 (s, 3H).

A mixture of 5-(2-methoxyphenyl)isoxazol-3-amine I2 (40 mg, 0.21 mmol) and cyclohexylsulfamoyl chloride (50 mg, 0.25 mmol) in pyridine (1 mL) was stirred at room temperature until LCMS analysis showed the starting material was consumed. The mixture was concentrated under reduced pressure and the residue was purified by prep. TLC (DCM/MeOH=20/1) to give the title compound (20 mg, 27%) as a white solid. LCMS-E (ES-API): $R_t$ 3.04 min; m/z 351.9 [M+H]$^+$. $^1$H NMR (400 MHz, DMSO-$d_6$) δ 10.7 (s, 1H), 7.81 (dd, J=7.8, 1.7 Hz, 1H), 7.71 (d, J=7.7 Hz, 1H), 7.54-7.47 (m, 1H), 7.23 (d, J=8.2 Hz, 1H), 7.14-7.07 (m, 1H), 6.79 (s, 1H), 3.94 (s, 3H), 3.12-3.04 (m, 1H), 1.82-1.73 (m, 2H), 1.70-1.60 (m, 2H), 1.54-1.45 (m, 1H), 1.22-1.14 (m, 4H), 1.09-0.99 (m, 1H).

Example 118: 2,6-Dimethoxy-N-(5-(2-methoxy-5-(1-methyl-1H-pyrazol-3-yl)phenyl)isoxazol-3-yl)benzenesulfonamide, 118

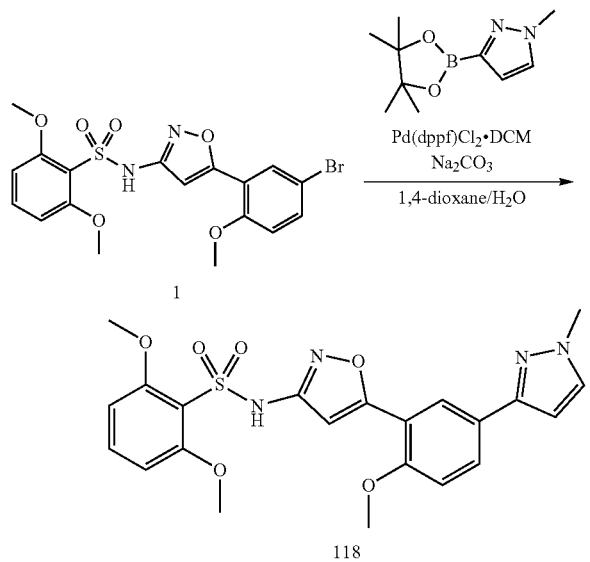

A mixture of N-(5-(5-bromo-2-methoxyphenyl)isoxazol-3-yl)-2,6-dimethoxybenzene sulfonamide 1 (50 mg, 0.11 mmol), 1-methyl-5-(4,4,5,5-tetramethyl-1,3,2-dioxaborolan-2-yl)-1H-pyrazole (55.6 mg, 0.27 mmol), Pd(dppf)Cl₂·DCM (8.0 mg, 0.01 mmol) and Na₂CO₃ (34 mg, 0.32 mmol) in 1,4-dioxane (8 mL) and water (2 mL) was heated at 100° C. under N₂ overnight. The mixture was adjusted to pH 5 with 1 M aqueous HCl and extracted with EtOAc. The combined organic extracts were washed with brine, dried over Na₂SO₄, filtered and concentrated under reduced pressure. The residue was purified by prep. TLC (Pet. Ether/EtOAc=2/1) to give the title compound (42 mg, 83%) as a white solid. LCMS-A (ES-API): $R_t$ 2.19 min; m/z 471.0 [M+H]⁺. ¹H NMR (400 MHz, DMSO-$d_6$) δ 11.1 (brs, 1H), 8.13 (d, J=2.3 Hz, 1H), 7.82 (d, J=8.4 Hz, 1H), 7.71 (d, J=2.2 Hz, 1H), 7.47-7.40 (m, 1H), 7.20 (d, J=8.7 Hz, 1H), 6.74 (d, J=8.5 Hz, 2H), 6.70 (s, 1H), 6.67 (d, J=2.3 Hz, 1H), 3.91 (s, 3H), 3.86 (s, 3H), 3.80 (s, 6H).

The following Examples (119-121) were synthesised from N-(5-(5-bromo-2-methoxyphenyl)isoxazol-3-yl)-2,6-dimethoxybenzenesulfonamide 1 and the appropriate boronic acid or ester according to the procedure described for Example 118.

| Example | Starting material | Name and structure | Analytical data | Notes |
|---|---|---|---|---|
| 119 | 1-Methyl-5-(4,4,5,5-tetramethyl-1,3,2-dioxaborolan-2-yl)-1H-pyrazole | 2,6-Dimethoxy-N-(5-(2-methoxy-5-(1-methyl-1H-pyrazol-5-yl)phenyl)isoxazol-3-yl)benzenesulfonamide | LCMS-A (ES-API): $R_t$ 2.15 min; m/z 471.0 [M + H]⁺, ¹H NMR (400 MHz, DMSO-$d_6$) δ 11.1 (br s, 1H), 7.77 (s, 1H), 7.60 (d, J = 8.3 Hz, 1H), 7.45 (s, 1H), 7.43-7.36 (m, 1H), 7.30 (d, J = 8.7 Hz, 1H), 6.73-6.71 (m, 3H), 6.39 (s, 1H), 3.95 (s, 3H), 3.82 (s, 3H), 3.79 (s, 6H). | Prep. TLC (Pet. Ether/EtOAc = 1/1) |
| 120 | (1H-Pyrazol-4-yl)boronic acid | 2,6-Dimethoxy-N-(5-(2-methoxy-5-(1H-pyrazol-4-yl)phenyl)isoxazol-3-yl)benzenesulfonamide | LC-MS-A (ES-API): $R_t$ 1.90 min; m/z 457.0 [M + H]⁺, ¹H NMR (400 MHz, DMSO-$d_6$) δ 12.9 (br s, 1H), 11.1 (br s, 1H), 8.16-9.96 (m, 2H), 7.92 (d, J = 2.3 Hz, 1H), 7.70 (dd, J = 8.7, 2.3 Hz, 1H), 7.49 (t, J = 8.5 Hz, 1H), 7.20 (d, J = 8.7 Hz, 1H), 6.78 (d, J = 8.5 Hz, 2H), 6.70 (s, 1H), 3.90 (s, 3H), 3.83 (s, 6H). | Prep. TLC (DCM/MeOH = 30/1) followed by prep. HPLC |

| Example | Starting material | Name and structure | Analytical data | Notes |
|---|---|---|---|---|
| 121 | 1-Methyl-4-(4,4,5,5-tetramethyl-1,3,2-dioxaborolan-2-yl)-1H-pyrazole | 2,6-Dimethoxy-N-(5-(2-methoxy-5-(1-methyl-1H-pyrazol-4-yl)phenyl)isoxazol-3-yl)benzenesulfonamide | LCMS-A (ES-API): R$_t$ 2.12 min; m/z 471.0 [M + H]$^+$. $^1$H NMR (400 MHz, DMSO-d$_6$) δ 11.1 (br s, 1H), 8.15 (s, 1H), 7.88 (d, J = 2.3 Hz, 1H), 7.84 (s, 1H), 7.65 (dd, J = 8.7, 2.3 Hz, 1H), 7.49 (t, J = 8.5 Hz, 1H), 7.20 (d, J = 8.7 Hz, 1H), 6.78 (d, J = 8.5 Hz, 2H), 6.71 (s, 1H), 3.90 (s, 3H), 3.84 (s, 3H), 3.83 (s, 6H). | Prep. TLC (DCM/MeOH = 70/1) |

Example 122: 2,6-Dimethoxy-N-(5-(3-methoxy-[1,1'-biphenyl]-2-yl)isoxazol-3-yl)benzenesulfonamide, 122

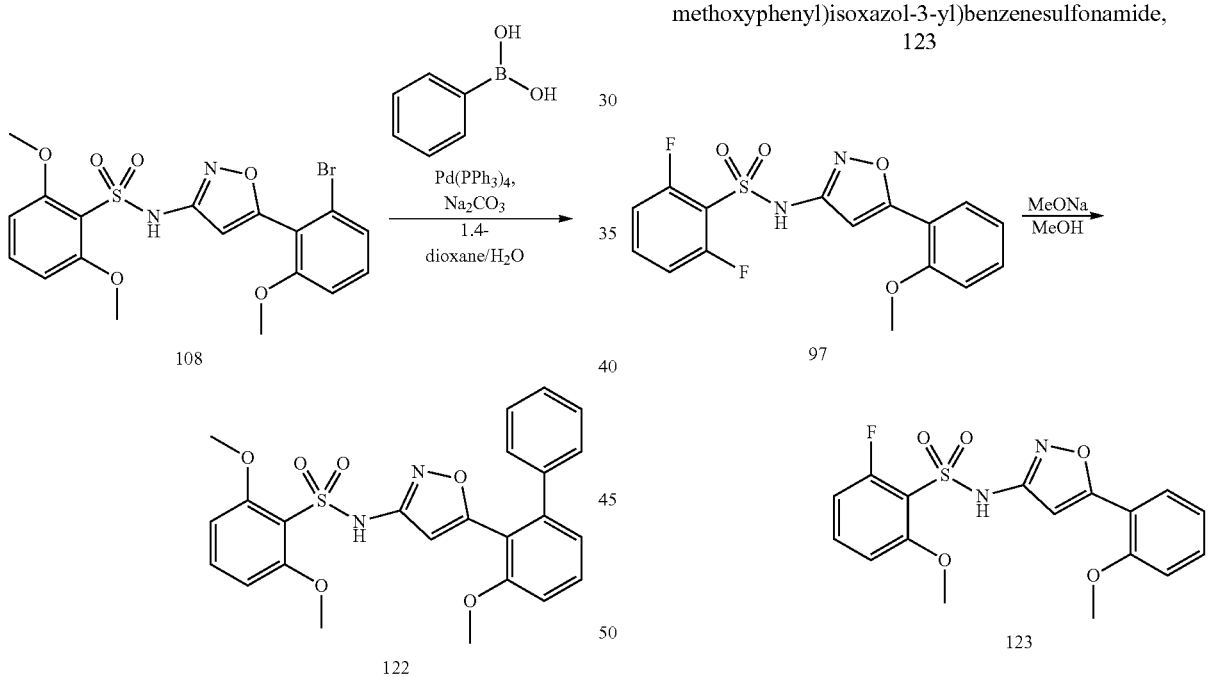

To a solution of N-(5-(2-bromo-6-methoxyphenyl)isoxazol-3-yl)-2,6-dimethoxybenzenesulfonamide 108 (30 mg, 0.06 mmol) in 1,4-dioxane (2.5 mL) and water (0.5 mL) was added phenylboronic acid (12 mg, 0.09 mmol), Pd(PPh$_3$)$_4$ (8 mg, 0.006 mmol) and Na$_2$CO$_3$ (27 mg, 0.26 mmol) and the mixture was heated at 100° C. under N$_2$ overnight. Water was added and the mixture was extracted with EtOAc (10 mL×3). The combined organic extracts were washed with brine, dried over Na$_2$SO$_4$, filtered and concentrated under reduced pressure. The residue was purified by prep. TLC (Pet. Ether/EtOAc=1/1) to give the title compound (10 mg, 36%) as a white solid. LCMS-A (ES-API): R$_t$ 2.41 min; m/z 467.0 [M+H]$^+$. $^1$H NMR (400 MHz, DMSO-d$_6$) δ 10.9 (br s, 1H), 7.60-7.40 (m, 2H), 7.28-7.09 (m, 4H), 7.00-6.97 (m, 3H), 6.74 (d, J=8.4 Hz, 2H), 6.08 (s, 1H), 3.76 (s, 3H), 3.72 (s, 6H).

Example 123: 2-Fluoro-6-methoxy-N-(5-(2-methoxyphenyl)isoxazol-3-yl)benzenesulfonamide, 123

To a solution of 2,6-difluoro-N-(5-(2-methoxyphenyl)isoxazol-3-yl)benzenesulfonamide 97 (50 mg, 0.14 mmol) in MeOH (3 mL) was added MeONa (54 mg, 0.84 mmol) and the mixture was heated at 120° C. in a sealed tube overnight. The mixture was adjusted to pH 5 with 1 M aqueous HCl and extracted with EtOAc. The organic extract was dried over Na$_2$SO$_4$, filtered and concentrated under reduced pressure. The residue was purified by prep. TLC (DCM/MeOH=50/1) to give the title compound (15 mg, 28%) as a white solid. LCMS-A (ES-API): R$_t$ 2.84 min; m/z 366.8 [M+H]$^+$. $^1$H NMR (400 MHz, DMSO-d$_6$) δ 11.6 (br s, 1H), 7.82-7.70 (m, 1H), 7.62-7.52 (m, 1H), 7.51-7.43 (m, 1H), 7.23-7.15 (m, 1H), 7.12-6.89 (m, 3H), 6.68 (s, 1H), 3.92 (s, 3H), 3.84 (s, 3H).

Example 124: 2-(Benzyloxy)-N-(5-(2-ethylphenyl)isoxazol-3-yl)-6-methoxybenzenesulfonamide, 124

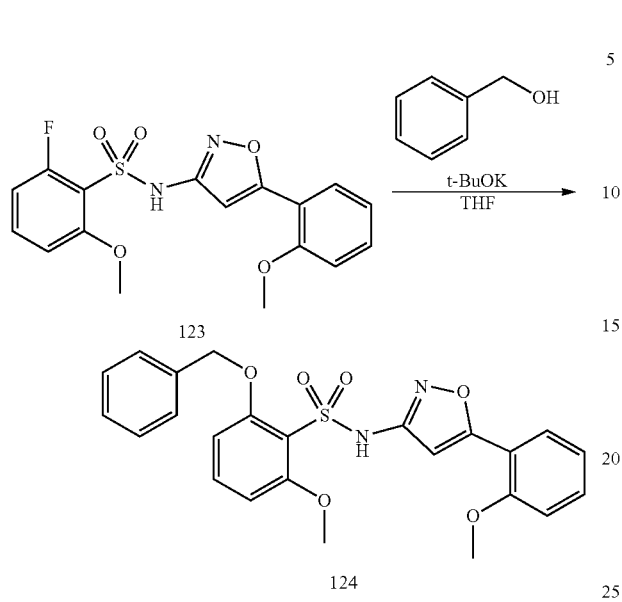

To a solution of 2-fluoro-6-methoxy-N-(5-(2-methoxyphenyl)isoxazol-3-yl)benzenesulfonamide 123 (50 mg, 0.13 mmol) in THF (50 mL) was added benzyl alcohol (29 mg, 0.26 mmol) and f-BuOK (30 mg, 0.26 mmol) and the mixture was heated at 50° C. under $N_2$ overnight. The mixture was acidified to pH 5 with 1 M aqueous HCl and extracted with EtOAc. The organic extract was dried over $Na_2SO_4$, filtered and concentrated under reduced pressure. The residue was purified by prep. TLC (DCM/MeOH=50/1) to give the title compound (20 mg, 33%) as a white solid. LCMS-B (ES-API): $R_t$ 4.19 min; m/z 467.1 [M+H]$^+$. $^1$H NMR (400 MHz, DMSO-d$_6$) δ 11.2 (br s, 1H), 7.74 (dd, J=7.9, 1.8 Hz, 1H), 7.53 (d, J=7.5 Hz, 2H), 7.51-7.39 (m, 2H), 7.33-7.25 (m, 3H), 7.17 (d, J=8.4 Hz, 1H), 7.06 (t, J=7.6 Hz, 1H), 6.81-6.74 (m, 3H), 5.28 (s, 2H), 3.82 (s, 3H), 3.76 (s, 3H).

Example 125: N-(5-(3,4-Dimethoxyphenyl)-1,3,4-oxadiazol-2-yl)-5-ethyl-2-methoxybenzenesulfonamide, 125

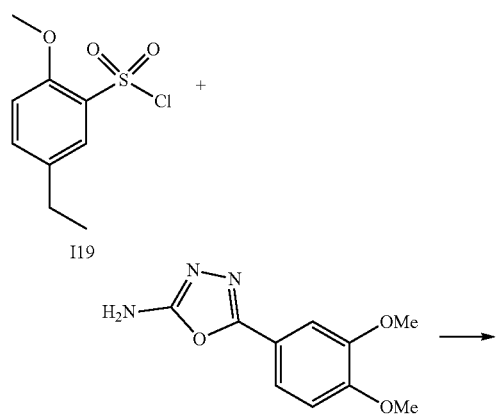

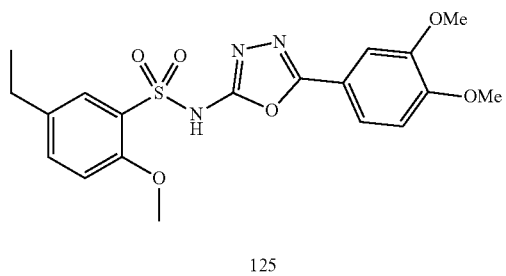

A suspension of 5-ethyl-2-methoxybenzene-1-sulfonyl chloride I19 (150 mg, 0.639 mmol) and 5-(3,4-dimethoxyphenyl)-1,3,4-oxadiazol-2-amine (141 mg, 0.639 mmol) in pyridine (2 mL) was irradiated in the microwave at 110° C. for 2 hours. The product was purified by column chromatography (0-100% EtOAc in petroleum benzine 40-60° C.) to give the title compound as a white solid (109 mg, 40%). LCMS-C: $R_t$ 6.167 min; m/z 420.1 [M+H]$^+$. $^1$H NMR (400 MHz, DMSO-d$_6$) δ 7.70 (d, J=2.3 Hz, 1H), 7.46-7.38 (m, 2H), 7.31 (d, J=2.0 Hz, 1H), 7.18-7.06 (m, 2H), 3.91-3.78 (m, 6H), 3.72 (s, 3H), 2.63 (q, J=7.6 Hz, 2H), 1.18 (t, J=7.5 Hz, 3H).

Example 126: 5-Ethyl-2-methoxy-N-(5-phenyl-1,3,4-oxadiazol-2-yl)benzenesulfonamide, 126

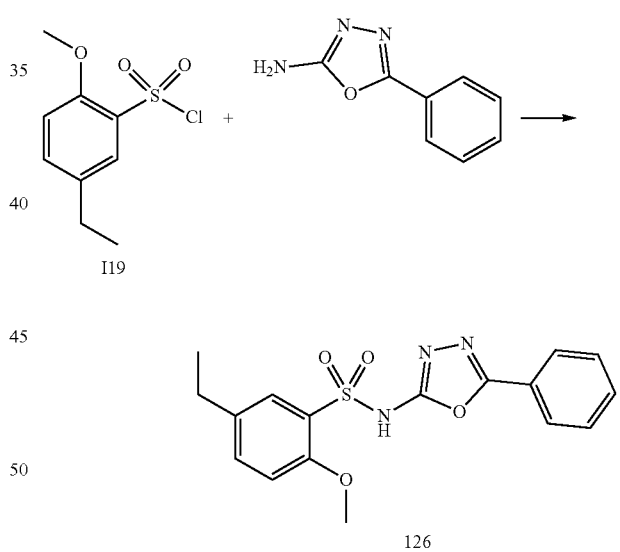

A suspension of 5-ethyl-2-methoxybenzene-1-sulfonyl chloride I19 (150 mg, 0.639 mmol) and 5-phenyl-1,3,4-oxadiazol-2-amine (103 mg, 0.639 mmol) in pyridine (2 mL) was irradiated in the microwave at 110° C. for 2 hours. The product was purified by column chromatography (0-100% EtOAc in petroleum benzine 40-60° C.) to give the title compound as a white solid (142 mg, 62%). LCMS-C: $R_t$ 6.308 min; m/z 360.1 [M+H]$^+$. $^1$H NMR (400 MHz, DMSO-d$_6$) δ 7.88-7.80 (m, 2H), 7.71 (d, J=2.3 Hz, 1H), 7.68-7.55 (m, 3H), 7.42 (dd, J=8.4, 2.3 Hz, 1H), 7.10 (d, J=8.5 Hz, 1H), 3.72 (s, 2H), 2.63 (q, J=7.6 Hz, 2H), 1.18 (t, J=7.6 Hz, 3H).

Example 127: N-(5-(2-methoxyphenyl)-1,3,4-thiadiazol-2-yl)tetrahydro-2H-pyran-4-sulfonamide, 127

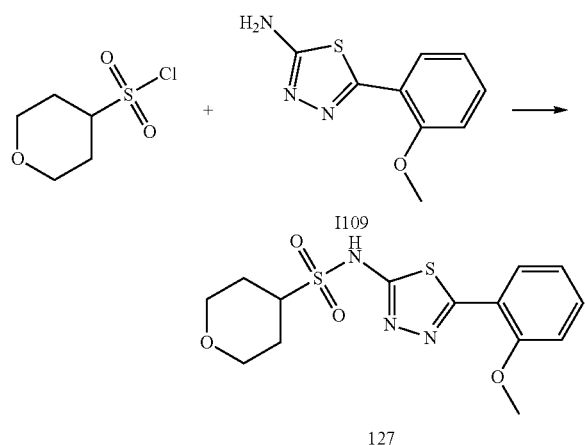

Lithium bis(trimethylsilyl)amide solution 1.0 M in THF (0.386 mL, 0.386 mmol) was added to a solution of 5-(2-methoxyphenyl)-1,3,4-thiadiazol-2-amine I109 (0.040 g, 0.193 mmol) in THF (0.965 mL) at 0° C. and the reaction was stirred for 15 min. A solution of tetrahydropyran-4-sulfonyl chloride (0.029 mL, 0.232 mmol) in THF (0.5 mL) was added dropwise, the resulting mixture was warmed to room temperature and stirred for 4 h. The reaction was quenched with 1 M HCl and extracted with EtOAc (3×). The combined organics were washed with brine, dried (MgSO$_4$) and concentrated. Purification by column chromatography (4 g silica cartridge, 20-60% ethyl acetate in petroleum benzine 40-60° C.) gave the title compound as a pale yellow solid. LCMS-D: rt 3.15 min, m/z 355.9 [M+H]$^+$

Example 128 and 129: tert-Butyl 4-(N-(5-(2-methoxyphenyl)-1,3,4-thiadiazol-2-yl)sulfamoyl)piperidine-1-carboxylate, 128 and N-(5-(2-methoxyphenyl)-1,3,4-thiadiazol-2-yl)piperidine-4-sulfonamide hydrochloride, 129

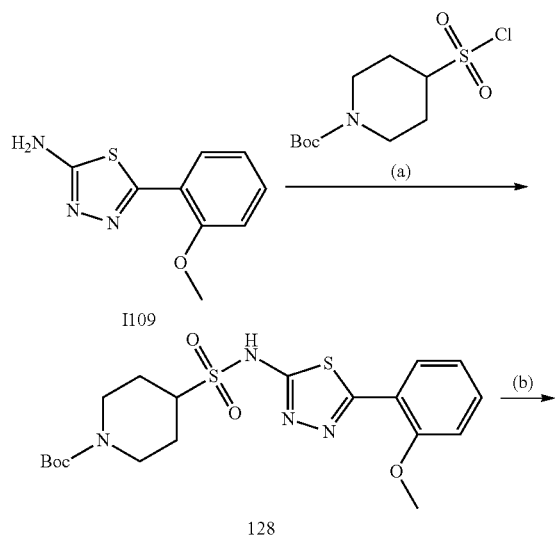

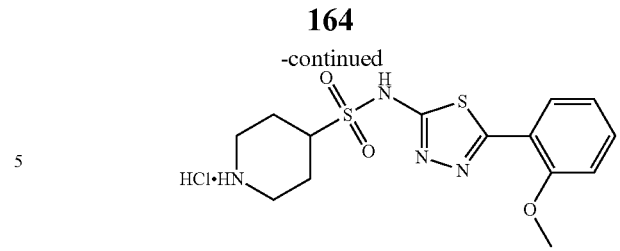

a) tert-butyl 4-(N-(5-(2-methoxyphenyl)-1,3,4-thiadiazol-2-yl)sulfamoyl)piperidine-1-carboxylate I28

Lithium bis(trimethylsilyl)amide solution 1.0 M in THF (0.386 mL, 0.386 mmol) was added to a solution of 5-(2-methoxyphenyl)-1,3,4-thiadiazol-2-amine I109 (0.040 g, 0.193 mmol) in tetrahydrofuran (1.93 mL) at −10° C. and the reaction was stirred for 10 min. A solution of tert-butyl 4-chlorosulfonylpiperidine-1-carboxylate (0.066 g, 0.232 mmol) in THF (0.5 mL) was added dropwise, the resulting mixture was warmed to room temperature and stirred overnight. The reaction was quenched with water (5 mL), acidified with 1 M HCl and extracted with EtOAc (3×10 mL). The combined organics were washed with brine, dried (MgSO$_4$) and concentrated. Purification by column chromatography (4 g silica cartridge, 50-90% ethyl acetate in petroleum benzine 40-60° C.) gave the title compound (0.013 g, 15% yield) as a pale yellow oil. LCMS-C: rt 6.14 min, m/z 453.2 [M−H]$^−$, $^1$H NMR (400 MHz, CDCl$_3$) δ 8.07 (dd, J=7.9, 1.7 Hz, 1H), 7.47 (ddd, J=8.4, 7.4, 1.7 Hz, 1H), 7.07 (td, J=7.6, 1.0 Hz, 1H), 7.02 (d, J=8.4 Hz, 1H), 4.34-4.18 (m, 2H), 3.98 (s, 3H), 3.16 (tt, J=11.9, 3.6 Hz, 1H), 2.80-2.69 (m, 2H), 2.17 (dd, J=13.6, 3.6 Hz, 2H), 1.77 (qd, J=12.5, 4.5 Hz, 2H), 1.46 (s, 9H).

b) N-(5-(2-methoxyphenyl)-1,3,4-thiadiazol-2-yl)piperidine-4-sulfonamide hydrochloride I29

HCl (4 M in 1,4-dioxane, 0.055 mL) was added to a solution of tert-butyl 4-(N-(5-(2-methoxyphenyl)-1,3,4-thiadiazol-2-yl)sulfamoyl)piperidine-1-carboxylate I28 (0.010 g 0.022 mmol) in DCM (0.06 mL). The reaction was stirred for 18 h and the solvent was removed to give title compound (6.0 mg, 70% yield) as a white solid. LCMS-D: rt 2.83 min, m/z 354.9 [M−Cl]$^+$.

Assays

Protein Preparation
KAT5

Molecular Biology: A codon optimized DNA sequence (for expression in *Escherichia coli*) encoding amino acid residues 2 to 461 (Uniprot Q92993-2) of human KAT5 isoform was synthesised by GenScript USA Inc (Piscataway, N.J., USA). This was ligated into a modified pET43a *E. coli* expression vector designed to encode an N-terminal hexa-histidine tag followed by a tobacco etch virus protease (TEV) cleavage site and by the KAT5 sequence. The resulting protein sequence is listed below.

MGHHHHHHGTENLYFQGSAEVGEIIEGCRLPVLRRNQDNEDEWPLAEILS

VKDISGRKLFYVHYIDFNKRLDEWVTHERLDLKKIQFPKKEAKTPTKNGL

-continued
PGSRPGSPEREVKRKVEVVSPATPVPSETAPASVFPQNGAARRAVAAQPG

RKRKSNCLGTDEDSQDSSDGIPSAPRMTGSLVSDRSHDDIVTRMKNIECI

ELGRHRLKPWYFSPYPQELTTLPVLYLCEFCLKYGRSLKCLQRHLTKCDL

RHPPGNEIYRKGTISFFEIDGRKNKSYSQNLCLLAKCFLDHKTLYYDTDP

FLFYVMTEYDCKGFHIVGYFSKEKESTEDYNVACILTLPPYQRRGYGKLL

IEFSYELSKVEGKTGTPEKPLSDLGLLSYRSYWSQTILEILMGLKSESGE

RPQITINEISEITSIKKEDVISTLQYLNLINYYKGQYILTLSEDIVDGHE

RAMLKRLLRIDSKCLHFTPKDWSKRGKWAS*

Protein Expression: To produce recombinant KAT5 protein, expression plasmid was transformed into *E. coli* BL21 DE3 strain and grown with shaking at 37° C. in 1 L volumes of Terrific broth (TB) supplemented with 100 µg/mL Ampicillin and 50 µM zinc until an OD600 of 0.8 was reached. Cultures were transferred to 18° C. and protein expression induced by the addition of Isopropyl β-D-1-thiogalactopyranoside to a final concentration of 0.5 mM and the cultures shaken overnight for further 16 hours. Following expression, cell cultures were centrifuged at 5000×g for 20 min and cell pellet stored frozen at −20° C.

Protein Purification: Protein purification was initiated by thawing the cell pellet (25 g wet weight) in Lysis buffer (50 mM Hepes pH 7.4, 500 mM NaCl, 5 mM imidazole, 5% [v/v]glycerol, 0.1% [w/v] CHAPS, 2 mM 2-mercaptoethanol, 3 mM MgCl$_2$ 0.5 mg/mL lysozyme, benzonase endonuclease [EMD Millipore], 1 mM PMSF, complete protease inhibitor tablets EDTA-free [Roche]) using a ratio of 6 mL of buffer per 1 g of cells. Cells were further lysed by sonication using a Misonix Liquid Processor (6×30 second pulses, amplitude 60 [70 watts]) and then centrifuged at 48,000×g at 4° C. Supernatant (cell lysate) was mixed with 20 mL of Q-Sepharose FF resin (GE Healthcare) pre-equilibrated with Q buffer (20 mM Hepes pH 7.4.1 M NaCl). The unbound fraction from Q-Sepharose FF was then incubated with 5 mL of complete His-Tag Purification Resin (Roche), pre-equilibrated with IMAC Wash Buffer (20 mM hepes pH 7.4, 500 mM NaCl, 35 mM imidazole). The resin was washed with IMAC Wash Buffer, and bound KAT5 eluted with IMAC Elution buffer (20 mM hepes pH 7.4, 500 mM NaCl, 300 mM imidazole). IMAC-eluted protein was immediately desalted into Storage buffer (50 mM Na citrate pH 6.5, 500 mM NaCl, 5% [v/v] glycerol) using 2× HiPrep 26/10 desalting columns (GE Healthcare) in series. Desalted protein was further purified by passing through a HiLoad 26/60 Superdex 75 column pre-equilibrated in Storage buffer. Finally, KAT5 protein was concentrated to 1.5 mg/mL using Amicon Ultra centrifugal filter unit (Utra-15 MWCO 10 kDa), flash-frozen in liquid nitrogen and stored in −70° C. freezer.

KAT6A

Molecular Biology: The DNA sequence encoding amino acid residues 507 to 778 (Uniprot Q92794-1) of human KAT6A was amplified by PCR and was ligated into a modified pET *E. coli* expression vector designed to encode a NusA solubility tag followed by a hexahistidine tag and a tobacco etch virus protease (TEV) cleavage site and by the KAT6A sequence. The resulting protein sequence is listed below.

MNKEILAVVEAVSNEKALPREKIFEALESALATATKKKYEQEIDVRVQID

RKSGDFDTFRRWLVVDEVTQPTKEITLEAARYEDESLNLGDYVEDQIESV

TFDRITTQTAKQVIVQKVREAERAMVVDQFREHEGEIITGVVKKVNRDNI

SLDLGNNAEAVILREDMLPRENFRPGDRVRGVLYSVRPEARGAQLFVTRS

KPEMLIELFRIEVPEIGEEVIEIKAAARDPGSRAKIAVKTNDKRIDPVGA

CVGMRGARVQAVSTELGGERIDIVLWDDNPAQFVINAMAPADVASIVVDE

DKHTMDIAVEAGNLAQAIGRNGQNVRLASQLSGWELNVMTVDDLQAKHQA

EAHAAIDTFTKYLDIDEDFATVLVEEGFSTLEELAYVPMKELLEIEGLDE

PTVEALRERAKNALATIAQAQEESLGDNKPADDLLNLEGVDRDLAFKLAA

RGVCTLEDLAEQGIDDLADIEGLTDEKAGALIMAARNICWFGDEATSGSG

HHHHHHSAGENLYFQGAMGRCPSVIEFGKYEIHTWYSSPYPQEYSRLPKL

YLCEFCLKYMKSRTILQQHMKKCGWFHPPVNEIYRKNNISVFEVDGNVST

IYCQNLCLLAKLFLDHKTLYYDVEPFLFYVLTQNDVKGCHLVGYFSKEKH

CQQKYNVSCIMILPQYQRKGYGRFLIDFSYLLSKREGQAGSPEKPLSDLG

RLSYMAYWKSVILECLYHQNDKQISIKKLSKLTGICPQDITSTLHHLRML

DFRSDQFVIIRREKLIQDHMAKLQLNLRPVDVDPECLRWTP

Protein Expression: To produce recombinant KAT6A protein, expression plasmid was transformed into *E. coli* BL21 DE3 strain and grown with shaking at 37° C. in 1 L volumes of Terrific broth (TB) supplemented with 100 µg/mL Ampicillin until an OD600 of 0.8 was reached. Cultures were transferred to 18° C. and protein expression induced by the addition of Isopropyl 3-D-1-thiogalactopyranoside to a final concentration of 0.5 mM and the cultures shaken overnight for further 16 hours. Following expression, cell cultures were centrifuged at 5000×g for 20 min and cell pellet stored frozen at −20° C.

Protein Purification: Protein purification was initiated by thawing the cell pellet (40 g wet weight) in Lysis buffer (25 mM Tris-HCl pH 7.8, 500 mM NaCl, 5 mM DTT, 0.01% [v/v] Triton-X 100, 5% [v/v] glycerol, 2 mM MgCl$_2$, 10 mM Imidazole, 0.5 mg/mL lysozyme, benzonase endonuclease [EMD Millipore], 1 mM PMSF, complete protease inhibitor tablets EDTA-free [Roche]) using a ratio of 5 mL of buffer per 1 g of cells. Cells were further lysed by 3 passes (at 15000 psi) through an ice cooled Avestin C5 cell crusher and then centrifuged at 48,000×g at 4° C. Supernatant (cell lysate) was filtered through a 5 µm filter and applied onto 5 mL HiTrap IMAC Sepharose FF column (GE Healthcare) pre-equilibrated with IMAC wash buffer (25 mM Tris-HCl pH 7.8, 500 mM NaCl, 5 mM DTT, 0.01% [v/v] Triton-X 100, 5% [v/v] glycerol, 20 mM Imidazole) using a Profinia Affinity chromatography purification system (Bio-Rad). The IMAC column was then washed with IMAC Wash buffer and bound KAT6A protein eluted with IMAC Elution buffer (25 mM Tris-HCl pH 7.8, 500 mM NaCl, 5% [v/v] glycerol, 5 mM DTT, 250 mM Imidazole). IMAC-eluted protein was further purified by passing through a HiLoad 26/60 Superdex 200 column pre-equilibrated in Storage buffer (25 mM Tris-HCl pH 7.8, 500 mM NaCl, 5 mM DTT, 5% [v/v] glycerol). Finally, KAT6A protein was concentrated to ≤1 mg/mL using Amicon Ultra centrifugal filter unit (Utra-15 MWCO 10 kDa), flash-frozen in liquid nitrogen and stored in −70° C. freezer.

KAT6B was obtained from SignalChem, catalog ID: K315-381BG

KAT7

Molecular Biology: A codon optimized DNA sequence encoding amino acid residues 325 to 611 (Uniprot O95251-1) of human KAT7 was synthesised by GenScript USA Inc (Piscataway, N.J., USA). This was ligated into a modified pET43a *E. coli* expression vector designed to encode an N-terminal hexahistidine tag followed by a tobacco etch virus protease (TEV) cleavage site and by the KAT7 sequence. The resulting protein sequence is listed below.

MGHHHHHHGTENLYFQGSRLQGQITEGSNMIKTIAFGRYELDTWYHSPYP

EEYARLGRLYMCEFCLKYMKSQTILRRHMAKCVWKHPPGDEIYRKGSISV

FEVDGKKNKIYCQNLCLLAKLFLDHKTLYYDVEPFLFYVMTEADNTGCHL

IGYFSKEKNSFLNYNVSCILTMPQYMRQGYGKMLIDFSYLLSKVEEKVGS

PERPLSDLGLISYRSYWKEVLLRYLHNFQGKEISIKEISQETAVNPVDIV

STLQALQMLKYWKGKHLVLKRQDLIDEWIAKEAKRSNSNKTMDPSCLKWT

PPKGTAS

Protein Expression: To produce recombinant KAT7 protein, expression plasmid was transformed into *E. coli* BL21 DE3 RIL strain and grown with shaking at 37° C. in 1 L volumes of Terrific broth (TB) supplemented with 100 µg/mL Ampicillin and 50 µM zinc until an OD600 of 0.8 was reached. Cultures were transferred to 18° C. and protein expression induced by the addition of Isopropyl β-D-1-thiogalactopyranoside to a final concentration of 0.5 mM and the cultures shaken overnight for further 16 hours. Following expression, cell cultures were centrifuged at 5000×g for 20 min and cell pellet stored frozen at −20° C. Protein Purification: Protein purification was initiated by thawing the cell pellet (10 g wet weight) in Lysis buffer (50 mM Hepes pH 7.5, 300 mM NaCl, 5 mM DTT, 5 mM Imidazole, 0.05% [v/v] Brij 35, 10% [v/v] glycerol, 3 mM MgCl$_2$ 0.5 mg/mL lysozyme, benzonase endonuclease [EMD Millipore], 1 mM PMSF, complete protease inhibitor tablets EDTA-free [Roche]) using a ratio of 10 mL of buffer per 1 g of cells. Cells were further lysed by sonication using a Misonix Liquid Processor (6×30 second pulses, amplitude 60 [70 watts]) and then centrifuged at 48,000×g at 4° C. Supernatant (cell lysate) was incubated with 1 mL of complete His-Tag Purification Resin (Roche), pre-equilibrated with IMAC Wash Buffer 1 (25 mM Hepes pH 7.5, 800 mM NaCl, 5 mM imidazole, 10% [v/v] glycerol, 5 mM DTT, 0.01% [v/v] Brij 35, 50 mM arginine, 50 mM glutamic acid). The resin was sequentially washed with IMAC Wash buffer 1 and IMAC Wash buffer 2 (25 mM hepes pH 7.5, 300 mM NaCl, 20 mM imidazole, 10% [v/v] glycerol, 5 mM DTT, 0.01% [v/v] Brij 35, 50 mM arginine, 50 mM glutamic acid). Bound KAT7 protein was eluted with IMAC Elution buffer (25 mM hepes pH 7.5, 200 mM NaCl, 500 mM imidazole, 10% [v/v] glycerol, 5 mM DTT 0.01% [v/v] Brij 35, 50 mM arginine, 50 mM glutamic acid). The eluting protein was collected directly into 4 volumes of Desalt Buffer (50 mM Na citrate pH 6.5, 200 mM NaCl, 0.01% [v/v] Brij 35, 10% [v/v] glycerol, 5 mM DTT) to bring the final imidazole concentration to 100 mM. IMAC-eluted protein was immediately desalted into Desalt buffer using 2× HiPrep 26/10 desalting columns (GE Healthcare) in series. Desalted protein was further purified by passing through a HiLoad 26/60 Superdex 75 column pre-equilibrated in Storage Buffer (50 mM Na citrate pH 6.5, 200 mM NaCl, 10% [v/v] glycerol, 5 mM DTT). Finally, KAT7 protein was concentrated to 3.5 mg/mL using Amicon Ultra centrifugal filter unit (Utra-15 MWCO 10 kDa), flash-frozen in liquid nitrogen and stored in −70° C. freezer.

KAT8

Molecular Biology: A codon optimized DNA sequence (for expression in *E. coli*) encoding amino acid residues 177 to 447 (Uniprot Q9H7Z6-1) of human KAT8 was synthesised by Thermo Fisher Scientific GENEART GmbH (Regensberg, Germany). This was ligated into pPROEX Hta *E. coli* expression vector designed to encode an N-terminal hexahistidine tag followed by a tobacco etch virus protease (TEV) cleavage site and by the KAT8 sequence. The resulting protein sequence is listed below.

MSYYHHHHHHDYDIPTTENLYFQGAKYVDKIHIGNYEIDAWYFSPFPEDY

GKQPKLWLCEYCLKYMKYEKSYRFHLGQCQWRQPPGKEIYRKSNISVYEV

DGKDHKIYCQNLCLLAKLFLDHKTLYFDVEPFVFYILTEVDROGAHIVGY

FSKEKESPDGNNVACILTLPPYQRRGYGKFLIAFSYELSKLESTVGSPEK

PLSDLGKLSYRSYWSWVLLEILRDFRGTLSIKDLSQMTSITQNDIISTLQ

SLNMVKYWKGQHVICVTPKLVEEHLKSAQYKKPPITVDSVCLKWAP*

Protein Expression: To produce recombinant KAT8 protein, expression plasmid was transformed into *E. coli* BL21 DE3 strain and grown with shaking at 37° C. in 1 L volumes of Terrific broth (TB) supplemented with 100 µg/mL Ampicillin until an OD600 of 0.8 was reached. Cultures were transferred to 18° C. and protein expression induced by the addition of Isopropyl β-D-1-thiogalactopyranoside to a final concentration of 0.5 mM and the cultures shaken overnight for further 16 hours. Following expression, cell cultures were centrifuged at 5000×g for 20 min and cell pellet stored frozen at −20° C.

Protein Purification: Protein purification was initiated by thawing the cell pellet (34 g wet weight) in Lysis buffer (20 mM Hepes pH 7.5, 500 mM NaCl, 5 mM Imidazole, 5% [v/v]glycerol, 0.01% [v/v] Triton-X 100, 5 mM 2-mercaptoethanol, 2 mM MgCl$_2$ 0.5 mg/mL lysozyme, benzonase endonuclease [EMD Millipore], 1 mM PMSF, complete protease inhibitor tablets EDTA-free [Roche]) using a ratio of 3 mL of buffer per 1 g of cells. Cells were further lysed by 3 passes (at 15000 psi) through an ice cooled Avestin C5 cell crusher and then centrifuged at 48,000×g at 4° C. Supernatant (cell lysate) was filtered through a 0.2 µm filter and applied onto 5 mL HiTrap IMAC Sepharose FF column (GE Healthcare) pre-equilibrated with IMAC wash buffer 1 (20 mM Hepes pH 7.5, 500 mM NaCl, 0.5 mM TCEP, 5 mM Imidazole) using a Profinia Affinity chromatography purification system (Bio-Rad). The IMAC column was then sequentially washed with IMAC Wash buffer 1 and IMAC Wash buffer 2 (20 mM Hepes pH 7.5, 500 mM NaCl, 0.5 mM TCEP, 10 mM Imidazole) and bound KAT8 protein eluted with IMAC Elution buffer (20 mM Hepes pH 7.5, 500 mM NaCl, 0.5 mM TCEP, 500 mM Imidazole). IMAC-eluted protein was further purified by passing through a HiLoad 26/60 Superdex 200 column pre-equilibrated in Storage buffer (20 mM Hepes pH 7.5, 500 mM NaCl, 1 mM TCEP). Finally, KAT8 protein was concentrated to ≤0.2 mg/mL using Amicon Ultra centrifugal filter unit (Utra-15 MWCO 10 kDa), flash-frozen in liquid nitrogen and stored in −70° C. freezer.

Acetyltransferase Biochemical Assay

To determine the inhibition of KAT enzymatic activity by test compounds, assay reactions were conducted in a volume of 8 µL in 384-well low volume assay plates. The reactions were performed in assay buffer (100 mM Tris-HCl, pH 7.8, 15 mM NaCl, 1 mM EDTA, 0.01% Tween-20, 1 mM Dithiothreitol, and 0.01% m/v chicken egg white albumin).

Reactions were set up with 1 µM Acetyl coenzyme A, 100 nM of full-length recombinant histone labelled by limited biotinylation (KAT6A, KAT6B, KAT7: H3.1, KAT5, KAT8: H4), 10/5/8/40/20 nM of KAT5/KAT6A/KAT6B/KAT7/KAT8 enzyme respectively, and an acetyl-lysine specific antibody (H3.1: Cell Signaling Technology, H4: Abcam). 11-point dilution series of the test compounds were prepared in DMSO; a volume of 100 nL was transferred using a pin tool into assay plates containing substrates, before adding enzyme to start the reaction. Positive (no compound, DMSO only) and negative (AcCoA omitted) control reactions were included on the same plates and received the same amount of DMSO as the compound treated wells. After adding all reagents, the plates were sealed with adhesive seals and incubated for 90 min at room temperature. An additional 4 µL of assay buffer containing AlphaScreen® Protein A acceptor beads and Streptavidin donor beads (PerkinElmer, Waltham, Mass.) to a final concentration of 8 µg/mL was then added. After incubation for 2 hours the plates were read using an EnVision 2103 multi label plate reader (PerkinElmer) in HTS AlphaScreen® mode. $IC_{50}$ values were obtained from the raw readings by calculating percent inhibition (% I) for each reaction relative to controls on the same plate (% I=(I−CN)/(CP−CN) where CN/CP are the averages of the negative/positive reactions, respectively), then fitting the % I data vs. compound concentration [I] to % I=(A+((B−A)/(1+((C/[I])^D)))) where A is the lower asymptote, B is the upper asymptote, C is the $IC_{50}$ value, and D is the slope.

The results are shown in tables 1 to 5 below:

TABLE 1

| (TIP60-KAT5) | |
|---|---|
| Example | IC50 (µM) |
| 1 | =0.2132 |
| 2 | =23.995 |
| 3 | =20.547 |
| 4 | =11.995 |
| 5 | =1.0012 |
| 6 | =0.1639 |
| 7 | =0.5856 |
| 8 | =0.4157 |
| 9 | =2.4311 |
| 10 | =5.2472 |
| 11 | =0.8673 |
| 12 | =3.0962 |
| 13 | =12.193 |
| 14 | =0.1421 |
| 15 | =0.315 |
| 16 | =0.2189 |
| 17 | =2.066 |
| 18 | =0.4446 |
| 19 | =2.6329 |
| 20 | =6.02 |
| 21 | =23.967 |
| 22 | =1.3355 |
| 23 | =0.1402 |
| 24 | =19.462 |
| 25 | =31.296 |
| 26 | =33.849 |
| 27 | =23.748 |
| 28 | =21.253 |

TABLE 1-continued

| (TIP60-KAT5) | |
|---|---|
| Example | IC50 (µM) |
| 29 | >125 |
| 30 | >125 |
| 31 | =87.893 |
| 32 | =116.16 |
| 34 | =50.713 |
| 35 | >125 |
| 36 | >125 |
| 37 | =113.95 |
| 38 | =36.993 |
| 39 | =58.497 |
| 40 | =28.962 |
| 41 | =64.168 |
| 42 | =55.488 |
| 43 | =86.4 |
| 44 | =82.907 |
| 45 | >125 |
| 46 | >125 |
| 47 | >125 |
| 48 | =71.151 |
| 49 | =42.835 |
| 50 | =41.352 |
| 51 | =75.275 |
| 52 | =56.669 |
| 53 | =54.783 |
| 54 | =38.286 |
| 55 | >125 |
| 56 | =1.6636 |
| 57 | =10.409 |
| 58 | =19.008 |
| 59 | =26.102 |
| 60 | =12.439 |
| 61 | =69.613 |
| 62 | =68.322 |
| 63 | =65.242 |
| 64 | =88.353 |
| 65 | =57.525 |
| 66 | =12.308 |
| 67 | =8.1757 |
| 68 | >125 |
| 69 | =0.8447 |
| 70 | =0.6959 |
| 71 | =0.4159 |
| 72 | =0.1063 |
| 73 | =1.1547 |
| 74 | =12.995 |
| 75 | =13.782 |
| 76 | >125 |
| 77 | =3.2648 |
| 78 | =2.5063 |
| 79 | =21.468 |
| 80 | =26.616 |
| 81 | =121.01 |
| 82 | =27.072 |
| 83 | =108.63 |
| 84 | =1.8407 |
| 85 | >125 |
| 86 | =25.909 |
| 87 | =19.221 |
| 88 | =27.863 |
| 89 | =21.206 |
| 90 | =21.184 |
| 92 | =61.856 |
| 93 | =81.2054 |
| 94 | =62.2136 |
| 95 | =22.1163 |
| 96 | =2.2549 |
| 97 | =31.9712 |
| 98 | =45.4491 |
| 99 | =19.0089 |
| 100 | =11.2055 |
| 101 | >125.0000 |
| 102 | =7.3324 |
| 103 | =64.7593 |
| 104 | =58.7659 |
| 105 | =1.0976 |
| 106 | =2.8637 |

TABLE 1-continued (TIP60-KAT5)

| Example | IC50 (μM) |
| --- | --- |
| 107 | =26.3454 |
| 108 | =67.7482 |
| 109 | =16.4566 |
| 110 | =4.2450 |
| 111 | =0.2384 |
| 112 | =14.4120 |
| 113 | =60.1489 |
| 114 | =19.8700 |
| 115 | =57.4577 |
| 116 | =34.0304 |
| 117 | =5.2586 |
| 118 | =41.8736 |
| 119 | =0.7878 |
| 120 | =1.4454 |
| 121 | =7.8697 |
| 122 | =68.8714 |
| 123 | =34.2996 |
| 124 | =12.9392 |
| 125 | >125.0000 |
| 126 | =14.5937 |
| 127 | >125.0000 |
| 128 | =97.3157 |
| 129 | >125.0000 |

TABLE 2

(MOZ-KAT6A)

| Example | IC50 (μM) |
| --- | --- |
| 1 | =0.0403 |
| 2 | =2.2179 |
| 3 | =2.1385 |
| 4 | =3.539 |
| 5 | =0.2765 |
| 6 | =0.0412 |
| 7 | =0.1888 |
| 8 | =0.0252 |
| 9 | =0.4228 |
| 10 | =1.6461 |
| 11 | =0.2826 |
| 12 | =0.6147 |
| 13 | =0.6818 |
| 14 | =0.1514 |
| 15 | =0.1642 |
| 16 | =0.1325 |
| 17 | =2.1009 |
| 18 | =0.9502 |
| 19 | =1.0903 |
| 20 | =8.1888 |
| 21 | =9.0707 |
| 22 | =0.3626 |
| 23 | =0.0464 |
| 24 | =7.5264 |
| 25 | =5.3321 |
| 26 | =10.536 |
| 27 | =7.6321 |
| 28 | =8.8399 |
| 29 | =95.979 |
| 30 | =81.289 |
| 31 | =25.061 |
| 32 | =37.747 |
| 34 | =14.26 |
| 35 | =109.99 |
| 36 | =30.644 |
| 37 | =32.484 |
| 38 | =9.2962 |
| 39 | =25.168 |
| 40 | =3.967 |
| 41 | =23.685 |
| 42 | =4.209 |
| 43 | =36.651 |
| 44 | =63.074 |

TABLE 2-continued (MOZ-KAT6A)

| Example | IC50 (μM) |
| --- | --- |
| 45 | =48.673 |
| 46 | =59.399 |
| 47 | =39.061 |
| 48 | =18.214 |
| 49 | =14.327 |
| 50 | =18.217 |
| 51 | =42.301 |
| 52 | =27.966 |
| 53 | =12.708 |
| 54 | =11.403 |
| 55 | =89.616 |
| 56 | =0.9422 |
| 57 | =4.1786 |
| 58 | =9.6181 |
| 59 | =2.4298 |
| 60 | =1.5219 |
| 61 | =23.847 |
| 62 | =52.623 |
| 63 | =20.08 |
| 64 | =28.968 |
| 65 | =17.886 |
| 66 | =10.855 |
| 67 | =8.3855 |
| 68 | =92.403 |
| 69 | =0.6479 |
| 70 | =0.2898 |
| 71 | =1.5592 |
| 72 | =0.0449 |
| 73 | =0.0273 |
| 74 | =5.6231 |
| 75 | =5.3545 |
| 76 | =91.183 |
| 77 | =2.1968 |
| 78 | =1.3038 |
| 79 | =28.351 |
| 80 | =14.84 |
| 81 | =22.581 |
| 82 | =9.3499 |
| 83 | =80.816 |
| 84 | =0.236 |
| 85 | =51.784 |
| 86 | =7.4115 |
| 87 | =2.1888 |
| 88 | =4.9095 |
| 89 | =9.8455 |
| 90 | =16.353 |
| 91 | =30.055 |
| 92 | =14.94 |
| 93 | =21.6029 |
| 94 | =7.2928 |
| 95 | =0.8699 |
| 96 | =4.8561 |
| 97 | =13.3500 |
| 98 | =0.6931 |
| 99 | =2.8105 |
| 100 | =0.9310 |
| 101 | >125.0000 |
| 102 | =21.0661 |
| 103 | =14.1291 |
| 104 | =38.3881 |
| 105 | =0.0760 |
| 106 | =0.7315 |
| 107 | =0.5002 |
| 108 | =20.0693 |
| 109 | =10.5520 |
| 110 | =0.9847 |
| 111 | =0.0691 |
| 112 | =0.1706 |
| 113 | =30.0982 |
| 114 | =2.5004 |
| 115 | =20.4316 |
| 116 | =31.4091 |
| 117 | =6.9326 |
| 118 | =10.8306 |
| 119 | =0.2265 |
| 120 | =0.1945 |

TABLE 2-continued (MOZ-KAT6A)

| Example | IC50 (μM) |
|---|---|
| 121 | =3.1157 |
| 122 | =15.4242 |
| 123 | =25.4151 |
| 124 | =1.2518 |
| 125 | =54.1379 |
| 126 | =9.4041 |
| 127 | >125.0000 |
| 128 | =23.0152 |
| 129 | =20.8982 |

TABLE 3

(HBO-KAT7)

| Example | IC50 (μM) |
|---|---|
| 1 | =0.0876 |
| 2 | =3.0005 |
| 3 | =3.2552 |
| 4 | =6.3614 |
| 5 | =0.1109 |
| 6 | =0.0422 |
| 7 | =0.1057 |
| 8 | =0.102 |
| 9 | =1.22 |
| 10 | =0.9356 |
| 11 | =0.4758 |
| 12 | =4.4653 |
| 13 | =1.5196 |
| 14 | =0.0256 |
| 15 | =0.1058 |
| 16 | =0.062 |
| 17 | =0.5652 |
| 18 | =0.8678 |
| 19 | =0.5014 |
| 20 | =3.7859 |
| 21 | =3.8705 |
| 22 | =0.0796 |
| 23 | =0.0102 |
| 24 | =10.876 |
| 25 | =16.267 |
| 26 | =29.326 |
| 27 | =16.652 |
| 28 | =16.816 |
| 29 | >125 |
| 30 | >125 |
| 31 | =22.412 |
| 32 | =34.805 |
| 34 | =10.192 |
| 35 | >125 |
| 36 | =49.835 |
| 37 | =43.085 |
| 38 | =33.199 |
| 39 | =22.237 |
| 40 | =15.577 |
| 41 | =47.961 |
| 42 | =9.9191 |
| 43 | =25.23 |
| 44 | =59.083 |
| 45 | =123.23 |
| 46 | =93.596 |
| 47 | =66.172 |
| 48 | =25.528 |
| 49 | =24.549 |
| 50 | =21.139 |
| 51 | =54.965 |
| 52 | =37.759 |
| 53 | =19.191 |
| 54 | =17.61 |
| 55 | =63.571 |
| 56 | =0.4731 |
| 57 | =3.4541 |
| 58 | =3.9555 |

TABLE 3-continued (HBO-KAT7)

| Example | IC50 (μM) |
|---|---|
| 59 | =5.9579 |
| 60 | =6.1869 |
| 61 | =45.521 |
| 62 | =53.147 |
| 63 | =33.046 |
| 64 | =32.457 |
| 65 | =46.869 |
| 66 | =13.639 |
| 67 | =9.7499 |
| 68 | >125 |
| 69 | =0.2615 |
| 70 | =0.1288 |
| 71 | =0.0354 |
| 72 | =0.0388 |
| 73 | =0.3688 |
| 74 | =9.1331 |
| 75 | =9.5078 |
| 77 | =0.4338 |
| 78 | =1.0779 |
| 79 | =10.099 |
| 80 | =27.003 |
| 81 | =47.292 |
| 82 | =27.683 |
| 83 | >125 |
| 84 | =0.3289 |
| 85 | =97.312 |
| 86 | =14.265 |
| 87 | =5.4145 |
| 88 | =5.4379 |
| 89 | =20.904 |
| 90 | =23.509 |
| 91 | =20.885 |
| 92 | =37.341 |
| 93 | =4.5750 |
| 94 | =4.7667 |
| 95 | =1.2967 |
| 96 | =0.0924 |
| 97 | =3.4862 |
| 98 | =3.1485 |
| 99 | =3.0790 |
| 100 | =2.8451 |
| 101 | =107.4056 |
| 102 | =0.9936 |
| 103 | =3.0305 |
| 104 | =18.5367 |
| 105 | =0.1321 |
| 106 | =1.5310 |
| 107 | =4.0861 |
| 108 | =20.3222 |
| 109 | =0.6718 |
| 110 | =0.3717 |
| 111 | =0.1376 |
| 112 | =1.4029 |
| 113 | =11.2556 |
| 114 | =3.4529 |
| 115 | =6.8021 |
| 116 | =3.3319 |
| 117 | =0.4537 |
| 118 | =3.0847 |
| 119 | =0.3216 |
| 120 | =0.2150 |
| 121 | =0.4527 |
| 122 | =75.5323 |
| 123 | =5.6804 |
| 124 | =1.0896 |
| 125 | =86.2109 |
| 126 | =7.4482 |
| 127 | =25.3925 |
| 128 | =9.6780 |
| 129 | =85.2041 |

TABLE 4

(MOF-KAT8)

| Example | IC50 (µM) |
|---|---|
| 1 | =1.2049 |
| 2 | =42.857 |
| 3 | =40.082 |
| 4 | =32.524 |
| 5 | =3.9631 |
| 6 | =0.7462 |
| 7 | =5.1154 |
| 8 | =4.034 |
| 9 | =12.561 |
| 10 | =20.628 |
| 11 | =8.8423 |
| 12 | =10.322 |
| 13 | =25.534 |
| 22 | =1.0461 |
| 31 | =50.349 |
| 40 | =26.272 |
| 42 | =43.575 |
| 45 | >125 |
| 55 | >125 |
| 56 | =35.954 |
| 57 | =78.111 |
| 58 | =39.034 |
| 59 | =31.02 |
| 62 | =16.153 |
| 63 | >125 |
| 73 | =5.7769 |
| 77 | =2.0273 |
| 78 | =0.7684 |
| 84 | =5.5111 |
| 87 | =76.623 |
| 88 | =21.759 |

TABLE 5

(QKF-KAT6B)

| Example | IC50 (µM) |
|---|---|
| 2 | =7.7689 |
| 4 | =23.731 |
| 14 | =0.1232 |
| 15 | =0.0854 |
| 16 | =0.3098 |
| 17 | =3.7189 |
| 18 | =1.0003 |
| 19 | =2.1125 |
| 56 | =3.1417 |
| 73 | =0.1174 |
| 84 | =1.5532 |

Histone H3 Lysine 23 Acetylation Biomarker Assay

Compounds may be tested for their ability to inhibit acetylation of the histone H3K23 marker in the following assay:

The cell line U2OS was seeded at a density of 9,000 cells per well in 96 well optical quality tissue culture plates in RPMI medium and 10% foetal bovine serum, and allowed to adhere for 24 hours under standard culture conditions (37 degree Celsius, 5% CO2). At the end of this period the medium was aspirated. Compound dilutions prepared in DMSO were added to medium, with negative control wells reserved for treatment with DMSO only and 100% inhibition positive controls receiving a potent inhibitor compound (e.g. cas 2055397-28-7, benzoic acid, 3-fluoro-5-(2-pyridinyl)-, 2-[(2-fluorophenyl)sulfonyl]hydrazide) (Baell, J., Nguyen, H. N., Leaver, D. J., Cleary, B. L., Lagiakos, H. R., Sheikh, B. N., Thomas. T. J., Aryl sulfonohydrazides, WO2016198507A1, 2016) at 10 µM concentration and 200 µL transferred to the cells. After incubation for 24 hours, the cells were fixed with 3.7% formaldehyde in PBS for 20 minutes at room temperature, washed (5×5 minutes) with phosphate buffer saline containing 0.1% Tween 20 and blocked with Odyssey blocking buffer (LI-COR, Lincoln, Nebr.) containing 0.1% TritonX100. Anti-H3K23ac specific antibody (Abeam ab177275) in Odyssey blocking buffer containing 0.1% Tween 20 was added and incubated for 16 hours at 4 degree Celsius. After washing (as above), a secondary antibody labelled with Alexa647 dye (LifeTechnologies) and Hoechst 33342 (1 µg/mL, SigmaAldrich) were added for 1 hour incubation. Plates were washed as previously and read on a PerkinElmer Phenix high content imaging platform. Using a Columbus image analysis pipeline, individual nuclei were located by Hoechst 33342 stain and the acetylation level was calculated from the Alexa647-related intensity in the same area. The resulting mean intensity per cell was directly converted to percent inhibition relative to controls on the same plate and the data fitted against a four-parameter logistic model to determine the 50% inhibitory concentration ($IC_{50}$).

The results are shown in table 6 below:

| Example | IC50 (µM) |
|---|---|
| 1 | =0.0284 |
| 2 | >10 |
| 3 | >10 |
| 4 | >10 |
| 5 | =0.8951 |
| 6 | =0.4709 |
| 7 | =0.0491 |
| 8 | =0.0518 |
| 14 | =0.1325 |
| 15 | =0.141 |
| 16 | =0.1169 |
| 17 | =2.2578 |
| 18 | =1.5344 |
| 19 | >10 |
| 22 | =2.131 |
| 23 | =0.1776 |
| 56 | =2.0667 |
| 70 | =0.2753 |
| 71 | =0.0693 |
| 72 | =0.2042 |
| 73 | =0.0171 |
| 84 | =0.6452 |
| 96 | =3.9408 |
| 105 | =0.1730 |
| 111 | =0.4745 |
| 112 | =0.1868 |
| 116 | >20.0000 |
| 117 | =5.5641 |
| 119 | =0.6337 |

Histone H3 Lysine 14 Acetylation Biomarker Assay

Compounds may be tested for their ability to inhibit acetylation of the histone H3 Lysine 14 marker in the following assay:

The cell line U2OS was seeded at a density of 3,000 cells per well in 384-well optical quality tissue culture plates in RPMI medium supplemented with 10% foetal bovine serum and 10 mM Hepes. The cells were allowed to adhere for 24 hours under standard culture conditions (37 degree Celsius, 5% CO2). At the end of this period the cells were washed with serum free medium. Compound dilutions prepared in DMSO were added to the serum free medium, with negative control wells reserved for treatment with DMSO only and 100% inhibition positive controls receiving a potent inhibitor compound (e.g. (Z)-4-fluoro-N-((3-hydroxyphenyl)sulfonyl)-5-methyl-[1,1'-biphenyl]-3-carbohydrazonic acid) at 10 µM concentration. After incubation for 24 hours, the cells were fixed with 4% formaldehyde in PBS for 15 minutes at room temperature, washed with phosphate buffer saline and blocked with blocking buffer containing 0.2% TritonX100 and 2% BSA. Anti-H3K14ac specific antibody (Cell Signalling Technologies) in blocking buffer was added and incubated overnight at 4 degree Celsius. After washing, a secondary antibody labelled with AlexaFluor 488 dye (ThermoFisher) and Hoechst 33342 (1 µg/mL, Life Technologies) were added for 2 hours incubation at room temperature. Plates were washed and read on a PerkinElmer Opera HCS high content imaging platform. Using a Columbus image analysis pipeline, individual nuclei were located by Hoechst 33342 stain and the acetylation level was calculated from the AlexaFluor 488-related intensity in the same area. The resulting mean intensity per cell was converted to percent inhibition relative to controls on the same plate and the data fitted against a four-parameter logistic model to determine the 50% inhibitory concentration ($IC_{50}$).

The results are shown in table 7 below

| Example | IC50 (µM) |
|---|---|
| 1 | =0.1245 |
| 3 | =39.233 |
| 5 | =2.328 |
| 6 | =0.5256 |
| 7 | =0.4958 |
| 8 | =0.3446 |
| 10 | =4.1416 |
| 11 | =2.7388 |
| 12 | >40 |
| 13 | =22.384 |
| 14 | =0.2197 |
| 15 | =0.4495 |
| 16 | =0.1926 |
| 17 | =3.1957 |
| 18 | =3.8432 |
| 21 | >40 |
| 22 | =0.762 |
| 23 | =0.2157 |
| 56 | =2.6426 |
| 57 | >40 |
| 58 | =22.414 |
| 72 | =0.5749 |
| 73 | =1.2902 |
| 84 | =0.8783 |
| 96 | =7.3834 |
| 102 | =25.6297 |
| 105 | =3.0025 |
| 116 | >40.0000 |

H2A.Z Lysine 7 Acetylation Biomarker Assay

Compounds may be tested for their ability to inhibit the histone H2A.Z Lysine 7 acetylation marker in the following assay:

The cell line U2OS was seeded at a density of 3,000 cells per well in 384-well optical quality tissue culture plates in RPMI medium supplemented with 10% foetal bovine serum and 10 mM Hepes. The cells were allowed to adhere for 24 hours under standard culture conditions (37 degree Celsius, 5% $CO_2$). At the end of this period the cells were washed with serum free medium. Compound dilutions prepared in DMSO were added to the serum free medium, with negative control wells reserved for treatment with DMSO only and 100% inhibition positive controls receiving a potent inhibitor compound enantiomer 1 of 7-iodo-N-(2-(oxazol-2-yl)-2-phenylethyl)-2H-benzo[e][1,2,4]thiadiazine-3-carboxamide 1,1-dioxide, which is compound 146 of co-pending application GB1713962.7, filed on 31 Aug. 2018, at 30 µM concentration. After incubation for 24 hours, the cells were fixed with 4% formaldehyde in PBS for 15 minutes at room temperature, washed with phosphate buffer saline and blocked with blocking buffer containing 0.2% TritonX100 and 2% BSA. Anti-H2A.ZK7ac specific antibody (Abcam) in blocking buffer was added and incubated overnight at 4 degree Celsius. After washing, a secondary antibody labelled with AlexaFluor 488 dye (ThermoFisher) and Hoechst 33342 (1 µg/mL, Life Technologies) were added for 2 hours incubation at room temperature. Plates were washed and read on a PerkinElmer Opera HCS high content imaging platform. Using a Columbus image analysis pipeline, individual nuclei were located by Hoechst 33342 stain and the acetylation level was calculated from the AlexaFluor 488-related intensity in the same area. The resulting mean intensity per cell was converted to percent inhibition relative to controls on the same plate and the data fitted against a four-parameter logistic model to determine the 50% inhibitory concentration ($IC_{50}$).

The results are shown in table 8 below:

| Example | IC50 (µM) |
|---|---|
| 1 | =2.2314 |
| 3 | >40 |
| 5 | =5.6448 |
| 6 | =1.3537 |
| 7 | =2.1859 |
| 8 | =3.2736 |
| 10 | >40 |
| 11 | =5.3163 |
| 12 | >40 |
| 14 | =2.5007 |
| 15 | =12.111 |
| 16 | =1.7681 |
| 17 | =29.343 |
| 18 | =19.891 |
| 19 | =5.4231 |
| 21 | >40 |
| 22 | =4.7723 |
| 23 | =9.9897 |
| 56 | =24.141 |
| 58 | >40 |
| 72 | =4.7343 |
| 73 | =35.244 |
| 84 | =3.1481 |
| 96 | =27.2425 |
| 102 | >40.0000 |
| 105 | =17.0797 |
| 116 | >40.0000 |

STATEMENTS OF INVENTION

1. A compound of formula (I), or a pharmaceutically acceptable salt thereof, for use in a method of therapy:

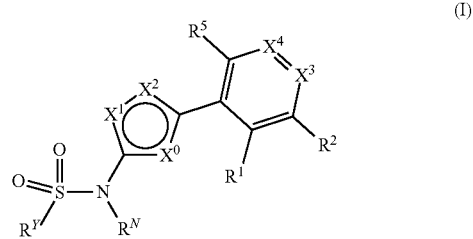

wherein either:
(i) $X^0=CR^C$, $X^1=N$, $X^2=O$; or
(ii) $X^0=CR^C$, $X^1=O$, $X^2=N$; or
(iii) $X^0=S$, $X^1=N$, $X^2=N$; or (iv) $X^0$=N, $X^1$=N, $X^2$=O; or
(v) $X^0$=O, $X^1$=N, $X^2$=N;
where $R^C$ is H, $CO_2CH_3$ or Cl;
$R^N$ is H or methyl;
$X^3$ is $CR^3$ or N;
$X^4$ is $CR^4$ or N;
$R^1$ to $R^5$ are independently selected from:
  (i) H;
  (ii) halo;
  (iii) cyano;
  (iv) $C_{1-3}$ alkyl, optionally substituted by one or more fluoro groups;
  (v) $(CH_2)_{n0}$—$C_{3-6}$ cycloalkyl, where n0=0 or 1;
  (vi) $(CH_2)_{n1}$—$C_{1-3}$ alkoxy, where n1=0 or 1, optionally substituted by one or more fluoro groups;
  (vii) $C_{1-3}$ alkylester;
  (vii) $(CH_2)_{n2}$-phenyl, where n2=0-2; and
  (viii) $(CH_2)_{n3}$—$C_5$ heteroaryl, wherein n3=0-1, optionally substituted by methyl; and
$R^Y$ is selected from:
  (i) $(CH_2)_{n4}$-phenyl, where n4=0-2, where phenyl is optionally substituted by
    (a) $C_{1-4}$ alkyl, optionally substituted by one or more fluoro groups;
    (b) $C_{1-4}$ alkoxy, optionally substituted by phenyl, or one or more fluoro groups;
    (c) halo;
    (d) cyano, nitro or amido;
    (e) phenyl; or
    (f) —$(CH_2)_{n5}$—, where n5 is 3 or 4;
  (ii) pyridyl;
  (iii) $C_{3-4}$ alkyl;
  (iv) $(CH_2)_{n6}$—$C_{3-6}$ cycloalkyl, where n6=0-2;
  (v) $C_6$ heterocyclyl, optionally substituted by $C_{1-4}$alkylester; and
  (vi) $NHR^{YN}$, where $R^{YN}$ is selected from phenyl or cyclohexyl.

2. A compound for use according to statement 1, wherein $X^0$=$CR^C$, $X^1$=N and $X^2$=O.

3. A compound for use according to statement 1, wherein $X^0$=$CR^C$, $X^1$=O and $X^2$=N.

4. A compound for use according to any one of statements 1 to 3, wherein $R^C$ is H.

5. A compound for use according to any one of statements 1 to 3, wherein $R^C$ is $CO_2CH_3$.

6. A compound for use according to any one of statements 1 to 3, wherein $R^C$ is Cl.

7. A compound for use according to statement 1, wherein $X^0$=S, $X^1$=N and $X^2$=N.

8. A compound for use according to statement 1, wherein $X^0$=N, $X^1$=N and $X^2$=O.

9. A compound for use according to statement 1, wherein $X^0$=O, $X^1$=N, and $X^2$=N.

10. A compound for use according to any one of statements 1 to 9, wherein $R^N$ is H.

11. A compound for use according to any one of statements 1 to 9, wherein $R^N$ is methyl.

12. A compound for use according to any one of statements 1 to 11, wherein $X^3$ is $CR^3$ and $X^4$ is $CR^4$.

13. A compound for use according to any one of statements 1 to 12, wherein when $R^1$ to $R^5$ is halo, it is selected from F, Cl and Br.

14. A compound for use according to any one of statements 1 to 13, wherein when $R^1$ to $R^5$ is $C_{1-3}$ alkyl, optionally substituted by one or more fluoro groups, it is selected from methyl, ethyl and propyl.

15. A compound for use according to any one of statements 1 to 13, wherein when $R^1$ to $R^5$ is $C_{1-3}$ alkyl, optionally substituted by one or more fluoro groups, the $C_{1-3}$ alkyl is perfluorinated.

16. A compound for use according to any one of statements 1 to 15, wherein when $R^1$ to $R^5$ is $(CH_2)_{n0}$—$C_{3-6}$ cycloalkyl, n0 is 0.

17. A compound for use according to any one of statements 1 to 15, wherein when $R^1$ to $R^5$ is $(CH_2)_{n0}$—$C_{3-6}$ cycloalkyl, n0 is 1.

18. A compound for use according to any one of statements 1 to 17, wherein when $R^1$ to $R^5$ is $(CH_2)_{n1}$—$C_{1-3}$ alkoxy, n1 is 0.

19. A compound for use according to any one of statements 1 to 17, wherein when $R^1$ to $R^5$ is $(CH_2)_{n1}$—$C_{1-3}$ alkoxy, n1 is 1.

20. A compound for use according to any one of statements 1 to 19, wherein when $R^1$ to $R^5$ is $C_{1-3}$ alkylester, it is selected from $CO_2CH_3$, $CO_2CH_2CH_3$ and $CO_2CH_2CH_2CH_3$.

21. A compound for use according to any one of statements 1 to 20, wherein when $R^1$ to $R^5$ is $(CH_2)_{n2}$-phenyl, it is phenyl.

22. A compound for use according to any one of statements 1 to 20, wherein when $R^1$ to $R^5$ is $(CH_2)_{n2}$-phenyl, it is $CH_2$-phenyl.

23. A compound for use according to any one of statements 1 to 20, wherein when $R^1$ to $R^5$ is $(CH_2)_{n2}$-phenyl, it is $C_2H_5$-phenyl.

24. A compound for use according to any one of statements 1 to 23, wherein when $R^1$ to $R^5$ is $(CH_2)_{n3}$—$C_5$ heteroaryl, where n3=0-1, optionally substituted by methyl; n3 is 0.

25. A compound for use according to any one of statements 1 to 23, wherein when $R^1$ to $R^5$ is $(CH_2)_{n3}$—$C_5$ heteroaryl, where n3=0-1, optionally substituted by methyl; n3 is 1.

26. A compound for use according to any one of statements 1 to 25, wherein when $R^1$ to $R^5$ is $(CH_2)_{n3}$—$C_5$ heteroaryl, it is selected from $(CH_2)_{n3}$-oxazolyl, $(CH_2)_{n3}$-isoxazolyl, $(CH_2)_{n3}$-thiazolyl, $(CH_2)_{n3}$-isothiazolyl, $(CH_2)_{n3}$-imidazolyl and $(CH_2)_{n3}$-pyrazolyl.

27. A compound for use according to statement 26, wherein when $R^1$ to $R^5$ is $(CH_2)_{n3}$—$C_5$ heteroaryl, it is selected from —$(CH_2)_{n3}$-oxazolyl and —$(CH_2)_{n3}$-pyrazolyl.

28. A compound for use according to any one of statements 1 to 11, wherein $R^2$ and $R^5$ are not H, and $R^1$, $R^3$ and $R^4$ are H.

29. A compound for use according to statement 28, wherein $R^2$ is selected from: halo;
$(CH_2)_{n0}$—$C_{3-6}$ cycloalkyl;
$(CH_2)_{n1}$—$C_{1-3}$ alkoxy;
$C_{1-3}$ alkylester; and
$(CH_2)_{n3}$—$C_5$ heteroaryl, optionally substituted by methyl.

30. A compound for use according to statement 29, wherein $R^2$ is selected from Br, Cl, cyclopropyl, methoxy and $CO_2CH_3$.

31. A compound for use according to statement 29, wherein $R^2$ is selected from:
pyrazol-1-yl;
pyrazol-3-yl; and
pyrazol-4yl;
each optionally substituted by methyl.

32. A compound for use according to any one of statements 28 to 30, wherein $R^5$ is selected from $C_{1-3}$ alkyl and $(CH_2)_{n1}$—$C_{1-3}$ alkoxy.

33. A compound for use according to statement 32, wherein $R^5$ is selected from ethyl, methoxy, $CH_2OCH_3$, isopropoxy, O—$CH_2CH_3$ and $OCF_3$.

34. A compound for use according to any one of statements 1 to 33, wherein $R^Y$ is $(CH_2)_{n4}$-phenyl, where n4=0-2, where phenyl is optionally substituted by:
   (a) $C_{1-4}$ alkyl, optionally substituted by one or more fluoro groups;
   (b) $C_{1-4}$ alkoxy, optionally substituted by phenyl, or one or more fluoro groups;
   (c) halo;
   (d) cyano, nitro or amido;
   (e) phenyl; or
   (f) —$(CH_2)_{n5}$—, where n5 is 3 or 4.

35. A compound for use according to claim 34, wherein n4 is 0.

36. A compound for use according to claim 34, wherein n4 is 1.

37. A compound for use according to claim 34, wherein n4 is 2.

38. A compound for use according to any one of claims 34 to 37, wherein the phenyl group in $R^Y$ is unsubstituted.

39. A compound for use according to any one of claims 34 to 37, wherein the phenyl group in $R^Y$ is substituted by one substituent.

40. A compound for use according to any one of claims 34 to 37, wherein the phenyl group in $R^Y$ is substituted by two substituents.

41. A compound for use according to any one of claims 34 to 37 and 39 to 40, wherein when $R^Y$ is substituted by $C_{1-4}$ alkyl, optionally substituted by one or more fluoro groups, the $C_{1-4}$ alkyl is unsubstituted by fluoro.

42. A compound for use according to any one of claims 34 to 37 and 39 to 40, wherein when $R^Y$ is substituted by $C_{1-4}$ alkyl, optionally substituted by one or more fluoro groups, the $C_{1-4}$ alkyl is perfluorinated.

43. A compound for use according to any one of claims 34 to 37 and 39 to 42, wherein when the phenyl group in $R^Y$ is substituted by $C_{1-4}$ alkoxy, optionally substituted by one or more fluoro groups, the $C_{1-4}$ alkyloxy is unsubstituted by fluoro.

44. A compound for use according to any one of claims 34 to 37 and 39 to 42, wherein when the phenyl group in $R^Y$ is substituted by $C_{1-4}$ alkoxy, optionally substituted by one or more fluoro groups, the $C_{1-4}$ alkyloxy is perfluorinated.

45. A compound for use according to any one of claims 34 to 37 and 39 to 44, wherein when the phenyl group in $R^Y$ is substituted by halo, the halo group is selected from F, Cl, Br and I.

46. A compound for use according to claim 45, wherein the halo group is F.

47. A compound for use according to claim 45, wherein the halo group is Cl.

48. A compound for use according to claim 45, wherein the halo group is Br.

49. A compound for use according to claim 45, wherein the halo group is I.

50. A compound for use according to any one of claims 34 to 37 and 39 to 49, wherein when the phenyl group in $R^Y$ is substituted by cyano.

51. A compound for use according to any one of claims 34 to 37 and 39 to 50, wherein when the phenyl group in $R^Y$ is substituted by nitro.

52. A compound for use according to any one of claims 34 to 37 and 39 to 51, wherein when the phenyl group in $R^Y$ is substituted by amido.

53. A compound for use according to any one of claims 34 to 37 and 39 to 52, wherein when the phenyl group in $R^Y$ is substituted by phenyl.

54. A compound for use according to any one of claims 34 to 37 and 39 to 53, wherein when the phenyl group in $R^Y$ is substituted by —$(CH_2)_{n5}$—, n5 is 3.

55. A compound for use according to any one of claims 34 to 37 and 39 to 53, wherein when the phenyl group in $R^Y$ is substituted by —$(CH_2)_{n5}$—, n5 is 4.

56. A compound for use according to any one of statements 1 to 33, wherein $R^Y$ is pyridyl.

57. A compound for use according to any one of statements 1 to 33, wherein $R^Y$ is $C_{3-4}$ alkyl.

58. A compound for use according to statement 57, wherein $R^Y$ is propyl.

59. A compound for use according to statement 57, wherein $R^Y$ is butyl.

60. A compound for use according to any one of statements 1 to 33, wherein $R^Y$ is —$(CH_2)_{n6}$—$C_{3-6}$ cycloalkyl, where n6=0-2.

61. A compound for use according to statement 60, wherein $R^Y$ is cyclopropyl.

62. A compound for use according to statement 60, wherein $R^Y$ is cyclobutyl.

63. A compound for use according to statement 60, wherein $R^Y$ is cyclopentyl.

64. A compound for use according to statement 60, wherein $R^Y$ is cyclohexyl.

65. A compound for use according to any one of statements 1 to 33, wherein $R^Y$ is $C_6$ heterocyclyl, optionally substituted by $C_{1-4}$ alkylester.

66. A compound for use according to statement 65, wherein $R^Y$ is tetrahydropyran-4-yl.

67. A compound for use according to statement 65, wherein $R^Y$ is 4-piperidyl.

68. A compound for use according to any one of statements 1 to 33, wherein $R^Y$ is $NHR^{YN}$ where $R^{YN}$ is selected from phenyl or cyclohexyl.

69. A compound for use according to statement 68, wherein $R^Y$ is —NH-phenyl.

70. A compound for use according to statement 68, wherein $R^Y$ is —NH-cyclohexyl.

71. A compound for use according to any one of statements 1 to 33, wherein $R^Y$ is 2,6-dimethoxyphenyl.

72. A compound for use according to any one of statements 1 to 33, wherein $R^Y$ is 2,6-dimethoxy or 4-phenylphenyl.

73. A compound for use according to any one of statements 1 to 33, wherein $R^Y$ is 2-methoxyphenyl.

74. A compound for use according to any one of statements 1 to 33, wherein $R^Y$ is 2-methoxy or 5-ethylphenyl.

75. A compound for use according to any one of statements 1 to 33, wherein $R^Y$ is $CH_2$phenyl.

76. A compound for use according to any one of statements 1 to 33, wherein $R^Y$ is $CH_2CH_2$phenyl.

77. A compound for use according to statement 1, with the proviso that when:
$X^0=CR^C$, $X^1=O$, $X^2=N$, $X^3=CR^3$, and $X^4=CR^4$,
$R^1$, $R^2$, $R^3$ $R^4$, $R^5$, $R^C$ and $R^N$ are H,
$R^Y$ is not 4-methylphenyl or 3,4-dimethoxyphenyl.

78. A compound for use according to statement 1, with the proviso that when:
$X^0=S$, $X^1=N$, $X^2=N$, $X^3=CR^3$, and $X^4=CR^4$, $R^1$, $R^2$, $R^3$ $R^4$, $R^5$ and $R^N$ are H,
$R^Y$ is not 4-methylphenyl or 3,4-dimethoxyphenyl.
79. A compound for use according to statement 1, with the proviso that when:
$X^0=S$, $X^1=N$, $X^2=N$, $X^3=CR^3$, and $X^4=CR^4$,
$R^1$, $R^2$, $R^4$, $R^5$ and $R^N$ are H, and $R^3$ is methyl or chloro,
$R^Y$ is not 3-chlorophenyl or 3-methylphenyl.
80. A compound for use according to statement 1, with the proviso that when:
$X^0=O$, $X^1=N$, $X^2=N$, $X^3=CR^3$, and $X^4=CR^4$,
$R^1$, $R^2$, $R^4$, $R^5$ and $R^N$ are H, and $R^3$ is $CF_3$,
$R^Y$ is not phenyl.
81. A compound for use according to statement 1, with the proviso that when:
$X^0=O$, $X^1=N$, $X^2=N$, $X^3=N$, and $X^4=CR^4$,
$R^1$, $R^2$, $R^4$, $R^5$ and $R^N$ are H,
$R^Y$ is not phenyl, 4-chlorophenyl, 4-bromophenyl or 4-iodophenyl.
82. A pharmaceutical composition comprising a compound as defined in any one of statements 1 to 81 and a pharmaceutically acceptable excipient.
83. A method of treatment of cancer, comprising administering to a patient in need of treatment, a compound as defined in any one of statements 1 to 81 or a pharmaceutical composition according to statement 82.
84. A method according to statement 83, wherein the compound is administered simultaneously or sequentially with radiotherapy and/or chemotherapy
85. The use of a compound as defined in any one of statements 1 to 81 in the manufacture of a medicament for treating cancer.
86. A compound as defined in any one of statements 1 to 81 or a pharmaceutical composition according to statement 82 for use in the treatment of cancer.
87. A compound or pharmaceutical composition according to statement 86, wherein the treatment is for simultaneous or sequential administration with radiotherapy and/or chemotherapy.
88. A compound as defined in any one of statements 1 to 81 or a pharmaceutically acceptable salt thereof.
89. A compound according to statement 88, wherein at least one of $R^1$ to $R^5$ is not H.
90. A compound according to either statement 88 or statement 89, wherein $R^2$ and $R^5$ are not H.
91. A compound according to any one of statements 88 to 90, wherein $R^Y$ is not $(CH_2)_{n4}$-phenyl, wherein the phenyl is substituted by a single group which is Cl, F or $NO_2$.
92. A compound according to any one of statements 88 to 91, wherein $R^Y$ is not $(CH_2)_{n4}$-phenyl, wherein the phenyl is substituted by $NO_2$.
93. A compound according to statement 88, with the proviso that when:
$X^0=S$, $X^1=N$, $X^2=N$, $X^3=CR^3$, and $X^4=CR^4$,
$R^1$, $R^2$, $R^4$, $R^5$ and $R^N$ are H, and $R^3$ is H or methyl,
$R^Y$ is not phenyl or 4-methylphenyl.
94. A compound according to statement 88, with the proviso that when:
$X^0=O$, $X^1=N$, $X^2=N$, $X^3=CR^3$, and $X^4=CR^4$,
$R^1$, $R^2$, $R^3$ $R^4$, $R^5$ and $R^N$ are H,
$R^Y$ is not phenyl or 4-nitrophenyl.
95. A compound according to statement 88, with the proviso that when:
$X^0=CR^C$, $X^1=O$, $X^2=N$, $X^3=CR^3$, and $X^4=CR^4$,
$R^1$, $R^2$, $R^3$ $R^4$, $R^5$, $R^C$ and $R^N$ are H,
$R^Y$ is not 4-methylphenyl or 3,4-dimethoxyphenyl.
96. A compound according to statement 88, with the proviso that when:
$X^0=S$, $X^1=N$, $X^2=N$, $X^3=CR^3$, and $X^4=CR^4$,
$R^1$, $R^2$, $R^3$ $R^4$, $R^5$ and $R^N$ are H,
$R^Y$ is not 4-methylphenyl or 3,4-dimethoxyphenyl.
97. A compound according to statement 88, with the proviso that when:
$X^0=S$, $X^1=N$, $X^2=N$, $X^3=CR^3$, and $X^4=CR^4$,
$R^1$, $R^2$, $R^4$, $R^5$ and $R^N$ are H, and $R^3$ is methyl or chloro,
$R^Y$ is not 3-chlorophenyl or 3-methylphenyl.
98. A compound according to statement 88, with the proviso that when:
$X^0=O$, $X^1=N$, $X^2=N$, $X^3=CR^3$, and $X^4=CR^4$,
$R^1$, $R^2$, $R^4$, $R^5$ and $R^N$ are H, and $R^3$ is $CF_3$,
$R^Y$ is not phenyl.
99. A compound according to statement 88, with the proviso that when:
$X^0=O$, $X^1=N$, $X^2=N$, $X^3=N$, and $X^4=CR^4$,
$R^1$, $R^2$, $R^4$, $R^5$ and $R^N$ are H,
$R^Y$ is not phenyl, 4-chlorophenyl, 4-bromophenyl or 4-iodophenyl.
100. A compound for use according to statement 1, wherein either:
  (i) $X^0=CR^C$, $X^1=N$, $X^2=O$; or
  (ii) $X^0=CR^C$, $X^1=O$, $X^2=N$; or
  (iii) $X^0=S$, $X^1=N$, $X^2=N$; or
  (iv) $X^0=N$, $X^1=N$, $X^2=O$; or
  (v) $X^0=O$, $X^1=N$, $X^2=N$;
where $R^C$ is H, $CO_2Me$ or Cl;
$R^N$ is H or Me;
$X^3$ is $CR^3$ or N;
$X^4$ is $CR^4$ or N;
$R^1$ to $R^5$ are independently selected from:
  (i) H;
  (ii) halo;
  (iii) cyano;
  (iv) $C_{1-3}$ alkyl, optionally substituted by one or more F;
  (v) $(CH_2)_{n0}$—$C_{3-6}$ cycloalkyl, where n0=0 or 1;
  (vi) $(CH_2)_{n1}$—$C_{1-3}$ alkoxy, where n1=0 or 1, optionally substituted by one or more F;
  (vii) $C_{1-3}$ alkylester;
  (vii) $(CH_2)_{n2}$-Ph, where n2=0-2;
  (viii) $C_5$ heteroaryl
$R^Y$ is selected from:
  (i) $(CH_2)_{n4}$Ph, where n4=0-2, where Ph is optionally substituted by
    (a) $C_{1-4}$ alkyl, optionally substituted by one or more F;
    (b) $C_{1-4}$ alkoxy, optionally substituted by one or more F;
    (c) halo;
    (d) cyano, nitro or amido;
    (e) phenyl; or
    (f) —$(CH_2)_{n5}$—, where n5 is 3 or 4;
  (ii) pyridyl;
  (iii) $C_{3-4}$ alkyl;
  (iv) $C_{3-6}$ cycloalkyl
101. A compound for use according to statement 100, wherein $X^0=CR^C$, $X^1=N$ and $X^2=O$ or $X^0=CR^C$, $X^1=O$ and $X^2=N$, and $R^C$ is H.
102. A compound for use according to any either statement 100 or statement 101, wherein $R^N$ is H.
103. A compound for use according to any one of statements 100 to 102, wherein $X^3$ is $CR^3$ and $X^4$ is $CR^4$.
104. A compound for use according to any one of statements 100 to 103, wherein $R^2$ and $R^5$ are not H, and $R^1$, $R^3$ and $R^4$ are H.

105. A compound for use according to statement 104, wherein $R^2$ is selected from halo, $(CH_2)_{n0}$—$C_{3-6}$ cycloalkyl, $(CH_2)_{n1}$—$C_{1-3}$ alkoxy and $C_{1-3}$ alkylester.
106. A compound for use according to statement 105, wherein $R^2$ is selected from Br, Cl, cyclopropyl, OMe and $CO_2$Me.
107. A compound for use according to any one of statements 104 to 106, wherein $R^5$ is selected from $C_{1-3}$ alkyl and $(CH_2)_{n1}$—$C_{1-3}$ alkoxy.
108. A compound for use according to statement 107, wherein $R^5$ is selected from Et, OMe, $CH_2$OMe, O-iPr, O-Et and $OCF_3$.
109. A compound for use according to any one of statements 100 to 108, wherein $R^Y$ is $(CH_2)_{n4}$Ph, where n4=0-2, where Ph is optionally substituted by:
    (a) $C_{1-4}$ alkyl, optionally substituted by one or more F;
    (b) $C_{1-4}$ alkoxy, optionally substituted by one or more F;
    (c) halo;
    (d) cyano, nitro or amido;
    (e) phenyl; or
    (f) —$(CH_2)_{n5}$—, where n5 is 3 or 4.
110. A compound for use according to statement 109, wherein the Ph group in $R^Y$ is unsubstituted.
111. A compound for use according to statement 109, wherein the Ph group in $R^Y$ bears a single substituent.
112. A compound for use according to statement 109, wherein the Ph group in $R^Y$ bears two substituents.
113. A compound for use according to any one of statements 100 to 108, wherein $R^Y$ is pyridyl.
114. A compound for use according to any one of statements 100 to 108, wherein $R^Y$ is $C_{3-4}$ alkyl.
115. A compound for use according to any one of statements 100 to 108, wherein $R^Y$ is $C_{3-6}$ cycloalkyl.
116. A compound for use according to any one of statements 100 to 108, wherein $R^Y$ is selected from:
    a) 2,6-dimethoxyphenyl;
    b) 2,6-dimethoxy, 4-phenylphenyl;
    c) 2-methoxyphenyl;
    d) 2-methoxy, 5-ethylphenyl;
    e) $CH_2$Ph; and
    f) $CH_2CH_2$Ph.
117. A pharmaceutical composition comprising a compound as defined in any one of statements 100 to 116 and a pharmaceutically acceptable excipient.
118. A compound as defined in any one of statements 100 to 116 or a pharmaceutical composition according to statement 117 for use in the treatment of cancer.
119. A compound or pharmaceutical composition according to statement 118, wherein the treatment is for simultaneous or sequential administration with radiotherapy and/or chemotherapy.
120. A compound as defined in any one of statements 100 to 116 or a pharmaceutical salt thereof.
121. A compound according to statement 120, wherein at least one of $R^1$ to $R^5$ is not H.
122. A compound according to either statement 120 or statement 121, wherein $R^2$ and $R^5$ are not H.
123. A compound according to any one of statements 120 to 122, wherein $R^Y$ is not $(CH_2)_{n4}$Ph, wherein the Ph is substituted by a single group which is Cl, F or $NO_2$.
124. A compound according to any one of statements 120 to 123, wherein $R^Y$ is not $(CH_2)_{n4}$Ph, wherein the Ph is substituted by $NO_2$.

REFERENCES

Aggarwal and Calvi, Nature, 2004, 430, 372-376 doi: 10.1038/nature02694

Avvakumov et al., Oncogene, 2007, 26, 5395-5407 doi: 10.1038/sj.one. 1210608

Berge et al., J. Pharm. Sci., 1977, 66, 1-19 doi: 10.1002/jps.2600660104

Borrow et al., Nat. Genet., 1996, 14, 33-41 doi:10.1038/ng0996-33

Dekker et al., Drug, Discov. Today, 2014, 19, 654-660 doi: 10.1016/j.drudis.2013.11.012

Doyon et al., Mol. Cell., 2006, 27, 51-64 doi:10.1016/j.molcel.2005.12.007

Dhuban et al., Sci. Immunol., 2017, 2, 9297 doi: 10.1126/sciimmunol.aai9297

Duong et al., Cancer Res., 2013, 73, 5556-5568 doi: 10.1158/0008-5472.CAN-13-0013

Ghizzoni et al., Eur. J. Med. Chem., 2012, 47, 337-344 doi:10.1016/j.ejmech.2011.11.001

Gil et al., J. Proteomics, 2017, 150, 297-309 doi:10.1016/j.jprot.2016.10.003

Gobert, M. et al., Cancer Research, 2009, 69, 2000-2009 doi: 10.1158/0008-5472.CAN-08-2360

Holbert et al., J. Biol. Chem., 2007, 282, 36603-36613 doi:10.1074/jbc.M705812200

Iizuka et al., Mol. Cell. Biol., 2006, 26, 1098-1108 doi: 10.1128/MCB.26.3.1098-1108.2006

Iizuka et al., Cancer Sci., 2013, 104, 1647-1655 doi: 10.1111/cas. 12303

Jeong, et al., Blood Res 2016 51(3), 152-154 doi:10.5045/br.2016.51.3.152

Joshi, et al., Immunity 2015, 43, 579-590 doi:10.1016/j.immuni.2015.08.006

Li, B. et al., PNAS, 2007, 104, 4571-4576 doi:10.1073/pnas.0700298104

Melero, et al. Nature Reviews Cancer, 2015, 15, 457-472 doi:10.1038/nrc3973

Merson et al., J. Neurosci., 2006, 26, 11359-11370 doi: 10.1523/JNEUROSCI.2247-06.2006

Miller, A. M. et al. J. Immunol., 2006, 177, 7398-7405 doi:10.4049/jimmunol.177.10.7398

Persa, E. et al. Cancer Letters, 2015 368(2), 252-261 doi: 10.1016/j.canlet.2015.03.003

Sheikh et al., Blood, 2015, 125(12), 1910-21 doi:10.1182/blood-2014-08-594655

Shi et al, Nature Biotech, 2015, 33, 661-667 doi:10.1038/nbt.3235

Su et al., Int. J. Mol. Sci., 2016, 17, 1-18 doi:10.3390/ijms17101594

Stern et al., Crit. Rev. Oncol. Hematol., 2005, 54, 11-29 doi:10.1016/j.critrevonc.2004.10.011

Thomas et al., Development, 2000, 127, 2537-2548 PMID: 10821753

Tao, H. et al., Lung Cancer, 2012, 75, 95-101 doi:10.1016/j.lungcan.2011.06.002

Turner-Ivey et al., Neoplasia, 2014, 16(8): 644-655 doi: 10.1016/j.neo.2014.07.007

Valerio et al., Cancer Research, 2017, 77(7), 1753-62 doi: 10.1158/0008-5472.CAN-16-2374

Vizmanos et al., Genes Chromosomes Cancer, 2003, 36(4), 402-405 doi:10.1002/gcc.10174

Voss et al., BioEssays, 2009, 31(10), 1050-1061 doi: 10.1002/bies.200900051

Wang, L., et al. EBioMedicine, 2016, 13, 99-112 doi: 10.1016/j.ebiom.2016.10.018

Wang, X. et al., Oncogene, 2017, 36, 3048-3058 doi: 10.1038/onc.2016.458

Xiao, Y. et al., Cell reports, 2014, 7, 1471-1480 doi:10.1016/j.celrep.2014.04.021

Yan, M. et al., *Breast Cancer Research*, 2011, 13, R47 doi: 10.1186/bcr2869

Zack et al., *Nature Genetics* 2013 45, 1134-1140 doi: 10.1038/ng.2760

Zhang et al., *Mini. Rev. Med. Chem.*, 2017, 17, 1-8 doi: 10.2174/1389557516666160923125031

The invention claimed is:

1. A compound of formula (I), or a pharmaceutically acceptable salt thereof:

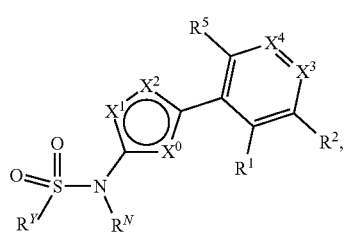

(I)

wherein either:
(i) $X^0=CR^C$, $X^1=N$, —$X^2=O$; or
(ii) $X^0=CR^C$, $X^1=O$, $X^2=N$; or
(iii) $X^0=S$, $X^1=N$, $X^2=N$; or
(iv) $X^0=N$, $X^1=N$, $X^2=O$; or
(v) $X^0=O$, $X^1=N$, $X^2=N$;
where $R^C$ is H, $CO_2CH_3$ or Cl;
$R^N$ is H or methyl;
$X^3$ is $CR^3$ or N;
$X^4$ is $CR^4$ or N;
$R^1$ to $R^5$ are independently selected from:
  (i) H;
  (ii) halo;
  (iii) cyano;
  (iv) $C_{1-3}$ alkyl, optionally substituted by one or more fluoro groups;
  (v) $(CH_2)_{n0}$—$C_{3-6}$ cycloalkyl, where n0=0 or 1;
  (vi) $(CH_2)_{n1}$—$C_{1-3}$ alkoxy, where n1=0 or 1, optionally substituted by one or more fluoro groups;
  (vii) $C_{1-3}$ alkylester;
  (viii) $(CH_2)_{n2}$-phenyl, where n2=0-2; and
  (ix) $(CH_2)_{n3}$—$C_5$ heteroaryl, where n3=0-1, optionally substituted by methyl; and
$R^Y$ is selected from:
  (i) $(CH_2)_{n4}$-phenyl, where n4=0-2, where phenyl is optionally substituted by:
    (a) $C_{1-4}$ alkyl, optionally substituted by one or more fluoro groups;
    (b) $C_{1-4}$ alkoxy, optionally substituted by phenyl, or one or more fluoro groups;
    (c) halo;
    (d) cyano, nitro or amido;
    (e) phenyl; or
    (f) —$(CH_2)_{n5}$—, where n5 is 3 or 4;
  (ii) pyridyl;
  (iii) $C_{3-4}$ alkyl;
  (iv) $(CH_2)_{n6}$—$C_{3-6}$ cycloalkyl, where n6=0-2;
  (v) $C_6$ heterocyclyl, optionally substituted by $C_{1-4}$ alkylester; and
  (vi) $NHR^{YN}$, where $R^{YN}$ is selected from phenyl or cyclohexyl.

2. A pharmaceutical composition comprising the compound or salt as defined in claim 1 and a pharmaceutically acceptable excipient.

3. The compound or salt according to claim 1, wherein at least one of $R^1$ to $R^5$ is not H.

4. The compound or salt according to claim 1, wherein $R^2$ and $R^5$ are not H.

5. The compound or salt according to claim 1, wherein $R^Y$ is not $(CH_2)_{n3}$-phenyl, wherein the phenyl is substituted by a single group which is Cl, F or $NO_2$.

6. The compound or salt according to claim 1, wherein $R^Y$ is not $(CH_2)_{n3}$-phenyl, wherein the phenyl is substituted by $NO_2$.

7. The compound or salt according to claim 1, with the proviso that when:
  (a) $X^0=S$, $X^1=N$, $X^2=N$, $X^3=CR^3$, and $X^4=CR^4$, $R^1$, $R^2$, $R^4$, $R^5$ and $R^N$ are H, and $R^3$ is H or methyl, $R^Y$ is not phenyl or 4-methylphenyl;
  (b) $X^0=O$, $X^1=N$, $X^2=N$, $X^3=CR^3$, and $X^4=CR^4$, $R^1$, $R^2$, $R^3$ $R^4$, $R^5$ and $R^N$ are H, $R^Y$ is not phenyl or 4-nitrophenyl;
  (c) $X^0=CR^C$, $X^1=O$, $X^2=N$, $X^3=CR^3$, and $X^4=CR^4$, $R^1$, $R^2$, $R^3$ $R^4$, $R^5$, $R^C$ and $R^N$ are H, $R^Y$ is not 4-methylphenyl or 3,4-dimethoxyphenyl;
  (d) $X^0=S$, $X^1=N$, $X^2=N$, $X^3=CR^3$, and $X^4=CR^4$, $R^1$, $R^2$, $R^3$ $R^4$, $R^5$ and $R^N$ are H, $R^Y$ is not 4-methylphenyl or 3,4-dimethoxyphenyl;
  (e) $X^0=S$, $X^1=N$, $X^2=N$, $X^3=CR^3$, and $X^4=CR^4$, $R^1$, $R^2$, $R^4$, $R^5$ and $R^N$ are H, and $R^3$ is methyl or chloro, $R^Y$ is not 3-chlorophenyl or 3-methylphenyl;
  (f) $X^0=O$, $X^1=N$, $X^2=N$, $X^3=CR^3$, and $X^4=CR^4$, $R^1$, $R^2$, $R^4$, $R^5$ and $R^N$ are H, and $R^3$ is $CF_3$, $R^Y$ is not phenyl; and
  (g) $X^0=O$, $X^1=N$, $X^2=N$, $X^3=N$, and $X^4=CR^4$, $R^1$, $R^2$, $R^4$, $R^5$ and $R^N$ are H, $R^Y$ is not phenyl, 4-chlorophenyl, 4-bromophenyl or 4-iodophenyl.

8. The compound or salt according to claim 1, wherein $X^0=CR^C$, $X^1=N$ and $X^2=O$ or $X^0=CR^C$, $X^1=O$ and $X^2=N$, and $R^C$ is H.

9. The compound or salt according to claim 1, wherein $R^N$ is H.

10. The compound or salt according to claim 1, wherein $X^3$ is $CR^3$ and $X^4$ is $CR^4$.

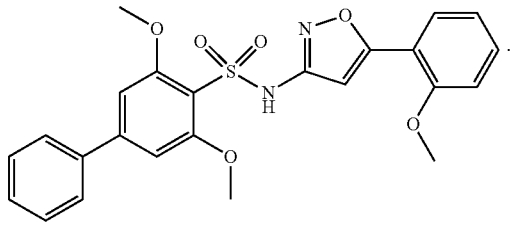 [SMILES: COc1ccccc1-c1cc(NS(=O)(=O)c2c(OC)cc(-c3ccccc3)cc2OC)no1]

11. A compound.
12. A salt of the compound of claim 11.
13. A pharmaceutically acceptable salt of the compound of claim 11.

* * * * *